US008841100B2

(12) United States Patent
Benjamin et al.

(10) Patent No.: US 8,841,100 B2
(45) Date of Patent: Sep. 23, 2014

(54) USE OF METHYLSULFONYLMETHANE (MSM) TO MODULATE MICROBIAL ACTIVITY

(75) Inventors: Rodney L. Benjamin, Camas, WA (US); Jeffrey Varelman, Moyie Springs, ID (US); Anthony L. Keller, Ashland, OR (US)

(73) Assignee: Biogenic Innovations, LLC, Vancouver, WA (US)

( * ) Notice: Subject to any disclaimer, the term of this patent is extended or adjusted under 35 U.S.C. 154(b) by 0 days.

(21) Appl. No.: 13/029,001

(22) Filed: Feb. 16, 2011

(65) Prior Publication Data

US 2011/0136210 A1    Jun. 9, 2011

Related U.S. Application Data

(63) Continuation of application No. PCT/US2010/054845, filed on Oct. 29, 2010.

(60) Provisional application No. 61/294,437, filed on Jan. 12, 2010, provisional application No. 61/259,098, filed on Nov. 6, 2009, provisional application No. 61/257,751, filed on Nov. 3, 2009, provisional application No. 61/256,935, filed on Oct. 30, 2009.

(51) Int. Cl.

| C12P 7/02 | (2006.01) |
| C12N 1/20 | (2006.01) |
| A61K 31/431 | (2006.01) |
| A61K 31/437 | (2006.01) |
| A61K 9/00 | (2006.01) |
| A61K 31/43 | (2006.01) |
| A61K 45/06 | (2006.01) |
| C12P 7/56 | (2006.01) |
| A61K 31/10 | (2006.01) |
| C12P 7/06 | (2006.01) |
| A01N 41/10 | (2006.01) |
| C12N 1/18 | (2006.01) |
| C12N 1/38 | (2006.01) |

(52) U.S. Cl.
CPC ............... *A61K 31/10* (2013.01); *A61K 31/431* (2013.01); *A61K 31/437* (2013.01); *A61K 9/0014* (2013.01); *A61K 31/43* (2013.01); *A61K 45/06* (2013.01); *C12P 7/56* (2013.01); *C12P 7/06* (2013.01); *C12N 1/20* (2013.01); *Y02E 50/17* (2013.01); *A01N 41/10* (2013.01); *Y02E 50/343* (2013.01); *C12N 1/18* (2013.01); *C12N 1/38* (2013.01)
USPC ...................... 435/155; 435/252.3

(58) Field of Classification Search
USPC ............................ 435/155, 252.3
See application file for complete search history.

(56) References Cited

U.S. PATENT DOCUMENTS

| 3,654,165 | A |  | 4/1972 | Bryant et al. |
| 4,112,946 | A |  | 9/1978 | Herschler |
| 4,296,130 | A |  | 10/1981 | Herschler |
| 4,477,469 | A |  | 10/1984 | Herschler |
| 4,514,421 | A |  | 4/1985 | Herschler |
| 4,559,329 | A |  | 12/1985 | Herschler |
| 4,568,547 | A |  | 2/1986 | Herschler |
| 4,616,039 | A |  | 10/1986 | Herschler |
| 4,863,748 | A |  | 9/1989 | Herschler |
| 4,902,517 | A | * | 2/1990 | Nakagawa et al. ............. 426/11 |
| 4,911,936 | A | * | 3/1990 | Kijima et al. ................. 426/62 |
| 4,914,135 | A |  | 4/1990 | Herschler |
| 4,973,605 | A |  | 11/1990 | Herschler |
| 5,071,878 | A |  | 12/1991 | Herschler |
| 5,753,696 | A |  | 5/1998 | Shealy et al. |
| 6,183,758 | B1 |  | 2/2001 | Scott |
| 6,328,987 | B1 |  | 12/2001 | Marini |
| 6,416,772 | B1 |  | 7/2002 | Van Engelen et al. |
| 6,426,370 | B1 |  | 7/2002 | Hofschneider |
| 6,579,543 | B1 |  | 6/2003 | McClung |
| 6,776,979 | B2 |  | 8/2004 | Frager et al. |
| 7,371,407 | B2 |  | 5/2008 | Farmer |
| 2001/0047038 | A1 |  | 11/2001 | Moorman et al. |

(Continued)

FOREIGN PATENT DOCUMENTS

| WO | WO 94/05272 | 3/1994 |
| WO | WO 01/73096 | 10/2001 |

(Continued)

OTHER PUBLICATIONS

Magnuson et al. (Pharmacokinetics and Distribution of [35S]Methylsulfonylmethane following Oral Administration to Rats., J. Agric. Food Chem., (2007), vol. 55, pp. 1033-1038.*

(Continued)

*Primary Examiner* — Alexander Kim
(74) *Attorney, Agent, or Firm* — Klarquist Sparkman, LLP

(57) ABSTRACT

Disclosed herein are methods of use of methylsulfonylmethane (MSM) to modulate microbial activity, such as to enhance or inhibit the activity of microorganisms. In one example, MSM (such as about 0.5% to 5% MSM) is used to enhance fermentation efficiency, such as to enhance fermentation efficiency associated with the production of beer, cider, wine, a biofuel, dairy product or any combination thereof. Also disclosed are in vitro methods for enhancing the growth of one or more probiotic microorganisms and methods of enhancing growth of a microorganism in a diagnostic test sample. Methods of inhibiting microbial activity are also disclosed. In one particular example, a method of inhibiting microbial activity includes selecting a medium that is susceptible to H1N1 influenza contamination; and contacting the medium with MSM at a concentration of about 10% to about 16% of weight by volume, thereby inhibiting H1N1 influenza microbial activity.

19 Claims, No Drawings

(56) References Cited

U.S. PATENT DOCUMENTS

| | | | |
|---|---|---|---|
| 2004/0001817 | A1 | 1/2004 | Giampapa |
| 2004/0126440 | A1 | 7/2004 | Frager et al. |
| 2005/0118291 | A1 | 6/2005 | Wang et al. |
| 2006/0040871 | A1 | 2/2006 | Levey et al. |
| 2006/0052438 | A1* | 3/2006 | Ho et al. ............ 514/453 |
| 2006/0084573 | A1 | 4/2006 | Grech et al. |
| 2006/0127508 | A1 | 6/2006 | Larkins |
| 2007/0110731 | A1 | 5/2007 | Riley |
| 2008/0038219 | A1 | 2/2008 | Mosbaugh et al. |
| 2008/0228161 | A1 | 9/2008 | Claussen et al. |
| 2008/0260708 | A1 | 10/2008 | Hall |
| 2009/0017438 | A1 | 1/2009 | Roy et al. |
| 2009/0017439 | A1 | 1/2009 | Shimko et al. |

FOREIGN PATENT DOCUMENTS

| | | | |
|---|---|---|---|
| WO | WO 2004/067013 | | 8/2004 |
| WO | WO 2004/100896 | | 11/2004 |
| WO | WO 2006/129149 | | 12/2006 |
| WO | WO2007/134294 | * | 11/2007 ............ B32B 27/04 |

OTHER PUBLICATIONS

MSM Alternative Medicine Review, (2003) vol. 8, pp. 438-441.*
Gorbach and Samtsov, "Therapeutic possibilities of inhalation of rifampicin with dimexide in phthisiopulmonology," *Probl Tuberk*, 3:34-36, 1991 (English Abstract).
Jagannath et al., "Enhancement of drug susceptibility of multi-drug resistant strains of *Mycobacterium tuberculosis* by ethambutol and dimethyl sulphoxide," *J of Antimicro Chemo*, 35(3):381-390, 1995.
Shaklee Health Network, "Methyl Sulfonyl Methane," retrieved from the internet on Dec. 16, 2010; URL:http://content.nhiondemand.com/shp/monoVMN.asp?objID=100028.
Mitinskaia et al., "BCG vaccination and increasing the effectiveness of treatment of post-vaccination complications by the use of fifampicin and dimexide," *Probl. Tuberk*, 5:4-7, 1994 (with English Abstract).
Mohamaddi and O'Mara, "Unusual patient odor interfering with care," *Ann. Emerg. Med.*, 27:391-392, 1996.
Müller and Urbanczik, "Influence of dimethyl Sulfoxide (DMSO) on restoring sensitivity of mycobacterial strains resistant to chemotherapeutic compounds," *J. Antimicrob. Chemother*. 5:326-327, 1979.
Muravyev et al., "Effect of dimethyl sulfoxide and dimethyl sulfone on a destructive preocess (sic) in the joints of mice with spontaneous arthritis," *Patol Fiziol Eksp*, 2:37-39, 1991 (with English Abstract).
Nash and Steingrube, "In vitro drug sensitivity of M. Avium-Intracellulare complex in the presence and absence of dimethyl sulphoxide," *Microbios.*, 35:7178, 1982.
Oshima et al., "The effect of distilled methylsulfonylmethane (MSM) on human chondrocytes in vitro," *Osteoarthritis and Cartilage*, 15:213, 2007.
Ostojic et al., "Laboratory testing of cabin air filters for the removal of reduced-sulfur odors," *New Engine Design and Automotive Filtration SAE Special Publications*, 1362:41-58, 1998.
Paul, "Interval therapy with dimethyl sulfoxide," *Ann. N.Y. Acad. Sci.*, 141:586-598, 1967.
Paulus, "FDA advisory committee meeting: methotrexate; guidelines for the clinical evaluation of anti-inflammatory drugs: DMSO in scleroderma," *Arthritis heum.*, 29:1289-1290, 1986.
Penrod et al., "Dimethyl sulfoxide for incisional pain after thoracotomy: Preliminary Report," *Ann. N.Y. Acad. Sci.*, 141:493-495, 1967.
Pottz et al., "The effect of dimethyl Sulfoxide (DMSO) on antibiotic sensitivity of a group of medically important microorganisms: preliminary report," *Ann. N.Y. Acad. Sci.*, 141:261-272, 1967.
Pratt et al., "A study of the absorption of OptiMSM (methylsulfonylmethane) in horses," *Proc. 17th Equine Nutr. Physiol. Soc.*, pp. 141-142, 2001.
Ropek et al., "Effects of dimethyl sulfoxide on *Tubercle bacilli* resistant to INH," *Gruzlica.*, 39:738-741, 1971.
Seibert, "DMSO and other combatants against bacteria isolated from leukemia and cancer patients," *Ann. N.Y. Acad. Sci.*, 141:175-201, 1967.
Shanmugam et al. "The effects of methylsulfonylmethane on hair growth promotion of magnesium ascorbyl phosphate for the treatment of alopecia," *Biomolecules and Ther.*, 17:241-248, 2009.
Simon et al., "Efficacy and safety of topical diclofenac containing dimethyl sulfoxide (DMSO) compared with those of topical placebo, DMSO vehicle and oral diclofenac for knee osteoarthritis," *Pain*, 143:238-245, 2009.
Smith et al., "Anti-inflammatory effects of topically applied dimethylsulphoxide gel on endotoxin-induced synovitis in horses," *Am. J. Vet. Res.*, 59:1149-52, 1998.
Steinberg, "The employment of DMSO as an anti-inflammatory agent and steroid transporter in diversified clinical diseases," *Ann. N.Y. Acad. Sci.*, 141:532-550, 1967.
Sturenberg, "Rapid detection of methicillin-resistant *Staphylococcus aureus* directly from clinical samples: methods, effectiveness and cost considerations," *GMS*, 7:1-19, 2009.
Szmant, "Physical properties of dimethyl sulfoxide and its function in biological systems," *Ann. N.Y. Acad. Sci.*, 243:20-23, 1975.
Szydlowska, "Studies on the role of dimethylsulfoxide in resensibilization of antibiotic-resistant bacterial strains," *Arch. Immunol. Ther. Exp. (Warsz)*, 20:193-202, 1972.
Szydlowska, "In vitro and in vivo Studies on the Role of Dimethylsulfoxide (DMSO) in Resensibilization of Bacterial Strains Resistant to Antibiotics and Chemotherapeutic Agents," *Abl. Bakt. Hyg.*, 239:270-274, 1977.
Szydlowska and Pawlowska, "Comparative studies on the influence of dimethylsulfoxide (DMSO) on reversion to sensitivity to isonicotinic acid hydrazide (INH) and rifampicin (RMP) in resistant strains of *Tubercle bacilli*," *Arch. Immunol. Ther. Exp. (Warsz)*, 24:575-577, 1976.
Szydlowska and Pawlowska, "In vivo studies on reversion to sensitivity of INH-resistant *Tubercle bacilli* under the influence of dimethylsulfoxide (DMSO)," *Arch. Immunol. Ther. Exp. (Warsz).*, 22(4):559-561, 1974.
Teigland and Saurino, "Clinical evaluation of dimethyl sulfoxide in equine applications," *Ann. N.Y. Acad. Sci.*, 141:471-477, 1967.
Tiews et al., "Metabolism and excretion of dimethyl sulfoxide in cows and calves after topical and parenteral application," *Ann. N.Y. Acad. Sci.*, 243:139-150, 1975.
Usha and Naidu, "Randomized, double-blind, parallel, placebo-controlled study of oral glucosamine, methylsulfonylmethane and their combination in osteoarthritis," *Clin. Drug. Invest.*, 24:353-363, 2004.
Vignes, "Dimethyl Sulfoxide: a superior solvent underutilized because of a safety myth," Semiconductor Safety Association Annual Meeting, Arlington, VA, Apr. 25-28, 2000.
Vuopala et al., "The analgesic action of DMSO ointment in arthrosis," *Acta. Rheum. Scand.*, 17:57-60, 1971.
Wierzbicki, "Homocysteine and cardiovascular disease: a review of the evidence" *Diabetes and Vascular Disease Research*, 4:143-149, 2007.
Williams et al., "Metabolism of dimethyl sulfide, dimethyl sulfoxide and dimethyl sulfone in the rabbit," *Arch. Biochem. Biophys.*, 117:84-87, 1966.
Windrum et al., "Variation in dimethyl sulfoxide use in stem cell transplantation: a survey of EBMT centres," *Bone Marrow Transplantation.*, 36:601-603, 2005.
Wong et al., "Absorption, excretion and biotransformation of dimethyl sulfoxide in man and miniature pigs after topical application as an 80% gel," *J. Invest. Dermatol.*, 56:44-48, 1971.
Wood and Wood, "Pharmacologic and biochemical consideration of dimethyl sulfoxide," *Ann. N.Y. Acad. Sci.*, 143, 7-19, 1975.
Zhang et al., "Assessment of methylsulfonylmethane as a permeability enhancer for regional EDTA chelation therapy," *Drug Delivery*, 16:243-248, 2009.
Zuckner et al., "Local application of dimethyl sulfoxide and DMSO combined with triacinolone acetonide in rheumatoid arthritis," *Ann. N.Y. Acad. Sci.*, 141:555-559, 1967.
"Additive Free MSM Methylsulfonylmethane," http://www.worldimagenaturals.com/products/msm/indes.php, 5 pages, downloaded Aug. 18, 2010.

(56) References Cited

OTHER PUBLICATIONS

"AloeCalm™ All-Natural and Organic Body Lotion," http://www.acne-answrs.org/products/aloe-calm.html, 6 pages, downloaded Jul. 5, 2010.
"How to Flush the Toxins out of Your Body from the Swine or H1N1 Flu Shot," http://www.ehow.com, 3 pages, downloaded Aug. 18, 2010.
"Methylsulfonylmethane," http://en.wikipedia.org/wiki/Methylsulfonylmethane, 5 pages, downloaded Jul. 5, 2010.
"MSM—MethylSulfonylMethane," http://pages.prodigy.net/naturedoctor/msm.html, 6 pages, downloaded Jul. 5, 2010.
"Sulfur (MSM): A Basic Essential Nutrient Needed, Now, More than Ever Before," http://www.all-natuarl.com/msm.html, 7 pages, downloaded Aug. 11, 2010.
Alekesvich et al., "Increase in the sensitivity of pathologic gum recessed microflora to streptomycin under effect of dimexide and trypsin," *Mikrobiol Zh.*, 35:766-769, 1973 (English Abstract).
Andrews, "Determination of minimum inhibitory concentrations," *J. of Antimicrobial Chemotherapy*, 48:5-16, 2001.
Barrager et al., "A multicentered, open-label trial on the safety and efficacy of methylsulfonylmethane in the treatment of seasonal allergic rhinitis," *J. Alt. Complem. Med.*, 8:167-173, 2002.
Beilke et al., "Effects of dimethyl sulphoxide on the oxidative function of human neutrophils," *J. Lab. Clin. Med.*, 110:91-96, 1987.
Berry et al., "Natural Gas Odorants Desulfurization," AIChE Ann. Meet. Conf. Proc., 2004 (8 pages).
Blumenthal and Fuchs, "The clinical use of dimethyl sulfoxide on various headaches, musculosekeletal, and other general medical disorders," *Ann. N.Y. Acad. Sci.*, 141:572-585, 1967.
Bookman et al., "Effect of a topical diclofenac solution for relieving symptoms of primary osteoarthritis of the knee: a randomized controlled trial," *JAMC*, 171(4):333-338, 2004.
Borodina et al., "Dimethylsulfone as a growth substrate for novel methylotrophic species of Hyphomicrobium and Arthrobacter," *Arch. Microbiol.*, 173:425-437, 2000.
Brandt, et al., "Selective affinity of dimethyl sulphoxide (DMSO) and 2-amino-4-phenyl sulphonylbenzenesulphonamide (NSD 3004) for the large intestinal mucosa of mice," *Acta. Pharmacol. Toxicol.*, 51:173-176, 1982.
Brayton, "Dimethyl Sulfoxide (DMSO): A Review," *The Cornel Veterinarian*, 76:61-69, 1986.
Brechner et al., "Dermal anesthesia by the topical application of tetracaine base dissolved in dimethyl sulfoxid," *Ann. N.Y. Acad. Sciences*, 141:524-531, 1967.
Brien et al., "Systematic review of the nutritional supplements dimethyl sulfoxide (DMSO) and methylsulfonylmethane (MSM) in the treatment of osteoarthritis" *Osteoarthritis and Cartilage*, 16:1277-1288, 2008.
Brien et al., "Meta-analysis of the related nutritional supplements dimethyl sulfoxide and methylsulfonylmethane in the treatment of osteoarthritis of the knee," *eCAM*, doi:10.1093/ecam/nep045, 10 pages, 2009.
Brown et al., "Guidelines for the laboratory diagnosis and susceptibility testing of methicillin-resistant *Staphylococcus aureus* (MRSA)," *J. Antimicrob. Chemother.*, 56, 1000-1018, 2005.
Brown, "Clinical experience with DMSO in acute musculoskeletal conditions comparing a non-controlled series with a controlled double blind study," *Ann. N.Y. Acad. Sci.*, 141:496-505, 1967.
Dancer, "The effect of antibiotics on methicillin-resistant *Staphylococcus aureus*," *J. Antimicrob. Chemother.*, 61:246-253, 2008.
De LenCastre et al., "Antibiotic resistant *Staphylococcus aureus*: a paradigm of adaptive power," *Curr. Opin. Microbiol.*, 10, 428-435, 2007.
Debi et al., "The role of MSM in knee osteoarthritis: a double blind, randomized prospective study," *Osteoarthritis and Cartilage*, 15:427, 2008.
Demos et al., "Dimethyl Sulfoxide in Musculoskeletal Disorders," *Ann. N.Y. Acad. Sci.*, 141:517-523, 1967.

Eberhardt et al., "DMSO in patients with activated gonarthrosis," *Fortschr. Med.*, 113:446-450, 1995 (Abstract only).
Evans et al., "Dimethylsulfoxide (DMSO) blocks conduction in peripheral nerve C fibers: a possible mechanism of analgesia," *Neurosci. Lett.*, 150:145-148, 1984.
Feldman et al., "In vivo and in vitro effects of dimethyl sulfoxide on streptomycin-sensitive and —resistant *Escherichia coli*," *Ann. N.Y. Acad. Sci.*, 243:269-277, 1975.
Gerhards and Gibian, "The metabolism of dimethyl sulfoxide and its metabolic effects in man and animals," *Ann. N.Y. Acad. Sci.*, 141:65-76, 1967.
Glasser, "Dimethylsulfoxide (DMSO) "resensibilization" as potential chemotherapy for opportunistic mycobacterial disease," *Am. Rev. Respir. Dis.*, 118:969-970, 1978.
Gorbach and Samtsov, "Therapeutic possibilities of inhalation of rifampicin with dimexide in phthisiopulmonolgy," *Probl. Tuberk.*, 3:34-36, 1991 (with English Abstract).
Gupta, "New delivery systems for topical nutraceutical (nutracosmetic) and cosmeceutical formulations," *Business Briefing: Global Cosmetic Manufacturing*, 1-5, 2004.
Haigler and Spring, "Comparison of the analgesic effect of dimethyl sulfoxide and morphine," *Ann. N.Y. Acad. Sci.*, 411:19-27, 1983.
Hasegawa, "Suppressive effects of methylsulfonylmethane (MSM) on type II collagen induced arthritis in DBA/iJ mice, *J. Pharmacol. Ther.*, 32:421-427, 2004.
Horvath et. al., "Toxicity of methylsulfonylmethane in rats," *Food Chem. Toxicol.*, 40:1459-62, 2002.
Hucker, et al., "Studies on the absorption, excretion and metabolism of dimethylsulfoxide (DMSO) in man," *J. Pharmacol. Exp. Therap.*, 155:309-317, 1967.
Jacob and Appleton, "MSM: The Definitive Guide: A comprehensive review of the science and therapeutics of Methylsulfonylmethane," *Freedom Press*, Topanga, CA, 2003 (51 pages).
Jacob and Herschler, "Dimethyl sulfoxide after twenty years," *Ann. N.Y. Acad. Sci.*, 411:14-18, 1983.
Jacob and Herschler, "Pharmacology of DMSO," *Cryobiology*, 23:14-27, 1986.
Jacob et al., "The miracle of MSM: the natural solution for pain," pp. 51-97; pp. 122-132; pp. 139-144; pp. 191-214, *Berkley Trade*, 1999.
Jacob and Wood, "Dimethyl sulfoxide (DMSO): toxicology, pharmacology, and clinical experience," *Am. J. Surg.*, 114:414-426, 1967.
Jagannath et al., "Enhancement of drug susceptibility of multi-drug resistant strains of *Mycobacterium tuberculosis* by ethambutol and dimethyl sulphoxide," *J. Antimicrob. Chemother.*, 35(3):381-390, 1995.
Jimenez and Willkens, "Dimethyl Sulphoxide: a perspective of its use in rheumatic diseases," *J. Lab. Clin. Med.*, 100:489-500, 1982.
John and Laudahn, "Clinical experiences with the topical application of DMSO in orthopedic diseases: evaluation of 4180 cases," *Ann. N.Y. Acad. Sci.*, 141:506-516, 1967.
Karlson and Ulrich, "Stability of rifampin in dimethylsulfoxide," *Appl. Microbiol.*, 18:692-693, 1969.
Kim et al., "Efficacy of methylsulfonylmethane (MSM) in osteoarthritis pain of the knee: a pilot clinical trial," *OsteoArthritis and Cartilage*, 14:286-294, 2006.
Knowles "Clinical experience with DMSO in small animal practice," *Ann. N.Y. Acad. Sci.*, 141:478-483, 1967.
Koenen et al., "Percutaneous therapy of activated osteoarthritis of the knee—comparison between DMSO and diclofenac," *Therapiestudie*, 38:534-538, 1996 (with English Abstract).
Layman and Jacob, "The absorption, metabolism, and excretion of dimethyl sulfoxide by *rhesus monkeys*" *Life Sciences*, 37:2431-2437, 1985.
Lee et al., "Evaluation of genotoxicity on plant derived dietary sulfur," *J. Microbiol. Biotech.*, 16:817-820, 2006.
Liubinets and Kruk, "Applying dimexide in treatment of endobronchitis in patients with destructive forms of pulmonary tuberculosis," *Zh Ushn Nos. Gorl. Bolesn.*, 29:68-71, 1969 (with English Abstract).
Lockie and Norcross, "A clinical study on the effects of dimethyl sulfoxide in 103 patients with acute and chronic musculoskeletal injuries and inflammations," *Ann. N.Y. Acad. Sci.*, 141:599-602, 1967.

(56) References Cited

OTHER PUBLICATIONS

Lu et al., "A mouse model for the evaluation of pathogenesis and immunity to Influenza A (H5N1) viruses isolated from humans," *J. Virol.*, 73:5903-5911, 1999.

Magnuson et al., Pharmacokinetics and distribution of [35S]-methylsulfonylmethane following oral administration in rats, *J. Agri. Food Chem.*, 55:2033-2038, 2006.

Magnuson et al., "Oral development toxicity of Methylsulfonylmethane in rats," *Food Chem. Toxicol.*, 45:977-984, 2007.

Martin and Hauthal, *Dimethyl Sulfoxide*, New York: John Wiley & Sons, 1971 (chapter 12, 21 pages).

Matsumoto, "Clinical trials of dimethyl sulfoxide in rheumatoid arthritis patients in Japan," *Ann. N.Y. Acad. Sci.*, 141:560-568, 1967.

\* cited by examiner

USE OF METHYLSULFONYLMETHANE (MSM) TO MODULATE MICROBIAL ACTIVITY

CROSS REFERENCE TO RELATED APPLICATIONS

This is a continuation of international patent application PCT/US2010/054845, filed Oct. 29, 2010, designating the United States, and claims priority to U.S. Provisional Applications No. 61/294,437 filed Jan. 12, 2010; No. 61/259,098 filed Nov. 6, 2009; No. 61/257,751 filed Nov. 3, 2009; and No. 61/256,935, filed Oct. 30, 2009; each of which is hereby incorporated by reference in its entirety.

FIELD OF THE DISCLOSURE

This disclosure relates to the field of methylsulfonylmethane (MSM), specifically to methods of use of MSM to modify biological activity, such as to enhance or inhibit microbial activity including bacterial growth.

BACKGROUND

Microorganisms (or microbes) are microscopic organisms that include bacteria, fungi, archaea, protists, plants (e.g., green algae), viruses, prions, parasites, and animals such as amoeba, plankton. Depending on the context, microorganisms may be viewed as either harmful or beneficial. In some cases, microorganisms may be harmful and lead to illness and disease in plants, animals or humans. Moreover, in addition to causing infections or diseases, undesired microbial growth may also occur in consumer products, such as food contamination. In other cases, microorganism growth is beneficial and is routinely exploited in biotechnology, modern diagnostic technologies, in chemical processes (e.g., fermentation), in food and beverage preparation, in environmental and industrial applications, and in maintaining and/or promoting human health.

SUMMARY

Disclosed herein are methods of modulating microorganism activity with MSM. MSM is an organosulfur compound with the formula $(CH_3)_2SO_2$. In particular, disclosed herein is the surprising capability of MSM to enhance or inhibit microorganism activity, such as microorganism growth or survival, depending upon the concentration of MSM provided to the microorganism (e.g., in the medium in which the organism is grown). MSM at a concentration of about 0.5% to about 5% by weight of medium or by weight of moisture content of the medium enhances microbial activity whereas MSM at a concentration of about 6% to about 17% by weight of medium or by weight of moisture content of the medium inhibits microbial activity.

Disclosed herein is the surprising discovery that MSM can both inhibit and enhance microbial activity, depending upon the concentration of MSM. For example, MSM concentrations between about 6 and about 17 percent by weight of medium (or of moisture content of medium inhibit microbial activity by reducing or otherwise impacting the growth, survival rate (e.g., by causing or expediting cell deterioration or death, such as programmed cell death), metabolism, reproduction (e.g., gene expression, protein expression, signal transduction, transcription, translation, protein folding, etc.), proliferation, vitality, robustness, action, and/or function of the microorganism. In contrast, MSM concentrations between about 0.04% to about 5% by weight enhance microbial activity, including enhancing microbial fermentation efficiency, microbial growth and/or culture efficiency.

As such, disclosed herein are methods of use of MSM to modulate microbial activity, such as to enhance or inhibit the activity of microorganisms.

In some embodiments, a method of enhancing fermentation efficiency of a microorganism is disclosed. For example, the method includes contacting medium containing a microorganism capable of fermentation with MSM, wherein the MSM is provided at a concentration of about 0.5% to about 5% by weight of the medium or at a concentration of about 0.5% to about 5% by weight of the moisture content of the medium, wherein the MSM increases the fermentation efficiency of the microorganism as compared to the fermentation efficiency in the absence of MSM.

In some embodiments, in vitro methods for enhancing the growth of one or more probiotic microorganisms are disclosed. In some examples, the method comprises contacting one or more probiotic microorganisms with a medium capable of supporting growth of one or more probiotic microorganisms; and providing MSM to the medium at about 0.4% to about 5% by weight of the medium or by weight of a moisture content of the medium thereby enhancing growth of the one or more microorganisms in vitro as compared to growth of the one or more microorganisms in vitro in the absence of MSM.

Also provided are methods for enhancing growth of a microorganism in a diagnostic test sample. In some examples, the method comprises contacting the diagnostic test sample comprising one or more microorganisms with a medium capable of supporting growth of the one or more microorganisms; providing MSM to the medium at a concentration of about 0.4% to about 5% by weight of the medium or by weight of a moisture content of the medium, thereby enhancing the growth of the one or more microorganisms in the diagnostic test sample as compared to growth of the one or more microorganisms in the absence of MSM.

Further disclosed are methods of inhibiting microbial activity. In some examples, the method comprises selecting a medium that is susceptible to H1N1 influenza contamination; and contacting the medium with MSM at a concentration of about 10% to about 16% of weight by volume, thereby inhibiting H1N1 influenza microbial activity.

The foregoing and other features of the disclosure will become more apparent from the following detailed description of a several embodiments.

DETAILED DESCRIPTION

I. Overview of Several Embodiments

Disclosed herein is the surprising discovery that MSM can both inhibit and enhance microbial activity, depending upon the concentration of MSM. For example, MSM concentrations between about 6 and about 17 percent by weight of medium (or of moisture content of medium inhibit microbial activity by reducing or otherwise impacting the growth, survival rate (e.g., by causing or expediting cell deterioration or death, such as programmed cell death), metabolism, reproduction (e.g., gene expression, protein expression, signal transduction, transcription, translation, protein folding, etc.), proliferation, vitality, robustness, action, and/or function of the microorganism. In contrast, MSM concentrations between about 0.04% to about 5% by weight enhance microbial activity, including enhancing microbial fermentation efficiency, microbial growth and/or culture efficiency.

As such, disclosed herein are methods of use of MSM to modulate microbial activity, such as to enhance or inhibit the activity of microorganisms.

In some embodiments, a method of enhancing fermentation efficiency of a microorganism is disclosed. For example, the method includes contacting medium containing a microorganism capable of fermentation with MSM, wherein the MSM is provided at a concentration of about 0.5% to about 5% by weight of the medium or at a concentration of about 0.5% to about 5% by weight of the moisture content of the medium, wherein the MSM increases the fermentation efficiency of the microorganism as compared to the fermentation efficiency in the absence of MSM. In some examples, enhancing fermentation efficiency comprises an at least 50% increase in alcohol, carbon dioxide or acid production in the presence of MSM by the microorganism as compared to alcohol or acid production in the absence of MSM. For example, enhancing fermentation efficiency comprises an at least 50% increase in production of ethanol, methanol or a combination of thereof as compared to production of ethanol, methanol or a combination of thereof in the absence of MSM.

In some examples, enhancing fermentation efficiency comprises an at least 50% increase in carbon dioxide production in the presence of MSM by the microorganism as compared to carbon dioxide production in the absence of MSM, the microorganism is yeast and the method of enhancing fermentation is for the production of bread.

In some examples, enhancing fermentation efficiency comprises an at least 50% increase in lactic acid production in the presence of MSM by the microorganism as compared to lactic acid production in the absence of MSM and the method of enhancing fermentation is for the production of a dairy product.

In some embodiments, the method of enhancing fermentation efficiency is for the production of beer, cider, wine, a biofuel, bread, dairy product or any combination thereof. In some examples, the microorganism is yeast and the method of enhancing fermentation is for the production of beer. In some examples, the microorganism is algae and the method of enhancing fermentation is for the production of biofuel.

In some embodiments, the concentration of MSM is about 0.5%. In some examples, the medium comprises a sodium chloride concentration of less than 5% of total moisture content.

Also disclosed are in vitro methods for enhancing the growth of one or more probiotic microorganisms. In some embodiments, the method comprises contacting one or more probiotic microorganisms with a medium capable of supporting growth of one or more probiotic microorganisms; and providing MSM to the medium at about 0.4% to about 5% by weight of the medium or by weight of a moisture content of the medium thereby enhancing growth of the one or more microorganisms in vitro as compared to growth of the one or more microorganisms in vitro in the absence of MSM.

In some examples, the concentration of MSM is about 1% to about 3% of the weight of the medium or the moisture content of the medium.

In some examples, the one or more probiotic microorganisms comprises *Lactobacillus acidophilus, Lactobacillus delbrueckii, Bacillus coagulans, Lactobacillus rhamnosus, Bifidobacteruim bifidum* or any combination thereof.

In some examples, the medium comprises a probiotic-containing product, such as milk, yogurt, rice yogurt, frozen yogurt, chocolate, cheese, beer, wine, vinegar, sauerkraut or any combination thereof.

Also disclosed are methods for enhancing growth of a microorganism in a diagnostic test sample. In some examples, the method comprises contacting the diagnostic test sample comprising one or more microorganisms with a medium capable of supporting growth of the one or more microorganisms; providing MSM to the medium at a concentration of about 0.4% to about 5% by weight of the medium or by weight of a moisture content of the medium, thereby enhancing the growth of the one or more microorganisms in the diagnostic test sample as compared to growth of the one or more microorganisms in the absence of MSM.

Further disclosed are methods of inhibiting microbial activity. In some examples, the method comprises selecting a medium that is susceptible to H1N1 influenza contamination; and contacting the medium with MSM at a concentration of about 10% to about 16% of weight by volume, thereby inhibiting H1N1 influenza microbial activity. In some examples, the medium comprises a bodily fluid, a bodily tissue, or a surface. In some examples, contacting the medium comprises spraying or wiping the medium susceptible to microbial contamination with MSM. In some examples, the surface is a household surface, bedding, coverings, industrial equipment or surface, blood, skin or a combination thereof. In some examples, MSM is provided in a composition, wherein said composition is free of bleach or free alcohol or consists essentially of water. In some examples, the method further comprises sterilizing the medium after adding said MSM. In some examples, the medium is free from preservatives. In some examples, the MSM inhibits the microbial activity by reducing growth rate of H1N1 influenza by at least 50% as compared to the growth rate of H1N1 influenza in the absence of MSM.

II. Abbreviations and Terms

DMEM: Dulbecco's modified eagle medium
DMSO: Dimethyl sulfoxide
DNA: Deoxyribonucleic acid
ELISA: Enzyme-linked immunosorbent assay
$IC_{50}$: Inhibitory concentration 50
LAB: Lactic acid bacteria
MIC: Minimum inhibitory concentration
MSM: Methylsulfonylmethane
PAGE: Polyacrylamide-gel electrophoresis
PBS: Phosphate buffered saline
PDA: Potato dextrose agar
SDS: Sodium dodecyl sulfate
TNTC: Too numerous to count
TSB: Tryptic soy broth The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a bacterial cell" includes single or plural bacterial cells and is considered equivalent to the phrase "comprising at least one bacterial cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. For example, conventional methods well known in the art to which a disclosed invention pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999; Loudon, *Organic Chemistry*, Fourth Edition, New York: Oxford University Press, 2002, pp. 360-361, 1084-1085; Smith and March, *March's Advanced Organic Chemistry Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978.

Additional terms commonly used in molecular genetics can be found in Benjamin Lewin, Genes V published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Additional terms commonly used in chemistry can be found in Loudon, *Organic Chemistry*, Fourth Edition, New York: Oxford University Press, 2002, pp. 360-361, 1084-1085; Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978.

Administration: To provide or give a subject a compound, such as MSM, by any effective route. Exemplary routes of administration include, but are not limited to, injection (such as subcutaneous, intramuscular, intradermal, intraperitoneal, and intravenous), oral, sublingual, rectal, transdermal (such as topical), intranasal, vaginal and inhalation routes. A particular type of administration is topical.

Bacterial pathogen: A bacteria that causes disease (pathogenic bacteria). Examples of pathogenic bacteria for which MSM may be used to modify include without limitation any one or more of (or any combination of) *Acinetobacter baumanii*, *Actinobacillus* sp., *Actinomycetes*, *Actinomyces* sp. (such as *Actinomyces israelii* and *Actinomyces naeslundii*), *Aeromonas* sp. (such as *Aeromonas hydrophila*, *Aeromonas veronii biovar sobria* (*Aeromonas sobria*), and *Aeromonas caviae*), *Anaplasma phagocytophilum*, *Alcaligenes xylosoxidans*, *Acinetobacter baumanii*, *Actinobacillus actinomycetemcomitans*, *Bacillus* sp. (such as *Bacillus anthracis*, *Bacillus cereus*, *Bacillus subtilis*, *Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae*, *Bifidobacterium* sp., *Bordetella* sp. (such as *Bordetella pertussis*, *Bordetella parapertussis*, and *Bordetella bronchiseptica*), *Borrelia* sp. (such as *Borrelia recurrentis*, and *Borrelia burgdorferi*), *Brucella* sp. (such as *Brucella abortus*, *Brucella canis*, *Brucella melintensis* and *Brucella suis*), *Burkholderia* sp. (such as *Burkholderia pseudomallei* and *Burkholderia cepacia*), *Campylobacter* sp. (such as *Campylobacter jejuni*, *Campylobacter coli*, *Campylobacter lari* and *Campylobacter fetus*), *Capnocytophaga* sp., *Cardiobacterium hominis*, *Chlamydia trachomatis*, *Chlamydophila pneumoniae*, *Chlamydophila psittaci*, *Citrobacter* sp. *Coxiella burnetii*, *Corynebacterium* sp. (such as, *Corynebacterium diphtheriae*, *Corynebacterium jeikeum* and *Corynebacterium*), *Clostridium* sp. (such as *Clostridium perfringens*, *Clostridium difficile*, *Clostridium botulinum* and *Clostridium tetani*), *Eikenella corrodens*, *Enterobacter* sp. (such as *Enterobacter aerogenes*, *Enterobacter agglomerans*, *Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), *Erysipelothrix rhusiopathiae*, *Eubacterium* sp., *Francisella tularensis*, *Fusobacterium nucleatum*, *Gardnerella vaginalis*, *Gemella morbillorum*, *Haemophilus* sp. (such as *Haemophilus influenzae*, *Haemophilus ducreyi*, *Haemophilus aegyptius*, *Haemophilus parainfluenzae*, *Haemophilus haemolyticus* and *Haemophilus parahaemolyticus*, *Helicobacter* sp. (such as *Helicobacter pylori*, *Helicobacter cinaedi* and *Helicobacter fennelliae*), *Kingella kingii*, *Klebsiella* sp. (such as *Klebsiella pneumoniae*, *Klebsiella granulomatis* and *Klebsiella oxytoca*), *Lactobacillus* sp., *Listeria monocytogenes*, *Leptospira interrogans*, *Legionella pneumophila*, *Leptospira interrogans*, *Peptostreptococcus* sp., *Moraxella catarrhalis*, *Morganella* sp., *Mobiluncus* sp., *Micrococcus* sp., *Mycobacterium* sp. (such as *Mycobacterium leprae*, *Mycobacterium intracellulare*, *Mycobacterium avium*, *Mycobacterium bovis*, and *Mycobacterium marinum*), *Mycoplasm* sp. (such as *Mycoplasma pneumoniae*, *Mycoplasma hominis*, and *Mycoplasma genitalium*), *Nocardia* sp. (such as *Nocardia asteroides*, *Nocardia cyriacigeorgica* and *Nocardia brasiliensis*), *Neisseria* sp. (such as *Neisseria gonorrhoeae* and *Neisseria meningitidis*), *Pasteurella multocida*, *Plesiomonas shigelloides*. *Prevotella* sp., *Porphyromonas* sp., *Prevotella melaminogenica*, *Proteus* sp. (such as *Proteus vulgaris* and *Proteus mirabilis*), *Providencia* sp. (such as *Providencia alcalifaciens*, *Providencia rettgeri* and *Providencia stuartii*), *Pseudomonas aeruginosa*, *Propionibacterium acnes*, *Rhodococcus equi*, *Rickettsia* sp. (such as *Rickettsia rickettsii*, *Rickettsia akari* and *Rickettsia prowazekii*, *Orientia tsutsugamushi* (formerly: *Rickettsia tsutsugamushi*) and *Rickettsia typhi*), *Rhodococcus* sp., *Serratia marcescens*, *Stenotrophomonas maltophilia*, *Salmonella* sp. (such as *Salmonella enterica*, *Salmonella typhi*, *Salmonella paratyphi*, *Salmonella enteritidis*, *Salmonella cholerasuis* and *Salmonella typhimurium*), *Serratia* sp. (such as *Serratia marcesans* and *Serratia liquifaciens*), *Shigella* sp. (such as *Shigella dysenteriae*, *Shigella flexneri*, *Shigella boydii* and *Shigella sonnei*), *Staphylococcus* sp. (such as *Staphylococcus aureus*, *Staphylococcus epidermidis*, *Staphylococcus hemolyticus*, *Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A *streptococci, Streptococcus pyogenes*, Group B *streptococci, Streptococcus agalactiae*, Group C *streptococci, Streptococcus anginosus, Streptococcus equismilis*, Group *D streptococci, Streptococcus bovis*, Group F *streptococci,* and *Streptococcus anginosus* Group G *streptococci*), *Spirillum minus, Streptobacillus moniliformi, Treponema* sp. (such as *Treponema carateum, Treponema petenue, Treponema pallidum* and *Treponema endemicum, Tropheryma whippelii, Ureaplasma urealyticum, Veillonella* sp., *Vibrio* sp. (such as *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio* fumisii), *Yersinia* sp. (such as *Yersinia enterocolitica*, and *Yersinia pestis*) and *Xanthomonas maltophilia* among others.

In some embodiments, MSM is used to modify, such as increase or decrease the biological activity of one or more of the organisms listed above.

Beta-lactam antibiotics: A class of antibiotic agents containing a β-lactam nucleus in its molecular structure. Examples include the penicillin, cephalosporin, monobactam, and carbapenem families of antibiotics. Methicillin and Oxacillin are Beta-lactam antibiotics.

Biological activity: An expression describing the beneficial or adverse effects of a substance on living matter. When the agent is a complex chemical mixture, this activity is exerted by the substance's active ingredient or pharmacophore, but can be modified by the other constituents. Activity is generally dosage-dependent and it is not uncommon to have effects ranging from beneficial to adverse for one substance when going from low to high doses. In one example, MSM alters, such as increase or decreases the biological activity of a microorganism, such as bacteria.

Biofuel: A fuel derived from a metabolic product of a living organism. It is a renewable energy source, unlike other natural resources such as petroleum, coal and nuclear fuels. A biodiesel fuel is a diesel-equivalent processed fuel derived from biological sources which can be used in unmodified diesel-engine vehicles. Biodiesels are attractive for fuels, and some other uses, because they have a low vapor pressure, are non-toxic, stable and do not deteriorate or detonate upon mild heating. Chemically, biodiesels are generally defined as the mono alkyl esters of long chain fatty acids derived from renewable lipid sources.

Bleach: A solution of approximately 3-6% sodium hypochlorite (NaClO), and oxygen bleach, which contains hydrogen peroxide or a peroxide-releasing compound such as sodium perborate, sodium percarbonate, sodium persulfate, tetrasodium pyrophosphate, or urea peroxide together with catalysts and activators, e.g., tetraacetylethylenediamine and/or sodium nonanoyloxybenzenesulfonate. Bleaching powder is calcium hypochlorite. Many bleaches have strong bactericidal properties, and are used for disinfecting and sterilizing Conditions that permit production: Any fermentation or culturing conditions that allow a microorganism to grow and/or produce a desired product, such as alcohols and carbon dioxide or organic acids. Such conditions usually include temperature ranges, levels of aeration, and media selection that, when combined, allow the microorganism to grow. Exemplary mediums include broths or gels. To determine if culture conditions permit product production, the microorganism can be cultured for 2, 4, 6, 8, 12, 24, 36, 48 or 72 hours and a sample can be obtained and analyzed. For example, the cells in the sample or the medium in which the cells were grown can be tested for the presence of the desired product. When testing for the presence of a product, assays can be used, such as those provided herein, including those presented in the Examples below.

Contacting: Placement in direct physical association; including in solid, liquid and gas form. Contacting includes contact between one molecule and another molecule. Contacting can occur in vitro with isolated cells, tissue or a solid surface (such as a household or industrial surface) or in vivo by administering to a subject.

Control: Samples believed to be normal (e.g., representative activity or function in the absence of the variable being tested) as well as laboratory values, even though possibly arbitrarily set, keeping in mind that such values can vary from laboratory to laboratory. A control group is practically identical to the treatment group, except for the single variable of interest whose effect is being tested, which is only applied to the treatment group.

Culturing: Maintaining a cell in a medium that allows the organism to continue to live. For example, culturing includes incubating a microorganism in a fermentation media, such as a fermentation broth or fermentation gel. One of ordinary skill in the art will appreciate that the time, temperature, and other physical conditions associated with culturing will depend upon the organism being cultured and the desired outcome from the culture. For example, a microorganism that is cultured to produce ethanol can be placed in a fermentation broth containing a carbohydrate source, various minerals and trace elements, as well as MSM and compounds useful for inducing the production, including less than 5% NaCl.

Decrease: To reduce the quality, amount, or strength of something. In one example, administration of MSM decreases or reduces one or more biological activities, such as growth, reproduction, proliferation, survival rate, metabolism, vitality, robustness, action, and/or function of microorganisms by at least 10%, at least 20%, at least 50%, or even at least 90%, including between 10% to 95%, 20% to 80%, 30% to 70%, 40% to 50%, such as 10%, 20%, 30%, 40%, 50%, 60%, 70%, 80%, 85%, 90%, 95%, 98%, or 100%. For example, administration of MSM decreases or inhibits bacterial growth, for example by at least 2-fold, for example at least 3-fold or at least 4-fold, as compared to a control (such as bacterial growth in the absence of MSM or a reference value known to be representative of bacterial growth in a subject afflicted with a bacterial infection). Such decreases can be measured using the methods disclosed herein as well as those known to one of ordinary skill in the art. In some embodiments, MSM is used to inhibit growth of specific microorganisms. In other embodiments, MSM is used to inhibit growth of a wide range of microorganisms in certain media or products. In some embodiments, log-scale reductions are realized after the first 24 hours.

Dimethyl sulfoxide (DMSO): Dimethyl sulfoxide (DMSO), also known as methylsulfinylmethane or methyl sulfoxide, is an organosulfur compound with the formula $(CH_3)_2SO$. This colorless liquid is a polar aprotic solvent that dissolves both polar and nonpolar compounds and is miscible in a wide range of organic solvents as well as water. It has a distinctive property of penetrating the skin very readily, so that one may taste it soon after it comes into contact with the skin. DMSO is well known as a nutritional supplement and as a pharmaceutical agent. One of skill in the relevant art will be familiar with these uses. Various grades of DMSO are available commercially (for example, product No. 472301 from Sigma-Aldrich, Corp., St. Louis, Mo.) and one of skill in the art will be familiar with a source of DMSO.

Enhance or increase: To increase the quality, amount, or strength of something. In one example, MSM increases or enhances the activity of a microorganism, for example relative to activity in the absence of MSM. In a particular example, MSM increases the activity of a microorganism, such as enhancing the growth, reproduction, proliferation, survival rate, metabolism, vitality, robustness, action, and/or function of a microorganism by at least 10%, at least 20%, at least 50%, or even at least 90%, including between 10% to 95%, 20% to 80%, 30% to 70%, 40% to 50%, such as 10%, 20%, 30%, 40%, 50%, 60%, 70%, 80%, 85%, 90%, 95%, 98%, or 100%. The terms activity and growth are used interchangeably in some contexts. In some examples, MSM is used to enhance growth of specific microorganisms. In other examples, MSM is used to enhance growth of a wide range of microorganisms in certain media or products. In some examples, enhancing microbial activity includes enhancing microbial products or microbial metabolites. For example, MSM increases or enhances fermentation efficiency or culturing efficiency such as by at least 10%, at least 20%, at least 50%, or even at least 90%, including between 10% to 95%, 20% to 80%, 30% to 70%, 40% to 50%, such as 10%, 20%, 30%, 40%, 50%, 60%, 70%, 80%, 85%, 90%, 95%, 98%, or 100%. Such increases can be measured using the methods disclosed herein.

Fermentation: A process of deriving energy from the oxidation of organic compounds, such as carbohydrates, and using an endogenous electron acceptor, which is usually an organic compound. During fermentation, pyruvate is metabolised to various different compounds. Homolactic fermentation is the production of lactic acid from pyruvate; alcoholic fermentation is the conversion of pyruvate into ethanol and carbon dioxide; and heterolactic fermentation is the production of lactic acid as well as other acids and alcohols. Fermentation does not necessarily have to be carried out in an anaerobic environment. For example, even in the presence of abundant oxygen, yeast cells prefer fermentation to oxidative phosphorylation, as long as sugars are readily available for consumption. Sugars are a common substrate of fermentation, and typical examples of fermentation products are ethanol, lactic acid, and hydrogen. However, more exotic compounds can be produced by fermentation, such as butyric acid and acetone. Yeast carries out fermentation in the production of ethanol in beers, wines and other alcoholic drinks, along with the production of large quantities of carbon dioxide.

Fermentation Broth: Any medium that supports microorganism life (for instance, a microorganism that is actively metabolizing carbon). A fermentation medium usually contains a carbon source. The carbon source can be anything that can be utilized, with or without additional enzymes, by the microorganism for energy.

Fermentation efficiency: An expression of how much fermentation product, such as alcohol, lactic acid, micro-organisms or other desired fermentation product, was produced relatively to a control (such as in the absence of MSM) or to an amount that could be theoretically produced.

Fermentation media: Any substance used to culture cells, such as mammalian cells and microorganisms. Fermentation media includes any growth medium (e.g., broth or gel) which supports microorganism life (e.g., a microorganism that is actively metabolizing carbon). A fermentation medium usually contains a carbon source, such as glucose, xylose, cellulosic material and the like. The carbon source can be anything that can be utilized, with or without additional enzymes, by the microorganism for energy.

Fungal pathogen: A fungus that causes disease. Examples of fungal pathogens for which MSM can be used to modify include without limitation any one or more of (or any combination of) *Trichophyton rubrum*, *T. mentagrophytes*, *Epidermophyton floccosum*, *Microsporum canis*, *Pityrosporum orbiculare* (*Malassezia furfur*), *Candida* sp. (such as *Candida albicans*), *Aspergillus* sp. (such as *Aspergillus fumigatus*, *Aspergillus flavus*, *Aspergillus glaucus*, *Aspergillus nidulans*, *Aspergillus oryzae*, *Aspergillus terreus*, *Aspergillus ustus*, *Aspergillus versicolor* and *Aspergillus clavatus*), *Cryptococcus* sp. (such as *Cryptococcus neoformans*, *Cryptococcus gattii*, *Cryptococcus laurentii* and *Cryptococcus albidus*), *Coccidioides* sp., *Histoplasma* sp. (such as *Histoplasma capsulatum*), *Pneumocystis* sp. (such as *Pneumocystis jirovecii*), *Stachybotrys* sp. (such as *Stachybotrys chartarum*), *Paracoccidioides*, *Blastomyce*, *Fusarium*, *Sporothrix*, *Trichosporon*, *Rhizopus*, *Pseudallescheria*, *Paecilomyces*, *Alternaria*, *Curvularia*, *Exophiala*, *Wangiella*, *Penicillium*, and *Cephalosphorium*. In some embodiments, MSM is administered to inhibit or prevent an infection or disorder associated with one or more of the aforementioned fungal pathogens.

Incubating: A term that includes a sufficient amount of time for an agent, such as MSM, to interact with a cell or tissue.

Inhalant device: A device capable of delivering a composition to a subject, for example to a subject's lung tissue. For example, an inhalant device may be an inhaler, a nebulizer or a ventilator. Inhalant devices described herein are constructed from a material adapted for contacting DMSO and/or MSM. In some embodiments, an inhalant device is disposable or replaceable. Inhalant devices described herein are configured to deliver a DMSO or MSM containing composition to directly contact bacterial pathogens in a subject's lung tissue. Inhalant devices are configured to generate particles of a composition that range in size. In some embodiments, an inhalant device is configured to generate particles of a composition that range in size from about 0.1 μm to about 10 μm or from about 0.5 μm to about 5 μm.

Inhibiting microbial activity or Inhibiting an Infection or Disease: The phrase "inhibiting microbial activity" refers to reducing the growth, reproduction, proliferation, survival rate, metabolism, vitality, robustness, action, and/or function of microorganisms. The phrase "inhibiting or treating an infection, disease or a condition" refers to preventing or reducing the full development of an infection, disease or condition, for example, in a subject who is at risk for developing an infection, such as a bacterial infection. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the infection/disease in a susceptible subject, a reduction in severity of some or all clinical symptoms of the infection/disease, a slower progression of the infection/disease, a reduction in the number of relapses of the infection/disease, an improvement in the overall health or well-being of the subject, or by other parameters well known in the art that are specific to the particular infection/disease, such as a particular bacterial infection.

Medium or media: An environment containing or suitable for supporting microorganisms, including, but not limited to, broths, agar, cultures, foods, beverages, cell suspensions, biological tissue, biological fluids, inorganic surfaces, organic surfaces, substrates, living cells, host cells, diagnostic assays, and other solid, liquid, matrix, gelatinous, or gaseous environments.

Methylsulfonylmethane (MSM): An organosulfur compound with the formula $(CH_3)2SO_2$. MSM has largely been marketed and sold as a dietary supplement. MSM is also known as $DMSO_2$, Dimethyl sulfone and methyl sulfone.

MSM is structurally related to dimethyl sulfoxide (DMSO), but the behavior of these two is different. DMSO is a highly polar solvent and an excellent ligand, with water-like dissolving properties whereas MSM is less polar and less reactive. MSM is also a metabolite of DMSO. MSM has the following chemical structure:

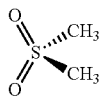

Microorganism. A member of the prokaryotic or eukaryotic microbial species from the domains Archaea, Bacteria, and Eucarya, the latter including yeast and filamentous fungi, protozoa, algae, or higher Protista. The terms "microbial cells" and "microbes" are used interchangeably with the term microorganism. Microbes can include wild-type, genetically-engineered or modified organisms. Microorganisms include viruses, prions, parasites, fungi, mold, yeast and bacteria. In some embodiments, MSM is used to enhance the activity of a wide spectrum of microorganisms including, but not limited to, viruses, prions, parasites, fungi, mold, yeast, algae and bacteria. In other embodiments, MSM is used to inhibit the activity of microorganisms, including, but not limited to, fungi, mold, yeast, bacteria and viruses.

Modulate or modulating: To adjust, alter, regulate an activity, a degree or rate of such including an increase or a decrease in biological activity of a molecule. In one example, MSM is administered to modulate, either increase or decrease microbial activity, such as bacterial growth.

Parasite: An organism that lives inside humans or other organisms acting as hosts (for the parasite). Parasites are dependent on their hosts for at least part of their life cycle. Parasites are harmful to humans because they consume needed food, eat away body tissues and cells, and eliminate toxic waste, which makes people sick. Examples of fungal pathogens for use in accordance with the disclosed methods and compositions include without limitation any one or more of (or any combination of) Malaria (*Plasmodium falciparum, P. vivax, P. malariae*), Schistosomes, Trypanosomes, Leishmania, Filarial nematodes, Trichomoniasis, Sarcosporidiasis, Taenia (*T. saginata, T. solium*), Leishmania, Toxoplasma gondii, Trichinelosis (*Trichinella spiralis*) or Coccidiosis (*Eimeria* species). MSM may be used to inhibit or prevent activity of one or more of the organisms listed above.

Pharmaceutical composition: A chemical compound or composition capable of inducing a desired therapeutic or prophylactic effect when properly administered to a subject. A pharmaceutical composition can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject). In a particular example, a pharmaceutical agent is an agent that significantly reduces one or more symptoms associated with an infection, such as a bacterial or viral infection. In some embodiments, a therapeutic agent is an antibiotic agent, such as methicillin or oxacillin.

Pharmaceutically Acceptable Carriers or vehicles: The pharmaceutically acceptable carriers (vehicles) useful in this disclosure are conventional. *Remington's Pharmaceutical Sciences*, by E. W. Martin, Mack Publishing Co., Easton, Pa., 19th Edition (1995), describes compositions and compositions suitable for pharmaceutical delivery of one or more therapeutic compounds or molecules, such as one or more peptides provided herein. In general, the nature of the carrier will depend on the particular mode of administration being employed. For instance, parenteral compositions usually comprise injectable fluids that include pharmaceutically and physiologically acceptable fluids such as water, physiological saline, balanced salt solutions, aqueous dextrose, glycerol or the like as a vehicle. In a particular embodiment the carrier is one that allows the therapeutic compound to cross the blood-brain barrier. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Prebiotic: A non-digestible food ingredient that stimulates growth and/or activity of bacteria in the digestive tract which are beneficial to the health of the body. Typically, prebiotics are carbohydrates (such as *oligosaccharides*); however, non-carbohydrates are also sources of such ingredients. Preboitoics can be short-chain, long-chain, and/or full-spectrum prebiotics. Short-chain prebiotics (such as oligofructose), contain 2-8 links per saccharide molecule, are typically fermented more quickly in the right-side of the colon providing nourishment to the bacteria in that area. Longer-chain prebiotics (such as inulin) contain 9-64 links per saccharide molecule, and tend to be fermented more slowly, nourishing bacteria predominantly in the left-side colon. Full-spectrum prebiotics provide the full range of molecular link-lengths from 2-64 links per molecule, and nourish bacteria throughout the colon (such as oligofructose-enriched inulin, OEI). In some examples, a prebiotic increases the number and/or activity of bifidobacteria and lactic acid bacteria. Bifidobacteria and the lactic acid bacteria (lactobacillus or LABs) are bacteria which improve digestion (including enhancing mineral absorption) and the effectiveness and intrinsic strength of the immune system. A product that stimulates bifidobacteri, such as MSM, is considered a bifidogenic factor. Traditional dietary sources of prebiotics include soybeans, inulin sources (such as Jerusalem artichoke, jicama, and chicory root), raw oats, unrefined wheat, unrefined barley, garlic, leeks, onion, asparagus, banana and yacon. Prebiotic *oligosaccharides* are increasingly added to foods for their health benefits. Some *oligosaccharides* that are used in this manner are *fructooligosaccharides* (FOS), *xylooligosaccharides* (XOS), polydextrose and *galactooligosaccharides* (GOS). Some *monosaccharides* such as tagatose are also used sometimes as prebiotics. As used herein, MSM is a prebiotic.

Probiotic: A microorganism that confers a health benefit on the host, including, but not limited to, conferring protection from or treatment of illness or undesired effects. Probiotics can confer health benefits to a product, such as increasing the nutritional quality of edible products, Probiotics include beneficial bacteria, such as lactic acid bacteria (such as *Lactobacillus bulgaricus, Lactobacillus rhamnosus, Lactobacillus casei* and *Lactobacillus johnsonii*) and bifidobacteria (such as *Lactobacillus bifidus*) which are the most common types of microbes used as probiotics; but certain yeasts and bacilli may also be probiotics. Probiotics are commonly consumed as part of fermented foods; such as in yogurt, soy products, or as dietary supplements. Live probiotic cultures are available in fermented dairy products and probiotic fortified foods. However, tablets, capsules, powders and sachets containing the bacteria in freeze dried form are also available. Exemplary probiotic strains include, but are not limited to *Bacillus coagulans* GBI-30, 6086 (Ganeden Biotech), *Bifidobacterium* LAFTI® B94 (Institut-Rosell-Lallemand), *Lactobacillus acidophilus* LAFTI® L10 (Institut-Rosell-Lallemand), *Lactobacillus casei* LAFTI® L26 (Institut-Rosell-Lallemand), *Bifidobacterium animalis* subsp. *lactis* BB-12, *Bifidobacterium breve* (Yakult), *Bifidobacterium infantis* 35624 (Procter & Gamble), *Bifidobacterium animalis* subsp. *lactis* HN019 (Danisco), *Bifidobacterium longum* BB536 (Morinaga Milk Industry), *Lactobacillus acidophilus* DDS-1 (Nebraska Cultures), *Lactobacillus acidophilus* LA-5, *Lactobacillus acidophilus* NCFM (Danisco), *Lactobacillus casei* DN114-001 (Danone), *Lactobacillus casei* 431, *Lactobacillus casei* F19 (Arla Foods), *Lactobacillus casei* (Yakult), *Lactobacillus paracasei* St11 (or NCC2461, Nestlé), *Lactobacillus johnsonii* La1 (*Lactobacillus* LC1, *Lactobacillus johnsonii* NCC533, Nestlé), *Lactococcus lactis* L1A (Norrmejerier), *Lactobacillus plantarum* 299v (Probi), *Lactobacillus reuteri* ATTC 55730 (*Lactobacillus reuteri* SD2112, BioGaia Biologics), *Lactobacillus rhamnosus* ATCC 53013 (Valio), *Lactobacillus rhamnosus* LB21 (Norrmejerier), *Bifidobacterium bifidum*, *Lactobacillus gasseri* PA16/8, *Bifidobacterium bifidum* MF20/5, *Bifidobacterium longum* SP07/3, *Streptococcus thermophilus*, *Lactobacillus salivarius*, *Bifidobacterium longum* Rosell-175, *Lactococcus lactis* Rosell-1058, *Bifidobacterium breve* Rosell-70, *Lactobacillus rhamnosus* Rosell-11, *Lactobacillus acidophilus* Rosell-52, *Bifidobacterium bifidum* rosell-71, *Bacillus subtilis* var natto, *Lactobacillus paracasei*, *Enterococcus faecium*, *Bifidobacterium animalis*, *Lactobacillus delbrueckii*, and *Saccharomyces cerevisiae*.

Quantitating: Determining or measuring a quantity (such as a relative quantity) of a molecule or the activity of a molecule, such as the quantity of analyte present in a sample.

Stem cell: A cell that has the ability to self replicate indefinitely and that, under the right conditions, or given the right signals, can differentiate into some or all of the different cell types that make up an organism. Stem cells have the potential to develop into mature, differentiated cells, such as heart cells, skin cells, or nerve cells. The fertilized egg is a stem cell because it has the potential to generate all the cells and tissues that make up an embryo and that support its development in utero. Adult mammals include more than 200 kinds of cells, for instance, neurons, myocytes, epithelial cells, erythrocytes, monocytes, lymphocytes, osteocytes, and chondrocytes. Other cells that are essential for embryonic development but are not incorporated into the body of the embryo include the extraembryonic tissues, placenta, and umbilical cord. All of these cells are generated from a single fertilized egg.

Pluripotent cells can give rise to cells derived from all three embryonic germ layers—mesoderm, endoderm, and ectoderm. Thus, pluripotent cells have the potential to give rise to any type of cell. Unipotent stem cells are capable of differentiating along only one lineage. Embryonic stem cells are pluripotent cells derived from the blastocyst. Adult stem cells are undifferentiated cells found in a differentiated tissue that can replicate and become specialized to yield all of the specialized cell types of the tissue from which it originated. Adult stem cells are capable of self-renewal for the lifetime of the organism. Sources of adult stem cells have been found in the bone marrow, blood stream, cornea, retina, dental pulp, liver, skin, gastrointestinal tract, and pancreas. MSM is used herein to increase the culture efficiency, stability and/or viability of stem cells.

Sterilization: A process that eliminates (removes) or kills all forms of life, including transmissible agents (such as fungi, bacteria, viruses, spore forms, etc.) present on a surface, contained in a fluid, in medication, or in a compound such as biological culture media. Sterilization can be achieved methods known to one of ordinary skill in the art, including by applying the proper combinations of heat, chemicals, irradiation, high pressure, and filtration.

Subject: Living multi-cellular vertebrate organisms, a category that includes human and non-human mammals.

Symptom and sign: Any subjective evidence of disease or of a subject's condition, e.g., such evidence as perceived by the subject; a noticeable change in a subject's condition indicative of some bodily or mental state. A "sign" is any abnormality indicative of disease, discoverable on examination or assessment of a subject. A sign is generally an objective indication of disease. Signs include, but are not limited to any measurable parameters such as tests for detecting a disorder or disease, such as a bacterial or viral infection. In one example, reducing or inhibiting one or more symptoms or signs associated with a bacterial or viral infection, includes reducing or inhibiting bacterial growth or viral infection by a desired amount, for example by at least 20%, at least 50%, at least 60%, at least 70%, at least 80%, at least 90%, at least 95%, at least 98%, or even at least 100%, as compared to the bacterial growth or viral infectivity in the absence of MSM.

Therapeutically effective amount or concentration: An amount of a composition that alone, or together with an additional therapeutic agent(s) sufficient to achieve a desired effect in a subject, or in a cell, being treated with the agent. The effective amount of the agent will be dependent on several factors, including, but not limited to the subject or cells being treated, and the manner of administration of the therapeutic composition. In one example, a therapeutically effective amount or concentration is one that is sufficient to prevent advancement, delay progression, or to cause regression of a disease, or which is capable of reducing symptoms caused by a condition or disease.

In one example, a desired effect is to reduce or inhibit one or more symptoms associated with the disease. The one or more symptoms do not have to be completely eliminated for the composition to be effective. For example, a composition can decrease the sign or symptom by a desired amount, for example by at least 20%, at least 50%, at least 80%, at least 90%, at least 95%, at least 98%, or even at least 100%, as compared to the sign or symptom in the absence of MSM. In one particular example, a desired response is to reduce or inhibit microorganism activity (such as bacterial growth) by a desired amount, for example by at least 20%, at least 50%, at least 60%, at least 70%, at least 80%, at least 90%, at least 95%, at least 98%, or even at least 100%, as compared to microorganism activity in the absence of MSM.

A therapeutically effective amount of a disclosed pharmaceutical composition can be administered in a single dose, or in several doses, for example daily, during a course of treatment. However, the therapeutically effective amount can depend on the subject being treated, the severity and type of the condition being treated, and the manner of administration. A therapeutically effective amount of an agent can be measured as the concentration (moles per liter or molar-M) of the agent in blood (in vivo) or a buffer (in vitro) that produces the desired effect(s). Alternatively, a therapeutically effective amount of an agent can be measured as the amount administered to a subject per body weight of the subject, for example, mg agent/kg body weight.

Untreated cell: A cell that has not been contacted with a desired agent, such as MSM. In an example, an untreated cell is a cell that receives the vehicle in which MSM was delivered.

Virus: A microscopic infectious organism that reproduces inside living cells. A virus consists essentially of a core of nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so. In some examples, a virus is a pathogen.

Specific examples of viral pathogens that might be treated in accordance with the disclosed methods and compositions include without limitation any one or more of (or any combination of); Arenaviruses (such as Guanarito virus, Lassa virus, Junin virus, Machupo virus and Sabia), Arteriviruses, Roniviruses, Astroviruses, Bunyaviruses (such as Crimean-Congo hemorrhagic fever virus and Hantavirus), Barnaviruses, Birnaviruses, Bornaviruses (such as Borna disease virus), Bromoviruses, Caliciviruses, Chrysoviruses, Coronaviruses (such as Coronavirus and SARS), Cystoviruses, Closteroviruses, Comoviruses, Dicistroviruses, Flaviruses (such as Yellow fever virus, West Nile virus, Hepatitis C virus, and Dengue fever virus), Filoviruses (such as Ebola virus and Marburg virus), Flexiviruses, Hepeviruses (such as Hepatitis E virus), human adenoviruses (such as human adenovirus A-F), human astroviruses, human BK polyomaviruses, human bocaviruses, human coronavirus (such as a human coronavirus HKU1, NL63, and OC43), human enteroviruses (such as human enterovirus A-D), human erythrovirus V9, human foamy viruses, human herpesviruses (such as human herpesvirus 1 (herpes simplex virus type 1), human herpesvirus 2 (herpes simplex virus type 2), human herpesvirus 3 (*Varicella zoster* virus), human herpesvirus 4 type 1 (Epstein-Barr virus type 1), human herpesvirus 4 type 2 (Epstein-Barr virus type 2), human herpesvirus 5 strain AD169, human herpesvirus 5 strain Merlin Strain, human herpesvirus 6A, human herpesvirus 6B, human herpesvirus 7, human herpesvirus 8 type M, human herpesvirus 8 type P and Human Cyotmegalovirus), human immunodeficiency viruses (HIV) (such as HIV 1 and HIV 2), human *metapneumoviruses*, human papillomaviruses (such as human papillomavirus-1, human papillomavirus-18, human papillomavirus-2, human papillomavirus-54, human papillomavirus-61, human papillomavirus-cand90, human papillomavirus RTRX7, human papillomavirus type 10, human papillomavirus type 101, human papillomavirus type 103, human papillomavirus type 107, human papillomavirus type 16, human papillomavirus type 24, human papillomavirus type 26, human papillomavirus type 32, human papillomavirus type 34, human papillomavirus type 4, human papillomavirus type 41, human papillomavirus type 48, human papillomavirus type 49, human papillomavirus type 5, human papillomavirus type 50, human papillomavirus type 53, human papillomavirus type 60, human papillomavirus type 63, human papillomavirus type 6b, human papillomavirus type 7, human papillomavirus type 71, human papillomavirus type 9, human papillomavirus type 92, and human papillomavirus type 96), human parainfluenza viruses (such as human parainfluenza virus 1-3), human parechoviruses, human parvoviruses (such as human parvovirus 4 and human parvovirus B 19), human respiratory syncytial viruses, human rhinoviruses (such as human rhinovirus A and human rhinovirus B), human spumaretroviruses, human T-lymphotropic viruses (such as human T-lymphotropic virus 1 and human T-lymphotropic virus 2), Human polyoma viruses, Hypoviruses, Leviviruses, Luteoviruses, Lymphocytic choriomeningitis viruses (LCM), Marnaviruses, Narnaviruses, Nidovirales, Nodaviruses, Orthomyxoviruses (such as Influenza viruses), Partitiviruses, Paramyxoviruses (such as Measles virus and Mumps virus), Picornaviruses (such as Poliovirus, the common cold virus, and Hepatitis A virus), Potyviruses, Poxviruses (such as Variola and Cowpox), Sequiviruses, Reoviruses (such as Rotavirus), Rhabdoviruses (such as Rabies virus), Rhabdoviruses (such as Vesicular stomatitis virus, Tetraviruses, Togaviruses (such as Rubella virus and Ross River virus), Tombusviruses, Totiviruses, Tymoviruses, and Noroviruses among others.

In some embodiments, MSM is used to inhibit a biological activity of one or more of the viruses listed above.

Yeast: A eukaryotic microorganism classified in the Kingdom Fungi, with about 1,500 species described. Most reproduce asexually by budding, although a few reproduce by binary fission. Yeasts generally are unicellular, although some species may become multicellular through the formation of a string of connected budding cells known as pseudohyphae, or false hyphae. Exemplary yeasts that can be used in the disclosed methods and compositions include but are not limited to *Saccharomyces cerevisiae, Candida albicans, Schizosaccharomyces pombe, Pichia, Cryptococcus, Zygosaccharomyces, Torulopsis, Hansenula*, and Debaryomyces.

III. Compositions of MSM

Disclosed herein are compositions of MSM for use in modulating microbial activity, such as enhancing or decreasing microbial activity. In some embodiments, a composition of MSM for use in enhancing microbial activity includes about 0.02% to about 5% MSM by weight of the medium (such as culture medium) or by weight of the moisture content of the medium (such as culture medium), such as about 0.04% to about 4%, about 1% to about 3%, including about 0.02%, about 0.03%, about 0.04%, about 0.05%, about 0.06%, about 0.07%, about 0.08%, about 0.09%, about 0.1%, about 3%, about 0.5%, about 1%, about 2%, about 2.5%, about 3%, about 4% or about 5% of the weight of the medium or the moisture content of the medium. In some examples, the percentages of MSM provided herein are calculated from the amount of a polar solvent, for example water in a product. By way of example, a composition with 5% MSM by weight of the medium would contain 5 grams of MSM per 100 grams or medium or a composition with 5% MSM by weight of the moisture content of the medium would contain 5 grams of MSM per 100 grams or the polar solvent in the medium, excluding solids.

In some embodiments, the disclosed compositions include a medium capable of supporting growth of a microorganism, a microorganism, and MSM. In some examples, a medium includes one or more of the following: probiotic-containing products, dairy products, milk, yogurt, rice yogurt, frozen yogurt, chocolate, cheese, fermented beverages (such as beer, cider, wine) and water. In some examples, the medium also includes other products, edible or not, that benefit from enhanced microbial activity.

In some embodiments, enhancing microbial activity include enhancing the fermentation of a microorganism. Thus in some particular examples, a composition includes a medium capable of supporting growth of fermentative microorganisms, a fermentative microorganism and MSM. In some examples, MSM is provided at a concentration of about 0.04% to about 5%, such as about 0.1% to about 4%, 0.5% to about 3%, about 1% to about 2%, including about 0.04%, to about 0.05%, about 0.06%, about 0.07%, about 0.08%, about 0.09%, about 0.1%, about 0.3%, about 0.5%, about 0.7%, about 1%, about 1.5%, about 2.0%, about 2.5%, about 3.0%, about 4%, or about 4.5% MSM by weight of medium or by weight of the moisture content of the medium, wherein the concentration of MSM is effective for enhancing the fermentation of the microorganisms. In some embodiments, the disclosed compositions are used to produce a fermented beverage, such as beer, cider and/or wine. In some embodiments, a composition for enhancing fermentation efficiency includes MSM added to yeast packages to generate rapid or quick-activating yeast for home or commercial use.

In some embodiments, enhancing microbial activity include enhancing the growth of probiotics. Thus, in some examples, a composition for enhancing the growth of probiotics includes a medium capable of supporting growth of probiotics and MSM at a concentration of about 0.04% to about 5% by weight of the medium or by weight of the moisture content of the medium, wherein the concentration of MSM is effective for enhancing the activity (e.g., growth) of the probiotics. Further, a composition for enhancing the growth of the probiotics includes about 0.04% to about 5% MSM, such as about 0.1% to about 4%, 0.5% to about 3%, about 1% to about 2%, including about 0.04%, to about 0.05%, about 0.06%, about 0.07%, about 0.08%, about 0.09%, about 0.1%, about 0.3%, about 0.5%, about 0.7%, about 1%, about 1.5%, about 2.0%, about 2.5%, about 3.0%, about 4%, or about 4.5% MSM by weight of medium or by weight of moisture content of the medium.

In some embodiments, enhancing microbial activity includes enhancing microbial production of biofuel. Thus, in some examples, a composition for enhancing microbial production of biofuel includes a medium capable of supporting growth of algae, algae capable of producing a biofuel and MSM at a concentration of about 0.04% to about 5%, such as about 0.1% to about 4%, 0.5% to about 3%, about 1% to about 2%, including about 0.04%, to about 0.05%, about 0.06%, about 0.07%, about 0.08%, about 0.09%, about 0.1%, about 0.3%, about 0.5%, about 0.7%, about 1%, about 1.5%, about 2.0%, about 2.5%, about 3.0%, about 4%, or about 4.5% MSM by weight of medium or by weight of the moisture content of the medium, wherein the concentration of MSM is effective for enhancing the production of the biofuel from the algae. In other examples, a composition includes algae and MSM, and optionally other ingredients for enhancing algae growth. In several embodiments, the composition is useful to enhance algae activity for biofuel, algal farming, aquaculture, medicaments, etc. In one embodiment, the method comprises exposing algae to MSM at e.g., a concentration of about 0.04% to about 5% by weight of medium or by weight of the moisture content of the medium.

Compositions of MSM for inhibiting microbial activity are disclosed. In some embodiments, a composition of MSM for inhibiting microbial activity includes about 6% to about 17%, such as about 7% to about 15%, about 10% to about 12%, such as about 6%, about 7%, about 8%, about 9%, about 10%, about 11%, about 13%, about 14%, about 15%, or about 16% MSM by weight of medium or by weight of the moisture content of the medium, wherein the concentration of MSM is effective for inhibiting microbial activity, including, but not limited to microbial growth, infection rate, or a combination thereof.

It is contemplated that any of the disclosed compositions including MSM to modulate microbial activity have a sodium chloride concentration of less than 5% of total moisture content of the medium, such as about 1% to about 3% sodium chloride, including 0%, 0.1%, 0.3%, 0.5%, 0.75%, 1%, 2%, 2.5%, 3% or 4%. In some examples, a disclosed composition of MSM is preservative free. For example, MSM is added to a food, cosmetic or beverage product that requires or desires an all-natural ingredient list. In some embodiments, a composition of MSM consists or consists essentially of MSM and all-natural non-toxic ingredients. In other examples, a disclosed composition of MSM includes one or more additional preservatives. Preservatives include, but are not limited to one or a combination of the following: formaldehyde, potassium sorbate, methylparaben, methylchloroisothiazolinone, phthalates, cocamidopropyl betain, parabens, decyl polyglucose, polyaminopropyl biguanide, phenoxyethanol, sodium laureth sulfate, tetrasodium EDTA, decyl glucoside, polyethylene glycol, and propylene glycol.

In several embodiments, MSM is used to extend the shelf-life of products and is capable of reducing microbial activity by at least 2-, 3-, 4-, 5-, 10-, 25-, 50-, 100-, 1000-fold as compared to products with no MSM or as compared to products with less effective antimicrobial agents. In other embodiments, MSM is able to achieve comparable levels of antimicrobial activity as compared to agents that produce undesired side effects. Thus, in one embodiment, MSM can be used instead of an undesired preservative. In several embodiments, compositions include preservative-free or reduced preservative formulations comprising MSM.

In several embodiments, MSM is used in products (for example, cosmetics) that have an acidic, basic or neutral pH. Because MSM can inhibit microbial activity, cosmetics and other products can have more flexibility in pH selection. Thus, a pH that is optimal for the product can be selected. In several embodiments, products comprising MSM do not require refrigeration and may be stored at room temperature. In other embodiments, products comprising MSM do not require sterilization, including but not limited to sterilization via chemicals, heating, radiation, filtration or ultraviolet light.

In several embodiments, disclosed compositions include MSM in addition to one or more thickening agents, emollients, and/or aromatic agents. In some embodiments, a product or other medium is supplemented with continuous or periodic additions of MSM to, for example, extend the inhibitory or stimulatory actions of MSM.

In certain embodiments, the addition of MSM is an effective antimicrobial agent. For example, in one embodiment, a composition comprising MSM has the same or enhanced antimicrobial effect as compared to a formulation with no MSM. In other embodiments, MSM serves as an antibacterial agent. In certain embodiments, MSM is used as a substitute for a chemical food preservative. In still other embodiments, MSM may be used in combination with a preservative. In certain such embodiments, the use of MSM reduces the amount of, or altogether replaces, traditional preservatives. In some embodiments, MSM may increase the shelf life of a product, including products that traditionally would not have a preservative. In yet other embodiments, MSM serves as a virucide, fungicide and/or bacterioside. In further embodiments, MSM is bacteriostatic. In some embodiments, MSM is a broad spectrum inhibitor of microbial activity. In other embodiments, MSM selectively kills a certain kingdom, genus or species. In some embodiments, MSM selectively inhibits aerobic bacteria. In other embodiments, MSM selectively inhibits anaerobic bacteria. In some embodiments, MSM selectively inhibits gram-positive bacteria. In other embodiments, MSM selectively inhibits gram-negative bacteria.

In several embodiments, MSM is used to inhibit the growth of microorganisms, including those found in cosmetics, health and beauty aids, parenterals, topically used products, and oral products. In several preferred embodiments, MSM is used to inhibit the growth of microorganisms in products packaged in single or multiple-dose containers. MSM formulations according to several of the embodiments described herein are in any suitable form, including but not limited to, powder, cream, liquid, paste, solid or gel form.

In several embodiments, MSM is added to cosmetic products susceptible to microbial contamination. Cosmetics may include, but are not limited to, lipstick, lip gloss, lip liner, lip plumper, lip balm, lip conditioner and lip boosters, foundation, powder, rouge, blush, bronzer, mascara, eye liner, eye shadow, eye shimmer, glitter eye pencils, eyebrow pencil, nail polish, concealer, skin care products, creams, lotions, serums, moisturizer, sunscreen, skin repair products (e.g., for acne, sunburn, wrinkles, dark circles), and sunscreen.

In several embodiments, MSM is added to a cosmetic cream matrix susceptible to microbial contamination. In some such embodiments, the cream includes jojoba, *aloe vera*, cocoa butter, shea butter, coconut oil, or combinations thereof.

In several embodiments, MSM is added to personal care products susceptible to microbial contamination. Such products include products used for daily moisturizing needs, products to treat psoriasis or eczema, products to treat dry or itchy skin, products to treat sun and wind burn, pre- and post-shave products, massage oils or creams, personal lubricants, acne treatment products and exfoliants or emollients. According to other embodiments, MSM is added to products to soften skin on the hands or feet (such as calluses), after swim skin care products, make-up remover, children's skin lotion, and diaper rash cream. In some embodiments, MSM inhibits contamination while simultaneously conferring a beneficial cosmetic effect or health benefit.

In several embodiments, MSM is added to medicinal products or equipment susceptible to microbial contamination. Medicinal products include, but are not limited to, cold or flu preventatives and treatment, allergy preventatives and treatment, nasal irrigants, medicinal drops, eye drops, inhalants, athletes foot treatments, herpes and cold sore medications, burn creams, ointments for cuts and infection, and bactericidal, fungicidal and virucidal sprays or lotions. In some embodiments, MSM is used to inhibit microbial activity on inhalers, nebulizers, ventilators, catheters, syringes, intubation tubes, hospital room equipment, furniture and surfaces, diagnostic equipment, fabric, bedding, and patient coverings. In several embodiments, MSM is used to disinfect bodily tissues and fluids. For example, MSM may be used as part of a dialysis system to inhibit microbial activity in blood, which may be particularly helpful for sepsis patients. In another embodiment, MSM is injected into a patient to inhibit microbial activity locally or systemically. In other embodiments, a composition including MSM is topically applied to a microbial infection present on a dermal surface.

In some embodiments, MSM products are used nasally. In other embodiments, such products are used orally and/or as a vapor. In still other embodiments, the product is a repeated use eye drop or other ocular medicinal product.

In several embodiments, MSM is added to medicinal products used to prevent or treat fungal infections. In some such embodiments, the product is used to prevent or treat athlete's foot. In some embodiments, the product is used topically. In some such embodiments, the product is a cream, ointment, spray, gel or powder. In other embodiments, the product is used orally.

In several embodiments, MSM inhibits the activity of mycotoxins, toxic metabolites produced by an organism of the fungus kingdom, including mushrooms, molds, and yeasts. Products comprising MSM are also useful for decontaminating surfaces and equipment that are susceptible to contamination by such organisms and/or metabolites. In some embodiments, MSM inhibits the activity of organisms of the fungus kingdom (e.g., mushrooms, molds, and yeasts). In yet other embodiments, MSM inhibits the toxins from microbes directly and/or indirectly by inhibiting the activity of the microbes. In one embodiment, MSM inhibits the formation and/or release of microbial metabolites.

In several embodiments, MSM is added to products used to prevent or treat viral infections. Anti-viral nasal sprays comprising MSM are provided in one embodiment. Products comprising MSM are also useful for decontaminating surfaces and equipment that are susceptible to viral contamination. In one embodiment, MSM is used to inhibit the flu virus, including H1N1, either in a biological tissue or on an external surface. In some embodiments, MSM is used to inhibit the human immunodeficiency virus, herpes simplex virus, papilloma virus, parainfluenza virus, influenza, hepatitis, and other viruses.

In some embodiments, MSM inhibits algae. In one embodiment, MSM inhibits algal blooms. In some embodiments, MSM inhibits undesired phytoplankton activity. In other embodiments, MSM inhibits macroalgal species. In another embodiment, MSM inhibits dinoflagellates of genus Alexandrium and Karenia. In several embodiments, MSM inhibits the toxic metabolites (including by-products) of algae.

In some embodiments, MSM is added to medicinal products used to treat a burn, cut or wound. Wounds may include, but are not limited to, lacerations, split lacerations, over stretching, grinding compression, cut lacerations, tearing, incisions, incised wounds, abrasions, puncture wounds, penetration wounds. In some embodiments, MSM is incorporated into a bandage used to cover a wound. In other embodiments, MSM is added to a cream or ointment. In some such embodiments, the product formulated with MSM acts an antiseptic.

Skin microflora (bacteria, fungi, viruses, phage, archaea) play a significant role in common dermatological conditions, such as atopic dermatitis (a common form of eczema). Typically, a specific microbe colonizes the skin to disrupt the balance of commensal microflora, or microbes release toxic substances or invade cells to induce an inflammatory response directly. Thus, in some embodiments, MSM is incorporated into a topical product that inhibits growth of such microflora. Subcutaneous administration of MSM is provided in other embodiments.

In other embodiments, MSM is added to optical products susceptible to microbial contamination and/or to optical products to enhance their antimicrobial activity. Optical products may include solutions for cleaning or disinfecting contact lenses. In some such embodiments, MSM is incorporated into various products applied to contact lenses such as a contact lens storage solution. In some embodiments, MSM is added to eye drops used in conjunction with contact lenses. In other embodiments, MSM is added to chemical solutions used in ocular diagnostic procedures, such as a multi-use pupillary dilation solution.

In several embodiments, MSM is added to oral products susceptible to microbial contamination and/or to oral products to enhance their antimicrobial activity. In some embodiments, such products are used for tooth cleaning. In some embodiments, MSM is incorporated into toothpaste or toothgel. In some embodiments, MSM is incorporated into or coated onto the bristles of a toothbrush. In other embodiments, MSM formulations are incorporated into or used to coat tooth floss. In other embodiments, the product is used for cleaning the tongue. In other embodiments, the product is a mouthwash, mouth-rinse or mouth-irrigant for at home or professional dental use. In yet other embodiments, the product is a gum or confectionary. In some embodiments, MSM is added to storage or cleaning solutions for dental implants, dentures, and the like.

In some embodiments, MSM is added to foods containing probiotic organisms, such as milk, yogurt, rice yogurt, frozen yogurt, kefir, juice, pickled vegetables, fermented cabbage, fermented bean paste, brined olives, chocolate, cheeses and other dairy products, and certain cereals. In some embodiments, MSM is added to products that are dietary supplements, including, but not limited to, probiotic pills, capsules, and liquids. In some such embodiments, MSM is added to a supplement for human ingestion. In other embodiments, MSM is added to a supplement for animals. In some embodiments, MSM is added to a product that is formulated as a capsule or tablet. In some embodiments, MSM is added to a product that is formulated as a solid or liquid. In other embodiments, MSM is added to a foodstuff during the production process, while in still other embodiments, MSM is added to finished food products.

In several embodiments, MSM is added to a food product that is susceptible to microbial infection. In some embodiments, MSM may be mixed, ad-mixed, compounded, or otherwise incorporated into the food product. In other embodiments, MSM is applied to the surface of a food product. For example, in some embodiments, MSM may be sprayed on a food product. Such food products may include, but are not limited to, fruits, vegetables, fish and meat products. In some embodiments, MSM is used in processing or packing facilities to extend the shelf-life of food products. In several embodiments, the addition of MSM (e.g., about 5% to about 25%) increases the time to spoilage of ingestible products. For example, MSM can be baked into or added to breads, pastries, or dough to increase the shelf life of the edible products by about 10% to 100% (e.g., 20%, 30%, 40%, 50%, 75%, 150%, 200% or more). For example, in one embodiment, if the shelf life of an edible product is 10 days, the addition of MSM will increase the shelf life to at least 11 days in some embodiments (e.g., 11 days, 14 days, 15 days, 20 days, or 25 days). As a further example, in another embodiment, if an edible product has a shelf life of 14 days at room temperature and/or 30 days in the refrigerator and/or 3 months in the freezer, the addition of MSM will increase the shelf life to 30 days at room temperature and/or 60 days in the refrigerator and/or 6 months in the freezer. In further embodiments, the use of MSM will permit the shipping and/or storage of an edible product at room temperature, where the product would otherwise have to be shipped and/or stored at colder temperatures. In yet other embodiments, the use of MSM will obviate the need for sterilization of edible products.

In some examples, any of the disclosed compositions of MSM consist essentially of water. For example, MSM is particularly effective when combined with water or other liquid components. In some examples, a disclosed composition of MSM is bleach-free, alcohol free or a combination thereof. In several embodiments, a composition for modulating microbial activity includes a MSM related compound instead of or in addition to MSM. Related compounds include, but are not limited to, DMSO and dimethylsulfide (DMS).

MSM used according to any of the embodiments provided herein may be isolated, purified or processed. MSM that is designated GRAS (Generally Recognized As Safe) is used for several embodiments described herein. Formulations for consumption by humans, domesticated animals and livestock are provided in accordance with several embodiments herein.

In some embodiments, MSM is combined with one or more of the following ingredients (or derivatives, metabolites, precursors, oils, extracts, esters, acids, salts, and related compounds thereof): abietic acid, acacia, acacia senegal gum, acai extract, acetic acid, acetone, acetyl glycosamine, acmella oleracea extract, adenophora stricta, alaria marginata (sea vegetable), albumin, alcohol, aldenine, alfalfa, algae extract, alkyl guanine transferase, alkyloamides, allantoin, aluminum hydroxide, almond, *aloe vera,* alpha lipoic acid, aluminum benzoate, aluminum chloride, amino acids, aminopropane sulfonic acid 3, ammonium glycolate, ammonium lauryl sulfate, anemarrhenae asphodeloides root extract, anise oil, antioxidants, apigenin, apricot, apricot kernel, arachidonic acid, arbutin, argan oil, *argania spinosa* leaf extract, arginine, argireline, arnica extract, *artemisia dracunculus* (tarragon) oil, ascorbic acid, ascorbyl palmitate, ascorbyl tetraisopalmitate, *aspergillus ferment, aspidosperma quebracho,* astaxanthin, atelocollagen, *avena sativa* (oat) kernel extract, avobenzone, azelic acid, azuki beans, balm mint extract, balsam peru, bamboo stem extract, barely (*hordeum vulgare*) extract, barium sulfate, barley, basil, bee pollen, beeswax, bentonite, benzoyl peroxide, *beta vulgaris* root extract (beet), betacarotene, bilberry, biotin, bismuth oxychloride, bladderwrack extract, borage oil, boric acid, boric oxide, bovine placenta liquid, brewers yeast, bronopol, butyl acetate, butyl stearate, butylated hydroxyanisole, butylated hydroxytoluene, butylene glycol, butylparaben, butyrospermum parkii, c18-36 acid triglyceride, caffeine, calamine, calcium, *calendula* extract, carnauba wax, *camellia oleifera* leaf extract, *camellia sinensis* leaf extract, camphor, *canaga odorata* (ylang ylang) flower oil, candelilla cera, candelilla wax, canola sterols, caprylic acid, caprylic/capric triglyceride, caprylyl glycol, caprylyl glycol, *capsicum oleoresin,* caramel, carmine, carotenoids, carrageenan, carrot oil, carrot seed oil, *carthamus tinctorius* (safflower) seed oil, castor oil, cellulose, centella asiatica, *calendula officinalis,* cera alba, cera carnauba, ceramide, cerebrosides, cerric ammonium ferrocyanide, ceteareth-3, cetearyl alcohol, cetearyl glucoside, cetearyl olivate, cetyl alcohol, cetyl lactate, chamomile oil, *chamomilla recutita* (matricaria) flower extract, chestnut, chestnut extract, chloroxylenol, chlorphenesin, cholesterol, choline, *chondrus crispus* (irish moss), chromium hydroxide green, chromium oxide greens, cinnamyl alcohol, citric acid, citronellol, *citrus, citrus nobilis* (green mandarin) oil, clove powder, clover blossom extract, clyceryl coconate, cocamidopropyl betaine, cocoa, cocoa butter, caprylate/caprate, coconut oil, coconut wax, cod liver oil, coenzyme q10, collagen, comfrey extract, coneflower extract, *copernica cerifera* (carnauba) wax, copper, coriander, *coriandrum sativum* (cilantro) oil, corn starch, cornflower extract, creatine, *crithmum* maritimum extract, cucumber, cyclomethicone, cyclopentasiloxane, dantoin 685, decyl glucoside, deionized water, diazolidinyl urea, dicalcium phosphate dehydrate, dicaprylyl carbonate, diethanolamine, dilaurate, dimethicone, dimethylaminoethanol, *dioscorea villosa* (wild yam) root extract, dipotassium glycyrrhizinate, disodium distyrylbiphenyl disulfonate, disodium edta, dmdm hydantoin, *echinacea angustifolia* (coneflower) extract, edta, eijitsu rose, elaeis oleifera, elastin, elder flower, emollients, enzymes, epilobium fleischeri extract (gravel willow), *equisetum hiemale* leaf extract (horsetail), erucate, essential fatty acids, essential oils, ethanol, ethoxydiglycol, ethyl acetate, ethylene/acrylic acid copolymer, ethylhexyl palmitate, ethylhexylglycerin, ethylparaben, eucalyptus extract, eukarion, euterpe oleracea fruit extract, evening primrose oil, exfoliants, fatty acids, fatty alcohols, fennel oil, ferric oxide, flavanoids, flavonolignan, fish oils, flax, floralozone, fluoride, formaldehyde, fruit acids, fruit extract, fruit extracts, gaba, gamma linolenic acid, gelatin, geraniol, geranium oil, *gigartina papillata* (wildcrafted seaweed), ginger, ginger oil, ginko biloba oil, ginseng, glucosamine, glucose oxidase, glucose sugar, glycereth, glycereth-26, glycerin, glycerol, glycerol stearate, glyceryl hydrogenated rosinate, glyceryl oleate, glyceryl stearate, glycol distearate, glycolic acid, gold, goldenseal extract, grape seed, grape seed oil, grapefruit, grapefruit oil, grapefruit seed extract, green tea, gums, hazelnut oil, hdi/trimethylol hexyllactone crosspolymer, hemp seed oil, hexamidine, hexylene glycol, homosalate, honey, *hordeum distychum* extract, hordihydroguaiaretic acid, hormones, humectant, *humulus lupulus* extract, hyaluronic acid, *hydrastis canadensis* extract (golden seal), hydrocortisone, hydrocotyl extract, hydrogenated castor oil laurate, hydrogenated polyisobutene, hydrogenated polysobulene, hydrolyzed animal protein, hydrolyzed keratin, hydrolyzed rhizobian gum, hydrolyzed soy protein, hydrolyzed wheat protein, hydroxy acids, hydroxyethylcellulose, hydroxyethyl-cellulose, hydroxyisohexyl 3-cyclohexene carboxaldehyde, hydroxypropyl-cellulose, hydroxypropyltrimonium honey, hydroquinone, hydroxystearate, *hypericum* extract, idebenone, imidazolidinyl urea, iodine, irish moss, iron oxides, isobutylparaben, isododecane, isohexadecane, isononyl isononanoate, isopentyldiol, isopropyl alcohol, isopropyl lanolate, isopropyl linoleate, isopropyl myristate, isostearate, isostearic acid, ivy extract, jasmine oil, jojoba butter, jojoba oil, juniper extract, juniper oil, kaolin, keratin, ketones, kinerase, kinetin, kojic acid, kukui nut oil, lactic acid, lactoperoxidase, lady's mantle leaf extract, *laminaria digitata* (kelp) extract, lanolin, *larix sibirica* wood extract, lauramide, laurate, laureth, lauryl alcohol, lauryl glucoside, lavender, lavender oil, lecithin, lemon oil, licorice, lime oil, limonene, linden extract, linoleic acid, linolenic acid, liposomes, locust bean, *lycium barbarum* fruit extract, *lycium barbarum* fruit extract (goji berry), lycopene, *macadamia* nut oil, matcha, magnesium aluminum silicate, magnesium ascorbyl phosphate, magnesium myristate, magnesium stearate, magnesium sulfate (epsom salts), malpighia punicifolia (acerola) fruit extract, manganese violet, mango butter, marigold, marshmallow extract, matcha tea powder, matricaria oil, mea, meadowsweet, melaleuca oil, melon extract, *mentha piperita* (organic peppermint) extract, menthol, methyl acetate, methyl ethyl ketone, methyldihydroj asmonate, methylparaben, mica, microdermabrasion compounds, milk protein, minerals, mineral oil, mipa, monoethanolamine, monostearate, montmorillonite (green clay), mugwort (artesemia vulgaris) extract, mulberry, mulberry (morus nigra) root extract, murumuru, mushrooms, myristate, myristate, myristic acid, myristyl myristate, *myrtus communis* (green myrtle) oil, n-acetyl glucosamine, nephrite powder, neroli oil, nettle leaf, neuropeptides, niacin, nitrosamines, nonyl nonoxynol-150, nucleic acids, nutmeg powder, nuts, oat, oatmeal, oats, *ocimum basilicum linalol* (basil linalol) oil, octinoxate, octsalate, oleate, oleic acid, oleyl alcohol, oligopeptides, *oligosaccharides,* olive fruit extract, olive oil, omega-3, orange peel oil, orthoboric acid, oxybenzone, ozokerite, padina pavonica thallus extract, palm oil, palmitate, palmitic acid, palmitoyl, pantethine, panthenol, para-aminobenzoic acid, paraben, paraffin, *passiflora incarnate* fruit extract, passionfruit, patchouli, peach stone, peat extract, pectin, peg, peppermint, peppermint oil, peptides, petroleum jelly, *phellodendron amurense* bark extract, phenoxyethanol, phenyl trimethicone, phenylethyl resorcinol, phosphoric acid, phytochemicals, pine tree extract derivative, pineapple extract, *plantago lanceolata* leaf extract, plantain leaf extract, pollen extract, *polygonum cuspidatum* root extract, polypeptides, polysaccharides, polysilicone, polysorbate, polysorbate, polyvinylpyrrolidone, progesterone, propylene glycol, propylheptyl caprylate, propylparaben, pumpkin seed extract, punica granatum (pomegranate) extract, punica granatum extract/punica granatum, pycnogenol, quaternium-15, *quillaja saponaria* (soap) bark extract, quillia extract, reserveratol, retinoic acid, retinoids, retinol, retinol palmate, *ribes rubrum* fruit extract, rice, rice bran wax, ricinoleate, rose oil, rosehips, rosemary, rosemary oil, rosewater, royal jelly, *rubus villosus* fruit extract, *saccharum officinarum* (cane sugar), salicylic acid, salvia, sandalwood oil, saponins, sassafras, saw palmetto, *saxifraga sarmentose* extract, sclareolide, *scutellaria baicalensis* extract, seaweed, *secale cereale* (rye) seed extract, *selaginella tamariscina* (spike moss) extract, selenium, sesame oil, sesquioleate, shavegrass herb, shea butter, silibinin, silica, silicone, sirtuins, sodium alginate, sodium ascorbate, sodium bisulphate, sodium borate, sodium carbonate, sodium chloride, sodium citrate, sodium dehydroaceatate, sodium ethylparaben, sodium glycyrrhetinate, sodium hyaluronate, sodium lactobionate, sodium lauryl sulfate, sodium methylparaben, sodium polystyrene sulfonate, sodium propylparaben, sodium stearate, sodium thioglycolate, sodium acrylodimethyl taurate, sorbitan isostearate, sorbitan olivate, sorbitan sesquioleate, sorbitan stearate, sorbitol, sorbitol, soy, soy wax, soybean oil, spearmint oil, squalane, st. paul's/john's wort, stearate, stem cells, sucrose stearate, sugar cane extract, sulfate, sunflower seed oil, sweet almond oil, *symphytum officinale* (comfrey) leaf extract, *symphytum officinale* leaf extract, synthetic fluorphlolopite, tamarindus indica seed extract, tea tree oil, thyme extract, tin oxide, titanium dioxide, titanium dioxide, tocopherol, tocopheryl acetate, tocopheryl acetate, toluene, tomato, tragacanth, tretinoin, tribehenin, triclosan, tridecyl trimellitate, triethanolamine, trihydroxystearin, triisostearyl citrate, trimethylolpropane triisostearate, trimethylsiloxysilicate, trimyristate, tripeptide, turmeric, tyrosine, ubiquinone, ultramarines, undecylenoyl phenylalanine, urea, uridine, *vaccinium macrocarpon* fruit extract, vegetable glycerin, vetiver oil, vitamin A, vitamin B1-B12, vitamin C, vitamin C ester, vitamin D, vitamin E, vitamin K, vitamins, walnut shell powder, water, wheat germ oil, whey protein (lactis proteinum), white birch bark extract, willowbark, wintergreen oil, witch hazel, xantham gum, xanthan gum, yarrow extract, yeast, yerba mate, yucca, zinc oxide, zinc stearate.

In some embodiments, the composition comprises, consists or consists essentially of MSM in combination with one, two, three, four, five or more of the above-identified ingredients. In several embodiments, MSM inhibits microbial activity in the formulation. In other embodiments, MSM offers the same or better antimicrobial effect when used to replace a preservative in the formulation (some of which are identified above). In certain embodiments, MSM offers the same or better antimicrobial effect when used with a reduced amount of preservative. In yet other embodiments, the addition of MSM to a formulation having a preservative enhances the effects of the preservative. The ingredients identified herein may be used with MSM in a cosmetic formulation (e.g., oral, injectable, or topical), or in other types of formulations (e.g., oral, injectable, or topical medical formulations).

In some embodiments, the composition includes MSM, but is free of one or more of the following compounds: sulfates, GMOs, synthetic fragrances, synthetic dyes, formaldehyde, potassium sorbate, methylparaben, methylchloroisothiazolinone, cocamidopropyl betain, parabens, decyl polyglucose, polyaminopropyl biguanide, phenoxyethanol, sodium laureth sulfate, tetrasodium EDTA, decyl glucoside, polyethylene glycol, propylene glycol, phthalates, and triclosan. In some embodiments, the use of MSM permits the manufacture of a formulation that is free of any synthetic ingredient. In yet other embodiments, the use of MSM permits the manufacture of a formulation that is free of any allergy-causing, immunosuppressant and/or inflammatory ingredient.

In several embodiments, the antimicrobial properties of MSM reduce or eliminate the need for sterilization, lowered temperatures, sterile environments, special closures, and/or special packaging, etc. MSM has a dual or multipurpose function according to some embodiments. For example, not only does MSM inhibit the growth of undesired microorganisms, MSM also beneficially affects the product to which it is added in several embodiments (e.g., MSM serves as an antioxidant, regenerative compound, anti-wrinkle compound, moisturizer, skin brightener, softener, circulation stimulant, neutralizer, reparative, hair/nail strengthener, healing catalyst, resurfacing agent, etc., or combinations of two or more thereof). In several embodiments, the antimicrobial properties of MSM increase the shelf-life, half-life, efficacy and/or stability of the formulation (or specific ingredient identified herein). The use of MSM may be particularly beneficial in some embodiments for cosmetic or other types of formulations that are shared by more than one person (e.g., cosmetics used by make-up artists or at cosmetic counters).

Cosmetics may include, but are not limited to, lipstick, lip gloss, lip liner, lip plumper, lip balm, lip conditioner and lip boosters, foundation, powder, rouge, blush, bronzer, mascara, eye liner, eye shadow, eye shimmer, glitter eye pencils, eyebrow pencil, nail polish, concealer, skin care products (e.g., microdermabrasion products, soothing gels) creams, lotions, serums, moisturizer, sunscreen, skin repair products (e.g., for acne, sunburn, wrinkles, dark circles), and scrubs. Face, hair, and body formulations (e.g., shampoo, soaps, conditioners, sprays, gels, serums, restorative treatments, deodorants, etc.) are provided in several embodiments. Cosmetics, such as cosmeceutical and nutraceutical products, are provided in several embodiments of the invention. Dermal fillers and other dermatological products (such as hyaluronic acid, waglerin 1, acetyl hexapeptide-8, palmitoyl tetrapeptide-7, palmitoyl oligopeptide, liposomes, collagen, calcium hydroxyl-apatite, poly-lactic acid, and botulinum toxin) are provided in several embodiments. Anti-wrinkle, anti-acne, anti-aging, exfoliating, moisturizing, and anti-stretch mark formulations, fragrances, mineral make-up, and primers are provided in several embodiments. Dermal gels, for cosmetic and medical use (e.g., inhibiting or preventing microbial infection and/or wound healing) are provided in some embodiments.

In several embodiments, products containing MSM can be shipped and/or stored in high temperature and high humidly conditions that would otherwise be favorable for microbial activity.

In some embodiments, products including MSM are packaged in containers adapted for multiple use applications and exposure to external microorganisms, such as from the air or contact with a body part (e.g., fingers). The use of MSM is particularly beneficial in several embodiments because it increases the shelf life of such products. In some embodiments, products comprising MSM are also packaged in single-use sealed containers. In one embodiment, a single-use product (such as a condiment packet, seasoning packet, a travel cosmetic package, etc.) will have a longer shelf life and/or will no longer need refrigeration if MSM is used in conjunction with the product and/or packaging.

In some embodiments, MSM is incorporated directly into packaging materials to, for example, enhance shelf life. For example, MSM may be incorporate into food storage bags to inhibit microbial growth. In other embodiments, MSM may be incorporated into containers and/or lids to enhance shelf life of foods, cosmetics and other products by inhibiting undesired microbial growth. In yet other embodiments, MSM may be incorporated into liner products such as plastic and cling wraps.

In several embodiments, a composition for inhibiting microbial activity in a cream or topical ointment includes MSM, wherein the MSM is configured for affecting the microbial contamination by inhibiting microbial activity. MSM is provided in a concentration of at least 5% according to one embodiment (e.g., 5-10%, 10-16%, 16-20%, 20-30%, 30-40%, 40-50%, 50-75% or higher, and overlapping ranges thereof). In some examples, the composition is a preservative-free cream. In one embodiment, MSM inhibits microbial activity by at least 50% in the cream at room temperature.

In some embodiments, pharmaceutical compositions include MSM, DMSO, and/or antimicrobial agents, or combinations thereof, which are formulated for use in human or veterinary medicine.

For example, the provided pharmaceutical compositions include about 0.01% MSM by weight to about 20% MSM by weight. In some embodiments, a pharmaceutical composition contains between about 0.01% to about 5% MSM by weight. Other embodiments contain between about 5% to about 10% MSM, about 10% to about 15% MSM, or about 15% to about 20% MSM., such as about 5%, about 6%, about 7%, about 8%, about 9%, about 10%, about 11%, about 12%, about 13%, about 14%, about 15%, about 16%, about 17%, about 18%, about 19% or about 20% MSM. Some embodiments include about 10-16% MSM, about 10-14% MSM or about 10-12% MSM.

Exemplary additional anti-microbial agents which can be included in a disclosed composition include, but are not limited to penicillin derivatives, cephalosporins, penems, monobactams, carbapenems, Beta-lactamase inhibitors and combinations thereof. Examples of penicillin derivatives include, but are not limited to, aminopenicillins (e.g., amoxacillin, ampicillin, and epicillin); carboxypenicillins (e.g., carbenicillin, ticarcillin, and temocillin); ureidopenicillins (e.g., azlocillin, piperacillin and mezlocillin); mecillinam, sulbenicillin, benzathine penicillin, penicillin G (benzylpenicillin), penicillin V (phenoxymethylpenicillin), penicillin O (allylmercaptomethylpenicillinic), procaine penicillin, oxacillin, methicillin, nafcillin, cloxacillin, dicloxacillin, flucloxacillin, pivampicillin, hetacillin, becampicillin, metampicillin, talampicillin, co-amoxiclav (amoxacillin plus clavulanic acid), and piperacillion. Examples of cephalosporins include, but are not limited to, cephalexin, cephalothin, cefazolin, cefaclor, cefuroxime, cefamandole, cefotetan, cefoxitin, ceforanide, ceftriaxone, cefotaxime, cefpodoxime proxetil, ceftazidime, cefepime, cefoperazone, ceftizoxime, cefixime and cefpirome. Examples of penems include, without limitation, faropenem. Examples of monobactams include, without limitation, aztreonam and tigemonam. Examples of carbapenems include, but are not limited to, biapenenvdoripenem, ertapenem, -imipenem, -meropenem, -and panipenem. Examples of Beta-lactamase inhibitors include, but are not limited to, tazobactam ([2S-(2alpha,3beta,5alpha)]-3-Methyl-7-oxo-3-(1H-1,2,3-triazol-1-ylmethyl)-4-thia-1-azabicyclo[3.2.0]heptane-2-carboxylic acid 4,4-dioxide sodium salt), sulbactam (2S,5R)-3,3-dimethyl-7-oxo-4-thia-1-azabicyclo[3.2.0]heptane-2-carboxylic acid 4,4-dioxide sodium), and clavulanic acid ((2R,5R,Z)-3-(2-hydroxyethylidene)-7-oxo-4-oxa-1-aza-bicyclo[3.2.0]heptane-2-carboxylic acid), or other Beta-lactam antibiotic.

Many antibiotics have an established minimum inhibitory concentration (MIC) at which they are effective in reducing or killing certain bacteria. In some embodiments, a disclosed pharmaceutical composition includes an amount of Beta-lactam antibiotic equal to about 0.001 to 100 MIC for the particular bacterial pathogens disclosed herein. In some embodiments the pharmaceutical composition comprises about 1-5, 5-10, 10-20, 20-30, 30-40, 40-50, 50-60, 60-70, 70-80, 80-90 or about 90-100 MIC of a Beta-lactam antibiotic. In some embodiments, the pharmaceutical composition comprises about 0.001, 0.01, 0.1, 0.5 or 1 MIC of a Beta-lactam antibiotic.

Pharmaceutical compositions provided herein also include combinations of MSM and antimicrobial compounds, for example a combination of MSM and a Beta-lactam antibiotic. In some embodiments, pharmaceutical compositions provided herein include 10-16% MSM and an amount of a Beta-lactam antibiotic equal to 1 MIC for a bacterial pathogen the composition will be contacting.

One of skill in the art will know the MIC of an antibiotic for a particular bacterial pathogen, or the skilled artisan will know how to determine the MIC of an antibiotic for a particular bacterial pathogen. Methods of determining a MIC of a particular antibiotic for a particular bacterial pathogen are disclosed herein, for example use of the Etest® antibiotic testing system (bioMérieux, Durham, N.C.).

The dosage form of the pharmaceutical composition will be influenced by the mode of administration chosen. For instance, in addition to injectable fluids, inhalational, topical, ophthalmic, peritoneal, and oral formulations can be employed. Inhalational preparations can include aerosols, particulates, and the like. In general, the goal for particle size for inhalation is about 1 μm or less in order that the pharmaceutical reach the alveolar region of the lung for absorption.

Pharmaceutical compositions that include MSM, DMSO, an antimicrobial agent or therapeutic compound as described herein such as an active ingredient, or which include a mixture of two or more thereof, with or without additional agent(s) as active ingredients, may be formulated with an appropriate solid or liquid carrier, depending upon the particular mode of administration chosen. Oral formulations may be liquid (for example, syrups, solutions, or suspensions), or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

For oral administration, the pharmaceutical compositions can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring, and sweetening agents as appropriate.

For administration by inhalation, the compounds for use according to the present disclosure are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

For topical administration, the compounds can be, for example, mixed with a liquid delivery agent for administration locally. The agents used therapeutically (such as DMSO, MSM and/or other therapeutic compounds as described herein) are readily soluble or suspendable in water, and as such this would be useful for delivery since water does not cause adverse biological tissue effects. This allows sufficiently high doses to be administered locally or systemically, without secondary toxicity from the delivery vehicle.

Pharmaceutical compositions that include a therapeutic amount of MSM as described herein as an active ingredient will normally be formulated with an appropriate solid or liquid carrier, depending upon the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

The pharmaceutical compositions that include a therapeutic effective amount of MSM, in some embodiments, will be formulated in unit dosage form, suitable for individual administration of precise dosages. The amount of MSM administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

Preparations for administration can be suitably formulated to give controlled release of the therapeutic agent(s) (e.g., DMSO, MSM, Beta-lactam antibiotic and so forth). For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features that allow a controlled release of the active substance. See, for example, U.S. Pat. No. 5,700,486.

Polymers can be used for controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of lipid-capsulated compounds (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

In several embodiments, pharmaceutical compositions include DMSO and/or MSM, and a therapeutic agent to treat an infectious disease, such as H1N1, herpes simplex virus, or HIV. In some embodiments, compositions including DMSO and/or MSM are provided as an inhalant to treat an infectious disease. In some embodiments, pharmaceutical compositions for treating an infectious disease include DMSO and/or MSM formulated as solids, while in several other embodiments, compositions including DMSO and MSM are formulated as liquids. In some embodiments, the compositions are consumed orally to treat the infectious disease, while in some other embodiments, the compositions are applied topically. In one particular embodiment, the compositions are delivered in an inhalant device which is configured to generate particles of the formulation that range in size from about 0.5 um to about 5 um.

In some embodiments, the pharmaceutical compositions including DMSO and/or MSM allow antibiotics (or other therapeutic agents) to penetrate lung tissue infected with an infectious disease. In one embodiment, such compositions including DMSO and/or MSM: (i) allow antibiotics to reach deeper levels of infected tissue; (ii) allow direct contact of infected tissue; (iii) lengthen the exposure time of the antibiotic to the infected tissue; and/or (iv) decrease the time to achieve a desired antibiotic effect. In one embodiment, DMSO and/or MSM achieves one or more of these desired effects through use as an inhalant, wherein the inhalant additionally comprises one or more antibiotics or other therapeutic agents.

In some embodiments, pharmaceutical compositions including DMSO and/or MSM formulations further include antiparasitic agents that are effective in treating infections caused by parasites, such as nematodes, cestodes, trematodes, protozoa, or amoebae.

In some embodiments, pharmaceutical compositions including DMSO and/or MSM formulations further include antifungal agents that are effective in treating fungal infections, such as those caused by ringworm, candidiasis, and *Cryptococcus* (cryptococcal meningitis, for example).

In some embodiments, pharmaceutical compositions including DMSO and/or MSM formulations further include antiviral agents that are effective in treating viral infections. In some embodiments, specific classes of antiviral agents are used to treat infections caused by a particular type of virus. In some embodiments, agents that target HIV, herpes viruses, hepatitis B or C viruses, and influenza viruses, such as H1N1, are used.

In several embodiments, DMSO and/or MSM compositions include antibiotics that are effective in treating bacterial infections by, for example, inhibiting bacterial growth, metabolism, proliferation, activity and/or function. In some embodiments, bacteriostatic antibiotics are used, while in other embodiments, bactericidal antibiotics are used. In still other embodiments, both bacteriostatic and bactericidal antibiotics are incorporated into a single formulation comprising DMSO and/or MSM. In some embodiments, antibiotics of one or more classes are incorporated into a composition including DMSO and/or MSM. In certain embodiments, a composition includes one or more of an: aminoglycoside, ansamycin, carbacephem, carbapenem, cephalosporin ($1^{st}$, $2^{nd}$, $3^{rd}$, $4^{th}$, or $5^{th}$ generation), glycopeptides, macrolide, monobactam, penicillin, polypeptide, quinolone, sulfonamide, tetracycline, and the like.

In some embodiments, specific diseases are targeted by incorporating specific antibiotics into a disclosed composition including DMSO and/or MSM. For example, macrolides, such as azithromycin or erythromycin are incorporated into formulations used to treat respiratory or mycoplasmal infections. Likewise, penicillins, such as amoxicillin or oxacillin are incorporated into formulations used to treat a broad range of streptococcal infections.

In still other embodiments, specific disease-causing microorganisms are targeted by the specific antibiotics incorporated into a formulation comprising DMSO and/or MSM. For example, aminoglycosides, such as neomycin are incorporated into formulations used to treat *Escherichia coli* infections. In several embodiments, antibiotics typically used to combat microbial infections are used. In certain embodiments, antibiotics including, but not limited to, isoniazid, rifampicin, pyrazinamide, and ethambutol are incorporated into formulations comprising one or more of DMSO and MSM, and are used to treat an infectious disease, including a drug-resistant infectious disease.

In several embodiments, compositions include DMSO, MSM and one or more of the following therapeutic agents: rifampicin, isoniazid, pyrazinamide, and ethambutol are provided. In other embodiments, compositions including DMSO and at least one of rifampicin, isoniazid, pyrazinamide, and ethambutol are provided. In further embodiments, compositions including MSM and at least one of rifampicin, isoniazid, pyrazinamide, and ethambutol are provided. In several embodiments, compositions including DMSO and/or MSM in combination with rifampicin, isoniazid, pyrazinamide, and ethambutol are provided to treat an infectious disease, including a drug-resistant infectious disease.

In some embodiments, rifampicin is provided in a total daily dose ranging from about 400 mg to about 800 mg per day. In some embodiments, rifampicin is provided in a total daily dose ranging from about 500 mg to about 700 mg per day, while in still other embodiments, it is provided in a total daily dose ranging from about 550 to about 650 mg per day, including 560, 570, 580, 590, 600, 610, 620, 630, and 640 mg per day.

In some embodiments, isoniazid is provided in a total daily dose ranging from about 100 mg to about 500 mg per day. In some embodiments, isoniazid is provided in a total daily dose ranging from about 200 mg to about 400 mg per day, while in still other embodiments, it is provided in a total daily dose ranging from about 250 mg to about 350 mg per day, including 260, 270, 280, 290, 300, 310, 320, 330, and 340 mg per day.

In some embodiments, pyrazinamide is provided in a total daily dose ranging from about 1.0 to about 4.0 g per day. In some embodiments, pyrazinamide is provided in a total daily dose ranging from about 2.0 to about 3.0 g per day, while in still other embodiments, it is provided in a total daily dose ranging from about 2.0 to 2.5 g per day, including 2.1, 2.2, 2.3, and 2.4 g.

In some embodiments, ethambutol is provided in a total daily dose ranging from about 0.5 to about 2.5 g per day. In some embodiments, ethambutol is provided in a total daily dose ranging from about 1.0 to 2.0 g per day, while in still other embodiments, it is provided in a total daily dose ranging from about 1.0 to about 1.5 g per day, including 1.1, 1.2, 1.3, and 1.4 g.

In some embodiments, pharmaceutical compositions including DMSO and/or MSM are used to pretreat a patient suffering from an infectious disease, such as H1N1. In some embodiments, the dose of DMSO and/or MSM used to pretreat patients ranges from about 10% to 50% weight to volume. In some embodiments, the pretreatment DMSO and/or MSM dose ranges from about 20% to about 40%, from about 25% to 35%, including 26, 27, 28, 29, 30, 31, 32, 33, and 34%. In some embodiments, about 50% to about 100% DMSO and/or MSM is used. In several embodiments, pretreatment with DMSO and/or MSM enhances the ability of an antibiotic to inhibit bacterial activity and/or sensitizes a drug-resistant strain to a drug that was previously ineffective.

In some embodiments, a pharmaceutical composition is prepared wherein antimicrobials are dissolved in DMSO and/or MSM prior to administration. This is particularly advantageous in certain embodiments because the antimicrobial and DMSO (and optionally MSM) can be administered to a subject via inhalation. Inhalants, according to some embodiments, provide direct access of the DMSO and/or MSM to infected lung tissue to sensitize bacterial cells to the antibiotic.

In one embodiment, an inhalant is provided to target the site of infection (e.g., lungs) of several infectious diseases. In some such embodiments, the inhalant device comprises a nebulizer. In other embodiments, an inhaler is used. In some embodiments, a pressurized metered-dose inhaler is used, and the formulation is inhaled in liquid aerosol form. In other embodiments, dry powder inhalers are used, and the formulation is inhaled in a powder aerosol form. In several embodiments, oral, intravenous, intramuscular, or subcutaneous administration is used in addition to or instead of inhalant therapy.

The ability to administer antimicrobial agents as an inhalant (e.g., in a powder aerosol form) with DMSO and/or MSM is especially advantageous in some embodiments because it allows for increased shelf-stability and pre-packaged dosages. This is particularly helpful for individuals in underdeveloped or developing nations who do not have regular access to healthcare facilities. Entire courses of treatment can be provided to an affected subject in a single visit to a healthcare practitioner without the need for a hospital stay or repeat visits. In several embodiments, formulations disclosed herein are suitable for self-administration (e.g., through inhalant devices) and are therefore especially appropriate for patients with limited access to healthcare.

In certain embodiments, the total volume of inhaled DMSO and/or MSM is about 2-8 mL. In some embodiments, the total volume of inhaled DMSO and/or MSM is about 2 mL to about 4 mL. In some embodiments, the total volume of inhaled DMSO and/or MSM is about 6 mL to about 8 mL. In still other embodiments, the total volume of inhaled DMSO and/or MSM is about 3 mL to about 7 mL, including 4, 5, and 6 mL. Thus, in some embodiments, the concentration of DMSO administered via inhalation ranges from about 65% to about 95%, including 70, 75, 80, 85, 86, 87, 88, 89, 90, 91, 92, 93, and 94%.

In several embodiments, MSM is included with the inhaled DMSO and antimicrobial compounds. In certain embodiments, the amount of inhaled MSM ranges from about 0.01% by weight to about 70% by weight of the inhalant. In other embodiments, the inhaled formulation contains between about 0.01% and 10% MSM by weight. Other embodiments contain between about 10 and 20% MSM, about 20-30% MSM, about 30-40% MSM, about 40-50% MSM, about 50-60% MSM, or about 60-70% MSM including 60, 61, 62, 63, 64, 65, 66, 67, 68, 69, and 70% MSM. Still other embodiments comprise a formulation containing about 7 and 15% MSM, about 15-25% MSM, about 25-35% MSM, about 35-45% MSM, about 55-60% MSM, about 60-65% MSM, or about 65-70% MSM. Thus, in some embodiments of the inhaled formulation containing MSM, the concentration of DMSO administered ranges from about 50% to about 95%, including 55, 60, 65, 70, 75, 80, 85, 86, 87, 88, 89, 90, 91, 92, 93, and 94%.

In several embodiments, the use of MSM reduces the amount of DMSO needed to achieve a comparable effect and/or enhances the efficacy of DMSO by at least 10%, 25%, 50%, 100%, 2-fold, 3-fold, 5-fold, 10-fold, 50-fold, or 100-fold. In other embodiments, the use of MSM reduces the amount of a therapeutic agent needed to achieve a comparable effect and/or enhances the efficacy of the therapeutic agent by at least 10%, 25%, 50%, 100%, 2-fold, 3-fold, 5-fold, 10-fold, 50-fold, or 100-fold. In further embodiments, the use of DMSO reduces the amount of a therapeutic agent needed to achieve a comparable effect and/or enhances the efficacy of the therapeutic agent by at least 10%, 25%, 50%, 100%, 2-fold, 3-fold, 5-fold, 10-fold, 50-fold, or 100-fold. In still other embodiments, the use of DMSO and MSM reduces the amount of a therapeutic agent needed to achieve a comparable effect and/or enhances the efficacy of the therapeutic agent by at least 10%, 25%, 50%, 100%, 2-fold, 3-fold, 5-fold, 10-fold, 50-fold, or 100-fold as compared to DMSO or MSM alone and/or the therapeutic agent alone.

In several embodiments, a pretreatment formulation including DMSO, alone or in combination with MSM, is administered to a subject intravenously, intramuscularly, topically or orally to enhance the effects of an inhalant therapy comprising DMSO and/or MSM with therapeutic agents, such as antibiotics. The pretreatment with DMSO, alone or in combination with MSM, enhances the inhalant's therapeutic effects by at least 10%, 25%, 50%, 100%, 2-fold, 3-fold, 5-fold, 10-fold, 50-fold, or 100-fold.

In several embodiments, subjects having an infectious disease re treated with a formulation comprising, consisting or consisting essentially of DMSO, alone or in combination with MSM, and one or more therapeutic agents, such as antibiotics. In some embodiments, the formulation additionally includes other therapeutics agents, carriers or excipients. In one embodiment, the formulation additionally includes arginine, vitamin D, antioxidants, macrolides, linezolid, thioacetazone, thioridazine, or combinations thereof.

DMSO readily disrupts the integrity of many materials (particularly plastics and polymers used in manufacturing disposable medical equipment). Accordingly, several embodiments of the invention comprise devices to facilitate the storage and administration of DMSO. In some embodiments, DMSO is stored in glass bottles and administered through non-reactive tubing. In other embodiments, inhalant devices are specially designed to be DMSO resistant. In some embodiments, portions of the inhalant devices are disposable or replaceable. According to several embodiments, formulations comprising DMSO are manufactured, stored and/or administered using materials and devices disclosed in U.S. patent application Ser. No. 12/066,480, which is the National Phase entry of International Application No.: PCT/US06/35499, filed Sep. 11, 2006, which is herein incorporated by reference in its entirety.

In certain embodiments, the delivery device delivers droplets or particles of the inhaled formulation of a size capable of reaching the bronchioles of the patient's lungs. In some embodiments, the delivery device is synchronized with a patient's breathing rhythm to carry the formulation to the bronchioles. Inhalant therapy according to one embodiment, enables more direct administration the inhaled formulation to infected pulmonary target tissues. Direct targeting is advantageous in some embodiments because it allows for reduction of the amount of antimicrobial compounds incorporated into the formulation while maintaining or improving efficacy of the formulation against infectious microorganisms. In other embodiments, direct administration increases the efficacy of a given antimicrobial regime against one or more drug-resistant strains of microorganism. Direct targeting, according to other embodiments, minimizes side effects by minimizing contact with non-targeted tissue.

The small droplet or particle size that is provided according to some embodiments reduces the volume of DMSO and/or MSM that is administered as compared to traditional ventilator therapy. For example, in one embodiment, the use of an inhalant device (e.g., nebulizer) will be efficacious with about 6 mg to about 25 mg DMSO and/or MSM daily, as compared to 50-100 mg daily when administered through certain other pathways. Reducing DMSO is beneficial in some embodiments because it reduces undesired side effects and odor. In other embodiments, higher amounts of DMSO are used and tolerated.

In several embodiments, the addition of MSM unexpectedly reduces the unpleasant odor normally experienced with DMSO use. For example, in certain embodiments, DMSO and MSM formulations produce no perceptible odor after use. In some other embodiments having DMSO concentrations approaching or exceeding 50%, the combination with MSM in the formulation reduces or eliminates the DMSO-based odor. Such a result is unexpected, given that DMSO use is normally associated with a strong unpleasant odor.

In some embodiments, the use of DMSO and/or MSM with therapeutic agents (such as antibiotics) permits the manufacture and/or administration of small droplets or particle sizes, thereby reducing the irritation of the mucosa of the mouth and throat, as the droplets or particles travel more deeply into the lungs of the patient. In some embodiments, the depth of travel of the droplets or particles increases the concentration of the dissolved antibiotics in the patient's lungs.

In several embodiments, DMSO and/or MSM compositions are combined with therapeutic agents (such as antibiotics) and provided as an aerosol to deliver locally-active drugs to the respiratory system to treat a respiratory disease. In one embodiment, the lower airways are contacted (or contacted exclusively) with the composition. In other embodiments, the composition is used to systemically treat illnesses. For systemically-active drugs, the aerosol particles are sized to reach the alveolar surface in peripheral areas of the lung.

In some embodiments, the use of DMSO and/or MSM compositions comprising a therapeutic agent (such as an antibiotic) is particularly advantageous because it provides rapid onset of action. In one embodiment, inhalation delivery provides a large absorption area of the lung. For locally acting drugs, the onset of action is immediate in some embodiments. Systemically-active inhaled formulations, according to some embodiments, reach the blood stream quickly. Inhalation therapy provides a therapeutic effect within about 1-90 minutes in some embodiments. In one embodiment, DMSO and/or MSM enhance the bioavailability of the therapeutic agent. In a further embodiment, DMSO and/or MSM reduce the degradation of the therapeutic agent. In another embodiment, aerosol formulations disclosed herein reduce the gastrointestinal side effects or skin irritation that may occur with oral or topical treatment.

In several embodiments, inhalant particles are sized to minimize the deposit of those particles by inertial impact into the upper airways without reaching the site of action. In several embodiments, the particles are sized to minimize deposit in the mouth and throat, thereby minimizing swallowing and undesired local or systemic side effects. In several embodiments, the particles are smaller than 2, 5 or 10 μm. In one embodiment, the particles are about 3-5 μm and are transported into the bifurcations and smaller airways of the bronchii and bronchioles. In another embodiment, the particles are less than 3 μm and follow the airflow into the alveoli. In several embodiments, the use of DMSO and/or MSM allows for optimizing the particle size of the therapeutic agent. Thus, diseases such as an infectious disease can be more effectively treated. Moreover, in several embodiments, the use of DMSO and/or MSM sensitizes drug-resistant microorganisms to antibiotics.

In several embodiments, DMSO and/or MSM form a solution, mixture, emulsion, suspension, or other suitable combination with the therapeutic agent. In one embodiment, homogenization, sonication, high shear fluid processing, or other mechanical methods are used to combine the therapeutic agent with the DMSO and/or MSM. In other embodiments, the therapeutic agent dissolves readily in DMSO. Unlike other strong solvents, DMSO is not harmful to lung tissue. Thus, DMSO is especially advantageous in some embodiments because it can both dissolve the therapeutic agent and deliver said agent without damaging lung tissue. In some embodiments, DMSO dissolves at least 50%, 75%, 90%, 95%, or 99% of the therapeutic agent, and in one embodiment, is able to prevent undesired precipitation of the therapeutic agent.

In some embodiments, sprays, gels or wipes comprising DMSO, alone or in combination with MSM, and antibacterial agents are provided for sanitizing medical equipment, surfaces and the body to minimize the spread of infectious disease.

In several embodiments, a pharmaceutical composition comprising DMSO and/or MSM and antimicrobial agents are used as a treatment for an infectious disease.

In certain embodiments, compositions disclosed herein are effective to treat various infectious diseases including, but not limited to, *acinetobacter* infection, actinomycosis, Adenovirus infection, African sleeping sickness (African trypanosomiasis), AIDS, amebiasis, anaplasmosis, Anthrax, Arcanobacterium haemolyticum infection, Argentine hemorrhagic fever, ascariasis, aspergillosis, astrovirus infection, babesiosis, *Bacillus cereus* infection, bacterial pneumonia, bacterial vaginosis (BV), *Bacteroides* infection, balantidiasis, Baylisascaris infection, BK virus infection, black piedra, Blastocystis hominis infection, blastomycosis, Bolivian hemorrhagic fever, *Borrelia* infection, botulism, Brazilian hemorrhagic fever, brucellosis, *Burkholderia* infection, Calicivirus infection, campylobacteriosis, candidiasis (moniliasis; thrush), cat-scratch disease, cellulitis, Chagas disease, chancroid, chickenpox, chlamydia, *Chlamydophila pneumoniae* infection, cholera, chromoblastomycosis, clonorchiasis, *clostridium difficile* infection, coccidioidomycosis, Colorado tick fever, common cold, creutzfeldt-Jacob disease, Crimean-Congo hemorrhagic fever, cryptococcosis, cryptosporidiosis, cutaneous larva migrans (CLM), cyclosporiasis, cysticercosis, cytomegalovirus infection, dengue fever, dientamoebiasis, diphtheria, diphyllobothriasis, dracunculiasis, ebola hemorrhagic fever, echinococcosis, ehrlichiosis, enterobiasis (Pinworm infection), *Enterococcus* infection, enterovirus infection, epidemic typhus, erythema infectiosum, exanthem subitum, fasciolopsiasis, fasciolosis, fatal familial insomnia (FFI), filariasis, food poisoning, free-living amebic infection, *Fusobacterium* infection, gas gangrene (Clostridial myonecrosis), geotrichosis, Gerstmann-Sträussler-Scheinker syndrome (GSS), giardiasis, glanders, gnathostomiasis, gonorrhea, granuloma inguinale (Donovanosis), Group A streptococcal infection, Group B streptococcal infection, *Haemophilus influenzae* infection, hand, foot and mouth disease (HFMD), Hantavirus, *Helicobacter pylori* infection, hemolytic-uremic syndrome (HUS), hemorrhagic fever with renal syndrome (HFRS), Hepatitis A, B, C, D, or E, herpes simplex, histoplasmosis, hookworm infection, human bocavirus infection, Hhman ewingii ehrlichiosis, human granulocytic anaplasmosis (HGA), human *metapneumovirus* infection, human monocytic ehrlichiosis, human papillomavirus (HPV) infection, human parainfluenza virus infection, and hymenolepiasis.

In certain embodiments, formulations disclosed herein are also effective in treating one or more of the following infectious diseases, Epstein-Barr Virus Infectious Mononucleosis (Mono), Influenza (flu), Isosporiasis, Kawasaki disease, Keratitis, Kingella kingae infection, Kuru, Lassa fever, Legionellosis, *Leishmaniasis,* Leprosy, Leptospirosis, Listeriosis, Lyme disease, Lymphatic filariasis, Lymphocytic choriomeningitis, Malaria, Marburg hemorrhagic fever (MHF), Measles, Melioidosis (Whitmore's disease), Meningitis, Meningococcal disease, Metagonimiasis, Microsporidiosis Microsporidia, Molluscum contagiosum (MC), Mumps, Murine typhus, *Mycoplasma pneumonia,* Mycetoma, Myiasis, Neonatal conjunctivitis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, Pneumocystis pneumonia (PCP), Pneumonia, Poliomyelitis, Poliovirus, Primary amoebic meningoencephalitis (PAM), Progressive multifocal leukoencephalopathy, Psittacosis, Q fever, Rabies, Rat-bite fever, Respiratory syncytial virus, Rhinosporidiosis, Rhinovirus infection, Rickettsial infection, Rickettsialpox, Rift Valley fever (RVF), Rocky mountain spotted fever (RMSF), Rotavirus infection, Rubella, Salmonellosis, SARS (Severe Acute Respiratory Syndrome), Scabies, Schistosomiasis, Sepsis, Shigellosis, Shingles (Herpes zoster), Smallpox, Sporotrichosis, Staphylococcal food poisoning, Staphylococcal infection, Strongyloidiasis, Syphilis, Taeniasis, Tetanus (Lockjaw), *Tinea barbae* (Barber's itch), *Tinea capitis* (Ringworm of the Scalp), *Tinea corporis* (Ringworm of the Body), *Tinea cruris* (Jock itch), *Tinea manuum* (Ringworm of the Hand), *Tinea nigra, Tinea pedis* (Athlete's foot), *Tinea unguium* (Onychomycosis), *Tinea versicolor* (Pityriasis versicolor), Toxocariasis (Ocular Larva Migrans (OLM)), Toxocariasis (Visceral Larva Migrans (VLM)), Toxoplasmosis, Trichinellosis, *Trichomoniasis,* Trichuriasis (Whipworm infection), Tularemia, Ureaplasma urealyticum infection, Venezuelan equine encephalitis, Venezuelan hemorrhagic fever, Viral pneumonia, West Nile Fever, White piedra, Yersiniosis, Yellow fever, and Zygomycosis.

In several embodiments, compositions disclosed herein are particularly effective in treating one or more infectious diseases that are resistant to drug therapies. In addition to those infectious diseases listed above, which may already be or may become drug resistant in the future, certain embodiments are effective in treating, among others, drug resistant: measles, tetanus, malaria, upper and lower respiratory infections, hepatitis, typhoid fever, vancomycin/glycopeptide-intermediate *Staphylococcus aureus* infection, vancomycin-resistant enterococci, methicillin-resistant *Staphylococcus aureus* (MRSA), and *streptococcus pneumoniae.*

In some embodiments, treatment of an infectious disease comprises the pretreatment of a patient with DMSO, followed by the administration of a pharmaceutical composition comprising DMSO and antimicrobial agents. In other embodiments, treatment of an infectious disease comprises the pretreatment of a patient with DMSO, followed by the administration of a formulation comprising DMSO, MSM, and antimicrobial agents. In some embodiments, DMSO pretreatment is administered intravenously via a fast drip IV catheter. In other embodiments, the DMSO is given in a bolus IV injection. In yet other embodiments, pretreatment with DMSO is not performed. Pretreatment compositions additionally include MSM, a therapeutic agent or a combination thereof in some embodiments.

In several embodiments, compositions including DMSO and antimicrobial agents, or DMSO, MSM and antimicrobial agents are administered orally, intravenously, intramuscularly, or subcutaneously. However, as the site of infection of several infectious diseases is the lungs, in some embodiments, formulations are administered by inhalation. In some such embodiments, the inhalant means comprises a nebulizer. In other embodiments, an inhaler is used.

In several embodiments, subjects are pretreated with DMSO using intravenous DMSO by fast drip within, e.g., a ten minute period. In one embodiment, DMSO will be provided in glass bottles with proprietary non-reactive tubing. Subjects will then receive antibiotics dissolved in DMSO in 3 mL doses through an inhaler or mouth spray three times a day with meals. In one embodiment, DMSO pretreatment is provided in the range of about 25 mg to about 75 mg (e.g., 30 mg, 40 mg, 50 mg, 60 mg, 70 mg) in 200 mL 5% dextrose and water. In one embodiment, 56 mg DMSO in 200 mL 5% dextrose and water is provided. In one embodiment, the following antibiotics are provided: rifampicin, isoniazid, pyrazinamide, and ethambutol. In one embodiment, about 600 mg rifampicin, 300 mg isoniazid, 2.4 g pyrazinamide, and 1.2 g ethambutol are administered per day, through an inhaler/nebulizer or mouth spray delivered in 3 mL dosages, three times daily. In one embodiment, the antibiotics are combined with DMSO for delivery via inhalation, with or without the pretreatment with DMSO. Pretreatment with MSM is also provided in several embodiments. Intravenous pretreatment of DMSO, MDM, or the combination of the two is provided in some embodiments. In some examples, pretreatment formulations include therapeutic agents.

In several embodiments, therapeutic effects are obtained within two weeks of treatment, within two months of treatment, and/or within six months of treatments. Other therapeutic windows are also provided.

In some embodiments, patients pretreated with DMSO show better improvement than those treated with inhalant DMSO and antibiotics without intravenous DMSO pretreatment. In some embodiments, patients treated with DMSO with inhalant DMSO and antibiotics show better improvement than those treated with antibiotics alone. In several embodiments, the addition of MSM to the formulation enhances the therapeutic effects or reduces side effects. In one embodiment, MSM is used alone as a pretreatment.

In several embodiments, compositions disclosed herein are used to not only treat undesired symptoms and illnesses, but can also act as a preventative agent. For example, formulation may be taken on a regular basis to prevent the onset of illness. In one embodiment, at risk subjects (e.g., family members or subjects who are exposed to patients having an infectious disease) are administered lower doses of DMSO and/or MSM and antibiotics to prevent the onset of infection.

IV. Methods of Use of MSM

Disclosed herein are methods of using any of the disclosed MSM compositions (as described in Section III) to modulate microbial activity, such as to enhance or inhibit the activity of microorganisms. For example, methods of enhancing microbial activity are disclosed which include methods of enhancing microbial growth, fermentation efficiency, culturing efficiency, microbial survival, or any combination thereof. Methods of inhibiting microbial activity are also disclosed which include methods of inhibiting microbial growth (such as bacterial growth) or infection. In some embodiments, MSM selectively enhances the activity (e.g., growth) of one microorganism (such as a probiotic microorganism) and inhibits the activity of undesired microbes (such as an undesired bacterial or fungal activity).

A. Methods of Enhancing Microbial Activity

Methods of enhancing microbial activity are disclosed. In one embodiment, a method for enhancing activity of a microorganism includes providing microorganisms, a medium capable of supporting growth of the microorganisms, and MSM in an amount sufficient to enhance the activity (e.g., fermentation efficiency, growth, culturing efficiency, and/or microbial survival) of the microorganisms and contacting the MSM with the medium, thereby enhancing the growth of the microorganisms in the medium. It is contemplated that the MSM can be added to the medium prior to, concurrent with or after the medium is contacted with the microorganisms. In one particular embodiment, MSM is provided at a concentration of about 0.04% to about 5% by weight of the medium or by weight of the moisture content of the medium. As such, in some examples, MSM (such as a composition including about 0.5% to about 5% MSM) is used to enhance microbial growth. For example, MSM is used to enhance fermentation efficiency, such as to enhance fermentation efficiency associated with the production of beer, cider, wine, a biofuel, dairy product or any combination thereof. In several examples, MSM enhances the production of certain food or beverage making processes that rely on microorganisms, such as beer brewing, winemaking, baking, pickling, dairy product production, and the like. In additional examples, MSM is used to enhance the growth of one or more probiotic microorganisms or a microorganism in a diagnostic test sample. In even further examples, MSM is used to enhance the culturing efficiency and/or survival of microorganisms.

i. Methods to Enhance Microorganism Fermentation Efficiency with MSM

In several embodiments, MSM is used to facilitate energy production. Thus, disclosed herein are methods of enhancing energy production, including methods of enhancing microorganism fermentation efficiency. For example, microorganisms may be used in a fermentation process to produce ethanol, and in biogas reactors to produce methane. Fermentation is an energy yielding process whereby organic or synthetic molecules are degraded through metabolism by microorganisms. Some forms of microorganisms, such as bacteria or yeast may be used to convert various forms of agricultural and urban waste into usable fuels. Microorganisms may be used as living microbial fuel cells. In some embodiments, MSM enhances bacterial growth and metabolism. In some embodiments, MSM enhances bacterial energy production. In some embodiments, MSM enhances yeast growth and metabolism. In some embodiments, MSM enhances yeast energy production.

In several embodiments, MSM is used to activate or enhance one or more of the following: (i) ethanol fermentation or other anaerobic respiration used primarily by yeast when oxygen is not present in sufficient quantity for normal cellular respiration; (ii) fermentative hydrogen production; (iii) industrial fermentation or other breakdown and re-assembly of biochemicals for industry; (iv) the conversion of carbohydrates into alcohols or acids under anaerobic conditions used for food preparation (e.g., breads, dairy, beans, vinegar, sauerkraut, kimchee, fish, and tofu); (v) fermentation for making brandy, whiskey, vodka, beer, wine or cider, (vi) fermentation for making glucosamine; and (vii) fermentation for the aerobic treatment of tea leaves to break down undesired chemicals and develop others that impact, e.g., the flavor and/or nutrients of tea.

In one embodiment, a method of enhancing fermentation efficiency of a microorganism includes contacting medium containing a microorganism capable of fermentation with MSM, wherein the MSM is provided at a concentration of about 0.04% to about 5% by weight of the medium or at a concentration of about 0.04% to about 5% by weight of the moisture content of the medium, wherein the concentration of MSM increases the fermentation efficiency of the microorganism as compared to the fermentation efficiency in the absence of MSM.

In one embodiment, enhanced fermentation efficiency is indicated by an at least 10%, such as about a 20% to 80% increase, about a 30% to 50% increase, including about a 10%, about a 20%, about a 30%, about a 40%, about a 50%, about a 60%, about a 70%, about a 80%, about a 90%, about a 100%, about a 150%, about a 200%, about a 300% increase in alcohol, carbon dioxide or acid production in the presence of MSM by the microorganism as compared to alcohol, carbon dioxide or acid production in the absence of MSM. For example, the method of enhancing fermentation efficiency is for the production of beer, cider, wine, a biofuel, bread, dairy product or any combination thereof. In some examples, enhancing fermentation efficiency includes an at least 10%, such as about a 20% to 80% increase, about a 30% to 50% increase, including about a 10%, about a 20%, about a 30%, about a 40%, about a 50%, about a 60%, about a 70%, about a 80%, about a 90%, about a 100%, about a 150%, about a 200%, about a 300% increase in production of ethanol, methanol or a combination of thereof as compared to production of ethanol, methanol or a combination of thereof in the absence of MSM. In one particular example, the microorganism is yeast and the method of enhancing fermentation is for the production of beer. In another example, the microorganism is algae and the method of enhancing fermentation is for the production of biofuel.

In some embodiments, enhancing fermentation efficiency includes an at least 10%, such as about a 20% to 80% increase, about a 30% to 50% increase, including about a 10%, about a 20%, about a 30%, about a 40%, about a 50%, about a 60%, about a 70%, about a 80%, about a 90%, about a 100%, about a 150%, about a 200%, about a 300% increase in carbon dioxide production in the presence of MSM by the microorganism as compared to carbon dioxide production in the absence of MSM. In a particular example, the microorganism is yeast and the method of enhancing fermentation is for the production of bread.

In additional embodiments, MSM is used to control the fermentation process in the production of cultured dairy products such as yogurt, milk, cheese and the like. For example, methods of enhancing fermentation efficiency include an at least 10%, such as about a 20% to 80% increase, about a 30% to 50% increase, including about a 10%, about a 20%, about a 30%, about a 40%, about a 50%, about a 60%, about a 70%, about a 80%, about a 90%, about a 100%, about a 150%, about a 200%, about a 300% increase in lactic acid production in the presence of MSM by the microorganism as compared to lactic acid production in the absence of MSM.

In some embodiments, the concentration of MSM effective for enhancing fermentation efficiency is about 0.04% to about 5%, such as about 0.1% to about 4%, 0.5% to about 3%, about 1% to about 2%, including about 0.04%, to about 0.05%, about 0.06%, about 0.07%, about 0.08%, about 0.09%, about 0.1%, about 0.3%, about 0.5%, about 0.7%, about 1%, about 1.5%, about 2.0%, about 2.5%, about 3.0%, about 4%, or about 4.5% by weight of medium or by moisture content of the medium. In some embodiments, MSM is added to yeast packages to generate rapid or quick-activating yeast for home or commercial use.

In some examples, the medium for the method of enhancing efficiency of a microorganism includes a sodium chloride concentration of less than 5% of total moisture content of the medium, such as about 1% to about 3% sodium chloride, including 0%, 0.1%, 0.3%, 0.5%, 0.75%, 1%, 2%, 2.5%, 3% or 4%.

In one certain embodiment, MSM is used for making beer. Yeast cultures are involved in the production of beer during the fermentation process to produce ethanol and carbon dioxide. In some examples, MSM is used to quicken or facilitate activation of the yeast culture, enhance fermentation, reduce potential environmental contamination (such as from undesirable airborne microorganism) or a combination thereof. For example, an increase in the efficiency to activate the yeast (such as an increase in the efficiency of the starter process), an increase in the efficiency of the fermentation process or combination thereof is indicated by an at least 10%, such as about a 20% to 80% increase, about a 30% to 50% increase, including about a 10%, about a 20%, about a 30%, about a 40%, about a 50%, about a 60%, about a 70%, about a 80%, about a 90%, about a 100%, about a 150%, about a 200%, about a 300% increase as compared to a control (such as efficiency of these processes in the absence of MSM).

In several embodiments, MSM is used for enhancing the activity of algae, including the fermentation process associated with generating biofuel from use of algae. In one embodiment, this is particularly beneficial for algaculture (farming algae) for making vegetable oil, biodiesel, bioethanol, biogasoline, biomethanol, biobutanol and/or other biofuels. In one embodiment, the addition of MSM increases the growth rate of algae by about 25%, about 30%, about 40%, about 50%, about 100%, about 200%, about 300%, about 400%, about 500% or higher. MSM may be particular advantageous because, by enhancing the activity of algae (such as algal growth), the production of biofuels may become scalable, economically competitive and/or commercially viable. In one embodiment, MSM enhances the process by which the algae product is harvested and converted into biodiesel. In other embodiments, MSM enhances the process by which the algae's carbohydrate content is fermented into bioethanol and biobutanol. In some embodiments, MSM enhances the algal process by (i) increasing algae yield, (ii) forming more robust algae colonies, (iii) shortening the time to harvest, (iv) shortening the fermentation time, (v) enhancing fermentation, and/or otherwise supporting or enhancing the growth, reproduction, proliferation, survival rate, metabolism, vitality, robustness, action, and/or function of the algae. Algae, including but not limited to, *Botryococcus braunii, Chlorella, Dunaliella tertiolecta, Gracilaria, Pleurochrysis carterae*, and *Sargassum* are enhanced by MSM according to several embodiments.

ii. Methods to Enhance Microbial Growth with MSM

In some embodiments, the addition of MSM is particularly advantageous because MSM promotes the growth of certain microorganisms (e.g., probiotics). In some embodiments, microorganisms grown with a media composition comprising MSM have a higher growth rate curve compared to a comparable composition without MSM. In some embodiments, microorganisms grown with a composition comprising MSM have an increased overall population density compared to a comparable composition without MSM. In certain embodiments, MSM significantly enhances the simultaneous growth of one or more microorganisms. In some embodiments, media supplemented with a composition of MSM for enhancing microbial activity (such as a concentration range of about 0.4% to about 5% or any of the compositions of MSM for enhancing microbial growth provided in Section III) enhances the growth of microorganisms.

Some microorganisms are anaerobic organisms (anaerobes). Anaerobes do not require oxygen for growth. Anaerobes may be used for fermentation and/or culturing. In some embodiments, MSM has a positive impact on anaerobes, such as *Bifidobacterium*, among others. In some such embodiments, MSM has a greater positive impact on growth of anaerobes than other microorganisms. In other embodiments, MSM has a greater positive impact on growth of aerobic bacteria as compared to other microorganisms. In still other embodiments, aerobes and anaerobes are both positively impacted by the presence of MSM.

Bacteria can be generally classified as gram-positive or gram-negative, depending on the structure of their cell wall. Gram negative bacteria include, but are not limited to, *Escherichia coli, Pseudomonas, Salmonella, Shigella, Enterobacteriaceae, Pseudomonas, Moraxella, Helicobacter, Stenotrophomonas, Bdellovibrio*, acetic acid bacteria, *Legionella*, alpha-proteobacteria, cyanobacteria, spirochaetes, green sulfur and green non-sulfur bacteria. Enterics are rod-shaped Gram-negative bacteria; most occur normally or pathogenically in the intestines of humans and other animals. In some embodiments, MSM has a positive impact on the growth of gram positive bacteria. In other embodiments, MSM has a positive impact on the growth of gram negative bacteria. In some such embodiments, MSM has a greater positive impact on gram negative bacteria than gram positive bacteria. In other embodiments, MSM has a greater positive impact on gram positive bacteria than gram negative bacteria. In yet other embodiments, MSM has a positive impact on both gram negative bacteria and gram positive bacteria.

Probiotics include live microorganisms thought to be healthy for the host organism. Lactic acid bacteria (LAB) and bifidobacteria are common types of microbes used as probiotics. Certain yeasts and bacilli are also used. In several embodiments, MSM is used to enhance the survival or growth of at least one probiotic. Effect on survival of probiotic organisms may be measured on three points according to some embodiments: survivability, colonization, and lactic-acid production. To be effective in maintaining the health of the gastrointestinal tract, probiotic bacteria must be able to survive. Bacterial that are dead on arrival, in most cases, provide no benefit. Thus in some embodiments, MSM positively affects probiotic survival. In certain embodiments, MSM improves initial survival upon exposure of bacteria to a new environment. Thus, in such embodiments, a product comprising a probiotic and MSM establishes a larger or more healthy (or both) population of probiotic bacteria in the gut as compared to probiotic products alone. In certain embodiments, MSM improves long-term survival of probiotics. Thus, in such embodiments, a product comprising a probiotic and MSM establishes a longer lasting, and based on growth, a larger population of probiotic bacteria in the gut as compared to probiotic products alone. Of those probiotic bacteria arriving in the gut alive, those that colonize (multiply in) the gut generally provide benefit. Thus, in several embodiments, MSM improves the speed and frequency of probiotic multiplication. In still other embodiments, MSM increases the production of lactic acid.

In some embodiments, MSM has a positive impact on probiotic growth. In some embodiments, MSM has a positive impact on the microbial flora of the gastrointestinal tract. In some such embodiments, MSM has a positive impact on intestinal health. In some embodiments, foods containing probiotics are supplemented with MSM, and the resulting probiotic levels achieved in the intestinal tract are greater than after ingestion of the probiotic-containing food alone. In some such embodiments, the addition of MSM results in higher level of probiotic organism in a shorter time frame with ingestion of probiotic-containing food alone. In some embodiments, probiotics that require 24 to 48 hours before effects are observed are rendered more efficacious because MSM increases their lifespan.

Bacterial growth typically has an initial lag phase where the bacteria adjust to the environment, before going into the log phase, where cells double. After the log phase there is a stationary phase. During the stationary phase, the growth rate slows as a result of nutrient depletion and accumulation of metabolic by-products. This phase is reached as the microbes begin to exhaust the resources that are available to them. This phase is a relatively constant value as the rate of microbial growth is equal to the rate of microbial death. In the death phase, bacteria typically exhaust nutrients and population numbers drop.

In some embodiments, MSM impacts the lag phase, log phase, stationary phase, death phase or any combination thereof. In certain embodiments, MSM shortens the lag phase, so that the bacteria, such as probiotic bacteria, begin the log phase at an earlier time. In several embodiments, MSM extends the stationary phase. In certain embodiments, the death rate is slowed in the presence of MSM. Certain embodiments of the disclosure as described herein positively affect one or more, and in certain embodiments all, phases of the growth of probiotic bacteria.

In some embodiments, MSM impacts metabolism of microbes (e.g., probiotics), in the lag phase. During the lag phase, microbes are maturing (growing in size) and not yet able to divide (thus not growing in number). During the lag phase of the microbial growth cycle, synthesis of RNA, enzymes and other molecules occurs. In some embodiments, MSM decreases the duration of the lag phase by accelerating the maturation (and adaptation of microorganisms to environmental stressors) of the microorganisms, thereby allowing microbial division sooner than in MSM-free media.

In some embodiments, MSM-supplementation results in an increase in the log phase of growth of microbes (e.g., probiotics). The exponential phase (sometimes called the log phase) of growth is a period characterized by cell doubling. The number of new microbes appearing per unit time is proportional to the present population. If growth is not limited, doubling will continue at a constant rate so both the number of cells and the rate of population increase doubles with each consecutive time period. Exponential growth cannot continue indefinitely, however, because the medium is soon depleted of nutrients and enriched with wastes. In some embodiments, MSM increases the overall duration of the exponential phase. In other embodiments, the presence of MSM in the growth media promotes microbial entry into the exponential phase more quickly than microorganisms in MSM-free media. The initial growth environment with MSM-supplemented media can be conducive to cell multiplication and survival.

In several embodiments, MSM affects the stationary phase of microbial (e.g., probiotic) growth. In one example, MSM-supplementation of media extends the stationary phase for microbes as compared to MSM-free media.

In some embodiments, MSM enhances probiotic growth, which in turn crowds out and takes nutrients from undesired microbes. In other embodiments, MSM enhances probiotic activity, which in turn enhances lactic and acetic acid production to lower the environmental pH and inhibit the activity of undesirable bacteria. In further embodiments, MSM enhances probiotic activity, which in turn stimulates the production of immunomodulating agents (e.g., cytokines), thereby enhancing the immune response. In certain embodiments, MSM enhances probiotic activity, which in turn enhances bactericidal activity with respect to undesired microbial contamination. In one embodiment, MSM enhances probiotic growth at a faster rate than undesired microbes, thereby allowing probiotics to preferentially colonize an environment (e.g., edible products, intestinal tract).

Without being bound by a particular theory, in several embodiments, MSM has a biochemical effect on microbial metabolism. For example, in some embodiments, the addition of MSM has a positive effect on metabolism of certain microorganisms such that certain microorganisms are better able to adapt and/or recover from environmental changes. In some embodiments, MSM serves as a substrate or cofactor for microbial metabolism and/or anapleurotic biochemical pathways. In some embodiments, MSM positively impacts the lag phase of growth. In some embodiments, MSM increases the log phase of microbial growth. In still further embodiments, MSM increases the duration of the stationary phase of microbial growth. In some embodiments, MSM decreases the rate of population decline of certain microbes. In certain embodiments, MSM provides a selective or semi-selective growth environment, so that certain microbial species grow more rapidly (or to attain larger population size, or both) as compared to other microbial species. In certain embodiments, MSM impacts the metabolic activity of microorganisms, while in other embodiments, MSM creates an environment more conducive to microbial growth.

As such, methods of enhancing microbial growth are provided. In some embodiments, methods of enhancing microbial growth include in vitro methods for enhancing the growth of one or more microorganisms. In one example, in vitro methods for enhancing growth of one or more microorganisms includes contacting one or more microorganisms with a medium capable of supporting growth of the one or more microorganisms; and providing MSM to the medium at about 0.4% to about 5% by weight of the medium or by weight of moisture content of the medium thereby enhancing the growth of the one or more microorganisms in vitro as compared to growth of the one or more microorganisms in vitro in the absence of MSM. It is contemplated that similar methods can be used for enhancing the growth of desired microorganisms (such as probiotics) in vivo. For example, an increase in microbial growth is indicated by an increase in weight of the microrganism or cell number such as an at least 10%, such as about a 20% to 80% increase, about a 30% to 50% increase, including about a 10%, about a 20%, about a 30%, about a 40%, about a 50%, about a 60%, about a 70%, about a 80%, about a 90%, about a 100%, about a 150%, about a 200%, about a 300% increase as compared to a control (such as weight of the microorganism or cell number in the absence of MSM). Increases in microorganism growth can be detected by methods known to those of skill in the art including those described in the Examples.

a. Methods for Enhancing Growth of a Probiotic Microorganism

Methods for enhancing growth of one or more probiotic microorganisms are disclosed. For example, methods of enhancing growth of one or more probiotic microorganisms include contacting one or more probiotic microorganisms with a medium capable of supporting growth of one or more probiotic microorganisms; and providing MSM to the medium at about 0.4% to about 5% by weight of the medium or by weight of moisture content of the medium thereby enhancing the growth of the one or more microorganisms as compared to growth of the one or more microorganisms in the absence of MSM. In one example, the concentration of MSM is about 1% to about 3% of the weight of the medium or by weight of the moisture content of the medium. An increase in probiotic growth is indicated by an at least 10%, such as about a 20% to 80% increase, about a 30% to 50% increase, including about a 10%, about a 20%, about a 30%, about a 40%, about a 50%, about a 60%, about a 70%, about a 80%, about a 90%, about a 100%, about a 150%, about a 200%, about a 300% increase in cell growth as compared to a control (such as cell growth in the absence of MSM)

In some examples, the medium for enhancing microbial growth, such as probiotic growth, include a probiotic-containing product, such as milk, yogurt, rice yogurt, frozen yogurt, chocolate, cheese, beer, wine, vinegar, sauerkraut or any combination thereof.

It is contemplated that the method can be used to enhance growth of any probiotic microorganism, including, but not limited to *Lactobacillus acidophilus*, *Lactobacillus delbrueckii*, *Bacillus coagulans*, *Lactobacillus rhamnosus*, *Bifidobacteruim bifidum* or any combination thereof. In one embodiment, the disclosed methods are used to enhance the activity of the bacteria *Lactobacillus rhamnosus*. In other embodiments, the disclosed methods are used to enhance the activity of species within the *Lactobacillus* genus. For example, a method of enhancing the activity (e.g., growth) of *Lactobacillus acidophilus* includes contacting *Lactobacillus acidophilus* with a medium capable of supporting growth of *Lactobacillus acidophilus*; and providing MSM to the medium at about less than about 1% (such as at about 0.04%, 0.05%. 0.1%, 0.2%, 0.3%, 0.4%, 0.5%. 0.6%, 0.75, 0.8% or 0.9%) by weight of the medium or by weight of a moisture content of the medium thereby enhancing the growth of *Lactobacillus acidophilus* as compared to growth of *Lactobacillus acidophilus* in the absence of MSM.

In other embodiments, the disclosed methods are used to enhance the activity of *Bifidobacterium bifidum*. For example, a method of enhancing the activity (e.g., growth) of *Bifidobacterium bifidum* includes contacting *Bifidobacterium bifidum* with a medium capable of supporting growth of *Bifidobacterium bifidum*; and providing MSM to the medium at about less than about 1% (such as at about 0.04%, 0.05%. 0.1%, 0.2%, 0.3%, 0.4%, 0.5%. 0.6%, 0.75, 0.8% or 0.9%) of weight of the medium or a moisture content of the medium thereby enhancing the growth of *Bifidobacterium bifidum* as compared to growth of *Bifidobacterium bifidum* in the absence of MSM.

An increase in probiotic growth is indicated by an increase in weight of the probiotic microorganism or cell number of such, including an at least 10%, such as about a 20% to 80% increase, about a 30% to 50% increase, including about a 10%, about a 20%, about a 30%, about a 40%, about a 50%, about a 60%, about a 70%, about a 80%, about a 90%, about a 100%, about a 150%, about a 200%, about a 300% increase as compared to a control (such as weight of the probiotic microorganism or cell number in the absence of MSM). Increases in probiotic microorganism growth can be detected by methods known to those of skill in the art including those described in the Examples.

b. Methods for Enhancing Growth of a Microorganism in a Diagnostic Test Sample or Industrial Test Sample Methods for enhancing growth of a microorganism in a diagnostic test sample or industrial test sample are disclosed. In one embodiment, a method for enhancing growth of a microorganism in a diagnostic test sample is provided. In one example, the method includes contacting a diagnostic test sample (e.g., blood, tissue, scrapings, bodily fluids and metabolic products, and the like) comprising one or more microorganisms with a medium capable of supporting growth of the one or more microorganisms; and providing MSM to the medium at a concentration sufficient to enhance microbial growth, thereby enhancing the growth of the one or more microorganisms in the diagnostic test sample as compared to growth of the one or more microorganisms in the absence of MSM.

In some embodiments, a method for enhancing growth of a microorganism in an industrial test sample is provided. In one example, the method includes contacting an industrial test sample (e.g., water sample, household mold or bacteria sample and other like samples) comprising one or more microorganisms with a medium capable of supporting growth of the one or more microorganisms; and providing MSM to the medium at a concentration sufficient to enhance microbial growth, thereby enhancing the growth of the one or more microorganisms in the industrial test sample as compared to growth of the one or more microorganisms in the absence of MSM.

In several embodiments, MSM is provided in a composition for facilitating diagnostic assays or industrial test sample assays, such as at a concentration of about 0.04% to about 5% by weight of the sample or by weight of the moisture content of the sample. In some embodiments, MSM is provided in a composition for facilitating diagnostic assays or industrial test sample assays such as any of the compositions of MSM capable of enhancing microbial activity which are described in Section III. In certain embodiments, MSM is added directly to the diagnostic or industrial test sample comprising microorganisms.

According to several embodiments described herein, MSM can shorten detection and/or analysis time by 10%, 20%, 30%, 40%, 50%, 60%, 70%, 80% or 90%. According to several embodiments described herein, MSM can enhance microbial activity (such as growth) by at least 10%, 20%, 30%, 40%, 50%, 60%, 70%, 80%, 90%, 100%, 2-fold, 5-fold, 100-fold, 500-fold or 1000-fold. For example, an increase in microbial growth is indicated by an increase in weight of the microorganism or cell number of such, including an at least 10%, such as about a 20% to 80% increase, about a 30% to 50% increase, including about a 10%, about a 20%, about a 30%, about a 40%, about a 50%, about a 60%, about a 70%, about a 80%, about a 90%, about a 100%, about a 150%, about a 200%, about a 300% increase as compared to a control (such as weight of the microorganism or cell number in the absence of MSM). Increases in microorganism growth can be detected by methods known to those of skill in the art including those described in the Examples.

In several embodiments, MSM is used in conjunction with medical screening tests and rapid diagnostic testing, such as in urine or blood samples. In many cases, diagnostic tests are performed to identify possible microbial infections. Several groups of microorganisms, including bacteria, viruses, mold, and yeast, can cause infections. If a microorganism is found, more testing is done to determine which antibiotics may be effective in treating the infection. In order diagnose such infections as early as possible, in some embodiments MSM is used to supplement the growth media used in diagnostic tests to increase the rate of growth of microorganisms in the patient sample, thereby improving the detection time of the test. In some embodiments, MSM may enhance detection sensitivity of a diagnostic test. In some embodiments, the diagnostic test is a urine test. In some embodiments, the diagnostic test is a blood test. In other embodiments, other patient samples can be grown for diagnostic purposes, such as sputum, saliva, skin scrapings, dental swaps, vaginal or cervical swabs, and the like. In one embodiment, MSM is used to provide a rapid strep test. For example, a sample of bodily fluid (the diagnostic test sample) is added to a test tube or culture dish (the medium). The medium supports the culture of any microbes that may exist in the bodily fluid. By providing a medium that is pre-dosed with MSM or by adding MSM prior to or after adding the bodily fluid to the test tube or culture dish, microbes in the bodily fluid (or their assayable products or metabolites) would increase, and would be easier to assay. Thus, diagnosis is facilitated.

In several embodiments, the use of MSM facilitates medical diagnosis of viral infections by supporting the growth of viruses for diagnostic assay. Viruses include, but are not limited to, human immunodeficiency virus, herpes simplex virus, papilloma virus, parainfluenza virus, influenza, hepatitis, and other viruses. Likewise, medical diagnosis of other infections, such as those caused by bacteria, fungi, yeast and parasites are also facilitated by MSM according to several embodiments. The use of MSM facilitates vaccine development in one embodiment.

In several embodiments, MSM is used to enhance detection of microbes in a commercial or industrial test. Microorganisms are a common water contaminant. Many water safety test kits evaluate quality of drinking water through Environmental Protection Agency (EPA) testing methods by testing for, among others, the presence of bacteria. Mold found in the home, office and school environments has been linked to pulmonary disorders, and allergic symptoms. However, some tests used to detect bacteria or mold can be time consuming for analysis while some tests additionally detect only viable (living) organisms. Thus, in several embodiments MSM is used to supplement growth media used in commercial detection tests. In some embodiments, MSM-supplemented media improves the detection time of tests. In some embodiments, MSM-supplemented media improves the detection sensitivity of such tests. In certain embodiments, MSM restores environmentally stressed bacteria which were previously nonviable. In still further embodiments, diagnostic test kits comprising microorganism-specific MSM-supplemented media are used to enhance the detection time or sensitivity of a test directed to detecting a particular microorganism. In other embodiments, MSM is used to supplement a broad spectrum growth media, such that a variety of microorganisms are detected more rapidly or with increased sensitivity.

iii. Methods for Enhancing Survivability of Microorganisms and Cells with MSM

Methods for enhancing survivability of microorganisms (including, but not limited to probiotic microorganisms) or cells (such as, stem cells or recombinant cells) are disclosed. For example, methods of enhancing survivability of microorganisms or cells, such as cells in culture, include contacting one or more microorganisms or selected cells with MSM at about 0.4% to about 5% by weight of the medium or by weight of a moisture content of the medium thereby enhancing the survivability of the one or more microorganisms or collection of cells as compared to survivability of the one or more microorganisms or collection of cells in the absence of MSM. In one example, the concentration of MSM is about 1% to about 3% of the weight of the medium or the moisture content of the medium. An increase in survivability is indicated by an at least 10%, such as about a 20% to 80% increase, about a 30% to 50% increase, including about a 10%, about a 20%, about a 30%, about a 40%, about a 50%, about a 60%, about a 70%, about a 80%, about a 90%, about a 100%, about a 150%, about a 200%, about a 300% increase in colony or cell number as compared to a control (such as colony or cell number in the absence of MSM).

According to several embodiments, MSM improves initial survival of the microorganisms (including, but not limited to, probiotic microorganisms). In one embodiment, MSM improves long-term survival of the microorganisms. In one embodiment, MSM extends the stationary phase of a growth curve of the microorganisms.

In several embodiments, MSM extends the shelf-life of a product by extending the lifespan of beneficial bacteria as compared to products without MSM. For example, a probiotic containing product may have a shelf-life of several weeks, after which time the probiotic organisms begin to decline in health and/or population. However, in some embodiments, the addition of MSM to a probiotic containing product increases the length of time from product packaging until the decline of probiotic health and/or population. In such embodiments, the probiotic product is functional (in terms of delivering a population of health and active probiotics to the GI tract of the consumer) for a longer period of time after packaging.

In several embodiments, the addition of MSM increases the time to spoilage of ingestible products by supporting or enhancing the activity of beneficial microbes, with a resulting decrease in the activity of undesired microbes. For example, MSM can increase the shelf life of edible products, such as a probiotic product, by about 10% to 100% (e.g., 20%, 30%, 40%, 50%, 75%, 150%, 200% or more). For example, in one embodiment, if the shelf life of an edible product is 10 days, the addition of MSM will increase the shelf life to at least 11 days in some embodiments (e.g., 11 days, 14 days, 15 days, 20 days, or 25 days). As a further example, in another embodiment, if an edible product has a shelf life of 14 days at room temperature and/or 30 days in the refrigerator and/or 3 months in the freezer, the addition of MSM will increase the shelf life to 30 days at room temperature and/or 60 days in the refrigerator and/or 6 months in the freezer. In some embodiments, the use of MSM unexpectedly enhances the activity of beneficial microbes and inhibits (either directly or indirectly) the activity of undesired bacteria, thereby reducing or eliminating the need for sterilization (e.g., by irradiation, filtration, heat, chemicals, etc.).

In some embodiments, MSM is provided to enhance the activity of genetic vectors, such as recombinant viral vectors in recombinant cells. This may be beneficial for diagnostics as well as therapeutics, such as gene therapy. In some embodiments, MSM is used to enhance the activity (e.g., growth, culture, or viability) of one or more plasmid vectors, binary vectors, cloning vectors, expression vectors, shuttle vector, and viral vectors. As such, methods for enhancing gene therapy are disclosed in which one more processes associated with gene therapy is enhanced or increased by treating the recombinant cell or microorganism with a concentration of MSM (such as a concentration of about 0.04% to about 5% MSM) capable of enhancing one or more processes of gene therapy (such as the expression, growth or survivability of recombinant cells or microorganisms), thereby increasing the effectiveness of the gene therapy.

iv. Methods of Enhancing Culturing Efficiency with MSM

Methods of enhancing culturing efficiency with MSM are disclosed herein. In one embodiment, methods for enhancing various types of cultures are provided, including, but not limited to enhancing antibiotic, steroid, cell (e.g., recombinant and wild-type), microorganism and fertilizer culturing efficiency. For example, in several embodiments, MSM is used to supplement culture media used for the growth or propagation of microbial organisms. In several embodiments, MSM-supplemented media enhances the culture efficiency by enhancing the growth of the cells.

In some embodiments, methods of enhancing culturing efficiency include enhancing/promoting microbial activity in environmental and industrial fields. Microorganisms participate in element cycles such as the carbon cycle and nitrogen cycle, as well as fulfilling other vital roles in virtually all ecosystems, such as recycling the waste products and/or remains of other organisms through decomposition. Thus, in some embodiments, the use of MSM may enhance waste decomposition and waste management. Many biological oxidation processes for treating industrial wastewaters have in common the use of oxygen (or air) and microbial action. Specially-cultured microbes are used in the biological treatment of sewage and industrial waste effluent, a process known as bioaugmentation. Bioaugmentation is used to ensure that the in situ microorganisms can degrade contaminants. In some embodiments, MSM enhances certain microorganisms' degradation of contaminants. In some embodiments, MSM is added to gardening products, such as soil, fertilizers, and compost bins, to enhance the activity of beneficial microorganisms. As such, MSM is used to increase the efficiency of fertilizers and compost reactions.

In one embodiment, a method for enhancing the efficiency of a fertilizer includes applying MSM to medium in an amount sufficient to enhance the activity of a fertilizer, thereby enhancing the activity of the fertilizer. In one particular embodiment, MSM is dissolved in a solution to a final concentration of about 0.04% to about 5%. This solution is then sprayed onto a plant surface either prior to, following or simultaneously as the fertilizer. An increase in fertilizer efficiency is indicated by an at least 10%, such as about a 20% to 80% increase, about a 30% to 50% increase, including about a 10%, about a 20%, about a 30%, about a 40%, about a 50%, about a 60%, about a 70%, about a 80%, about a 90%, about a 100%, about a 150%, about a 200%, about a 300% increase in plant growth as compared to a control (such as plant growth in the absence of MSM).

In another embodiment, a method for enhancing the efficiency of composting is disclosed. This method includes applying MSM to the compost in amount sufficient to enhance the activity of one or more microorganisms or substances present in the compost. In one particular embodiment, MSM is dissolved in a solution to a final concentration of about 0.04% to about 5%. This solution is then applied to the compost (such as by pouring or spraying the solution) and allowed time sufficient to enhance the efficiency of the composting. An increase in compost efficiency is indicated by an at least 10%, such as about a 20% to 80% increase, about a 30% to 50% increase, including about a 10%, about a 20%, about a 30%, about a 40%, about a 50%, about a 60%, about a 70%, about a 80%, about a 90%, about a 100%, about a 150%, about a 200%, about a 300% increase in nitrate levels as compared to a control (such as nitrate levels in the absence of MSM). In other examples, an increase in compost efficiency is indicated by an at least 10%, such as about a 20% to 80% increase, about a 30% to 50% increase, including about a 10%, about a 20%, about a 30%, about a 40%, about a 50%, about a 60%, about a 70%, about a 80%, about a 90%, about a 100%, about a 150%, about a 200%, about a 300% decrease in the amount of time that decomposition of organic matter occurs as compared to a control (such as decomposition rate in the absence of MSM).

B. Methods of Inhibiting Microbial Activity

Methods of inhibiting microbial activity are disclosed. In one embodiment, a method for inhibiting microbial activity includes selecting a medium that is susceptible to contamination; and contacting the medium with MSM at a concentration of about 6% to about 16% of weight by volume, thereby inhibiting microbial activity as compared to microbial activity in a control (such as microbial activity in the absence of MSM). By an at least 10%, such as about a 20% to 80% decrease, about a 30% to 50% decrease, including about a 10%, about a 20%, about a 30%, about a 40%, about a 50%, about a 60%, about a 70%, about a 80%, about a 90%, about a 100%, about a 150%, about a 200%, about a 300% decrease as compared to a control (such as microbial activity in the absence of MSM).

In some embodiments, a method for inhibiting microbial activity includes selecting a medium that is susceptible to bacterial contamination; and contacting the medium with MSM at a concentration of about 6% to about 16% of weight by volume, thereby inhibiting bacterial activity. In some embodiments, a method for inhibiting microbial activity includes selecting a medium that is susceptible to viral contamination (such as contamination by human immunodeficiency virus, H1N1, herpes simplex virus, papilloma virus, parainfluenza virus, influenza, hepatitis, or other like viruses); and contacting the medium with MSM at a concentration of about 6% to about 16% of weight by volume, thereby inhibiting viral activity.

In one particular example, a method of inhibiting microbial activity includes selecting a medium that is susceptible to H1N1 influenza contamination; and contacting the medium with MSM at a concentration of about 10% to about 16% of weight by volume, thereby inhibiting H1N1 influenza microbial activity. In some embodiments, MSM inhibits the microbial activity by reducing growth rate of H1N1 influenza by at least 10%, such as by about a 20%, about a 30%, about a 40%, about a 50%, about a 60%, about a 70%, about a 80%, about a 90%, about a 100%, about a 150%, about a 200%, about a 300% decrease in H1N1 influenza growth or infectivity as compared to a control (such as H1N1 influenza activity or infectivity in the absence of MSM).

In several embodiments, the methods include MSM at about 8% (by weight) or greater, of a product's total weight or moisture content. In certain embodiments, MSM is an effective antimicrobial agent when used at concentrations between about 5% and about 16%. In certain embodiments, MSM is an effective antimicrobial agent when used at concentrations (based on a product's total weight or moisture content)

between about 9% and about 16%, between about 10% and about 16%, between about 12% and about 16%, between about 9% and about 13%, and between about 10% and about 12%. In certain embodiments MSM is an effective antimicrobial agent when used at concentrations between about 5% and about 16%, including 6%, 7%, 8%, 9%, 10%, 11%, 12%, 13%, 14, and 15%. In several embodiments disclosed herein, percentages of MSM are based on a product's moisture content. In some embodiments, MSM is particularly effective when combined with water or other liquid components. In several embodiments, the percentages of MSM provided herein are based on the amount of a polar solvent in a product or other medium.

In some embodiments, the disclosed methods of inhibiting microbial activity include inhibition of growth of specific microorganisms. In some examples, the methods include inhibiting growth of a wide range of microorganisms in certain media or products. In some embodiments, log-scale reductions are realized after the first 24 hours. In some other embodiments, significant log-scale reductions are evident within 24-48 hours. In some embodiments, the disclosed methods include MSM formulations which yield reduction in microbial (e.g., bacterial) levels ranging from about 0.5 log to about 5 log or more within two weeks. In some embodiments, the disclosed methods of inhibiting microbial activity result in a log reduction between about 1 log reduction and about 3 log or more reductions. In other embodiments, the disclosed methods of inhibiting microbial activity lethally inhibit the growth of certain microorganisms. In one embodiment, a method using a formulation of MSM between about 12% and about 16% lethally kills certain microbes (e.g., bacteria) within about 48 hours. In another embodiment, a formulation comprising MSM between about 8% and about 12% lethally kills certain microbes (e.g., bacteria) within about three to seven days. In other embodiments, the methods employ a formulation of MSM between about 5% and about 8%, combined with a reduced amount of conventional preservative, which lethally kills certain microbes (e.g., bacteria) within about 48 hours. With higher preservative concentrations, MSM levels may be reduced further.

In some embodiments, the disclosed methods of inhibiting microbial activity with MSM (such as with about 6% to about 16% MSM) impact metabolism of microbes in the lag phase. For example, the disclosed method increases the duration of the lag phase. An alteration, such as an increase in the lag phase, may be detected by methods of those known to skill in the art including those described in the Examples.

In some embodiments, MSM-supplementation results in a decrease in the log phase of growth of microbes. The exponential phase (sometimes called the log phase) of growth is a period characterized by cell doubling. The number of new microbes appearing per unit time is proportional to the present population. If growth is not limited, doubling will continue at a constant rate so both the number of cells and the rate of population increase doubles with each consecutive time period. Exponential growth cannot continue indefinitely, however, because the medium is soon depleted of nutrients and enriched with wastes. In some embodiments, MSM decreases the overall duration of the exponential phase. In other embodiments, the presence of MSM in the growth media inhibits microbial entry into the exponential phase.

In several embodiments, the disclosed methods of inhibiting microbial activity include modulating the stationary phase of microbial growth. During stationary phase, the growth rate slows as a result of nutrient depletion and accumulation of metabolic by-products. This phase is reached as the microbes begin to exhaust the resources that are available to them. This phase is a relatively constant value as the rate of microbial growth is equal to the rate of microbial death. MSM-supplementation of media at certain concentrations shortens the stationary phase for microbes in one embodiment.

It is contemplated that a medium includes any medium or environment containing or suitable for supporting contamination including, but not limited to, cosmetics, broths, agar, cultures, foods, beverages, cell suspensions, biological tissue, biological fluids, inorganic surfaces, organic surfaces, substrates, living cells, host cells, diagnostic assays, and other solid, liquid, matrix, gelatinous, or gaseous environments. In some examples, the medium is a bodily fluid, a bodily tissue, or a surface.

In some embodiments, contacting the medium include topical, oral, intravenous, intramuscular, or subcutaneous administration of MSM to the medium susceptible to microbial contamination. In other embodiments, contacting the medium includes spraying or wiping the medium susceptible to microbial contamination with a disclosed MSM composition/formulation. For example, a surface can include any surface susceptible to contamination including, but not limited to, a household surface, an industrial surface (such as surfaces in public restrooms, door handles, floors, walls, hand railings, shopping carts and the like), bedding, coverings, industrial equipment or surface, blood, skin or a combination thereof. For example, a household surface may include a door handle, door knob, a trash can, a counter top, floor, toilet seat or any surface which is commonly touched or exposed to possible contaminates.

Unintended microbial growth may occur in many cosmetics, health and beauty aids, topical products, and oral products. Acute or continued use of products with microbial contamination can lead to adverse health effects for the user. Contamination may occur, for example, during manufacturing, packaging, or repetitive use by a consumer which includes repeated opening and closing of containers, contact with hands, skin, or mucous membranes, or repeated withdrawal/administration of individual doses. In the absence of antimicrobial properties, these products may allow the unintended growth of many different, and potentially deleterious, microorganisms.

Antimicrobial preservatives may be added to products to protect them from microbial growth. Common general use antimicrobial preservatives include calcium propionate, sodium nitrate, sodium nitrite, sulfites (sulfur dioxide, sodium bisulfite, potassium hydrogen sulfite, etc.) and disodium EDTA. Cosmetic preservatives include formaldehyde, potassium sorbate, methylparaben, and methylchloroisothiazolinone.

In many cases, preservatives must be added in a minimum effective concentration, as adverse reactions may occur at certain concentrations or doses. Thus, while preservatives may inhibit microbial growth, they also have the potential to cause chemical burns and/or irritate the skin and mucous membranes. Some modern synthetic preservatives have become controversial because they have been shown to cause respiratory or other health problems. Addition of certain preservatives to commercial products may present unique complications with solubility, pH limits, de-activation by some polyethylene glycol (PEG) compounds, and a shift in the color, consistency or fragrance of a product. Some preservatives have only limited activity against particular classes of microorganisms.

Methods of inhibiting microbial activity in a consumer product are also disclosed. In one embodiment, the method includes selecting a medium that is susceptible to microbial contamination, such as a consumer product, and adding MSM to the medium to affect the microbial contamination by inhibiting microbial activity. MSM is provided in a concentration of at least 10% according to one embodiment (e.g., 10-16%, 16-20%, 20-30%, 30-40%, 40-50%, 50-75% or higher, and overlapping ranges thereof). The medium is free from preservatives in some embodiments.

In some embodiments, methods of inhibiting microbial activity in a cosmetic cream at room temperature are provided. In one embodiment, the method includes selecting a medium that is susceptible to microbial contamination; and adding MSM to the medium to affect the microbial contamination by inhibiting microbial activity. MSM is added in a concentration of at least 5% according to one embodiment (e.g., 5-10%, 10-16%, 16-20%, 20-30%, 30-40%, 40-50%, 50-75% or higher, and overlapping ranges thereof). The medium is free from preservatives in some embodiments. The medium includes a cosmetic cream in some embodiments. In one example, MSM inhibits microbial activity by at least 50% in the cosmetic cream at room temperature.

In some examples, the medium includes one or more of the following: cosmetics, broths, agar, cultures, foods, beverages, cell suspensions, biological tissue, biological fluids, inorganic surfaces, organic surfaces, substrates, living cells, host cells, diagnostic assays, and other solid, liquid, matrix, gelatinous, or gaseous environments. For example, in one embodiment, the medium includes an optical product or a product for oral hygiene or health. The medium may also include a bodily fluid or tissue, such as blood. In one example, the medium is sterilized before adding MSM and/or after adding MSM. In other examples, no sterilization is needed. In some examples, the antimicrobial properties of MSM reduce or eliminate the need for sterilization.

In some examples, microbial contamination is caused by bacteria, such as gram positive bacteria and/or gram negative bacteria, fungi, parasites, yeast, mold, viruses, or combinations thereof (e.g., bacteria and mold, or other combinations). In several embodiments, microbial contamination is caused by one or more of the following genera: *Candida, Aspergillus, Escherichia, Pseudomonas, Staphylococcus*, and *Streptococcus*, or combinations thereof. In other embodiment, microbial contamination is caused by an infectious disease including any of the infectious diseases described herein.

In several embodiments, methods for treating an infectious disease are disclosed including, but not limited to H1N1, herpes simplex virus, or HIV. In one embodiment, the method includes administering a therapeutic effective amount of a therapeutic agent and DMSO alone, MSM alone or a combination of DMSO and MSM. The concentration of DMSO and/or MSM ranges from about 6% to about 17% in a composition.

In some embodiments, MSM inhibits microbial activity by reducing the growth rate of one or more microbes by more than 50% which in turn increases the shelf life of the medium. It is contemplated that MSM can confer a therapeutic and/or aesthetic benefit. In some embodiments, the therapeutic or aesthetic benefit is unrelated to the microbial inhibition.

In some embodiments, the disclosed methods of inhibition of microbial activity inhibit microbial activity at temperatures conducive to microbial activity, including 20-25° C., 25-30° C., 30-40° C., 40-50° C. and higher (and overlapping ranges thereof). In some embodiments, MSM inhibits microbial activity at humidity levels favorable for microbial activity, including 50%-60%, 60-70%, 70-80%, 80-95%, and higher (and overlapping ranges thereof).

MSM is particularly advantageous in several embodiments because it may be used in higher concentrations than other preservatives, which when used even in low concentrations can cause adverse effects. For example, preservatives have been implicated in atopic dermatitis, rashes, flushing, abdominal pain, nausea, asthma, rhinitis, muscle aches, joint aches, fatigue, numbness, migraines, attention deficit and hyperactivity disorder, palpitations and arrhythmias. By contrast, MSM is not known to cause such effects in concentrations provided according to preferred embodiments herein. Moreover, MSM has a dual function according to some embodiments. Not only does MSM inhibit the growth of undesired microorganisms, MSM also beneficially affects the product to which it is added in several embodiments.

In some embodiments, the disclosed methods of inhibiting microbial activity not only inhibit microbial activity, but provide one or more beneficial effects, including, but not limited to, reduction of muscle cramps, skin irritation, reduction of pain, joint lubrication, reduction of inflammation, rheumatoid arthritis and osteoarthritis treatment, cardiovascular improvements, skin lubrication, improved wound healing, and improved scalp, hair, cuticle, and nails.

In some embodiments, the disclosed methods of inhibiting microbial activity are used to prevent or minimize the formation of new microbes. In other embodiments, the methods are used to kill or reduce existing microbes. In one embodiment, MSM can convert an otherwise unusable contaminated product into a usable product.

According to several embodiments, the methods inhibit microbial activity instantaneously. In other embodiments, the methods inhibits microbial activity at and up to 1 day, 2 days, 3 days, 4 days, 5 days, 7 days, 10 days, 14 days, 1 month, 3 months, 6 months, 1 year, 2 years, 3 years, 4 years, 5 years and longer.

In several embodiments, MSM is added to cleaning agents to enhance antimicrobial activity (e.g., to inhibit microorganism activity). In some embodiments, MSM is added to a soap formulation. In some embodiments, the product is a dry soap while in other embodiments, the product is a liquid soap. In some embodiments, MSM is added to a gel formulation to yield a sanitizer. For example, methods of inhibiting microbial activity include methods of sanitizing a surface, such as the body, equipment, floors, materials, walls, etc. In certain embodiments, the resultant sanitizer is an instant sanitizer. In other embodiments, the sanitizer acts non-instantaneously (e.g., is effective over time). In some embodiments, the sanitizer is applied to the body. In yet other embodiments, the product is applied to a surface. Surfaces include, but are not limited to, commercial surfaces, medical devices, medical surfaces, production equipment, production floors and food preparation surfaces. Surfaces may include, but not limited to household surfaces, vehicles, computers, clothing, and toys.

In some further embodiments, methods of inhibiting microbial activity include spraying or incorporating MSM (e.g., about 5% to about 50% into face masks or filters. Filters may include, but are not limited to, air-conditioner filters, air filters, water filters. Environments with recycled air, such as airplanes, may especially benefit from MSM filtration systems. Waste treatment and water filtration plants may also incorporate MSM to inhibit microbial activity. In some embodiments, MSM is provided to reduce microbial contamination in flower arrangements and gardening products (such as fertilizers and soils).

In some embodiments, methods of inhibiting microbial activity include inhibiting microbial activity of a microorganism present on animal feed and to prevent microbial growth during storage or processing of the feed. Types of animal feed include, but are not limited to, compound feed, fodder, or forage. Animal feed may consist of raw materials and/or additives. Raw feed may be provided as hay or grains. Alternatively, raw material may be manufactured and provided as meal, pellets or crumbles. In some embodiments, MSM is applied to animal feed to reduce mold growth. In other embodiments, MSM is applied to animal feed to reduce fungal growth. In some embodiments, MSM is applied to raw feed materials and thus incorporated into a finished feed product. In further embodiments, the product is applied to feed during or after manufacturing. In some embodiments, the product is applied to feed for long-term storage.

V. Methods of Making Products Including MSM

Methods of making products including MSM are disclosed herein. In some embodiments, MSM is incorporated at a stage that will reduce crystallization of MSM. In one embodiment, MSM is incorporated into a product prior to emulsification of said product. In another embodiment, MSM is encapsulated (e.g., in a lipid, polymer, or other material) prior to addition to a product. Microencapsulated MSM, according to some embodiments, may be designed to time or dose-release MSM. In yet other embodiments, MSM is combined with the aqueous portion of a product prior to mixing of the wet and dry ingredients. In one embodiment, MSM in dry powder form is mixed in a matrix with an aqueous or polar liquid to activate the MSM.

In yet another embodiment, MSM is added to a product at an elevated temperature (e.g., greater than 25° C., 30° C., 40° C., 50° C., 75° C., or higher). In some embodiments, MSM is materially unaffected by heat, and can be added prior to heating. Solutions that have a temperature of greater than about 35° C. support MSM concentrations greater than 50% in some embodiments. In several embodiments, MSM does not substantially impact the pH of the product to which it is added. In one embodiment, hygroscopic solid products and other products with low moisture content comprise MSM in the range of about 15% or higher.

Methods for manufacturing a product having a reduced preservative concentration are also disclosed herein. In one embodiment, the method includes providing a medium that is susceptible to microbial contamination, wherein the medium comprises a preservative and adding MSM to the medium, wherein the MSM affects the microbial contamination by inhibiting microbial growth. MSM is added in a concentration of at least 5% to about 20% according to one embodiment (e.g., 5-8%, 8-12%, 12-15%, 15-20%, or higher, and overlapping ranges thereof). In one embodiment, MSM and the preservative inhibit microbial growth by at least 50% in the medium at room temperature, and MSM supplements or enhances the ability of the preservative to inhibit microbial growth, thereby reducing the concentration of preservative needed to inhibit microbial growth. In one embodiment, the medium is emulsified or otherwise mixed. In one embodiment, MSM is added to the medium prior emulsification (or other mixing).

The following examples are provided to illustrate certain particular features and/or embodiments. These examples should not be construed to limit the disclosure to the particular features or embodiments described.

EXAMPLES

Example 1

MSM-based Modulation of Microbial Activity

This example describes MSM-based modulation of microbial activity, such as enhancing or inhibiting microbial growth depending upon the concentration of MSM.

Side-by-side microbial growth studies were conducted in media supplemented with MSM at a concentration of 0.1% to 10% and a control sample containing 0% MSM. The microorganisms evaluated were *Aspergillus niger, Candida albicans, Staphylococcus aureus, Pseudomonas aeruginosa, Escherichia coli,* and *Salmonella cholerasuis.* All microorganisms were grown in tryptic soy broth (TSB) and with the exception of *Candida* and *Aspergillus,* all were successively transferred into fresh media each day for 4 consecutive days prior to inoculation to maintain organisms in an exponential growth phase. *Candida* and *Aspergillus* had 48-58 hours of growth in TSB prior to inoculation into the test media. *Aspergillus* was also grown on multiple potato dextrose agar plates (PDA) for 48-58 hours. The *Aspergillus* inoculum was prepared by taking a surface rinse with TSB off of the PDA plates with a lawn of *Aspergillus,* and then added to the 48-58 hour culture until turbid. For each test microorganism, 90 mL aliquots of TSB were prepared with either 10% or 0% MSM. Once each set of test media was plated for sterility, they were inoculated at a level of 5 μl of inoculum per 10 mLs of broth (1:2000 inoculum dilution) with each respective microorganism. Bacterial organisms were incubated at 30° C.±2° C. and fungal organisms were incubated at 25° C.±2° C.

Fungal organisms were plated daily on PDA at days 0 through day 7 every 24 hours. Preparation and plating were conducted at room temperature. Fungal plates were incubated at 25° C.±2° C. for at least 3 days. Test samples were plated in triplicate at each test date and the averages are reported. Data are expressed as recovered colony forming units per milliliter (cfu/mL).

The effects of MSM on *Aspergillus niger* growth and *Candida albicans* growth are shown in Tables 1-1(a) and 1-1(b), respectively. Ten percent MSM inhibited *Aspergillus niger* growth by day 4 of treatment as represented by a dramatic reduction in colony formation on such date. A reduction in growth was also observed in *Candida albicans* MSM treated samples; however the reduction was not as dramatic as compared with the *Aspergillus niger.* For example, 10% MSM supplemented media resulted in reduced yeast viability as compared to lower concentrations of MSM as early as 2 days (plating day 2 for *Candida*). *Candida* growth was reduced early on in the study, with substantial reductions in fungal population at Day 4. After these time points, the divergence in growth curves continued throughout the study for *Candida.* These data indicate that a concentration of 10% MSM provides a significant negative effect on the growth of various fungal organisms over time.

TABLE 1-1(a)

Effect of MSM on *Aspergillus niger* Growth.

| *Aspergillus niger* | 0% MSM | 0.1% MSM | 0.5% MSM | 1.0% MSM | 10% MSM |
|---|---|---|---|---|---|
| Day 0 | $1.0 \times 10^3$ | $9.1 \times 10^2$ | $7.6 \times 10^2$ | $8.9 \times 10^2$ | $1.2 \times 10^3$ |
| Day 1 | $1.3 \times 10^3$ | $2.3 \times 10^3$ | $2.7 \times 10^3$ | $2.0 \times 10^3$ | $7.0 \times 10^2$ |
| Day 2 | $4.3 \times 10^3$ | $3.0 \times 10^2$ | $4.0 \times 10^3$ | $2.0 \times 10^3$ | $1.6 \times 10^2$ |
| Day 3 | $2.0 \times 10^3$ | $7.5 \times 10^2$ | $1.3 \times 10^3$ | $1.0 \times 10^3$ | $4.6 \times 10^2$ |
| Day 4 | $1.4 \times 10^4$ | $5.0 \times 10^3$ | $3.7 \times 10^3$ | $3.3 \times 10^3$ | 20 |
| Day 5 | $1.3 \times 10^4$ | $4.3 \times 10^3$ | $9.7 \times 10^3$ | $6.0 \times 10^3$ | 10 |
| Day 6 | $4.4 \times 10^4$ | $1.1 \times 10^4$ | $7.0 \times 10^3$ | $4.7 \times 10^3$ | 3 |
| Day 7 | $4.1 \times 10^4$ | $1.3 \times 10^4$ | $7.0 \times 10^3$ | $5.7 \times 10^3$ | 3 |

TABLE 1-1(b)

Effect of MSM on *Candida albicans* Growth.

| *Candida albicans* | 0% MSM | 0.1% MSM | 0.5% MSM | 1.0% MSM | 10% MSM |
|---|---|---|---|---|---|
| Day 0 | $2.2 \times 10^4$ | $2.1 \times 10^4$ | $1.8 \times 10^4$ | $2.5 \times 10^4$ | $2.6 \times 10^4$ |
| Day 1 | $1.0 \times 10^5$ | $4.7 \times 10^6$ | $4.9 \times 10^6$ | $5.0 \times 10^6$ | $<1.0 \times 10^5$ |
| Day 2 | $1.0 \times 10^7$ | $9.8 \times 10^6$ | $1.1 \times 10^7$ | $9.8 \times 10^6$ | $4.0 \times 10^3$ |
| Day 3 | $1.3 \times 10^7$ | $1.2 \times 10^7$ | $1.3 \times 10^7$ | $1.2 \times 10^7$ | $<1.0 \times 10^5$ |
| Day 4 | $1.9 \times 10^7$ | $1.3 \times 10^7$ | $1.4 \times 10^7$ | $1.2 \times 10^7$ | $7.0 \times 10^4$ |
| Day 5 | $1.6 \times 10^7$ | $1.3 \times 10^7$ | $1.4 \times 10^7$ | $1.3 \times 10^7$ | $1.7 \times 10^4$ |
| Day 6 | $8.8 \times 10^6$ | $1.3 \times 10^7$ | $1.4 \times 10^7$ | $1.6 \times 10^7$ | $2.8 \times 10^3$ |
| Day 7 | $1.7 \times 10^7$ | $1.4 \times 10^7$ | $1.6 \times 10^7$ | $1.7 \times 10^7$ | $3.3 \times 10^3$ |

The effect of MSM on *Staphylococcus aureus* growth is illustrated in Table 1-2. A difference in viability in the presence of higher concentrations of MSM was observed. In particular, 10% MSM appeared to both slow the growth rate and the maximum population size of *Staphylococcus aureus*.

TABLE 1-2

Effect of MSM on *Staphylococcus aureus* Growth.

| *Staphylococcus aureus* | 0% MSM | 0.1% MSM | 0.5% MSM | 1.0% MSM | 10% MSM |
|---|---|---|---|---|---|
| Day 0 | $2.4 \times 10^5$ | $2.4 \times 10^5$ | $2.5 \times 10^5$ | $2.3 \times 10^5$ | $2.5 \times 10^5$ |
| Day 1 | $3.6 \times 10^8$ | $4.6 \times 10^8$ | $4.1 \times 10^8$ | $6.0 \times 10^8$ | $5.3 \times 10^7$ |
| Day 2 | $7.5 \times 10^8$ | $8.5 \times 10^8$ | $7.8 \times 10^8$ | $8.2 \times 10^8$ | $3.0 \times 10^8$ |
| Day 3 | $9.6 \times 10^8$ | $9.1 \times 10^8$ | $8.4 \times 10^8$ | $9.6 \times 10^8$ | $5.1 \times 10^8$ |
| Day 4 | $6.4 \times 10^8$ | $7.9 \times 10^8$ | $4.7 \times 10^8$ | $4.5 \times 10^8$ | $3.7 \times 10^8$ |
| Day 7 | $2.6 \times 10^8$ | $1.8 \times 10^8$ | $1.7 \times 10^8$ | $3.3 \times 10^8$ | $9.0 \times 10^7$ |

The effect of MSM on *Pseudomonas aeruginosa* growth is illustrated in Table 1-3. Ten percent MSM media supplementation resulted in substantial divergence in *Pseudomonas aeruginosa* viability over time. For example, 10% MSM supplemented media yielded a population reduction that lasted for the first 4 days of the study, but did not persist after such time.

TABLE 1-3

Effect of 10% MSM on *Pseudomonas aeruginosa* Growth.

| *Pseudomonas aeruginosa* | 0% MSM | 0.1% MSM | 0.5% MSM | 1.0% MSM | 10% MSM |
|---|---|---|---|---|---|
| Day 0 | $4.0 \times 10^5$ | $4.8 \times 10^5$ | $4.8 \times 10^5$ | $4.2 \times 10^5$ | $4.0 \times 10^5$ |
| Day 1 | $4.4 \times 10^8$ | $5.1 \times 10^8$ | $5.4 \times 10^8$ | $5.8 \times 10^8$ | $1.0 \times 10^5$ |
| Day 2 | $1.1 \times 10^9$ | $6.0 \times 10^8$ | $9.2 \times 10^8$ | $5.7 \times 10^8$ | $5.8 \times 10^3$ |
| Day 3 | $1.6 \times 10^9$ | $1.4 \times 10^9$ | $1.2 \times 10^9$ | $1.0 \times 10^9$ | $5.3 \times 10^3$ |
| Day 4 | $1.6 \times 10^9$ | $2.0 \times 10^9$ | $1.4 \times 10^9$ | $1.9 \times 10^9$ | $3.7 \times 10^6$ |
| Day 7 | $1.4 \times 10^9$ | $2.1 \times 10^9$ | $1.6 \times 10^9$ | $1.2 \times 10^9$ | $6.0 \times 10^6$ |

The effect of MSM on *Pseudomonas aeruginosa* growth is illustrated in Table 1-4. Ten percent MSM media supplementation resulted in substantially less growth of *E. coli* over time.

TABLE 1-4

Effect of 10% MSM on *Escherichia coli* Growth.

| *Escherichia coli* | 0% MSM | 0.1% MSM | 0.5% MSM | 1.0% MSM | 10% MSM |
|---|---|---|---|---|---|
| Day 0 | $6.9 \times 10^5$ | $6.4 \times 10^5$ | $7.0 \times 10^5$ | $6.7 \times 10^5$ | $6.8 \times 10^5$ |
| Day 1 | $9.2 \times 10^8$ | $1.0 \times 10^9$ | $1.4 \times 10^9$ | $1.2 \times 10^9$ | $3.0 \times 10^4$ |
| Day 2 | $1.3 \times 10^9$ | $1.4 \times 10^9$ | $1.6 \times 10^9$ | $3.2 \times 10^9$ | $1.2 \times 10^5$ |
| Day 3 | $1.6 \times 10^9$ | $2.0 \times 10^9$ | $1.9 \times 10^9$ | $1.8 \times 10^9$ | $3.9 \times 10^7$ |
| Day 4 | $1.4 \times 10^9$ | $1.4 \times 10^9$ | $1.4 \times 10^9$ | $1.4 \times 10^9$ | $1.2 \times 10^8$ |
| Day 7 | $1.3 \times 10^9$ | $1.2 \times 10^9$ | $2.8 \times 10^9$ | $1.5 \times 10^9$ | $7.0 \times 10^7$ |

The effect of MSM on *Salmonella cholerasuis* growth is illustrated in Table 1-5. Media supplemented with 10% MSM reduced the growth of *Salmonella cholerasuis* for the majority of the time points of the study.

TABLE 1-5

Effect of 10% MSM on *Salmonella cholerasuis* Growth.

| *Salmonella cholerasuis* | 0% MSM | 0.1% MSM | 0.5% MSM | 1.0% MSM | 10% MSM |
|---|---|---|---|---|---|
| Day 0 | $6.8 \times 10^5$ | $8.7 \times 10^5$ | $5.9 \times 10^5$ | $5.5 \times 10^5$ | $7.6 \times 10^5$ |
| Day 1 | $9.6 \times 10^8$ | $1.2 \times 10^9$ | $9.7 \times 10^8$ | $1.1 \times 10^9$ | $1.7 \times 10^6$ |
| Day 2 | $1.3 \times 10^9$ | $1.0 \times 10^9$ | $1.2 \times 10^9$ | $1.3 \times 10^9$ | $7.7 \times 10^7$ |
| Day 3 | $1.2 \times 10^9$ | $1.2 \times 10^9$ | $1.5 \times 10^9$ | $1.5 \times 10^9$ | $3.2 \times 10^8$ |
| Day 4 | $7.8 \times 10^8$ | $6.0 \times 10^8$ | $7.1 \times 10^8$ | $8.0 \times 10^8$ | $1.9 \times 10^8$ |
| Day 7 | $3.0 \times 10^8$ | $3.4 \times 10^8$ | $3.6 \times 10^8$ | $9.2 \times 10^8$ | $2.3 \times 10^8$ |

These studies indicate that certain concentrations of MSM inhibit growth, including *Aspergillus niger, Candida albicans, Staphylococcus aureus, Pseudomonas aeruginosa* and *E. coli* growth.

Example 2

Antimicrobial Effectiveness Testing of MSM-Supplemented Media

This example describes the antimicrobial effectiveness testing results of MSM-supplemented media.

Compounds or formulated products having antimicrobial activity may be evaluated with the United States Pharmacopeia (USP) Antimicrobial Effectiveness Test (AET). The AET involves the addition of specified microorganisms (*Candida albicans, Aspergillus niger, Escherichia coli, Pseudomonas aeruginosa* and *Staphylococcus aureus*) directly to a test product at relatively high concentrations to simulate contamination. The product is held for one month, with weekly analysis of microorganism levels. Depending on the route of administration of a product, satisfaction of the AET generally requires a 1 to 3 log reduction in bacteria from initial levels, which should occur in one to two weeks, with no further increase in bacteria after two weeks. For yeast and mold, no increase from the initial inoculums level is permitted. Successfully meeting the criteria of the AET demonstrates that a product, optionally supplemented with an antimicrobial compound under evaluation, can withstand an inoculation of up to one million microorganisms per gram of product without becoming contaminated. The AET demonstrates the effectiveness of a preservative system in a product and/or may be used as part of a stability study to determine if a preservative system will affect a product's shelf life.

The AET was performed by adding the specified microorganisms directly to MSM supplemented test media at concentrations simulating microbial contamination. Fresh, active cultures standardized to a concentration between 100,000 to 1,000,000 cells per mL of the test product, were added to the MSM supplemented media. Inoculations were made using *Candida albicans, Aspergillus niger, Escherichia coli, Pseudomonas aeruginosa* and *Staphylococcus aureus*. Tryptic soy broth (TSB) was used as the culturing media. MSM was diluted 1/1, 1/5, 1/10, 1/100, and 1/1000 and each used to supplement the media. The inoculated media was held for one month, during which time the added microorganisms were enumerated weekly to determine if they were growing, dying off, or remaining near the initial inoculation level. Data points were measured in triplicate at 48 hours, 3, 5, 14, 20, 28, and 30 days. The results of these studies are shown in Tables 2-1 through 2-8. The acceptance criteria for antimicrobial effectiveness are described in detail in the USP, herein incorporated by reference.

TABLE 2-1

AET test results for 1:1 dilution of MSM.

| Test Organism | Initial Inoculum | 48 hrs | 3 days | 5 days | 14 days | 20 days | 28 days | 30 days |
|---|---|---|---|---|---|---|---|---|
| *Aspergillus Niger* | $3 \times 10^5$ | $3.5 \times 10^5$ | $3.2 \times 10^5$ | $3.1 \times 10^5$ | $2.3 \times 10^3$ | <10 | <10 | <10 |
| *Candida Albicans* | $2.5 \times 10^5$ | $2.8 \times 10^5$ | $2.6 \times 10^5$ | $2.4 \times 10^5$ | $1.2 \times 10^3$ | <10 | <10 | <10 |
| *Escherichia coli* | $1.3 \times 10^5$ | $1.3 \times 10^5$ | $1.2 \times 10^5$ | $1.1 \times 10^5$ | $1.8 \times 10^3$ | <10 | <10 | <10 |
| *Pseudomonas aeruginosa* | $1.5 \times 10^5$ | $1.8 \times 10^5$ | $1.9 \times 10^5$ | $1.6 \times 10^5$ | $4.0 \times 10^3$ | <10 | <10 | <10 |
| *Staphylococcus aureus* | $5.5 \times 10^5$ | $5.4 \times 10^5$ | $5.6 \times 10^5$ | $5.2 \times 10^5$ | $3.7 \times 10^3$ | <10 | <10 | <10 |
| *Salmonella typhimurium* | $4.6 \times 10^5$ | $4.9 \times 10^5$ | $5.1 \times 10^5$ | $4.7 \times 10^5$ | $2.5 \times 10^3$ | <10 | <10 | <10 |

TABLE 2-2

Log Reduction from Initial Microorganism Inoculum with 1:1 dilution of MSM.

| Test Organism | 14 Days | 28 Days |
|---|---|---|
| *Aspergillus Niger* | 3.4 | 4.5 |
| *Candida Albicans* | 3.0 | 4.4 |
| *Escherichia coli* | 3.3 | 4.1 |
| *Pseudomonas aeruginosa* | 3.6 | 4.2 |
| *Staphylococcus aureus* | 3.6 | 4.7 |
| *Salmonella typhimurium* | 3.4 | 4.7 |

TABLE 2-3

AET test results for 1:5 dilution of MSM.

| Test Organism | Initial Inoculum | 48 hrs | 3 days | 5 days | 14 days | 20 days | 28 days | 30 days |
|---|---|---|---|---|---|---|---|---|
| *Aspergillus Niger* | $3 \times 10^5$ | $4.0 \times 10^5$ | $4.2 \times 10^5$ | $3.8 \times 10^5$ | $3 \times 10^3$ | <10 | <10 | <10 |

TABLE 2-3-continued

AET test results for 1:5 dilution of MSM.

| Test Organism | Initial Inoculum | 48 hrs | 3 days | 5 days | 14 days | 20 days | 28 days | 30 days |
|---|---|---|---|---|---|---|---|---|
| Candida Albicans | $2.5 \times 10^5$ | $2.9 \times 10^5$ | $3.1 \times 10^5$ | $3.2 \times 10^5$ | $2 \times 10^3$ | <10 | <10 | <10 |
| Escherichia coli | $1.3 \times 10^5$ | $1.4 \times 10^5$ | $1.7 \times 10^5$ | $2 \times 10^5$ | $1 \times 10^3$ | <10 | <10 | <10 |
| Pseudomonas aeruginosa | $1.5 \times 10^5$ | $1.6 \times 10^5$ | $2.0 \times 10^5$ | $2.2 \times 10^5$ | $1.2 \times 10^3$ | <10 | <10 | <10 |
| Staphylococcus aureus | $5.5 \times 10^5$ | $5.7 \times 10^5$ | $6.0 \times 10^5$ | $5.9 \times 10^5$ | $2.3 \times 10^3$ | <10 | <10 | <10 |
| Salmonella typhimurium | $4.6 \times 10^5$ | $5.0 \times 10^5$ | $5.2 \times 10^5$ | $5.4 \times 10^5$ | $3.2 \times 10^3$ | <10 | <10 | <10 |

TABLE 2-4

Log Reduction from Initial Microorganism Inoculum with 1:5 dilution of MSM.

| Test Organism | 14 Days | 28 Days |
|---|---|---|
| Aspergillus Niger | 3.5 | 4.5 |
| Candida Albicans | 3.3 | 4.4 |
| Escherichia coli | 3.0 | 4.1 |
| Pseudomonas aeruginosa | 3.2 | 4.2 |
| Staphylococcus aureus | 3.4 | 4.7 |
| Salmonella typhimurium | 3.5 | 4.7 |

TABLE 2-5

AET test results for 1:10 dilution of MSM.

| Test Organism | Initial Inoculum | 48 hrs | 3 days | 5 days | 14 days | 20 days | 28 days | 30 days |
|---|---|---|---|---|---|---|---|---|
| Aspergillus Niger | $3 \times 10^5$ | $5 \times 10^5$ | $5.2 \times 10^5$ | $5.4 \times 10^5$ | $2 \times 10^4$ | <10 | <10 | <10 |
| Candida Albicans | $2.5 \times 10^5$ | $3 \times 10^5$ | $3.4 \times 10^5$ | $4 \times 10^5$ | $1.5 \times 10^4$ | <10 | <10 | <10 |
| Escherichia coli | $1.3 \times 10^5$ | $2 \times 10^5$ | $2.3 \times 10^5$ | $3.2 \times 10^5$ | $2.5 \times 10^3$ | <10 | <10 | <10 |
| Pseudomonas aeruginosa | $1.5 \times 10^5$ | $1.9 \times 10^5$ | $2.2 \times 10^5$ | $2.9 \times 10^5$ | $4 \times 10^5$ | <10 | <10 | <10 |
| Staphylococcus aureus | $5.5 \times 10^5$ | $5.9 \times 10^5$ | $6.1 \times 10^5$ | $6.3 \times 10^5$ | $2.9 \times 10^4$ | <10 | <10 | <10 |
| Salmonella typhimurium | $4.6 \times 10^5$ | $5.0 \times 10^5$ | $5.2 \times 10^5$ | $5.5 \times 10^5$ | $3.2 \times 10^3$ | <10 | <10 | <10 |

TABLE 2-6

Log Reduction from Initial Microorganism Inoculum with 1:10 dilution of MSM.

| Test Organism | 14 Days | 28 Days |
|---|---|---|
| Aspergillus Niger | 4.3 | 4.5 |
| Candida Albicans | 4.2 | 4.4 |
| Escherichia coli | 3.4 | 4.1 |
| Pseudomonas aeruginosa | 3.6 | 4.2 |
| Staphylococcus aureus | 4.5 | 4.7 |
| Salmonella typhimurium | 3.5 | 4.7 |

TABLE 2-7

AET test results for 1:100 dilution of MSM.

| Test Organism | Initial Inoculum | 48 hrs |
|---|---|---|
| Aspergillus Niger | $3 \times 10^5$ | TNTC* |
| Candida Albicans | $2.5 \times 10^5$ | TNTC |
| Escherichia coli | $1.3 \times 10^5$ | TNTC |
| Pseudomonas aeruginosa | $1.5 \times 10^5$ | TNTC |
| Staphylococcus aureus | $5.5 \times 10^5$ | TNTC |
| Salmonella typhimurium | $4.6 \times 10^5$ | TNTC |

*Colonies too numerous to count (TNTC)

TABLE 2-8

AET test results for 1:1000 dilution of MSM.

| Test Organism | Initial Inoculum | 48 hrs |
|---|---|---|
| Aspergillus Niger | $3 \times 10^5$ | TNTC* |
| Candida Albicans | $2.5 \times 10^5$ | TNTC |
| Escherichia coli | $1.3 \times 10^5$ | TNTC |
| Pseudomonas aeruginosa | $1.5 \times 10^5$ | TNTC |
| Staphylococcus aureus | $5.5 \times 10^5$ | TNTC |
| Salmonella typhimurium | $4.6 \times 10^5$ | TNTC |

The 1:1, 1:5, and 1:10 dilutions of MSM (Tables 2-1 to 2-6, above), indicate that these concentrations of MSM in the media killed microorganisms and do not simply have a static effect on growth. Based on the culture populations at day 5, bactericidal effects were unexpected, as the culture populations were stable or showed signs of increasing growth. However, by 14 days, reduction in initial inoculation levels were observed, and by 20 days, a total kill of all microorganisms was observed using at least 10% MSM. These results were confirmed by spiking a 90 mL TSB blank with 10 mLs of the tested dilution matrix (e.g., the media believed to no longer contain any living microorganisms). None of the microorganisms could be cultured and contamination was not observed. These results demonstrate that MSM, at certain concentrations, is bactericidal to these organisms.

Example 3

Bactericidal Effects of Sterile and Non-Sterile MSM on Escherichia coli

This example describes the bactericidal effects of sterile and non-sterile MSM on E. coli growth.

The USP <51> AET test methodology as described in Example 2 was used as the basis to evaluate the lethality to Escherichia coli (ATCC strain 8739) of various concentrations of MSM ranging from 5 to 16% in TSB or saline. The USP <51> AET is a compendial (United States Pharmacopeia) antimicrobial effectiveness test method for determining if a preservative is effective based upon a verified and validated methodology. The parameters of the AET are described above. In this study, after the designated incubation period, cultures were evaluated visually and were then streaked and grown on selective MacConkey agar for qualitative analysis of the effects of the various MSM concentrations. This study also evaluated the effect of pre-sterilizing the MSM (by steam autoclaving at 121° C. for 15 minutes) prior to media preparation. Test media were prepared by weighing an appropriate amount of MSM and adding it to 25 mL of TSB media or saline. Media compositions were coded as provided in Table 3-1.

TABLE 3-1

Media compositions tested against E. coli.

| Media Code | Preparation |
|---|---|
| NS | Sterile saline added to non-sterile MSM |
| NSA | Saline + MSM, then sterilized |
| TSB | Sterile TSB added to non-sterile MSM |
| TSBA | TSB + MSM, then sterilized |
| TSBC | TSB without MSM, spiked with E. coli |
| (−)TSBC | negative control (no E. coli) |
| NSC | Saline without MSM, spiked with E. coli |
| (−)NSC | negative control (no E. coli) |

All tubes except the negative controls were spiked with 250 μl of a $1.2 \times 10^8$ culture, which yields an initial E. coli population density of $1.2 \times 10^6$/mL. Tubes were incubated at 25° C.

At 24 hours, visible signs of growth were observed in the 5-9% MSM in TSB/TSBA media (see Table 3-2 below). In contrast, no signs of growth were seen in the tubes with 10-16% MSM in TSB/TSBA media (see Table 3-2 below). Saline tubes did not show any signs of growth. When streaked on MacConkey media, heavy growth resulted in all media containing 5-9% MSM, while fewer colonies were detected on the streaked plates from the 10% MSM in TSB/TSBA media. Little to no growth resulted from the streaking of the 11-16% MSM in TSB/TSBA media. Growth was detected in the TSB and saline positive control (TSB or saline without MSM, spiked with E. coli), while no growth was detected on the plates streaked from the non-spiked media.

TABLE 3-2

Growth profile of E. coli in MSM-containing media after 24 hours.

| MSM Concentration | TSB | TSBA | NS | NSA |
|---|---|---|---|---|
| 5% | Heavy | Heavy | Heavy | Heavy |
| 6% | Heavy | Heavy | Heavy | Heavy |
| 7% | Heavy | Heavy | Heavy | Heavy |
| 8% | Heavy | Heavy | Heavy | Heavy |
| 9% | Heavy | Heavy | Heavy | Heavy |
| 10% | Moderate | Moderate | Heavy | Heavy |
| 11% | Few | Few | Heavy | Heavy |
| 12% | Few | Few | Moderate | Moderate |
| 13% | Few | Few | Moderate | Moderate |
| 14% | Few | Few | Moderate | Moderate |
| 15% | Few | Few | Moderate | Moderate |
| 16% | Few | Few | Moderate | Moderate |

As shown in Table 3-3, at 48 hours signs of heavy growth were observed in the 5-10% MSM in TSB/TSBA culture tubes. Apparent growth was observed in the 11% MSM in TSB/TSBA culture tubes. Similar to the 24 hour time point, little to no observable signs of growth were observed in the 12-15% MSM in TSB/TSBA culture tubes. After streaking, heavy bacterial growth occurred in all media containing 5-10% MSM. 11% MSM in TSB/TSBA allowed moderate growth, while the same concentration of MSM added to saline allowed heavy growth. At concentrations from 12-16% MSM in TSB/TSBA, little to no growth was detected on the plates. Moderate growth was observed from similar concentrations of MSM in saline media.

TABLE 3-3

Growth profile of E. coli in MSM-containing media after 48 hours.

| MSM Concentration | TSB | TSBA | NS | NSA |
|---|---|---|---|---|
| 5% | Heavy | Heavy | Heavy | Heavy |
| 6% | Heavy | Heavy | Heavy | Heavy |
| 7% | Heavy | Heavy | Heavy | Heavy |
| 8% | Heavy | Heavy | Heavy | Heavy |
| 9% | Heavy | Heavy | Heavy | Heavy |
| 10% | Heavy | Heavy | Heavy | Heavy |
| 11% | Moderate | Moderate | Heavy | Heavy |

TABLE 3-3-continued

Growth profile of *E. coli* in MSM-containing media after 48 hours.

| MSM Concentration | TSB | TSBA | NS | NSA |
|---|---|---|---|---|
| 12% | Few | Few | Moderate | Moderate |
| 13% | Few | Few | Moderate | Moderate |
| 14% | Few | Few | Moderate | Moderate |
| 15% | Few | Few | Moderate | Moderate |
| 16% | Few | Few | Moderate | Moderate |

After 72 hours of culturing, signs of heavy growth were observed in the 5-10% MSM in TSB/TSBA culture tubes (Table 3-4). Apparent growth was observed in the 11% MSM in TSB/TSBA culture tubes. Similar to the 24 hour time point, little to no observable signs of growth were observed in the 12-15% MSM in TSB/TSBA culture tubes. After streaking, heavy bacterial growth occurred in all media containing 5-10% MSM. 11% MSM in TSB/TSBA allowed moderate growth, while the same concentration of MSM added to saline allowed heavy growth. At concentrations from 12-16% MSM in TSB/TSBA, little to no growth was detected on the plates. Moderate growth was observed from similar concentrations of MSM in saline media.

TABLE 3-4

Growth profile of *E. coli* in MSM-containing media after 72 hours.

| MSM Concentration | TSB | TSBA | NS | NSA |
|---|---|---|---|---|
| 5% | Heavy | Heavy | Heavy | Heavy |
| 6% | Heavy | Heavy | Heavy | Heavy |
| 7% | Heavy | Heavy | Heavy | Heavy |
| 8% | Heavy | Heavy | Heavy | Heavy |
| 9% | Heavy | Heavy | Heavy | Heavy |
| 10% | Heavy | Heavy | Heavy | Heavy |
| 11% | Moderate | Moderate | Heavy | Heavy |
| 12% | Few | Few | Moderate | Moderate |
| 13% | Few | Few | Moderate | Moderate |
| 14% | Few | Few | Moderate | Moderate |
| 15% | Few | Few | Moderate | Moderate |
| 16% | Few | Few | Moderate | Moderate |

These results show that concentrations of MSM from about 10-16% are effective at killing bacteria at certain time points. At 24 hours, 10% MSM reduced the viable bacterial population, while at 48-72 hours higher concentrations were more effective at killing the majority of the bacterial population. The 10-16% concentrations of MSM in TSB/TSBA were more effective than the same concentration in a saline based media. The data further suggest that steam sterilization does not inherently impact the effectiveness of MSM.

Example 4

Comparison of MSM Bactericidal Effectiveness in Saline or Tryptic Soy Broth(TSB)-based Media This example compares MSM bactericidal effectiveness in saline and TSB-based media.

As presented in Examples 2 and 3, the USP <51> AET test methodology was used as the basis to evaluate the lethality to *E. coli* of various concentrations of MSM (flaked or microprill) ranging from 5 to 16% in TSB or saline. Each media composition was inoculated with $1.25 \times 10^6$/mL of *E. coli* and then cultured for seven days at 35° C. At the end of the incubation period, cultures were evaluated visually and were then grown on trypto-soy agar at serially diluted concentrations to ensure bacterial growth (if any) at a density that was able to be quantified. Plated cultures were grown for 24 hours at 35° C. before analysis. Media compositions were coded as shown in Table 4-1 and results of these studies are provided in Table 4-2.

TABLE 4-1

Media compositions

| Media Code | Preparation |
|---|---|
| PS | Microprill MSM added to saline |
| FS | Flaked MSM added to saline |
| PTSB | Microprill MSM added to TSB |
| FTSB | Flaked MSM added to TSB |
| TSBC | TSB without MSM, spiked with *E. coli* |
| (−)TSBC | negative control (no *E. coli*) |
| NSC | Saline without MSM, spiked with *E. coli* |
| (−)NSC | negative control (no *E. coli*) |

TABLE 4-2

Log growth of *E. coli* in different media with various concentrations of MSM.

| MSM Concentration | FTSB | FS | PTSB | PS |
|---|---|---|---|---|
| 16% | 1 | 4.5 | 1 | 4.8 |
| 15% | 2.6 | 4.8 | 2.3 | 5.1 |
| 14% | 2.9 | 4.9 | 2.1 | 5.6 |
| 13% | 2.6 | 5.5 | 3 | 5.6 |
| 12% | 2.7 | 5.1 | 3 | 5.8 |
| 11% | 3.6 | 5.4 | 3.3 | 5.9 |
| 10% | 6 | 5.5 | 6 | 5.8 |
| 9% | 6 | 5.6 | 6 | 5.9 |
| 8% | 6 | 5.7 | 6 | 6 |
| 7% | 6 | 5.9 | 6 | 6 |
| 6% | 6 | 5.9 | 6 | 6.2 |
| 5% | 6 | 5.7 | 6 | 6.4 |

Concentrations in the range from 11-16% MSM have a negative effect on the growth of *E. coli* in cultured for 7 days. As the concentration of MSM increased above 10% in either the FTSB or PTSB media, *E. coli* growth was reduced. Both forms of MSM showed efficacy in inhibiting bacterial growth.

Example 5

Effect of Sodium Chloride-Free Media on Bactericidal Effect of MSM

This example shows the effect of sodium chloride-free media on bactericidal effects of MSM.

A study employing MUller-Hinton broth media, which does not contain NaCl, was performed. Standard MUller-Hinton media was compared to MUller-Hinton media supplemented with NaCl to the same level as the saline-based media of Example 4. MSM was added to each media in concentrations ranging from 5-16%. After inoculation of each MSM-containing media type with $1.9 \times 10^7$ cfu/mL of *E. coli*, the cultures were incubated at 35° C. for seven days. Aliquots of each culture were taken at 24 and 48 hours, as well as 7 days. Aliquots were grown on trypto-soy agar at serially diluted concentrations to ensure bacterial growth (if any) at a density that was able to be quantified. Plated cultures were grown for 24 hours at 35° C. before analysis. Media compositions were coded as provided in Table 5-1. Results of these studies are provided in Tables 5-2 through 5-4.

TABLE 5-1

Media compositions

| Media Code | Preparation |
|---|---|
| PMHS | Microprill MSM added to Müller-Hinton media plus NaCl |
| FMHS | Flaked MSM added to Müller-Hinton media plus NaCl |
| PMH | Microprill MSM added to Müller-Hinton media |
| FMH | Flaked MSM added to Müller-Hinton media |
| MHC | Müller-Hinton media without MSM, spiked with E. coli |
| (−)MHC | negative control (no E. coli) |
| MHNSC | Müller-Hinton media plus NaCl without MSM, spiked with E. coli |
| (−)MHNSC | negative control (no E. coli) |

After 24 hours in culture, an approximately 1 log reduction from the initial inoculum was detected in all media having MSM concentrations great than 13% (Table 5-2). Further, at 12% MSM, all media compositions reduced the *E. coli* growth, except the PMHS composition. At 11% MSM, only the FMH media reduced *E. coli* growth.

TABLE 5-2

Log growth of *E. coli* in MSM supplemented Müller-Hinton media or Müller-Hinton (plus NaCl) after 24 hours

| MSM Concentration | PMHS | FMHS | PMH | FMH |
|---|---|---|---|---|
| 16% | 6.2 | 6.1 | 6.1 | 6.2 |
| 15% | 6.0 | 6.1 | 6.0 | 6.2 |
| 14% | 6.0 | 6.0 | 5.9 | 6.3 |
| 13% | 6.3 | 6.2 | 5.8 | 5.9 |
| 12% | 7.2 | 5.7 | 5.8 | 5.9 |
| 11% | 7.9 | 7.8 | 7.4 | 5.9 |
| 10% | 8.7 | 8.2 | 7.9 | 7.8 |
| 9% | 8.3 | 8.3 | 8.3 | 8.2 |
| 8% | 8.2 | 8.4 | 8.4 | 8.4 |
| 7% | 8.3 | 8.4 | 8.4 | 8.5 |
| 6% | 8.1 | 8.4 | 8.5 | 8.5 |
| 5% | 8.2 | 8.4 | 8.6 | 8.6 |

After 48 hours in culture, media compositions with MSM concentrations greater than 13% reduced *E. coli* growth by 1-2 logs. Certain concentrations of MSM are effective at reducing bacterial growth, which is surprising because other concentrations of MSM are effective at supporting increased bacterial activity.

TABLE 5-3

Log growth of *E. coli* in MSM supplemented Müller-Hinton media or Müller-Hinton (plus NaCl) after 48 hours

| MSM Concentration | PMHS | FMHS | PMH | FMH |
|---|---|---|---|---|
| 16% | 6.0 | 5.9 | 6.0 | 5.9 |
| 15% | 6.0 | 5.9 | 5.8 | 4.6 |
| 14% | 5.7 | 5.9 | 5.4 | 5.3 |
| 13% | 5.9 | 5.9 | 5.4 | 5.2 |
| 12% | 6.7 | 6.9 | 5.6 | 5.3 |
| 11% | 7.8 | 7.8 | 7.2 | 7.1 |
| 10% | 7.9 | 8.0 | 7.9 | 8.2 |
| 9% | 8.2 | 8.1 | 8.1 | 8.2 |
| 8% | 8.1 | 8.1 | 8.2 | 8.3 |
| 7% | 8.2 | 8.2 | 8.0 | 8.4 |
| 6% | 8.1 | 8.2 | 8.4 | 8.4 |
| 5% | 8.4 | 8.3 | 8.3 | 8.4 |

After 7 days in culture, media compositions containing as low as 12% MSM substantially inhibited the growth of *E. coli* (Table 5-4). FMHS media was most efficacious at 12% MSM, yielding a 3 log reduction in *E. coli*.

TABLE 5-4

Log growth of *E. coli* in MSM supplemented Müller-Hinton media or Müller-Hinton (plus NaCl) after 7 days

| MSM Concentration | PMHS | FMHS | PMH | FMH |
|---|---|---|---|---|
| 16% | 4.4 | 4.7 | 3.9 | 7.8 |
| 15% | 4.7 | 4.7 | 3.8 | 7.9 |
| 14% | 4.9 | 4.7 | 3.3 | 7.6 |
| 13% | 3.9 | 4.4 | 3.2 | 7.2 |
| 12% | 6.0 | 4.1 | 6.0 | 6.5 |
| 11% | 6.8 | 6.2 | 6.6 | 7.0 |
| 10% | 6.8 | 6.9 | 7.0 | 7.0 |
| 9% | 6.9 | 7.0 | 7.0 | 6.5 |
| 8% | 7.2 | 7.0 | 7.8 | 7.2 |
| 7% | 7.5 | 6.8 | 6.7 | 7.6 |
| 6% | 8.0 | 8.0 | 7.5 | 7.6 |
| 5% | 8.0 | 8.1 | 8.0 | 7.8 |

Example 6

Bactericidal Effect of MSM in Low Protein and Sodium Chloride-Free Media

This example shows the bactericidal effect of MSM in low protein and sodium chloride-free media.

Lactose broth, free of both NaCl and of proteins, was used as the media in this experiment. MSM was added to lactose broth in concentrations ranging from 5-16%. A duplicate set of MSM-containing media were supplemented with DMSO to a final concentration of 1%. Each media composition was initially inoculated with $6.75 \times 10^6$ cfu/mL of *E. coli*. Cultures were incubated at 25° C. for seven days. Aliquots of each culture were taken after 24 hours of culturing and at the end of seven days in culture. Aliquots were serially diluted (with Modified Letheen diluent) and plated on trypto-soy agar plates. Plated cultures were grown for 24 hours at 35° C. and then analyzed. Media compositions were coded as shown in Table 6-1. Results of these studies are shown in Tables 6-2 and 6-3.

TABLE 6-1

Media compositions

| Media Code | Preparation |
|---|---|
| LBM | MSM added to lactose broth |
| LBMD | MSM added to lactose broth supplemented with 1% DMSO |
| LB | Lactose broth without MSM, spiked with E. coli. |
| (−)LB | negative control (no E. coli.) |

Lactose broth containing from 11-16% MSM reduced bacterial growth from about 1 log (16% MSM) to a maximum of about 2.2 logs (11% MSM) as shown in Table 6-2. Inhibition of bacterial growth was reduced by 1 log or more from 9-16% MSM.

TABLE 6-2

Log of 24 hour *E. coli* growth in MSM-lactose broth with or without DMSO

| MSM Concentration | LBM | LBMD |
|---|---|---|
| 16% | 5.8 | 5.3 |
| 15% | 5.6 | 5.5 |
| 14% | 5.5 | 5.3 |
| 13% | 5.1 | 5 |

TABLE 6-2-continued

Log of 24 hour E. coli growth in MSM-lactose broth with or without DMSO

| MSM Concentration | LBM | LBMD |
|---|---|---|
| 12% | 5.5 | 4.9 |
| 11% | 4.6 | 5.6 |
| 10% | 7 | 4.8 |
| 9% | 7.1 | 5.7 |
| 8% | 8 | 7.8 |
| 7% | 8 | 9.2 |
| 6% | 8.1 | 8.4 |
| 5% | 8.4 | 8.8 |

After 7 days of culturing, a more defined pattern of bacterial growth inhibition was evident (Table 6-3). 10% MSM in lactose broth held the *E. coli* population approximately equivalent to the initial inoculum.

TABLE 6-3

Log of 7-day E. coli growth in MSM-lactose broth with or without DMSO

| MSM Concentration | LBM | LBMD |
|---|---|---|
| 16% | 4 | 4 |
| 15% | 3.9 | 3.6 |
| 14% | 4 | 3.6 |
| 13% | 3.3 | 3.2 |
| 12% | 3.4 | 2.9 |
| 11% | 2.5 | 3.1 |
| 10% | 6.9 | 4.2 |
| 9% | 7.9 | 7.9 |
| 8% | 8.2 | 8.4 |
| 7% | 8.4 | 8.6 |
| 6% | 8.4 | 8.6 |
| 5% | 8.5 | 8.6 |

Example 7

Evaluation of Bactericidal Effect of MSM in Cosmetics

This example shows the bactericidal effect of MSM in cosmetics.

An initial evaluation of the bactericidal effect of MSM in a cosmetic matrix was performed. The cosmetic matrix was a cream base (jojoba) that is used in many cosmetic products. MSM was incorporated into the cream at concentrations ranging from 5-16% MSM. Each of these concentrations was then spiked with *E. coli* at a level of $4.6 \times 10^5$ cfu/mL and incubated at 25° C. for 48 hours. After 48 hours, aliquots of each culture were diluted and plated on tryptic-soy agar, which was then incubated at 35° C. for 24 hours before counting. The results of these studies are shown in Table 7-1.

TABLE 7-1

Log of 48 hour E. coli growth in MSM-containing cosmetic matrix

| MSM Concentration | Cream |
|---|---|
| 16% | 1 |
| 15% | 1 |
| 14% | 1 |
| 13% | 1 |
| 12% | 1 |
| 11% | 0.78 |

TABLE 7-1-continued

Log of 48 hour E. coli growth in MSM-containing cosmetic matrix

| MSM Concentration | Cream |
|---|---|
| 10% | 1.5 |
| 9% | 1.9 |
| 8% | 1.8 |
| 7% | 2.5 |
| 6% | 2 |
| 5% | 3.16 |

These data indicate that bacteria growing in a cosmetic cream are particularly sensitive to MSM. Surprisingly, lower concentrations of MSM (e.g., the 5-9% concentration range) substantially inhibited bacterial growth in this study. Thus, in several embodiments, MSM in concentrations greater than 5% is used to inhibit microbial activity.

Example 8

Evaluation of Bactericidal Activity of 10% MSM in a Cosmetic Base with or Without Preservative over 28 Days This example shows the bactericidal activity of 10% MSM in a cosmetic base with or without preservative over a 28 day period.

To evaluate the ability of MSM to function as a long term antimicrobial in a cosmetic base, 10% MSM was incorporated into a cosmetic cream matrix spiked with *E. coli*, which was evaluated for a 28 day time period using the USP <51> AET protocol. The cosmetic cream matrix into which the MSM was incorporated was preservative free. An additional cream, with a preservative, was also spiked with *E. coli* and evaluated. The results of these studies are shown in Table 8-1 through 8-4.

TABLE 8-1

Effect of 10% MSM on Microbial Growth in a Cosmetic Cream Without Preservative

| Test Organism | Initial Inoculum | 48 hrs | 7 days | 14 days | 28 days |
|---|---|---|---|---|---|
| *Aspergillus Niger* | $1.1 \times 10^5$ | $8 \times 10^3$ | $8 \times 10^3$ | $6 \times 10^3$ | $5 \times 10^2$ |
| *Candida Albicans* | $2.1 \times 10^5$ | <10 | <10 | <10 | <10 |
| *Escherichia coli* | $4.8 \times 10^6$ | <10 | <10 | <10 | <10 |
| *Pseudomonas aeruginosa* | $1.89 \times 10^6$ | <10 | <10 | <10 | <10 |
| *Staphylococcus aureus* | $4.0 \times 10^6$ | <10 | <10 | <10 | <10 |

TABLE 8-2

Log Reduction from Initial Microorganism Inoculum with 10% MSM in Preservative-free Jojoba Cosmetic Cream dilution of MSM

| Test Organism | 14 Days | 28 Days |
|---|---|---|
| *Aspergillus Niger* | 1.2 | 2.3 |
| *Candida Albicans* | 4.3 | 4.3 |
| *Escherichia coli* | 5.7 | 5.7 |
| *Pseudomonas aeruginosa* | 5.3 | 5.3 |
| *Staphylococcus aureus* | 5.6 | 5.6 |

TABLE 8-3

Microbial Growth in a Cosmetic Cream Containing a Preservative

| Test Organism | Initial Inoculum | 48 hrs | 7 days | 14 days | 28 days |
|---|---|---|---|---|---|
| Aspergillus Niger | $1.1 \times 10^5$ | $2 \times 10^6$ | $1.6 \times 10^2$ | $18 \times 10^1$ | $3 \times 10^1$ |
| Candida Albicans | $2.1 \times 10^5$ | <10 | <10 | <10 | <10 |
| Escherichia coli | $4.8 \times 10^6$ | <10 | <10 | <10 | <10 |
| Pseudomonas aeruginosa | $1.89 \times 10^6$ | <10 | <10 | <10 | <10 |
| Staphylococcus aureus | $4.0 \times 10^6$ | $3 \times 10^4$ | $1.6 \times 10^4$ | <10 | <10 |

TABLE 8-4

Log Reduction from Initial Microorganism Inoculum in Jojoba Cosmetic Crème Containing a Preservative

| Test Organism | 14 Days | 28 Days |
|---|---|---|
| Aspergillus Niger | 2.7 | 3.5 |
| Candida Albicans | 4.3 | 4.3 |
| Escherichia coli | 5.7 | 5.7 |
| Pseudomonas aeruginosa | 5.3 | 5.3 |
| Staphylococcus aureus | 5.6 | 5.6 |

These studies show that a cosmetic cream base containing MSM is effective in substantially inhibiting microbial growth over a period of 28 days. Further, these studies illustrated that under some conditions MSM is a more efficient antimicrobial agent than a standard cosmetic preservative. For example, 10% MSM reduced the microbial load to a greater degree at 48 hours as compared to preservative containing cream. Moreover, S. aureus was reduced to nearly undetectable levels at 48 hours in the MSM containing cream. In contrast, the preservative-containing cream showed a modest bacterial population of $3 \times 10^4$ bacteria after 48 hours. Despite a less robust initial phase, preservative containing cream bacterial load was reduced to the same extent by the end of the study as compared to the preservative containing cream.

Example 9

Evaluation of MSM Antimicrobial Activity in Two Preservative-Free Cosmetic Compositions This example describes MSM antimicrobial activity in two preservative-free cosmetic compositions.

As described in Example 8, above, 10% MSM was incorporated into the cosmetic matrices, which were spiked with various initial inoculations of microbes. In accordance with the USP <51> AET test, these spiked microbe cultures were incubated for 28 days, with samples removed at 48 hours, 7 days, 14 days, and 28 days for plating and subsequent colony counting. The results of these studies are shown in Tables 9-1 through 9-4 below.

TABLE 9-1

Effect of 10% MSM on Microbial Growth in Preservative Free Cosmetic Composition #1

| Test Organism | Initial Inoculum | 48 hrs | 7 days | 14 days | 28 days |
|---|---|---|---|---|---|
| Aspergillus Niger | $8.0 \times 10^5$ | $9.0 \times 10^3$ | $4.0 \times 10^3$ | $5.0 \times 10^1$ | <10 |
| Candida Albicans | $2.0 \times 10^6$ | $2.1 \times 10^3$ | <10 | <10 | <10 |
| Escherichia coli | $5.8 \times 10^6$ | $5.4 \times 10^4$ | <10 | <10 | <10 |
| Pseudomonas aeruginosa | $5.7 \times 10^6$ | $7.3 \times 10^3$ | <10 | <10 | <10 |
| Staphylococcus aureus | $5.3 \times 10^6$ | $1.9 \times 10^4$ | <10 | <10 | <10 |

TABLE 9-2

Log Reduction from Initial Microorganism Inoculum with 10% MSM Preservative Free Cosmetic Composition #1

| Test Organism | 14 Days | 28 Days |
|---|---|---|
| Aspergillus Niger | 4.2 | 4.9 |
| Candida Albicans | 5.3 | 5.3 |
| Escherichia coli | 5.8 | 5.8 |
| Pseudomonas aeruginosa | 5.8 | 5.8 |
| Staphylococcus aureus | 5.7 | 5.7 |

TABLE 9-3

Effect of 10% MSM on Microbial Growth in Preservative Free Cosmetic Composition #2

| Test Organism | Initial Inoculum | 48 hrs | 7 days | 14 days | 28 days |
|---|---|---|---|---|---|
| Aspergillus Niger | $8.0 \times 10^5$ | $9.0 \times 10^3$ | $3.0 \times 10^3$ | $1.3 \times 10^3$ | $6.0 \times 10^1$ |
| Candida Albicans | $2.0 \times 10^6$ | $9.0 \times 10^2$ | <10 | <10 | <10 |
| Escherichia coli | $5.8 \times 10^6$ | $1.7 \times 10^5$ | <10 | <10 | <10 |
| Pseudomonas aeruginosa | $5.7 \times 10^6$ | $2.1 \times 10^3$ | <10 | <10 | <10 |
| Staphylococcus aureus | $5.3 \times 10^6$ | $1.5 \times 10^5$ | <10 | <10 | <10 |

TABLE 9-4

Log Reduction from Initial Microorganism Inoculum with 10% MSM Preservative Free Cosmetic Composition #2

| Test Organism | 14 Days | 28 Days |
|---|---|---|
| Aspergillus Niger | 2.8 | 5.1 |
| Candida Albicans | 5.3 | 5.3 |
| Escherichia coli | 5.8 | 5.8 |
| Pseudomonas aeruginosa | 5.8 | 5.8 |
| Staphylococcus aureus | 5.7 | 5.7 |

These studies show that MSM exhibited effective antimicrobial properties in the absence of a preservative.

Example 10

Selected Concentrations of MSM Supports Microbial Activity

This example shows that selected concentrations of MSM support microbial activity.

Side-by-side growth studies in media fortified with MSM at a concentration of 0, 0.04, 0.1, 0.2, 0.4, and 1% MSM were compared to the growth curve of various microorganisms to a 0% MSM concentration control sample. Each organism (*Lactobacillus rhamnosus*, *Lactobacillus acidophilus*, and *Bifidobacterium bifidum*) was grown in MRS bacterial growth medium (broth) and plated on MRS agar at different time intervals. Results are expressed in colony forming units per milliliter (cfu/mL).

For each test organism, 100 mL aliquots of MRS broth were prepared with the respective concentration of MSM as outlined. Initially, a 1%, 0.4%, and 0.2% MSM (+/−0.01%) test solution was prepared by adding 1 g or 0.45 g of MSM into 110 g of MRS broth and 0.20 g of MSM into 100 g, respectively. The 0.1% and 0.04% test concentrations were prepared by making a 1:10 dilution of the 1% and 0.4% test solutions. Once each set of test media was plated for sterility, they were inoculated at a level of 100 μl of inoculum per 100 g or mLs of test broth (1:1000 inoculum dilutions) with each respective microorganism. All bacterial organisms were incubated at 35° C.+/−2° C. for the duration of the study.

All samples were plated on MRS agar at time 0, 12, 36, 48, 60 and 72 hours (+/−45 minutes). All preparations and plating were conducted at room temperature. All plating events were incubated at 35° C.+/−2° C. for at least 2 days or 3 days for *Bifidobacterium*. Test samples were plated in triplicate at each test date and the averages are reported. The results of these studies are provided in Tables 10-1 through 10-3.

For *Lactobacillus rhamnosus* samples (Table 10-1), within the first 12 hours all MSM samples had recovered at least 12% or more than the 0% control. The 0.2% and 1% concentrations were 41% and 47% higher respectively within the first 12 hours. All test values were in line at 24 hours before leveling off, cultures were highly turbid suggesting the organism was headed into stationary phase. However, after leveling off slightly at 36 and 48 hours, the counts in the samples with MSM continued to rise whereas the 0% control started to drop.

TABLE 10-1

Growth of *Lactobacillus rhamnosus*

| Time (hours) | 0% MSM | 0.04% MSM | 0.1% MSM | 0.2% MSM | 0.4% MSM | 1% MSM |
|---|---|---|---|---|---|---|
| 0 | $1.4 \times 10^6$ | $1.7 \times 10^6$ | $1.7 \times 10^6$ | $1.9 \times 10^6$ | $2.2 \times 10^6$ | $1.5 \times 10^6$ |
| 12 | $1.7 \times 10^7$ | $2.1 \times 10^7$ | $1.9 \times 10^7$ | $2.4 \times 10^7$ | $2.2 \times 10^7$ | $2.5 \times 10^7$ |
| 24 | $1.4 \times 10^9$ | $1.5 \times 10^9$ | $1.3 \times 10^9$ | $1.4 \times 10^9$ | $1.4 \times 10^9$ | $1.4 \times 10^9$ |
| 36 | $2.0 \times 10^9$ | $1.8 \times 10^9$ | $1.8 \times 10^9$ | $2.0 \times 10^9$ | $2.1 \times 10^9$ | $2.7 \times 10^9$ |
| 48 | $2.0 \times 10^9$ | $2.1 \times 10^9$ | $2.3 \times 10^9$ | $2.3 \times 10^9$ | $2.1 \times 10^9$ | $2.4 \times 10^9$ |
| 60 | $3.0 \times 10^9$ | $2.6 \times 10^9$ | $3.0 \times 10^9$ | $2.3 \times 10^9$ | $2.8 \times 10^9$ | $2.6 \times 10^9$ |
| 72 | $2.7 \times 10^9$ | $2.6 \times 10^9$ | $3.0 \times 10^9$ | $3.2 \times 10^9$ | $3.0 \times 10^9$ | $3.8 \times 10^9$ |

These studies suggest that MSM concentrations of about 0.1% to about 1% enhance the growth/function of *Lactobacillus rhamnosus*, with microbial levels ranging from 11% to 41% higher by the end of 72 hours.

For *Lactobacillus acidophilus* samples (Table 10-2), the 0.04% and 0.1% MSM concentrations were the first to yield growth, followed by 0.2% and 0.4% MSM at 36 hours and the 1% MSM sample by 48 hours. No growth was recovered from the 0% control, suggesting MSM had a positive impact on the recovery. Lower MSM concentrations revealed a shorter recovery time than the higher concentrations of MSM. The 0.04% and 0.4% MSM samples resulted in high levels of growth for *Lactobacillus acidophilus*. These studies illustrate that MSM affects microbial metabolism in a manner that promotes microbial adaptability and recovery.

TABLE 10-2

Growth of *Lactobacillus acidophilus*

| Time (hours) | 0% MSM | 0.04% MSM | 0.1% MSM | 0.2% MSM | 0.4% MSM | 1% MSM |
|---|---|---|---|---|---|---|
| 0 | $1.0 \times 10^3$ | $1.0 \times 10^3$ | $1.0 \times 10^3$ | $1.0 \times 10^3$ | $1.0 \times 10^3$ | $1.0 \times 10^3$ |
| 12 | $1.0 \times 10^3$ | $1.0 \times 10^3$ | $1.0 \times 10^3$ | $1.0 \times 10^3$ | $1.0 \times 10^3$ | $1.0 \times 10^3$ |
| 24 | $1.0 \times 10^3$ | $1.5 \times 10^4$ | $1.2 \times 10^4$ | $1.0 \times 10^5$ | $1.0 \times 10^5$ | $1.0 \times 10^5$ |
| 36 | $1.0 \times 10^3$ | $8.7 \times 10^7$ | $3.4 \times 10^7$ | $7.3 \times 10^5$ | $1.6 \times 10^8$ | $1.0 \times 10^3$ |
| 48 | $1.0 \times 10^3$ | $2.2 \times 10^8$ | $2.1 \times 10^8$ | $7.4 \times 10^6$ | $2.2 \times 10^8$ | $4.7 \times 10^4$ |
| 60 | $1.0 \times 10^5$ | $3.4 \times 10^8$ | $1.7 \times 10^8$ | $1.7 \times 10^7$ | $3.1 \times 10^8$ | $2.8 \times 10^7$ |
| 72 | $1.0 \times 10^5$ | $4.7 \times 10^8$ | $2.7 \times 10^8$ | $8.9 \times 10^6$ | $3.6 \times 10^8$ | $1.6 \times 10^8$ |

*Bifidobacterium bifidum*, a common microbe used in probiotics, was also tested. All *Bifidobacterium* samples were incubated under anaerobic conditions. Oxygen indicators were used to verify anaerobic conditions between plating intervals for the *Bifidobacterium* test samples and plating events.

By 48 hours, the 0.04% and 0.2% MSM samples were 1 log higher than the 0% MSM control. The 0.2% MSM sample had the highest level of growth for *Bifidobacterium bifidum*, followed by the 0.04% MSM sample.

As observed with the *Lactobacillus* rhamnosus (Table 10-2), the 0.1% to 1% MSM samples continued to grow while the control was headed into a downward stationary growth phase (Table 10-3). One and 2 log increases of *Bifidobacterium* were observed with the 0.04% and 0.2% MSM concentrations, respectively (Table 10-3).

TABLE 10-3

Growth of *Bifidobacterium bifidum*

| Time (hours) | 0% MSM | 0.04% MSM | 0.1% MSM | 0.2% MSM | 0.4% MSM | 1% MSM |
|---|---|---|---|---|---|---|
| 0  | $8.7 \times 10^4$ | $6.6 \times 10^4$ | $7.0 \times 10^4$ | $7.0 \times 10^4$ | $1.1 \times 10^5$ | $6.8 \times 10^4$ |
| 12 | $2.0 \times 10^3$ | $3.5 \times 10^3$ | $4.4 \times 10^4$ | $3.1 \times 10^4$ | $2.0 \times 10^3$ | $2.3 \times 10^4$ |
| 24 | $1.4 \times 10^5$ | $1.2 \times 10^5$ | $1.3 \times 10^5$ | $1.3 \times 10^5$ | $1.0 \times 10^5$ | $2.0 \times 10^5$ |
| 36 | $2.4 \times 10^5$ | $2.3 \times 10^5$ | $2.0 \times 10^5$ | $2.3 \times 10^5$ | $2.3 \times 10^5$ | $4.0 \times 10^5$ |
| 48 | $2.6 \times 10^5$ | $5.2 \times 10^6$ | $2.3 \times 10^5$ | $5.8 \times 10^6$ | $4.0 \times 10^5$ | $3.1 \times 10^5$ |
| 60 | $3.3 \times 10^5$ | $3.4 \times 10^7$ | $4.7 \times 10^5$ | $4.8 \times 10^7$ | $8.7 \times 10^5$ | $3.7 \times 10^5$ |
| 72 | $1.6 \times 10^6$ | $8.0 \times 10^7$ | $5.3 \times 10^5$ | $1.2 \times 10^8$ | $1.2 \times 10^6$ | $5.7 \times 10^5$ |

Also tested by observation were the general growth characteristics of probiotic organisms in MSM-supplemented and MSM-free media. Colony size of *Bacillus coagulans* grown on 0% media and 5% MSM-containing media were compared (see Example 13 for detailed description).

Example 11

Evaluation of MSM Influence on Shelf-Life

This example describes MSM effect on the shelf-life of milk.

MSM as an additive has been shown to increase the growth and recovery of beneficial microorganisms in a product. This example examined whether MSM modified the microorganisms that affect the shelf life stability of a product based on microbial count. Milk which has a relative short shelf life was used as the product to evaluate in this study. Milk with concentrations of fat were analyzed to study the effects of how the solid concentration in the product may affect the MSM. The standard shelf life for milk is 18 to 21 days, the study was carried out to 28 days.

Shelf-life study on milk products fortified with MSM at the 0.0%, 0.5%, 1.0%, 2.5%, 5.0% and 10% was conducted. The time intervals for plating of solutions in days were on day 0, 7, 14, 21, 24 and 28. The influences of the percent solids on MSM concentrations at the following percents were evaluated: 0.0%, 1.0%, 2%, 10.5% and 40%. The growth curves of recovered colony forming units per milliliter (cfu/mL) of microorganisms were compared between the MSM concentrations, with the 0% MSM concentration as a sample control. The MSM stock powder was supplied by Bergstrom Nutrition with certificate of analysis. The powder was the microprill formula, lot #0806809, expiration date Oct. 31, 2013. All media, water and stock MSM powder was sterility checked prior to the study. The working MSM concentrations were prepared from a single 10.0% MSM solution and were diluted accordingly with bottled milk to get the desired final concentration of MSM. The product was supplied by a local milk processing plant. The samples were collected and the study began on the day of processing. The product included two bottles of each product type for each MSM concentration for each day of analysis. Total bottles for one product type were 72 for the entire experiment. All bottles of the same product type came from one lot of production.

The microorganisms analyzed were the normal flora found in the product after processing. The product samples were held at 4° C. during the duration of the study. All prep and plating was conducted at room temperature. Each concentration of MSM was performed in duplicate. Each dilution was plated in duplicate for each time interval sampled. To capture the appropriate colonies per milliliter, each organism at each time interval was plated at three dilutions. All plates were incubated at 37° C.±0.5° C. for 48 hours before examination. The appropriate dilution plate was used for enumeration and averaged for reporting. The appropriate plate for enumeration contained between 25 and 250 cfu/mL.

The MSM stock sample and all media prepared with MSM were tested for background levels of microorganisms on Tryptic Soy agar. The MSM stock was <10 cfu/g and all test media were negative in all instances prior to inoculation. All time intervals for plating included negative control plates during pouring for quality control purposes. All of the negative control plates were absent for microorganism growth. The results of these studies are shown in Tables 11.1-15.1 below.

TABLE 11.1

Log Growth of Nonfat Milk

| MSM Conc. | Time (days) | | | | | |
|---|---|---|---|---|---|---|
| | 0 | 7 | 14 | 21 | 24 | 28 |
| 0%   | 1.50 | 2.05 | 0.94 | 4.40 | 1.44 | 2.20 |
| 0.5% | 0.00 | 1.00 | 0.70 | 4.41 | 4.68 | 3.79 |
| 1%   | 0.74 | 0.70 | 0.00 | 4.56 | 1.28 | 2.02 |
| 2.5% | 0.74 | 0.70 | 1.65 | 4.37 | 3.69 | 0.00 |
| 5%   | 0.00 | 0.70 | 0.00 | 1.15 | 3.20 | 0.00 |
| 10%  | 0.92 | 0.70 | 0.59 | 0.00 | 0.00 | 0.00 |

TABLE 12.1

Log Growth of 1% Milk Fat

| MSM Conc. | Time (days) | | | | | |
|---|---|---|---|---|---|---|
| | 0 | 7 | 14 | 21 | 24 | 28 |
| 0.0%  | 0.35 | 1.36 | 0.00 | 4.44 | 4.44 | 5.74 |
| 0.5%  | 1.05 | 0.50 | 0.70 | 4.37 | 3.27 | 6.09 |
| 1.0%  | 0.35 | 1.23 | 0.70 | 4.37 | 5.27 | 5.36 |
| 2.5%  | 0.00 | 0.00 | 0.00 | 4.28 | 4.28 | 2.53 |
| 5.0%  | 0.00 | 2.55 | 0.59 | 0.59 | 1.28 | 0.00 |
| 10.0% | 0.70 | 0.00 | 0.50 | 0.85 | 0.50 | 0.00 |

TABLE 13.1

Log Growth of 2% Milk Fat

| MSM | Time (days) | | | | | |
|---|---|---|---|---|---|---|
| Conc. | 0 | 7 | 14 | 21 | 24 | 28 |
| 0.0% | 1.90 | 1.60 | 2.44 | 4.45 | 4.44 | 4.93 |
| 0.5% | 1.26 | 1.59 | 2.09 | 4.43 | 3.27 | 5.48 |
| 1.0% | 1.04 | 3.21 | 0.00 | 4.07 | 5.27 | 6.56 |
| 2.5% | 1.06 | 0.00 | 0.70 | 2.96 | 4.28 | 5.81 |
| 5.0% | 1.39 | 0.35 | 0.00 | 3.97 | 1.28 | 0.59 |
| 10.0% | 0.35 | 0.50 | 0.70 | 1.97 | 0.50 | 1.66 |

TABLE 14.1

Log Growth of 10.5% Milk Fat

| MSM | Time (days) | | | | | |
|---|---|---|---|---|---|---|
| Conc. | 0 | 7 | 14 | 21 | 24 | 28 |
| 0.0% | 0.35 | 0.42 | 1.98 | 4.43 | 2.94 | 4.7 |
| 0.5% | 0.00 | 1.09 | 0.00 | 4.36 | 2.73 | 3.84 |
| 1.0% | 0.50 | 0.00 | 0.94 | 3.30 | 2.24 | 3.91 |
| 2.5% | 0.35 | 0.35 | 0.00 | 2.34 | 3.14 | 1.84 |
| 5.0% | 0.00 | 0.85 | 0.00 | 0.35 | 1.99 | 0.00 |
| 10.0% | 1.00 | 0.85 | 0.35 | 2.14 | 0.35 | 0.00 |

TABLE 15.1

Log Growth of 40% Milk Fat

| MSM | Time (days) | | | | | |
|---|---|---|---|---|---|---|
| Conc. | 0 | 7 | 14 | 21 | 24 | 28 |
| 0.0% | 0.00 | 1.89 | 2.08 | 4.47 | 4.23 | 4.75 |
| 0.5% | 0.00 | 0.35 | 2.32 | 4.46 | 4.02 | 1.95 |
| 1.0% | 0.74 | 0.00 | 2.37 | 4.35 | 3.33 | 3.86 |
| 2.5% | 0.00 | 0.00 | 0.00 | 2.16 | 3.79 | 0.95 |
| 5.0% | 0.00 | 0.80 | 0.50 | 1.25 | 1.03 | 0.35 |
| 10.0% | 0.00 | 0.00 | 1.95 | 4.45 | 0.85 | 0.35 |

When evaluating all milk without the MSM, there was a spike in the counts at day 21. This is a standard spike typical with milk products. The increase in the normal flora reaches a 2 log point and there is a start to the degradation of the product. At 4 logs the product shelf life is questionable and the sensory factors make the product undesirable.

The evaluation study takes into consideration the nature of the product being used. The product was taken from one lot production day. Microbial counts for a single lot from milk products can vary by 0.5 to 1.5 logs. Looking at the day 0 growth, the ranges for each product are within 1.5 logs of each other.

Day 7 shows that for the control and the MSM concentrations there was a slight increase in the microbial counts. There was one microbial count that was higher than the other for each sample, except for the 10.5% milkfat product. The 10.5% product microbial counts were all within 0.75 logs of each other, (control and MSM concentrations). The 40% and nonfat milk products had an increase in the control sample. While the 1% milk product had a spike in the 5% MSM sample and the 2% milk product had a spike in the 1% MSM sample.

On Day 14, the products show normal microbial counts and growth rates. No abnormal growth is seen in the products. The lower milk fat products are within expected microbial load variabilities, when comparing the blank to the MSM concentrations. 40% milk product demonstrates a lower microbial count for the 5.00% and 2.50% MSM concentrations, while the blank and the other MSM concentrations are all within 0.40 logs in microbial counts. 10.5% milk product demonstrates the blank being 1 log higher than the MSM concentrations, with the 1.00% and 10.0% MSM being the only two with a microbial count.

On Day 21, the products microbial counts separated out with regards to the blank and MSM concentrations. The 1% and nonfat milk products indicated that MSM in the higher concentrations (5.0% and 10.0%) slowed down the growth of the normal flora. While the control and the lower MSM concentrations microbrial counts increased to 4 logs. In the 2% milk product, the 10.0% MSM concentration and the 2.50% MSM concentration slowed the normal flora growth rate. The 0.50%, 1.00%, 5.00% MSM and the blank control microbial counts were at 4 logs. The 10.5% milk product showed the 5.00% MSM at 0.35 logs, slowing the growth rate compared to the control, which was at 4.43 logs. The 0.50% MSM concentration was at 4.36 logs, 1.00% MSM was at 3.30 logs, 2.50% MSM was at 2.34 logs and 10.0% MSM was at 2.14 logs. With the increase in MSM concentrations the microbial counts decreased, with the exception of the 5.00% MSM. The 40% milk product microbial load was relatively equal in count for the control, 0.5%, 1.0% and 10% MSM. The 2.5% MSM concentration was two logs lower than the control at 2.16 logs, while the 5.0% MSM was lower by 3.22 logs.

On Day 24, the control and the 1.0% MSM for the nonfat milk product dropped to around 1.3 logs, while the 0.50% MSM maintaned microbial counts. The 2.50% MSM microbial counts dropped, while the 5.0% MMS increased. There was no growth observed in the 10.0% MSM. The 1% milk product had a microbial count decreased in the 0.50% MSM, increased in the 1.00% MSM, and no alteration in the control and 2.5% MSM. The 5.0% MSM increased and the 10.0% MSM decreased. These two higher MSM concentrations maintained a low microbial count. For the 2% milk product all MSM concentrations and control continued to increase in the microbial load. The 10% MSM continued to lag behind in the microbial count. The 10.5% milk product demonstrated a decrease in the control and the MSM concentrations; 0.5%, 1.0%, and 10.0%. The 2.5% MSM and 5.0% MSM continued to grow. The 40% milk product showed a slight decrease in growth for the control, 5.0% MSM and the two lower MSM concentrations. 2.5% MSM microbial counts increased at 24 hours, while the 10.0% MSM had a significant decrease in microbial growth. 5.0% MSM and 10.0% MSM were at count close to the initial day 0 microbial loads.

On Day 28, the nonfat milk products were greater than 2 logs microbial load. The 0.5% MSM concentration was at 3.79 logs. The higher concentrations of MSM, 2.50%, 5.0% and 10.0% were at no growth for day 28. The 1% milk product shows an increase for the control, 0.5% and 1.0% MSM. The 2.5% MSM sample had a decrease in microbial load, while the 5.0% and 10.0% MSM were at no growth. The 2% milk product had an increase for the 1.0% MSM, a slight decrease for the control, 0.50% and 2.5% MSM. The 5.0% MSM and 10.0% MSM decreased to 0.59 logs and 1.66 logs respectivefully. The higher fat milk products, 10.5% and 40%, show the control continuing to increase in microbial counts. Both products have the 1.0% MSM increasing, while the 10.5% product also had the 0.5% MSM increase in microbial counts, the 40% product had the 0.5% MSM decrease. The 2.5% MSM decreased in microbial load for both products. The 5.0% and 10% for the 10.5% milk product were no growth. The 40% product had a microbial count of 0.35 logs for the 5.0% and 10.0% MSM concentrations.

These studies indicate that use of MSM as an additive to milk does not adversely effect the shelf life of milk. In particular, at day 21 there was no MSM concentration that had a microbial count higher than the control. Moreover, these studies indicate that in certain milk products, a concentration of 5.0% MSM or 10.0% MSM actually held the microbial load significantly lower than the control. These studies suggest that MSM at such concentrations can be used to increase the shelf-life of a product, such as milk.

Example 12

Acidophilus Milk and Bacillus coagulans Growth in Simulated Gastric Acid Supplemented with MSM This example describes acidophilus milk and Bacillus coagulans growth in simulated gastric acid supplemented with MSM.

To analyze the effects of methylsulfonylmethane (MSM) on the growth of probiotic microorganisms in fortified with MSM in a simulated stomach fluid. Previous studies have shown that the addition of MSM to growth media, aid in the growth rate of microorganisms. The study will measure the effect of probiotic growth fortified with MSM in a simulated gastric acid fluid.

Microbial growth studies were performed in the presence of 0%, 0.25%, 2.0% and 5%. Time intervals for plating were pulled every 3 hours for 15 hours, then at 24 and 48 hours. The growth curves of recovered colony forming units per milliliter (cfu/mL) of the microorganisms were compared between the MSM concentrations with the 0% MSM concentration as a sample control for each microorganism. The MSM stock powder was supplied by Bergstrom Nutrition with certificate of analysis. The powder was the microprill formula, lot #0806809, expiration date Oct. 31, 2013. All media and stock MSM powder was sterility checked prior to the study. The study was run on two organisms over a two week period. The microorganisms analyzed included Lactobacillus acidophilus milk and Bacillus coagulans (15BB Lot #90BC004A1MZ supplied by Ganeden).

For the lactobacillus acidophilus milk, 11 mLs of milk with a count of 81,000 cfu/mL was added to 99 mLs of simulated gastric acid. For the Bacillus coagulans 1 gram of powder was added to 99 mL of a Tryptic Soy Broth (TSB) to get a count of 108,000 cfu per mL of Bacillus coagulans. Eleven milliliters of the Bacillus coagulans TSB was added to 99 mLs of simulated gastric acid. The working MSM concentrations were prepared from a single 5.0% MSM solution and were diluted accordingly with milk or TSB to get the desired final concentration of MSM. All solutions were verified for sterility before proceeding with the study. The working simulated gastric acid was incubated at 35.0±0.2° C. during the study. The pH of the simulated gastric acid was at 1.2.

Lactobacillus acidophilus milk was inoculated on MRS agar at the times listed previously. Bacillus coagulans was inoculated on Tryptic Soy Agar (TSA) at the times listed previously. All prep and plating was conducted at room temperature. Each concentration of MSM in the simulated gastric acid was performed in duplicate. Each dilution for each organism was plated in triplicate for each time interval sampled. To capture the appropriate colonies per milliliter, each organism at each time interval was plated at six different dilutions. All plates were incubated at 35° C.±0.5° C. for 72 hours for all organisms, except for Bacillus which was incubated for 48 hours, before examination. The appropriate dilution plate was used for enumeration and averaged for reporting. The appropriate plate for enumeration contains between 25 and 250 cfu/mL.

The MSM stock sample and all media prepared with MSM were tested for background levels of microorganisms on MRS agar and TSA. The MSM stock were <10 cfu/g and all test media were <1 cfu/mL in all instances prior to inoculation (see Table below). All time intervals for plating included negative control plates during pouring for quality control purposes. All of the negative control plates were clean for microorganism growth. The results of these studies are provided in Tables 16.1 through 18.2 below.

TABLE 16.1

Stock culture Numbers Control Prior to Test Sample Inoculation

|  | Lactobacillus acidophilus Milk | Bacillus coagulans |
|---|---|---|
| cfu/mL inoculum | $8.1 \times 10^4$ | $1.08 \times 10^5$ |
| Cfu added to 99 mL | $8.1 \times 10^5$ | $1.08 \times 10^6$ |
| Cfu/mL in media at time 0 | $8.1 \times 10^3$ | $1.08 \times 10^4$ |

The numbers control is derived from growth of specific organism on appropriate media. The inoculating liquids were plated for enumeration on the appropriate media. To capture the appropriate colonies per milliliter, each liquid was plated in triplicate at four different dilutions. The appropriate dilution plate was used for enumeration and averaged for reporting. The appropriate plate for enumeration contains between 25 and 250 cfu/mL.

TABLE 17.1

Log Growth of L. acidophilus in milk in duplicate

| | Time in (Hours) | MSM Concentration in percentage | | | | | | |
|---|---|---|---|---|---|---|---|---|
| | | 0 | 0 | 0.25 | 0.25 | 2.5 | 2.5 | 5 | 5 |
| Log Growth | 0 | 0 | 0 | 0 | 0 | 0 | 0 | 0 | 0.82 |
| | 3 | 0 | 0 | 0 | 0 | 1.3 | 1 | 0 | 0.82 |
| | 6 | 0 | 0 | 0.52 | 0.52 | 0 | 0 | 0.82 | 1 |
| | 9 | 0 | 0 | 0.82 | 0 | 0.82 | 0 | 0.52 | 0.52 |
| | 12 | 0 | 1.00 | 1.00 | 0 | 1.22 | 0.82 | 0.82 | 1.37 |
| | 15 | 0.52 | 1.43 | 1.56 | 1.3 | 1.3 | 1.37 | 1.43 | 1.43 |
| | 24 | 0.52 | 0.82 | 1.37 | 1.27 | 1.67 | 1.6 | 1.67 | 1.64 |
| | 48 | 0 | 0 | 0 | 0 | 1.3 | 1.22 | 1.22 | 1.43 |

TABLE 17.2

Log Growth of L. acidophilus in milk average

| | Time in (Hours) | MSM Concentration in percentage | | | |
|---|---|---|---|---|---|
| | | 0 | 0.25 | 2.5 | 5 |
| Log Growth | 0 | 0 | 0 | 0 | 0.41 |
| | 3 | 0 | 0 | 1.15 | 0.41 |
| | 6 | 0 | 0.52 | 0 | 0.91 |
| | 9 | 0 | 0.41 | 0.41 | 0.52 |
| | 12 | 0.5 | 0.5 | 1.02 | 1.10 |
| | 15 | 0.98 | 1.43 | 1.34 | 1.43 |
| | 24 | 0.67 | 1.32 | 1.64 | 1.66 |
| | 48 | 0 | 0 | 1.26 | 1.33 |

*Acidophilus* milk placed in simulated gastric acid was aided by MSM in the recovery of the *Lactobacillus acidophilus*. Initial recovery was less than the detection limit of the method. MSM at 5.0% had an initial log recovery of 0.41. Hour 3 showed a spike in the recovery for the 2.5% MSM, will maintaining the 5.0% MSM growth log. Hour 6 the 0.25% MSM has a recovery of 0.52 logs, 5.0% MSM showed a recovery of 0.91 logs. The 2.5% MSM had a decrease in growth to non-detectable. At hour 9, there was a significant detection for all concentrations of MSM. The 0% control is remained below the detectable limit. At hour 12, the control grew to 0.5 logs matching the 0.25% MSM. The 2.5% and 5.0% MSM samples had growth rates at 1.02 and 1.10 logs, respectively. Hour 15 demonstrated continual growth with the MSM concentrations at 1.43, 1.34, and 1.43 logs. The 0% MSM control increased by 0.48 logs to 0.98 logs. The 0% MSM and 0.25% MSM at 24 hours decreased in growth by 0.31 logs and 0.11 logs, respectfully. The 0.25% MSM increased by 0.30 logs and 5.0% MSM increased by 0.23 logs. At Hour 48, the 0.25% MSM and the 0% MSM control decreased to below detectable limits. The 2.5% MSM decreased by 0.38 logs and the 5.0% MSM decreased by 0.33 logs.

TABLE 18.1

Log Growth of *Bacillus coagulans* in duplicate

| | Time (Hours) | MSM Concentration in percentage | | | | | | | |
|---|---|---|---|---|---|---|---|---|---|
| | | 0 | 0 | 0.25 | 0.25 | 2.5 | 2.5 | 5 | 5 |
| Log Growth | 0 | 0 | 0.52 | 0.52 | 0 | 0 | 0 | 0.52 | 0 |
| | 3 | 0 | 0 | 0.52 | 0 | 0 | 0 | 0 | 0 |
| | 6 | 0 | 0 | 0.52 | 0.52 | 0 | 0 | 0 | 0 |
| | 9 | 0 | 0 | 0 | 0 | 0 | 0 | 0 | 0 |
| | 12 | 0 | 0 | 1.12 | 0.52 | 0 | 0 | 0 | 0 |
| | 15 | 0 | 0 | 0 | 0 | 0 | 0 | 0.52 | 0 |
| | 24 | 0 | 0 | 0 | 0 | 0 | 0 | 0 | 0 |
| | 48 | 0 | 0 | 0 | 0 | 0 | 0 | 0 | 0 |

TABLE 18.2

Log Growth of *Bacillus coagulans* average

| | Time (Hours) | MSM Concentration in percentage | | | |
|---|---|---|---|---|---|
| | | 0 | 0.25 | 2.5 | 5 |
| Log Growth | 0 | 0 | 0.26 | 0 | 0.26 |
| | 3 | 0 | 0.26 | 0 | 0 |
| | 6 | 0 | 0.52 | 0 | 0 |
| | 9 | 0 | 0 | 0 | 0 |

TABLE 18.2-continued

Log Growth of *Bacillus coagulans* average

| | Time (Hours) | MSM Concentration in percentage | | | |
|---|---|---|---|---|---|
| | | 0 | 0.25 | 2.5 | 5 |
| | 12 | 0 | 0.82 | 0 | 0 |
| | 15 | 0 | 0 | 0 | 0.26 |
| | 24 | 0 | 0 | 0 | 0 |
| | 48 | 0 | 0 | 0 | 0 |

The initial recovery of *Bacillus coagulans* indicated no recovery. The 0.25% and 5.0% MSM samples had an average of 0.26 logs however. A low recovery was seen throughout the study for 0.25% MSM and at hour 15 for the 5.0% MSM. The recovery was too low to come to a conclusion about the Gastric Acid study for *Bacillus coagulans*. It is possible that the initial 3 hour exposure killed the organism.

These studies reveal that in regards to the *Acidophilus* milk there is a positive impact on bacterial growth with the milk containing MSM. In the first 3 to 6 hours there is a slight increase in the log phase growth of each *L. acidophilus* in the 0.25%, 2.5% and 5.0% MSM concentrations. At hour 9, there is a significant recovery of the *L. acidophilus* from the milk in the MSM concentrations versus the control. Hour 12 is when there was the first indication of recovery of the *L. acidophilus* in the control milk at 0.5 logs, matching the 0.25% MSM. MSM concentrations of 2.5% and 5.0% are at a 1 log recovery growth rate. Hour 15 the control maximizes out its' growth at 0.98 logs. The 0.25% MSM concentration maxs out at 1.43 logs. 2.5% and 5.0% MSM maxs out at hour 24 at 1.64 and 1.66 logs, respectively. Hour 24 shows a die off for the control and 0.25% MSM. At 48 hours the control and 0.25% MSM go below the detectable limit for the method and the 2.5% and 5.0% MSM are still above a 1 log of organism. MSM seems to be aiding this process by accelerating the adaptation and allows for the microorganisms to adapt quicker to environmental stressors.

MSM treated samples showed an increase in the log phase of growth. This log phase increase is seen easiest in the 5.0% MSM concentration. The 5.0% MSM is 0.45 logs higher than the control at hour 15, which is the maximum growth recovery for the control. The 5.0% MSM reached a maximum of 1.66 logs or 0.68 logs higher than the control. This indicates a survival rate of daughter cell at a higher percentage than the 0% control sample. Thus, suggesting that the environment with MSM is conducive to cell multiplication and survival.

MSM also affected the stationary phase and die off phase. The control stationary phase was shorter than the stationary phase of the 2.5% and 5.0% MSM. From hour 15 to 24, the samples not only maintained the growth rate, but continued to increase in logs by a minimum of 0.24 logs. These results indicate that MSM as an additive allowed the *L. acidophilus* to thrive longer, allowing the organism to establish itself for a better health benefit. The control was nondetectable at hour 48. The 2.5% and 5.0% MSM growth was still above 1 log. This indicates that survivability of the *L. acidophilus* in milk was greater with the MSM additive.

The *Bacillus coagulans* study indicated no recovery. This was possibly due to the time exposure in the gastric fluid. A shorter time of exposure would be beneficial for the survivability of the *Bacillus coagulans*. The difference between the *Lactobacillus acidophilus* study and the *Bacillus coagulans* was the matrix. Milk provided enough of a buffer to allow the survival of the *L. acidophilus* in the gastric fluid.

Example 13

Measure of Viability of *Bacillus coagulans* Supplemented with MSM

This example describes the effect of MSM on *Bacillus coagulans* viability and colony formation.

Microbial robust colony formation studies were conducted in the presence of 0%, 1.0%, 2.0% and 5% MSM. The microorganisms were grown for 72 hours in 30 milliliters of tryptic soy broth. At the end of the 72 hours, the broth was measured for colony formation, with photographic documentation of colony formation on tryptic soy agar. Percent transmittance was also measured on a 25 mm×25 mm area of the tryptic soy agar placed between two microscope slides in a spectrophotometer.

The growth curves of recovered colony forming units per milliliter (cfu/mL) of the microorganisms were compared between the MSM concentrations with the 0% MSM concentration as a sample control for each microorganism. The MSM stock powder was supplied by Bergstrom Nutrition with certificate of analysis. The powder was the microprill formula, lot #0806809, expiration date Oct. 31, 2013. All media and stock MSM powder was sterility checked prior to the study. The microorganisms analyzed included *Bacillus coagulans* 9BB Lot #0109E002 supplied by Ganeden.

For the *Bacillus coagulans*, the organism was isolated and grown for 24 hours before harvesting. The harvested microorganism was placed into a sterile 100 mL bottle called dilution A. Dilution A was further diluted into one working solution, with a count of 210 *Bacillus coagulans* per 1 mL, called dilution B. One milliliter of Dilution B was used to inoculate the 30 mL of TSB concentrations stated above. The working MSM concentrations were prepared from a single 5.0% MSM solution and were diluted accordingly with TSB to get the desired final concentration of MSM. All solutions were verified for sterility before proceeding with the study.

*Bacillus coagulans* was inoculated on Tryptic Soy Agar (TSA) at 35° C.±0.5° C. for 72 hours for colony verification and population density. All prep and plating was conducted at room temperature. Each concentration of MSM in the study was performed in duplicate. Each dilution for the microorganism was plated in triplicate for each sample. To capture the appropriate colonies per milliliter, the microorganism was plated at six different dilutions. All plates were incubated at 35° C.±0.5° C. for 48 hours for the microorganism. The appropriate dilution plate was used for enumeration and averaged for reporting. The appropriate plate for enumeration contained between 25 and 250 cfu/mL.

The MSM stock sample and all media prepared with MSM were tested for background levels of microorganisms on MRS agar and TSA. The MSM stock were <10 cfu/g and all test media were <1 cfu/mL in all instances prior to inoculation. All time intervals for plating included negative control plates during pouring for quality control purposes. All of the negative control plates were clean for microorganism growth. The results of these studies are provided below.

TABLE 19.1

Stock culture Numbers Control Prior to Test Sample Inoculation

|  | *Bacillus coagulans* |
|---|---|
| cfu/mL inoculum | $2.1 \times 10^4$ |
| Cfu added to 99 mL | $2.1 \times 10^4$ |
| Cfu/mL in media at time 0 | $2.1 \times 10^2$ |

The numbers control is derived from growth of specific organism on appropriate media. The inoculating liquids were plated for enumeration on the appropriate media. To capture the appropriate colonies per milliliter, each liquid was plated in triplicate at four different dilutions. The appropriate dilution plate was used for enumeration and averaged for reporting. The appropriate plate for enumeration contains between 25 and 250 cfu/mL.

TABLE 20.1

*Bacillus coagulans* Population Table

| MSM Concentration in Percentage | Population Count Average |
|---|---|
| 0 | $4.3 \times 10^{10}$ |
| 1.0 | $1.01 \times 10^{11}$ |
| 2.5 | $3.3 \times 10^{11}$ |
| 5.0 | $2.8 \times 10^{11}$ |

The population count was based on the dilution of the tryptic soy broth after 72 hours and inoculation on to tryptic soy agar plates. The plates were incubated for 48 hours and enumerated.

TABLE 21.1

*Bacillus coagulans* weight

| MSM Concentration in Percentage | Population Weight Average |
|---|---|
| 0 | 0.0586 |
| 1.0 | 0.1363 |
| 2.5 | 0.9828 |
| 5.0 | 0.1260 |

The tryptic soy broth after 72 hours was centrifuged down in a conical vial. The supernatant was pulled off and the pellet was washed. The centrifuging and washing was repeated three times. At the end of the third wash, the vials with pellet were weighed. Each vial was weighed empty and recorded. The corresponding vial weight was then subtracted from the ending weight of the pellet and vial, to get the weight of the *Bacillus coagulans* population. A 25×25 mm section of agar was cut out of each plate at the end of the 72 hour period and placed between two microscope slides. The slides were sealed to prevent the agar plug from slipping. The wavelength was set at 546 nm, and two empty slides were used as a blank. When examining the plates, one *Bacillus coagulans* colony was observed to be larger and more robust looking with the 5.0% MSM compared to the 0% MSM control. The weights indicated a heavier growth or a colony that was larger in size adding to the weight of the biomass.

TABLE 22.1

*Bacillus coagulans* percent transmittance

| MSM Concentration in Percentage | Percent Transmittance |
|---|---|
| Agar | 61.1% |
| 0.0 | 52.3% |
| 1.0 | 51.5% |
| 2.5 | 49.8% |
| 5.0 | 45.6% |

The percent transmittance was used to indicate *Bacillus coagulans* colony size in which a decrease in transmittance indicates an increase in colony size as the colony inhibited light from passing through the agar. The addition of 1 to 5% MSM appeared to cause a decrease in the percent transmittance. It was observed that the percent transmittance result may be influenced by the sample size, sample location and agar variables.

From visual observation, it was noted that the colonies were larger in size following treatment with MSM as compared to the blank control. The colonies also resulted in a higher weight total when measuring the biomass of the MSM treated samples compared to the blank control. These two results combined with the measured percent transmittance indicate that MSM as an additive (at certain concentrations) positively influences the viability, health and size of *Bacillus coagulans*.

Example 14

Effect of MSM on *Lactobacillus acidophilus* Growth and Recovery in a Simulated Intestinal Tract Environment This example describes the effect of MSM on *Lactobacillus acidophilus* growth and recovery in a simulated intestinal tract environment.

Microbial growth studies fortified with MSM were conducted at the following concentrations: 0%, 0.25%, 2.0% and 5%. The time intervals for plating of solutions in hours were 0, 3, 8, 24, 30, 36, 48, 54, 60 and 72. The growth curves of recovered colony forming units per milliliter (cfu/mL) of the microorganisms were compared between the MSM concentrations with the 0% MSM concentration as a sample control for each microorganism. The MSM stock powder was supplied by Bergstrom Nutrition with certificate of analysis. The powder was the microprill formula, lot #0806809, expiration date Oct. 31, 2013. All media, water and stock MSM powder was sterility checked prior to the study. The pH of the simulated gastric acid was at 1.2. The pH of the simulated intestinal fluid was 6.8. The microorganisms analyzed included *Lactobacillus acidophilus* ATCC #4356:

For the *Lactobacillus acidophilus*, bottled milk was used as the product. One milliliter of a 9 log solution of organism was placed into a 99 mL of bottled milk and mixed by hand shaking. This was repeated for each concentration of MSM. The suspension was enumerated for each concentration of MSM and is referred to as the starting inoculum. Ten milliliters of each MSM concentration and *Lactobacillus acidophilus* milk was placed into 90 mL of simulated gastric acid for 20 minutes. The gastric acid was pre-warmed to 35° C. and kept at 35° C. for the duration of the 20 minutes. At the end of the 20 minute period, 10 mL of the simulated gastric acid, *Lactobacillus acidophilus* and milk mixture was placed into 90 mL of simulated intestinal fluid. The simulated intestinal fluid was pre-warmed to 35° C. and kept at 35° C. during the duration of the study. The working MSM concentrations were prepared from a single 5.0% MSM solution and were diluted accordingly with bottled milk to get the desired final concentration of MSM. All solutions were verified for sterility before proceeding with the study.

*Lactobacillus acidophilus* intestinal solution was inoculated on MRS agar at the times listed previously. All prep and plating was conducted at room temperature. Each concentration of MSM was performed in duplicate. Each dilution for each organism was plated in triplicate for each time interval sampled. To capture the appropriate colonies per milliliter, each organism at each time interval was plated at four dilutions. All plates were incubated at 37° C.±0.5° C. for 72 hours in a $CO_2$ environment, before examination. The appropriate dilution plate was used for enumeration and averaged for reporting. The appropriate plate for enumeration contained between 25 and 250 cfu/mL.

The MSM stock sample and all media prepared with MSM were tested for background levels of microorganisms on MRS agar and Tryptic Soy agar. The MSM stock was <10 cfu/g and all test media were negative in all instances prior to inoculation. All time intervals for plating included negative control plates during pouring for quality control purposes. All of the negative control plates were absent for microorganism growth. The results of these studies are provided in the below Tables.

TABLE 23.1

Log Growth of *Lactobacillus acidophilus*

| | MSM concentration | | | |
|---|---|---|---|---|
| Time | 0% MSM | 0.25% MSM | 2.5% MSM | 5.0% MSM |
| Starting Inoculum | 6.83 | 6.86 | 6.86 | 7.02 |
| 20 min Gastric | <1.00 | <1.00 | <1.00 | <1.00 |
| Hour 3 | 1.33 | 1.30 | 1.46 | 1.62 |
| Hour 8 | 2.22 | 2.18 | 2.30 | 2.33 |
| Hour 24 | 4.47 | 4.40 | 5.94 | 6.39 |
| Hour 30 | 4.10 | 4.66 | 5.39 | 6.63 |
| Hour 36 | 4.00 | 4.38 | 5.32 | 8.65 |
| Hour 48 | 4.59 | 8.03 | 11.17 | 10.17 |
| Hour 54 | 8.97 | 8.02 | 13.23 | 13.33 |
| Hour 60 | 9.23 | 9.14 | 11.27 | 12.76 |
| Hour 72 | 9.21 | 9.34 | 12.87 | 12.78 |

Reviewing the data there is a benefit with the addition of MSM to the product in the growth and recovery of *Lactobacillus acidophilus*. Comparing the 0% MSM control versus the 5.0% MSM there is a significant increase in the log phase of growth with *Lactobacillus acidophilus*. Within the first 24 hours the 5.0% MSM was 1.81 logs higher than the control. Over the next 12 hours the control, the 0.25% and 2.5% decreased. The 5.0% MSM continued to increase over the same time period. At the end of the time frame the 5.0% MSM was at 8.65 logs, 4.65 logs higher than the control. From hour 36 to hour 48 the MSM concentrations grew at a faster rate than the blank control. 0.25% MSM increased by 3.65 logs and 2.5% MSM increased by 5.85 logs compared to 0.59 logs for the 0.0% MSM. That trend changed in the next 8 hours with the control increasing by 4.38 logs. The 0.25% MSM decreased, while the 2.5% and 5.0% MSM did not increase as significantly at the control, there was an increase of 2.07 and 3.16 logs. From hour 60 to hour 72 the blank control dropped while the MSM concentrations increased.

Analyzing the data, another 24 hour period of testing would have helped to better predict a die off stage. At 72 hours the graph indicates the *Lactobacillus acidophilus* reaching the stationary phase. With no indication of a die off stage, it is hard to predict if the MSM concentration would extend life of the population longer than the control. What we do see is a increase of growth rate, with a higher population achieved with the 2.5% and 5.0% MSM. MSM as an additive to the *Lactobacillus acidophilus* products would increase the probability of the organism establishing itself in the intestinal tract. More organisms faster would increase the benefit of taking a probiotic.

With the addition of MSM there is a benefit in *Lactobacillus acidophilus* recovery after a decrease if population growth. At hour 24 to hour 36 there is a decrease in growth for the 0.25% MSM, 2.5% MSM and the 0.0% MSM. While the 0.25% MSM and 2.5% MSM recovered in twelve hours with a significant growth rate increase, the 0.0% MSM took another twelve hours to show a significant growth rate. For the 5.0% MSM there was no decrease in recovery for this time frame, just a slight decrease in growth rate. The 5.0% MSM took only 6 hours to produce a substantial growth rate increase after the slight decrease in growth rate at hour 24. This shows how the MSM influences the recovery time for *Lactobacillus acidophilus*. Increasing the recovery time for *Lactobacillus acidophilus* would be a benefit to helping it to establish a intestinal colony sooner, increasing health benefit.

The study needs to be extended to 96 hours and beyond to observe if MSM as an additive can extend the *Lactobacillus acidophilus* population longer. A population that can establish itself for a longer time in the intestinal tract would be added benefit to probiotic products and to the people who take them.

MSM as a supplement with *Lactobacillus acidophilus* helps the organism to establish itself faster, grow at faster rate and reaching a higher population. These attributes would benefit people taking *Lactobacillus acidophilus* as a probiotic.

Example 15

Effect of MSM on Grass Growth and Nutrient Value

This example describes the effect of MSM on grass growth and nutrient value of such grass.

The effect of MSM on grass growth and nutrient value was evaluated by monitoring grass growth under the following conditions: (1) fertilizer alone; (2) MSM alone (OptiMSM® GNC—Lot# 0922904, rate of 1:500 or 2 lbs per 1,000 sq. ft.); and (3) fertilizer and MSM (MSM at the rate of 1:500 or 2 lbs per 1,000 sq. ft. in the presence of fertilizer) applied to the same field but through a separate application. The fertilizer tested was Urea (45-0-0) and type of pasture included the following mix of grasses (tall fescue, perennial rye grass, orchard grass, Timothy, white clover, medium red clover and intermediate rye grass; seeds for such formulation are commercially available on the World Wide Web at web address oregroseeds.com/allnatdairy.html). The field to be tested was measured and the marked to denote different levels of MSM application and control. Using a controlled broadcast spreader, the MSM and/or fertilizer were applied. The field was irrigated as usual (sprinkler irrigated every four days). The grass was allowed to grow for seven weeks and three days before being cut for testing. The sampled grass was cut one inch from the soil and placed in plastic bags for drying before shipment. The results of these tests on nutrient value are shown in the Table 23.2 below.

TABLE 23.2

| | MSM/Fert Percent | MSM Percent | Fertilizer Percent | AOAC Method |
|---|---|---|---|---|
| Dry Matter | 43.26 | 39.57 | 44.62 | 934.02 |
| Moisture | 56.74 | 60.43 | 55.33 | 934.02 |
| Crude Protein | 20.03 | 24.36 | 22.26 | 2001.11 |
| Acid Detergent Fiber | 30.95 | 25.77 | 29.44 | 973.18 |
| Neutral Detergent Fiber | 52.84 | 35.23 | 48.44 | 2002.04 |
| Cell Solubles | 47.16 | 64.71 | 51.56 | Calc |
| Lignin | 4.21 | 4.62 | 3.98 | 973.18 |
| Ash | 10.89 | 11.25 | 11.26 | 942.05 |
| Estimated TDN/DDM | 64.47 | 68.39 | 65.61 | Calculation |
| Net Energy lact (Mcal/lb) | 0.66 | 0.71 | 0.67 | NFTA calc |
| Est Net Energy (Mcal/lb) | 0.55 | 0.6 | 0.57 | NFTA calc |
| Calcium | 0.47 | 0.96 | 0.55 | 968.08 |
| Phosphorus | 0.46 | 0.43 | 0.42 | 964.06 |

TABLE 23.2-continued

| | MSM/Fert Percent | MSM Percent | Fertilizer Percent | AOAC Method |
|---|---|---|---|---|
| Magnesium | 0.16 | 0.28 | 0.17 | 968.08 |
| Potassium | 3.97 | 3.48 | 4.09 | 968.08 |
| Sodium | 0.03 | 0.3 | 0.05 | 983.04 |
| Copper | 14.57 | 8.82 | 8.18 | 968.08 |
| Iron | 94.51 | 157.77 | 128.15 | 968.08 |
| Zinc | 25.75 | 24.79 | 25.76 | 968.08 |
| Manganese | 40.23 | 33.08 | 33.73 | 968.08 |
| Selenium | 2.61 | 3.23 | 2.87 | 996.17 |
| Quantitative Nitrate | 0.3 | 0.05 | 0.64 | 968.07 |
| Relative Feed Value | 114.06 | 181.73 | 126.68 | NFTA calc |
| Est. RFV-Ash Corrected | | 191.08 | 132 | Calculation |
| Chloride | 0.94 | 0.62 | 0.34 | 915.01 |
| Sulfur | 0.32 | 0.25 | 0.36 | 923.01 |
| Protein Solubility | 46.48 | 59.52 | 52.56 | 923.04 |
| Non Structural Carbo | 12.74 | 25.66 | 14.54 | Calculation |

1:500; Results reported on a Dry basis

Also, it was noted that while all of the grasses evaluated grew at equal rates, the rye grass grew 2 to 3" taller in the MSM treated areas. Further, it was noted that there was no visible color variation between the MSM and non-MSM treated grass. Moreover, it was noted that horses preferred the MSM-treated pasture grass over the non-MSM treated grass.

These studies indicate that MSM can alter the nutrient value of grass (for example, it can increase the relative feed value as compared to fertilizer alone), possibly the flavoring of grass as well as grass height depending upon the type of grass.

Example 16

Effect of 0.5% MSM on Fermentation Efficiency Related to the Production of Beer (Scotch Ale)

This example describes the effect of 0.5% MSM on the fermentation efficiency related to the production of beer, in particular Scotch Ale.

It has been demonstrated herein that MSM at certain concentrations has a positive effect on microorganisms, including microorganism growth. This positive impact includes such organisms as fungi, yeast, and bacteria. Yeast cultures are involved in the production of beer during the fermentation process to produce ethanol and carbon dioxide. This study was determined if 0.5% MSM by weight had a positive impact, such as increasing efficiency of the brewing process. MSM was added to the Yeast Starter (1000 mL $H_2O$, 100 g dried malt extract, 1 vial of white labs Edinburgh Ale Yeast) and to the wort. Wort is the liquid extracted from the mashing process during the brewing of beer or whisky. Wort contains the sugars that are fermented by the brewing yeast to produce alcohol.

First, the Yeast Starter was prepared according to standard methods known to those of skill in the art except 0.5% MSM was added to a treatment group and no MSM added to a control group. This Procedure is detailed below. Materials included the following: 2, 64ounce glass jugs; funnel; 2-standard type brewing air-locks; 5.0 grams MSM; 2000 mLs of Water; 200 grams of Dried Malt Extract (DME); 2-vials of White Labs Edinburgh Ale WLPO28 yeast extract; and brewing sanitizer (San Star).

Preparation of Treatment Starter batch included the following steps: (1) glass jugs, airlocks and funnel were thoroughly cleaned and then rinsed with beer sanitizer; (2) 1000 mLs of water was boiled then 100 grams of DME was added; (3) sample was boiled for 10 minutes; (4) sample was removed from heat and 5.0 grams of MSM added; and (5) solution was allowed to cool to 72° F. The Treatment Starter batch was then placed in a sanitized 64 ounce glass jug using to which 1-vial of White Labs Edinburgh Ale yeast was added. The airlock was applied and the entire vessel was placed in a dark room at room temperature for 48 hours.

Preparation of Control Starter Batch included the following steps: (1) glass jugs, airlocks and funnel were thoroughly cleaned and then rinsed with beer sanitizer; (2) 1000 mLs of water was boiled then 100 grams of DME was added; (3) sample was boiled for 10 minutes; (4) sample was removed from heat; and (5) solution was allowed to cool to 72° F. The Treatment Starter batch was then placed in a sanitized 64 ounce glass jug using to which 1-vial of White Labs Edinburgh Ale yeast was added. The airlock was applied and the entire vessel was placed in a dark room at room temperature for 48 hours.

The MSM Treatment Starter showed signs of activity (bubbling through trap) at approximately 2 hours after yeast was pitched. Control starter showed no sign of activity until approximately 10 hours after yeast was pitched.

On Brew Day (2-days after Yeast starter was made) the mash was prepared. Materials to prepare the mash included the following: 18 lb of American 2-Row base grain; 3 lb of Crystal Malt 40L specialty grain; 1 lb Cara-Pils Malt specialty grain; and water. A mash tun (a vessel used in the mashing process to convert the starches in crushed grains into sugars for fermentation) and Brew kettle were cleaned with powdered brewers wash and rinsed thoroughly. The mash tun was then sanitized (San Star Brewing Sanitizer). The following grains were crushed and milled for mashing: 18 lb of American 2-Row base grain; 3 lb of Crystal Malt 40L specialty grain; and 1 lb Cara-Pils Malt specialty grain. Seven gallons of water were heated to 163° F. and then combined with preheated mash tun. The crushed grains were then added and the solution was mixed thoroughly. The lid was attached and the solution allowed to mash for 60 minutes. After 60 minutes, 4.25 gallons of work was drained from the mash tun into the brew kettle. Strike water was preheated to 168° F., added to the mash tun and mix thoroughly with grain. The mixture was allowed to incubate for 10 minutes. This process repeated two more times until a total pre-boil volume of 12.75 gallons was achieved in the brew kettle.

After preparing the mash, the brewing process was started. The following materials were used for the brewing process: 3.0 oz Cascade hops; 2 tsp. of Irish moss; 105 grams of MSM; brew kettle containing 12.75 gallons of wort; wort chiller; 2 fermentation vessels; refractometer; brewing sanitizer; powdered brewers wash (PBW); and a filtered air stone. Equipment was cleaned thoroughly with PBW. The wort chiller and filtered air stone were sanitized with brewing sanitizer (San Star Brewing Sanitizer). The wort (12.75 gallons) was brought to a boil in a brew kettle and a 1$^{st}$ aliquot of Cascade hops (1.5 ounces) was added to the solution. At 30 minutes of boil, a second aliquot (0.5 ounces) of Cascade hops was added. At 40 minutes of boil, third aliquot (0.5 ounces) of Cascade hops was added as well as 2 teaspoons of fish Moss. At 50 minutes of boil, a fourth aliquot (0.5 ounces) of Cascade hops was added. Wort was decanted from the brew kettle to the wort chiller and chilled to 74° F. The wort was then divided into two fermentors (each 21 liters in volume). 0.5% MSM (105 grams) was added to the treatment fermentor. Brix reading of both fermentors was taken and the base point was recorded (Treatment fermentor=15 Brix; Control fermentor=14.75 Brix). Each fermentor was Brix tested every 24 hours for 21 days. Both fermentors were aerated for 25 minutes with sanitized filtered air stone. MSM infused yeast was pitched into treatment fermentor vessel while unaltered yeast was pitched into control fermentor vessel. Blow-off tubes were attached to both fermentors and fermentation was allowed to proceed for 21 days. Results of these studies are provided in the Table 23.3 below.

TABLE 23.3

| Day | MSM F.G. (Adjusted for Alc and Temp) | Control F.G. (Adjusted for Alc and Temp) |
| --- | --- | --- |
| 1 | 1.026 | 1.028 |
| 2 | 1.018 | 1.020 |
| 3 | 1.016 | 1.018 |
| 4 | 1.016 | 1.017 |
| 5 | 1.015 | 1.017 |
| 6 | 1.015 | 1.015 |
| 7 | 1.015 | 1.015 |
| 8 | 1.015 | 1.015 |
| 9 | 1.015 | 1.015 |
| 10 | 1.015 | 1.015 |
| 11 | 1.015 | 1.015 |
| 12 | 1.015 | 1.015 |
| 13 | 1.015 | 1.015 |
| 14 | 1.015 | 1.015 |
| 15 | 1.015 | 1.015 |
| 16 | 1.015 | 1.015 |
| 17 | 1.015 | 1.015 |
| 18 | 1.015 | 1.015 |
| 19 | 1.015 | 1.015 |
| 20 | 1.015 | 1.015 |
| 21 | 1.015 | 1.015 |

When making a yeast starter the faster activation of the yeast culture takes place the better for efficiency and for minimizing potential environmental contamination from undesirable airborne micro-organisms. The MSM treated starter batch showed activity 80% sooner than the control (2 hours compared to 10 hours). The study also indicated that MSM aided in the fermentation process. Like the yeast starter, the faster the activation of the yeast fermentation process the better for efficiency and for minimizing potential environmental contamination from undesirable airborne microorganisms. The MSM treated fermentor showed activity 58% sooner than the control (3.5 hours compared to 9 hours). The MSM treatment batch also reached maximum fermentation in 5 days where the control batch took 6 days (a 17-25% sooner time of completion).

These results indicate that MSM is useful in the process of beer brewing.

Example 17

Growth of *Lactobacillus acidophilus* in *Acidophilus* Milk Supplemented with MSM This example describes growth of *Lactobacillus acidophilus* in *Acidophilus* milk supplemented with MSM.

Microbial growth studies were conducted in *Acidophilus milk* fortified with MSM at 0%, 0.5%, 2.5% and 5%. Time intervals for evaluation were at 8 and 16 hours for a total of 104 hours. Then samples were evaluated every 7 days for a total of 28 days. The growth curves of recovered colony forming units per milliliter (cfu/mL) of the microorganisms were compared between the *Acidophilus* milk with MSM concentrations with the *Acidophilus* milk with 0% MSM concentration as a sample control. The MSM stock powder was supplied by Bergstrom Nutrition with certificate of analysis. The powder was the microprill formula, lot #0806809, expiration date Oct. 31, 2013. The milks were bought at a local store. The *Acidophilus* milk was low fat (Darigold). The *Acidophilus* plus Bifidus milk contained 2% milkfat (Lucerne). *Acidophilus* plus Bifidus milk was run simultaneously with a MSM concentration of 2.5% and 0% as a product containing two microorganisms. The working solutions were held at 4° C. during the study. The MSM milk working solutions were run in duplicate.

All prep and plating was conducted at room temperature. All dilutions for all solutions were plated in triplicate for all time intervals sampled. To capture the appropriate colonies per milliliter, all organisms at all time intervals were plated at three different dilutions. All plates were incubated at 35° C.±0.5° C. in $CO_2$ for 72 hours for all solutions. The appropriate dilution plate was used for enumeration and averaged for reporting. The appropriate plate for enumeration contains between 25 and 250 cfu/mL.

The MSM stock sample and all media prepared with MSM were tested for background levels of microorganisms on MRS agar and TSA. The MSM stock were <10 cfu/g and all test media were <1 cfu/mL in all instances prior to inoculation. All time intervals for plating included negative control plates during pouring for quality control purposes. All of the control plates were clean for microorganism growth. At 72 hours, MSM concentrations and negative control solutions were verified negative for contamination. The results of these studies are provided in Table 24 below.

control increased by 0.19 logs, while the MSM concentrations were stable. Hour 80 had a significant increase in growth. The control showed an increase of 1.44 logs. The MSM treated samples showed an increase of growth at 0.5% (1.1 logs), 2.5% (1.09 logs), and 5% (1.1 logs). At Hour 96 the control stabilized. All MSM concentrations increased on average (0.5%, 0.38 logs; 2.5%, 0.51 logs; and 5.0%, 0.41 logs) for Hour 96. At Hour 96, the 2.5% MSM concentration was 0.23 logs higher than the control. At Hour 104, the decrease in log growth was comparable between the control and the MSM concentrations (control decreased 0.57 logs; 0.5% MSM decreased 0.60 logs; 2.5% MSM decreased 0.62 logs; and 5.0% MSM decreased 0.64 logs). Comparing final growth recovery between control and MSM concentrations, the study showed the 0.5% MSM at 0.05 logs higher than the control, the 2.5% MSM at 0.18 logs higher than the control, and the 5% MSM at 0.11 logs higher than the control.

Day 7 showed a growth increase from hour 104 for all working solutions. The control increased 0.84 logs, 0.5% MSM increased 1.19 logs, 2.5% MSM increased 0.87 logs and 5.0% MSM increased 1.15 logs. 0.5% MSM was 0.39 logs higher than the control, 2.5% MSM was 0.21 logs higher than the control and 5.0% MSM was 0.42 logs higher than the control. Day 14 showed a significant decrease in growth. The largest decrease in growth was the 0.5% MSM at 4.46 logs.

TABLE 24

Log Growth of *Lactobacillus acidophilus* in Milk fortified with MSM

| | | | MSM Concentration in percentage in *acidophilus* Milk | | | | | | |
|---|---|---|---|---|---|---|---|---|---|
| Time | *Acido* Milk | A/B 0 | A/B 2.5% | 0.50% | 0.50% | 2.50% | 2.50% | 5% | 5% |
| 0 | 8.82 | 5.33 | 6.41 | 7.33 | 6.62 | 6.67 | 6.7 | 6.56 | 6.47 |
| 8 | 9.08 | 8.36 | 8.67 | 9.06 | 9.00 | 9.06 | 8.97 | 8.73 | 9.08 |
| 24 | 9.17 | 8.19 | 9.16 | 9.41 | 9.35 | 9.24 | 9.01 | 9.32 | 9.26 |
| 32 | 8.85 | 8.73 | 8.87 | 9.2 | 9.12 | 9.06 | 9.11 | 9.33 | 9.19 |
| 48 | 8.54 | 8.15 | 8.3 | 8.55 | 8.69 | 8.93 | 8.77 | 8.78 | 8.72 |
| 56 | 8.46 | 8.51 | 8.56 | 8.77 | 8.69 | 8.7 | 8.81 | 8.88 | 8.7 |
| 72 | 8.65 | 8.45 | 8.45 | 8.56 | 8.67 | 8.71 | 8.6 | 8.75 | 8.63 |
| 80 | 10.09 | 9.66 | 9.82 | 9.92 | 9.51 | 9.52 | 9.96 | 9.87 | 9.71 |
| 96 | 10.02 | 9.68 | 8.61 | 9.93 | 10.25 | 10.18 | 10.31 | 10.14 | 10.26 |
| 104 | 9.45 | 8.83 | 8.92 | 9.47 | 9.52 | 9.8 | 9.45 | 9.74 | 9.38 |
| Day 7 | 10.29 | 10.1 | 10.42 | 10.64 | 10.72 | 10.4 | 10.59 | 10.89 | 10.52 |
| Day 14 | 6.96 | 6.83 | 5.70 | 6.81 | 5.63 | 8.00 | 6.66 | 7.82 | 8.26 |
| Day 21 | 5.30 | 5.60 | 5.37 | 5.37 | 5.37 | 5.56 | 5.37 | 5.64 | 5.48 |
| Day 28 | 4.00 | 3.82 | 3.94 | 2.52 | 3.48 | 3.43 | 3.22 | 2.52 | 2.52 |

At hour 0 there was at least 1 log higher growth of *Lactobacillus acidophilus* in the milk without MSM compared to milk fortified with MSM. The significance is, at hour 8, the milk fortified with MSM showed a minimum of a 1.73 log increase in growth, while the milk without MSM showed a 0.26 increase in growth rate. The MSM within the first 8 hours of growth gave a significant increase in compared to the control. The highest increase in growth is the 5% MSM with an average log increase of 2.39, while the 2.5% MSM was an increase average of 2.33 logs. Hour 24 shows a growth rate that leveled off between control and the MSM concentrations. The control had a 0.32 log decrease in growth at hour 32. The MSM concentrations of 2.5% and 5% had a 0.04 and 0.03 log decrease in growth, while the 0.5% was decreased by a 0.22 log at hour 32. At hour 48 the control has a decrease of 0.31 logs, while the MSM decrease is 0.54 logs for 0.5%, 0.24 logs for 2.5% and 0.51 logs for 5%. The MSM concentrations maintained a higher recovery rate compared to the control. MSM concentration of 2.5% was on average 0.31 logs higher and the 5% was 0.21 logs higher. Hour 56 showed no significant change in growth increase or decrease. Hour 72 the The control was next with a decrease of 3.33 logs, 2.5% MSM at 3.17 and 5% MSM at 2.67 logs. 0.5% MSM was 0.74 logs lower than the control, while the 2.5% MSM was 0.37 logs higher. The 5.0% MSM sample was a full log higher than the control at 1.08 logs. Day 21 continued the decrease in growth. The control was 1.66 logs lower, 0.5% MSM was 0.85 logs lower, 2.5% was 1.87 lower and 5.0% MSM was 2.48 logs lower. 0.5% MSM and the control were equal in log growth, with 2.5% MSM 0.17 logs higher than the control and 5.0% MSM 0.26 logs higher than the control. On Day 28, the decreased growth continued with a decrease of 1.3 logs for the control, 2.37 logs for 0.5% MSM, 2.14 logs for 2.5% MSM and 3.04 logs for 5.0% MSM. The growth for the negative control at Day 28 was 1.00 logs higher than 0.5% MSM, 0.68 logs higher than 2.5% MSM and 1.48 logs higher than 5.0% MSM.

The *Acidophilus* plus Bifidus milk over the course of the study demonstrated similar growth rates. From Hour 0 to Hour 8 both showed a significant increase in growth. At Hour 24, the control decreased 0.17 logs, while the 2.5% MSM increased 0.49 logs, giving the 2.5% MSM a 0.97 log higher count than the control. At Hour 32, the 2.5% MSM decreased 0.29 logs and the control increased 0.54 logs, with the 2.5% MSM having a 0.14 higher log count than the control. From Hour 48 to Hour 72 there was a continual pattern of increase and decrease in growth, with the 2.5% MSM having an increase growth of 0.15 and 0.5 logs over the control. Hour 72 the growth was equal between the control and the 2.5% MSM. Hour 80 showed a growth increase of 1.21 logs for the control and 1.37 logs for the 2.5% MSM, with the 2.5% MSM having a 0.16 log increase in growth. At Hour 96, there was a significant decrease in growth for the 2.5% MSM of 1.21 logs. The control showed no significant difference from hour 80, resulting in a 1.07 log higher growth for the control compared to the 2.5% MSM. At Hour 104, the control growth decreased by 0.85 logs and the 2.5% MSM samples increased by 0.31 logs. Hour 104 showed the 2.5% MSM samples at 0.09 logs higher than the control. Day 7 had an increase of 1.27 logs for the milk and 1.5 logs for the 2.5% MSM, with the 2.5% MSM being 0.32 logs higher than the milk. Day 14 showed a decrease in growth, 3.27 logs for milk, 4.72 logs for 2.5% MSM. The milk had a 1.13 increase in growth compared to the 2.5% MSM. Day 21 the decrease slowed down, milk decreased by 1.23 logs and 2.5% MSM by 0.33 logs, with the milk being 0.23 logs higher in growth than the MSM. Day 28 milk decreased by 1.78 logs and 2.5% MSM decreased by 1.43 logs, with MSM being 0.12 logs higher than milk with no MSM. Table 25 displays the data by averaging the duplicates.

TABLE 25

Growth of Lactobacillus acidophilus in Milk fortified with MSM average.

| | MSM Concentration in percentage in *acidophilus* Milk | | | | | |
|---|---|---|---|---|---|---|
| Time | *Acido* Milk | A/B | A/B 2.5% | 0.50% | 2.50% | 5.00% |
| 0 | 8.82 | 5.33 | 6.41 | 6.98 | 6.69 | 6.52 |
| 8 | 9.08 | 8.36 | 8.67 | 9.03 | 9.02 | 8.91 |
| 24 | 9.17 | 8.19 | 9.16 | 9.38 | 9.13 | 9.29 |
| 32 | 8.85 | 8.73 | 8.87 | 9.16 | 9.09 | 9.26 |
| 48 | 8.54 | 8.15 | 8.3 | 8.62 | 8.85 | 8.75 |
| 56 | 8.46 | 8.51 | 8.56 | 8.73 | 8.76 | 8.79 |
| 72 | 8.65 | 8.45 | 8.45 | 8.62 | 8.66 | 8.69 |
| 80 | 10.09 | 9.66 | 9.82 | 9.72 | 9.74 | 9.79 |
| 96 | 10.02 | 9.68 | 8.61 | 10.09 | 10.25 | 10.20 |
| 104 | 9.45 | 8.83 | 8.92 | 9.50 | 9.63 | 9.56 |
| Day 7 | 10.29 | 10.1 | 10.42 | 10.68 | 10.50 | 10.71 |
| Day 14 | 6.96 | 6.83 | 5.7 | 6.22 | 7.33 | 8.04 |
| Day 21 | 5.3 | 5.6 | 5.37 | 5.37 | 5.465 | 5.56 |
| Day 28 | 4.00 | 3.82 | 3.94 | 3.00 | 3.325 | 2.52 |

The *Acidophilus* plus Bifidus milk started with a higher count at Day 0 than what is typically expected. This caused the end values to be elevated. The *Acidophilus* milk product at Day 0 was at expected values. The *Acidophilus* milk maintained adequate growth rates through out the study and were equivalent to typical growth rates seen in milk products. The 5.0% MSM did not allow any significant growth throughout the study.

MSM as an additive to this product played a significant role in increasing the population of the probiotic, *Lactobacillus acidophilus* in a product. Within the first eight hours of fortifying a product with MSM, there was a significant influence on probiotic in the product. There was a significant increase in the growth rate of the probiotic. *Acidophilus* milk without MSM had a 0.26 long increase in growth within the first 8 hours. While the *Acidophilus* milk with MSM had a minimum of 1.73 logs of growth. The 2.5% MSM milk sample had an increase of 2.27 and 2.39 logs. The 5.0% MSM sample had an increase of 2.17 and 2.61 logs.

Throughout the study there was a continual increase of growth when comparing the *Acidophilus* milk control to the *Acidophilus* milk fortified with MSM. The increase growth rate ranges from 0.04 to 1.08 logs over the control. Only at two time points was there data that shows the control growth higher than the MSM solutions, Hour 80 and Day 28. When analyzing the data, the reason for the higher growth at Hour 80 was due to the peak growth curve. *Acidophilus* milk without MSM peaked before the milk with MSM. Therefore, the MSM was still in the growth phase, while the *Acidophilus* milk had reached the peak of its growth. With the increase in growth due to the MSM, there was a higher rate of die off at the end of the study. Therefore, Day 28 showed a lower growth for the MSM solutions than the control.

Peak growth was reached with the *Acidophilus* milk fortified with 5.0% MSM, with a log of 10.89. *Acidophilus* Milk reached a peak growth of 10.29 logs. Every concentration of MSM exceeded the growth of the *Acidophilus* milk. 2.5% MSM had a peak growth of 10.59 logs and 0.5% MSM had a peak growth rate of 10.72 logs. This further establishes the influence of MSM on a probiotic. The product once fortified with MSM exceeded the growth of the product without MSM. With the peak growth being higher, there was an increase growth seen at Day 14, a full week pass the peak growth rate. The *Acidophilus* milk growth was 6.96 logs; the milk fortified with MSM was 7.82 and 8.26 logs, an increase of 0.86 and 1.3 logs respectively.

Probiotic effectiveness is based on three points; Survivability, Colonization and Lactic Acid Production. MSM demon-

TABLE 26

Growth of non-probiotic microorganisms in *Acidophilus* Milk cfu per mL.

| | | | MSM Concentration in percentage | | | | | | |
|---|---|---|---|---|---|---|---|---|---|
| Day | *Acido* Milk | A/B 0 | A/B 2.5% | 0.50% | 0.50% | 2.50% | 2.50% | 5% | 5% |
| 0 | 10 | 300 | 370 | 20 | 30 | 10 | 10 | 10 | 20 |
| 3 | 20 | 830 | 480 | 10 | 10 | 30 | 10 | 10 | 10 |
| 7 | 10 | 1250 | 570 | 10 | 10 | 20 | 10 | 10 | 20 |
| 14 | 20 | 2500 | 1460 | 20 | 20 | <10 | <10 | 20 | 10 |
| 21 | 20 | 8000 | 3500 | 20 | 40 | 60 | 170 | 20 | 10 |
| 28 | 650 | 120000 | 110000 | 30 | 2250 | 2460 | 2700 | 10 | 10 |

Table 26 shows the data for standard plate counts analyzed on the working solutions. This was performed to look at how MSM would affect the normal flora found in the milks. Day 0 was the day the samples were setup for the start of the study. strates the ability to affect the survivability and colonization of the probiotic bacteria. Within the first eight hours the ability to colonize was seen with the increase growth rate. At Day 14 the ability to survive was seen with the increase log growth. The ability to increase Lactic Acid production was the third component of the effectiveness of a probiotic that will be studied. In this study, there was an observed reaction of increased foam production in the MSM solutions.

The statement of MSM being a beneficial dietary supplement additive is supported by this study. Microbial flora of the gastrointestinal tract can be impacted in a positive way with the addition of MSM in the human diet. There was an increase in probiotic bacteria growth, with an increase in survivability. Increasing the likelihood that MSM when used in a probiotic product would increase the benefit to the consumer.

Example 18

Recovery of Lactobacillus acidophilus in Acidophilus Milk Supplemented with MSM

This example shows recovery of Lactobacillus acidophilus in acidophilus milk supplemented with MSM.

To analyze the effects of MSM on the recovery of Lactobacillus acidophilus in Acidophilus milk, after a specified time of incubation a diluted portion of the original growth solutions were transferred to the appropriate broth and sampled at time intervals analyzing for recovery rates. Microbial growth was determined in Acidophilus milk fortified with MSM at 0%, 0.5%, 2.5% and 5%. At day 7, 14, 21 and 28 the Acidophilus milk samples fortified with MSM were diluted and transferred to the appropriate broths without MSM for the recovery study. Time intervals for plating were pulled at every 24 hours over a 72 hour period. The growth curves of recovered colony forming units per milliliter (cfu/mL) of the microorganisms were compared between the Acidophilus milk with MSM concentrations with the Acidophilus milk with 0% MSM concentration as a sample control. All media and stock MSM powder was sterility checked prior to the study. The study was run on four organisms over a two week period. The microorganisms were split into two runs, each a week long analyzing two microorganisms each week.

The Acidophilus milk was low fat (Darigold). The Acidophilus plus Bifidus milk contained 2% milkfat (Lucerne). The Acidophilus Bifidus milk was run simultaneously with a MSM concentration of 2.5% and 0% as a product containing two microorganisms. The working solutions were held at 4° C. during the study. The MSM milk working solutions were run in duplicate. All preparations and plating was conducted at room temperature. All dilutions for all solutions were plated in triplicate for all time intervals sampled. To capture the appropriate colonies per milliliter, all organisms at all time intervals were plated at three different dilutions. All plates were incubated at 35° C.±0.5° C. in $CO_2$ for 72 hours for all solutions. The appropriate dilution plate was used for enumeration and averaged for reporting. The appropriate plate for enumeration contains between 25 and 250 cfu/mL.

The MSM stock sample and all media prepared with MSM were tested for background levels of microorganisms on MRS agar and TSA. The MSM stock were <10 cfu/g and all test media were <1 cfu/mL in all instances prior to inoculation. All time intervals for plating included negative control plates during pouring for quality control purposes. All of the control plates were clean for microorganism growth. At 72 hours, MSM concentrations and negative control solutions were verified negative for contamination.

The study looks at the effect of MSM on the recovery of Lactobacillus acidophilus from Acidophilus milk fortified with MSM. The recovery study was run parallel to the study done on the affects of MSM on growth of Lactobacillus acidophilus in Acidophilus milk fortified with MSM. The recovery growth rate was analyzed on Day 7, Day 14, Day 21 and Day 28. For Table 27, the growth for Day x with no time is calculated from the initial growth study with the dilution factor into the log growth. The Table 28 growth was calculated from the log growth Day x with no time subtracted from the log growth for the subsequential analyzyed dates, e.g., Day 28 had a result of 4.00 logs, calculating the dilution the Day 28 time 0 value is 2.00 logs for Table 27. Table 28 takes the value of 2.00 as the starting value. Subsequential data for the hours analyzed, takes the counts in logs and subtracts the initial value of 2.00, e.g., Day 28-24 is 11.29 logs, subtracting 2.00 logs the increase growth rate is 9.29 logs.

TABLE 27

Lag Recovery of Lactobacillus acidophilus in Milk fortified with MSM Day 7

| | MSM Concentration in percentage | | | | | | | | |
|---|---|---|---|---|---|---|---|---|---|
| Day -Hour | 0% | A/B 0% | A/B 2.5% | 0.50% | 0.5% | 2.50% | 2.5% | 5% | 5% |
| Day 7 -24 | 11.29 | 12.88 | 13.44 | 13.1 | 12.78 | 13.16 | 13.15 | 12.12 | 13.29 |
| Day 7 - 48 | 12.71 | 13.42 | 12.5 | 12.7 | 12.67 | 12.04 | 12.67 | 13.09 | 13.25 |
| Day 7 - 72 | 12.17 | 13.47 | 12.77 | 12.4 | 13.74 | 11.92 | 13.28 | 13.1 | 12.87 |

TABLE 28

Recovery of Lactobacillus acidophilus in Milk fortified with MSM Day 7 with average recovery by percentage of MSM with initial start data

| | MSM Concentration in percentage | | | | | |
|---|---|---|---|---|---|---|
| Day -Hour | Acidophilus Milk | Ac/Bf Milk | Ac/Bf 2.5% MSM | 0.5% MSM | 2.5% MSM | 5.0% MSM |
| Day 7 | 8.29 | 8.1 | 8.42 | 8.68 | 8.50 | 8.71 |
| Day 7 -24 | 11.29 | 12.88 | 13.44 | 12.94 | 13.16 | 12.71 |
| Day 7 - 48 | 12.71 | 13.42 | 12.50 | 12.69 | 12.36 | 13.17 |
| Day 7 - 72 | 12.17 | 13.47 | 12.77 | 13.07 | 12.60 | 12.99 |

Day 7 recovery shows that all MSM concentrations within the first 24 hours of growth have a greater than 1 log increase over the control, 0.5% MSM 1.65, 2.5% MSM 1.87, and 5.0% MSM 1.42. Hour 48, the control was slightly higher in growth compared to the 0.5% MSM at 0.03 logs, and 0.36 logs higher than the 2.5% MSM, but 0.46 logs lower than the 5.0% MSM. Hour 72, the MSM concentrations exceeded the growth of the control; 0.5% MSM at 0.9 logs, 2.5% MS at 0.43 logs and 5.0% at 0.82 logs.

Acidophilus plus bifidus control in the first 24 hours was at 12.88 logs for growth, while the Acidophilus plus bifidus with 2.5% MSM was at 13.44 logs growth. The 2.5% MSM milk was 0.56 logs higher than the control. In the next two 24 hour periods the Acidophilus plus bifidus control had growth at 13.42 logs and 13.47 logs. The Acidophilus plus bifidus with 2.5% MSM had growth at 12.50 logs and 12.77 logs over the same time period. The control was 0.92 logs higher than the 2.5% MSM in the second 24 hour period and was 0.7 logs higher in the third 24 hour period.

TABLE 29

Recovery of *Lactobacillus acidophilus* in Milk fortified with MSM Day 7 in log recovery growth rate increase from start time of zero.

| | MSM Concentration in percentage | | | | | |
|---|---|---|---|---|---|---|
| Hour | *Acidophilus* Milk | Ac/Bf Milk | Ac/Bf 2.5% MSM | 0.5% MSM | 2.5% MSM | 5.0% MSM |
| 0 | 0.00 | 0.00 | 0.00 | 0.00 | 0.00 | 0.00 |
| 24 | 3.00 | 4.78 | 5.02 | 4.26 | 4.66 | 4.00 |
| 48 | 1.42 | 0.54 | −0.94 | −0.26 | −0.8 | 0.47 |
| 72 | −0.54 | 0.05 | 0.27 | 0.39 | 0.25 | −0.19 |

Analyzing Day 7 recovery based on rate of growth increase in logs, there was a significant increase within the first 24 hours of growth. The control increased by 3 logs from the initial inoculation, while the MSM concentrations increased by 4.26 logs for the 0.5% MSM, 4.66 logs for the 2.5% MSM, and 4.00 logs for the 5.0% MSM. In the second twenty fours there was a decrease in the growth with respect to 0.5% MSM and 2.5% MSM. The control growth increased by 1.42 logs and the 5.0% MSM growth increased by 0.47 logs. The third twenty four hour period, the control growth decreased by 0.54 logs and the 5.0% MSM growth decreased by 0.19 logs. The 0.5% MSM and 2.5% MSM increased in log growth, 0.39 and 0.25 logs, respectively.

The *Acidophilus* plus bifidus milk control showed a 4.78 log increase in the first 24 hours, compared to a 5.02 increase for the *Acidophilus* plus bifidus milk fortified with 2.5% MSM. The second 24 hour period the *Acidophilus* plus bifidus control increased by 0.54 logs, while the 2.5% MSM milk decreased by 0.94 logs. In the third 24 hour period, the *Acidophilus* plus bifidus control increased by 0.05 logs, while the 2.5% MSM milk increased by 0.27 logs.

TABLE 30

Lag Recovery of *Lactobacillus acidophilus* in Milk fortified with MSM Day 14.

| | MSM Concentration in percentage | | | | | | | | |
|---|---|---|---|---|---|---|---|---|---|
| Day -Hour | 0% | A/B 0% | A/B 2.5 | 0.5% | 0.5% | 2.50% | 2.50% | 5.0% | 5.0% |
| Day 14 - 24 | 10.62 | 13.38 | 13.35 | 10.19 | 10.10 | 10.00 | 9.73 | 9.6 | 9.6 |
| Day 14 - 48 | 12.37 | 13.52 | 13.47 | 12.95 | 12.72 | 12.43 | 12.2 | 12.99 | 13.04 |
| Day 14 - 72 | 12.43 | 13.31 | 13.43 | 13.02 | 12.70 | 12.51 | 12.63 | 12.65 | 12.21 |

TABLE 31

Recovery of *Lactobacillus acidophilus* in Milk fortified with MSM Day 14 with average recovery by percentage of MSM with initial start data

| | MSM Concentration in percentage | | | | | |
|---|---|---|---|---|---|---|
| Day - Hour | *Acidophilus* Milk | Ac/Bf Milk | Ac/Bf 2.5% MSM | 0.5% MSM | 2.5% MSM | 5.0% MSM |
| Day 14 - 0 | 4.96 | 4.83 | 3.70 | 4.22 | 5.33 | 6.04 |
| Day 14 - 24 | 10.62 | 13.38 | 13.35 | 10.15 | 9.87 | 9.60 |
| Day 14 - 48 | 12.37 | 13.52 | 13.47 | 12.84 | 12.32 | 13.02 |
| Day 14 - 72 | 12.43 | 13.31 | 13.43 | 12.86 | 12.57 | 12.43 |

Day 14 the control exceeded the growth of the MSM concentrations in the first 24 hours. The control was 0.48 logs higher than the 0.5% MSM, 0.75 logs higher than the 2.5% MSM and 1.02 logs higher than the 5.0% MSM. Hour 48 the control solution was 0.05 logs higher than the 2.5% MSM. 0.5% MSM was 0.47 logs higher than the control and 5.0% MSM was 0.65 logs higher than the control. Hour 72 the 0.5% MSM was 0.43 logs higher, 2.5% MSM was 0.14 logs higher than the control and 5.0% MSM was equal to the control.

*Acidophilus* plus bifidus fortified with 2.5% MSM was 0.03 logs lower than the *Acidophilus* plus bifidus control at hour 24. Hour 48 the *Acidophilus* plus bifidus control was 0.05 logs higher than the *Acidophilus* plus bifidus with 2.5% MSM. Hour 72 the *Acidophilus* plus bifidus with 2.5% MSM was 0.12 logs higher than the *Acidophilus* plus bifidus control.

TABLE 32

Recovery of *Lactobacillus acidophilus* in Milk fortified with MSM Day 14 in log recovery growth rate increase from start time of zero.

| | MSM Concentration in percentage | | | | | |
|---|---|---|---|---|---|---|
| Hour | *Acidophilus* Milk | Ac/Bf Milk | Ac/Bf 2.5% MSM | 0.5% MSM | 2.5% MSM | 5.0% MSM |
| 0 | 0.00 | 0.00 | 0.00 | 0.00 | 0.00 | 0.00 |
| 24 | 5.66 | 8.55 | 9.65 | 5.93 | 4.54 | 3.56 |
| 48 | 1.75 | 0.14 | 0.12 | 2.69 | 2.45 | 3.42 |
| 72 | 0.06 | −0.21 | −0.04 | 0.03 | 0.26 | −0.59 |

Analyzing Day 14 recovery based on rate of growth increase in logs, the following was observed; the control increased by 5.66 logs from the initial inoculation, while the MSM concentrations increased by 5.93 logs for the 0.5% MSM, 4.54 logs for the 2.5% MSM, and 3.56 logs for the 5.0% MSM. In the second twenty fours, the control growth increased by 1.75 logs while the 0.5% MSM increased by 2.69 logs, the 2.5% MSM increased by 2.45 logs and the 5.0% MSM increased by 3.42 logs. The third twenty four hour period, the control growth increased by 0.06 logs and the 5.0% MSM growth decreased by 0.59 logs. The 0.5% MSM and 2.5% MSM increased in log growth, 0.0.03 and 0.26 logs respectively.

The *Acidophilus* plus bifidus milk control showed an 8.55 log increase in the first 24 hours, compared to 9.65 increase for the *Acidophilus* plus bifidus milk fortified with 2.5% MSM. The second 24 hour period the *Acidophilus* plus bifidus control increased by 0.14 logs, while the 2.5% MSM milk decreased by 0.12 logs. In the third 24 hour period, the *Acidophilus* plus bifidus control decreased by 0.21 logs, while the 2.5% MSM milk decreased by 0.04 logs.

TABLE 33

Lag Recovery of *Lactobacillus acidophilus* in Milk fortified with MSM Day 21

| | MSM Concentration in percentage | | | | | | | |
|---|---|---|---|---|---|---|---|---|
| Day - Hour | 0% | A/B 0% | A/B 2.5% | 0.50% | 0.50% | 2.50% | 2.50% | 5% | 5.00% |
| Day 21 - 24 | 12.94 | 12.43 | 13.08 | 12.89 | 12.93 | 10.62 | 10.95 | 9.52 | 9.85 |
| Day 21 - 48 | 13.02 | 12.16 | 12.08 | 12.94 | 13.1 | 12.44 | 13.12 | 13.08 | 13.07 |
| Day 21 - 72 | 10.32 | 10.86 | 12.33 | 12.29 | 10.31 | 13.14 | 13.05 | 13.26 | 13.04 |

TABLE 34

Recovery of *Lactobacillus acidophilus* in Milk fortified with MSM Day 21 with average recovery by percentage of MSM with initial start data

| | MSM Concentration in percentage | | | | | |
|---|---|---|---|---|---|---|
| Day - Hour | Acidophilus Milk | Ac/Bf Milk | Ac/Bf 2.5% MSM | 0.5% MSM | 2.5% MSM | 5.0% MSM |
| Day 21 | 3.30 | 3.60 | 3.37 | 3.37 | 3.47 | 3.56 |
| Day 21 - 24 | 12.94 | 12.43 | 13.08 | 12.91 | 10.79 | 9.69 |
| Day 21 - 48 | 13.02 | 12.16 | 12.08 | 13.02 | 12.78 | 13.08 |
| Day 21 - 72 | 10.32 | 10.86 | 12.33 | 11.30 | 13.10 | 13.15 |

Day 21 the *Acidophilus* control in the first 24 hours had a log growth of 12.94. 0.5% MSM the growth was 12.91 logs, 2.5% MSM was 10.79 logs and 5.0% MSM was 9.69. The next 24 hour period the control was equal in growth to 0.5% MSM milk, 0.24 logs higher than the 2.5% MSM and 0.05 logs lower than the 5.0% MSM. The final 24 hour period shows a significant increase in the MSM concentrations compared to the control. 0.5% MSM was 0.98 logs higher than the control, 2.5% MSM was 2.78 logs higher than the controla and the 5.0% MSM was 2.83 logs higher than the control.

*Acidophilus* plus bifidus with 2.5% MSM was 0.65 logs higher than the *Acidophilus* plus bifidus control in the first 24 hours. Hour 48 the *Acidophilus* plus bifidus control was 0.08 logs higher. In the final 24 hours the *Acidophilus* plus bifidus 2.5% MSM out grew the *Acidophilus* plus bifidus control by 1.47 logs.

TABLE 35

Recovery of *Lactobacillus acidophilus* in Milk fortified with MSM Day 21 in log recovery growth rate increase from start time of zero.

| | MSM Concentration in percentage | | | | | |
|---|---|---|---|---|---|---|
| Hour | Acidophilus Milk | Ac/Bf Milk | Ac/Bf 2.5% MSM | 0.5% MSM | 2.5% MSM | 5.0% MSM |
| 0 | 0.00 | 0.00 | 0.00 | 0.00 | 0.00 | 0.00 |
| 24 | 9.64 | 8.83 | 9.71 | 9.54 | 7.32 | 6.13 |
| 48 | 0.08 | −0.27 | −1.00 | 0.11 | 2.00 | 3.39 |
| 72 | −2.70 | −1.30 | 0.25 | −1.72 | 0.32 | 0.08 |

Reviewing the log increase for Day 21, in the first 24 hours the *Acidophilus* milk control had an increase of 9.64 logs. 0.5% MS had an increase of 9.54 logs, 2.5% MSM had an increase of 7.32 logs and 5.0% MSM had an increase of 6.13 logs. In the second 24 hours the control increased by 0.08 logs. 0.5% MSM increased by 0.11 logs, 2.5% MSM increased by 2.00, and 5.0% MSM increased by 3.39 logs. The final 24 hours shows the control decreasing by 2.70 logs. 0.5% MSM decreased by 1.72 logs. 2.5% MSM increased by 0.32 logs and 5.0% MSM increased by 0.08 logs.

*Acidophilus* plus bifidus with 2.5% MSM increased by 9.71 logs and the *Acidophilus* plus bifidus control increased by 8.83 logs. In the final two 24 hour periods the *Acidophilus* plus bifidus control decrease 0.27 logs and 1.30 logs. The *Acidophilus* plus bifidus with 2.5% MSM decreased 1.00 logs in the second 24 hour period and increased 0.25 logs in the final 24 hour period.

TABLE 36

Lag Recovery of *Lactobacillus acidophilus* in Milk fortified with MSM Day 28

| | MSM Concentration in percentage | | | | | | | |
|---|---|---|---|---|---|---|---|---|
| Day -Hour | 0% | A/B 0 | A/B 2.5% | 0.50% | 0.50% | 2.50% | 2.50% | 5.0% | 5.0% |
| Day 28 - 24 | 13.1 | 13.41 | 12.67 | 6.11 | 6.47 | 6.37 | 6.37 | 5.64 | 5.48 |
| Day 28 - 48 | 11.04 | 13.42 | 13.19 | 13.66 | 12.99 | 12.52 | 12.62 | 12.58 | 13.16 |
| Day 28 - 72 | 12.47 | 10.31 | 12.00 | 12.99 | 13.01 | 12.98 | 12.34 | 12.49 | 12.47 |

TABLE 37

Recovery of *Lactobacillus acidophilus* in Milk fortified with MSM Day 28 with average recovery by percentage of MSM with initial start data

| | MSM Concentration in percentage | | | | | |
|---|---|---|---|---|---|---|
| Day - Hour | Acidophilus Milk | Ac/Bf Milk | Ac/Bf 2.5% MSM | 0.5% MSM | 2.5% MSM | 5.0% MSM |
| Day 28 | 2.00 | 1.82 | 1.94 | 1.00 | 1.33 | 0.52 |
| Day 28 - 24 | 13.10 | 13.41 | 12.67 | 6.29 | 6.37 | 5.56 |
| Day 28 - 48 | 11.04 | 13.42 | 13.19 | 13.33 | 12.57 | 12.87 |
| Day 28 - 72 | 12.47 | 10.31 | 12.00 | 13.00 | 12.66 | 12.48 |

Day 28 recovery data shows in the first 24 hour period the *Acidophilus* milk control had a log growth of 13.10. The MSM concentrations were; 6.29 logs for 0.5% MSM, 6.37 logs for 2.5% MSM, and 5.56 logs for 5.0% MSM. Hour 48 the 0.5% MSM log growth was 13.33, the 2.5% MSM was 12.57 logs and the 5.0% MSM was 12.87 logs. The control at Hour 48 was 12.71 logs. The control decreased to 12.17 logs at Hour 72. 0.5% MSM decreased to 13.00 logs and 5.0% MSM decreased to 12.48 logs. 2.5% MSM improved to 12.66 logs. This was a 0.53 log increase over the control.

*Acidophilus* plus bifidus control was 13.41 logs at Hour 24, 0.74 logs higher than the *Acidophilus* plus bifidus with 2.5% MSM. At Hour 48, the difference was less with the control 0.23 logs higher than the *Acidophilus* plus bifidus with 2.5% MSM. At Hour 72, the *Acidophilus* plus bifidus with 2.5% MSM was 1.69 logs higher than the control, which was at 10.31 logs.

TABLE 38

Recovery of *Lactobacillus acidophilus* in Milk fortified with MSM Day 28 in log recovery growth rate increase from start time of zero.

| | | | MSM Concentration in percentage | | | |
|---|---|---|---|---|---|---|
| Time | *Acidophilus* Milk | Ac/Bf Milk | Ac/Bf 2.5% MSM | 0.5% MSM | 2.5% MSM | 5.0% MSM |
| 0 | 0.00 | 0.00 | 0.00 | 0.00 | 0.00 | 0.00 |
| 24 | 11.10 | 11.59 | 10.73 | 5.29 | 5.04 | 5.04 |
| 48 | −2.06 | 0.01 | 0.52 | 7.04 | 6.20 | 7.31 |
| 72 | 1.43 | −3.11 | −1.19 | −0.32 | 0.09 | −0.39 |

At Day 28, growth rate increased in which the *Acidophilus* milk control in the first 24 hour period increased 11.10 logs, 0.5% MSM increased 5.29 logs, 2.5% MSM increased 5.04 logs, and 5.0% MSM increased 5.04 logs. In the second 24 hour period, there was a shift to the control decreasing by 2.06 logs, while the MSM fortified milk concentrations increased 0.5% by 7.04 logs, 2.5% by 6.20 logs, and 5.0% MSM by 7.31 logs. The final 24 hour period showed the control increased by 1.43, the 2.5% MSM increased by 0.09 logs, the 0.5% MSM decreased by 0.32 logs and 5.0% MSM decreased by 0.39 logs.

*Acidophilus* plus bifidus milk control increased 11.59 logs in the first 24 hours and the *Acidophilus* plus bifidus with 2.5% MSM increased 10.73 logs. In the second 24 hour period, the *Acidophilus* plus bifidus control increased 0.01 logs and *Acidophilus* plus bifidus with 2.5% MSM increased 0.52 logs. In the final 24 hour period, the *Acidophilus* plus bifidus control decreased 3.11 logs, while the *Acidophilus* plus bifidus with 2.5% MSM decreased 1.19 logs.

These studies show that MSM as an additive to this product played a significant role in the recovery of the probiotic, *Lactobacillus acidophilus*. In every instance of recovery, there was an increase in the growth rate of *Lactobacillus acidophilus* with product fortified with MSM versus the product without MSM.

Day 7 recovery data showed in the first 24 hours MSM had a 0.99 log to 1.66 log increase compared to the control. In the second 24 hour period for Day 7 even though the MSM growth rate was lower than the control, the overall growth numbers were higher for the 5.0% MSM, 0.46 logs higher. The third 24 hour period for Day 7, the MSM growth rate was higher than the control, by 0.36 logs, 0.79 logs and 0.93 logs.

At Day 14, only the 0.5% MSM out grew the control by 0.27 logs the growth rate in the first 24 hours. The 2.5% MSM and 5.0% MSM samples were 1.13 and 2.10 logs, respectively, lower than the control. This is where the control started to outgrow the MSM concentrations in the first 24 hours. On Days 21 and 28, the control out grew all of the MSM concentrations in the first 24 hours.

The second 24 hours for every data point that was collected after Day 7 showed the MSM concentrations outperforming the control. Day 14 second period data showed MSM growth rates at 0.70, 0.94, and 1.67 logs higher than the control. Day 21 second period data showed MSM growth rates 0.03, 1.92, and 3.31 logs higher than the control. Day 28 second period data showed MSM growth rates at 9.10, 8.26, and 9.37 logs higher than the control. This increase growth rate did not always translate to a higher concentration of *Lactobacillus acidophilus* in the recovery broth. At Day 14, the 0.5% and 5.0% MSM concentrations were higher than the control, while the 2.5% MSM was lower. Day 21 only the 5.0% MSM was higher. On Day 28, all three MSM concentrations were significantly higher than the control, by 2.29, 1.53, and 1.83 logs.

The third period data for Day 14 demonstrated that only the 2.5% MSM concentration growth rate was greater, by 0.20 logs. Even with the lower growth rates, a higher log of growth was seen for the MSM concentrations, except for 5.0% MSM which was equal to the control. On Day 21, the third period data showed the MSM concentrations growth rate exceeding the control by 0.98, 3.02, and 2.78 logs. This growth rate increase did translate to a higher concentration of *Lactobacillus acidophilus* for the MSM fortified samples. The growth recovery counts were 0.98, 2.78, and 2.83 logs higher than the control. The control exceeded the MSM concentrations for Day 28's growth rate in the third period. Although the growth recovery counts for the MSM concentrations of 0.5, 2.5 and 5% were 0.53, 0.19 and 0.01 logs, respectively, higher than the control.

With growth curves of bacteria there is an initial lag phase where the bacteria adjust to the environment, before going into Exponential or log phase, where cells double. After the log phase there is a stationary phase were growth rate slows. In this phase spikes and valleys are seen as growth slows. Finally, there is the death phase where bacteria run out of nutrients and die.

This study provides indicators of how MSM aids in the lag phase, log phase, stationary phase and death phase. MSM at different stages shortens the lag phase, so that the probiotic bacteria begin the log phase at an earlier time. The log phase was extended beyond the control in this study, so that the product with the MSM additive had a higher peak value. The stationary phase was effected by the MSM as there was an extension of higher values for a longer period of time. The death rate was slowed with MSM. At different points there was a slower rate of decline in growth. These different observations show that MSM as an additive positively effects on probiotic bacteria. The benefit of ingesting a probiotic product fortified with MSM would be a faster response time with a longer lasting effect. The consumer would get a product that increases their body responds to the added benefits of probiotic bacteria.

MSM consistently aided in the recovery and growth of probiotic bacteria in the product studied. Within the first 24 hours of growth, there was an increase in rate of recovery indicating that stressed microorganisms responded to a new environment better with MSM as an additive.

Example 19

*Bifidobacterium bifidum* Growth in Media Fortified with MSM

This example shows the effects of MSM on the growth of *Bifidobacterium bifidum* in microbial growth media fortified with MSM.

Microbial growth studies were conducted in media fortified with MSM at 0%, 0.125%, 0.25%, 0.5%, 1.0%, 2.5% and 5%. Time intervals for plating were pulled every 8 hours for a total of 96 hours. The growth curves of recovered colony forming units per milliliter (cfu/mL) of the microorganisms were compared between the MSM concentrations with the 0% MSM concentration as a sample control for each microorganism. The MSM stock powder was supplied by Bergstrom Nutrition with certificate of analysis. The powder was the microprill formula, lot #0806809, expiration date Oct. 31, 2013. All media and stock MSM powder was sterility checked prior to the study. The microorganism analyzed was *Bifidobacterium bifidum* ATCC #29521.

*Bifidobacterium bifidum* (99 mL of MRS broth with the addition of 0.05% L-cysteine) was prepared with respective MSM concentrations. The working MSM concentrations were prepared from a single 5% MSM in MRS broth solution and were diluted accordingly with MRS broth to get the desired final concentration of MSM. The solutions were verified for sterility before proceeding with the study.

The working solutions were inoculated at a level of 1.5 to 2 logs of microorganism per 100 mL of broth. *Bifidobacterium bifidum* was incubated under anaerobic conditions at 35° C.±0.5° C. for 72 hours. Oxygen indicators were used to verify anaerobic conditions between plating intervals for the *Bifidobacterium* test samples.

*Bifidobacteruim* was inoculated on MRS agar supplemented with L-cysteine at the times listed previously to lower the oxidation-reduction potential of media. All prep and plating was conducted at room temperature. All dilutions for all organisms were plated in triplicate for all time intervals sampled. To capture the appropriate colonies per milliliter, all organisms at all time intervals were plated at six different dilutions. All plates were incubated at 35° C.±0.5° C. for 72 hours. The appropriate dilution plate was used for enumeration and averaged for reporting. The appropriate plate for enumeration contains between 25 and 250 cfu/mL. The MSM stock sample and all media prepared with MSM were tested for background levels of microorganisms on MRS agar and TSA. The MSM stock were <10 cfu/g and all test media were <1 cfu/mL in all instances prior to inoculation. All time intervals for plating included negative control plates during pouring for quality control purposes. All of the negative control plates were clean for microorganism growth. At 72 hours, MSM concentrations and control solutions were verified for negative for contamination of strains and the strains were verified to original species.

TABLE 39

Stock culture Numbers Control Prior to Test Sample Inoculation

|  | *Bifidobacterium bifidum* |
|---|---|
| cfu/mL inoculum | $1.48 \times 10^4$ |
| Cfu added to 100 mL | $1.48 \times 10^4$ |
| Cfu/mL in media at time 0 | $1.48 \times 10^2$ |

The numbers control was derived from growth of specific organism on appropriate media. After incubation, the colonies were washed off the media and captured in a sterile vial. The vial was used as the starting solution for the number control (stock). The stock solution was then diluted to get an appropriate reading on spectrophotometer, using wavelength of 420 with percent light transmission. Bacterial concentrations were determined according to AOAC Method 960.09, table 960.09A. Preparation of culture suspension from stock culture was determined by spectrophotometer reading or comparison to McFarland standard.

TABLE 40

Log Growth of *Bifidobacteruim bifidum* in Media Fortified with MSM.

| Hr | MSM Concentration in percentage |  |  |  |  |  |  |
|---|---|---|---|---|---|---|---|
|  | 0 | 0.125 | 0.25 | 0.5 | 1 | 2.5 | 5 |
| 0  | 1.22  | 1.12  | 1.00  | 1.00  | 1.00  | 1.30  | 1.12  |
| 8  | 2.55  | 2.89  | 2.93  | 2.84  | 2.73  | 2.71  | 2.04  |
| 16 | 7.16  | 7.85  | 8.07  | 7.45  | 7.73  | 7.56  | 6.10  |
| 24 | 8.94  | 9.06  | 8.49  | 8.81  | 8.81  | 8.64  | 8.43  |
| 32 | 10.81 | 11.45 | 11.41 | 11.22 | 11.49 | 11.56 | 11.13 |
| 40 | 11.03 | 10.80 | 10.31 | 12.09 | 11.19 | 11.73 | 11.78 |
| 48 | 11.54 | 8.22  | 8.10  | 9.39  | 10.43 | 10.72 | 10.70 |
| 56 | 10.64 | 7.25  | 7.22  | 9.51  | 10.57 | 11.34 | 10.59 |
| 64 | 9.97  | 8.86  | 6.77  | 10.34 | 10.66 | 12.26 | 14.32 |
| 72 | 8.56  | 6.59  | 6.39  | 8.35  | 8.34  | 10.26 | 8.65  |
| 80 | 10.56 | 9.12  | 8.52  | 10.38 | 9.43  | 9.52  | 12.20 |
| 88 | 10.64 | 9.12  | 8.52  | 9.70  | 10.41 | 10.64 | 12.31 |
| 96 | <6.00 | <6.00 | <6.00 | 8.82  | <6.00 | <6.00 | 9.60  |

The growth observed with *Bifidobacterium bifidum* show a 0.2 to 0.4 log increase in growth rate for the MSM concentrations of 0.125% to 2.5% at hour 8. MSM concentrations of 0.125% to 2.5% at hour 16 increased to 0.3 to 0.7 logs. Hour 24 showed the MSM concentrations of 0.125% to 2.5% slowing to be equal to or lower than the control. MSM at a concentration of 5% showed slower growth rate compared to the control for the first 24 hours. Hour 32 there was an increase in growth rate ranging from 0.3 to 0.75 logs for all concentrations of MSM compared to the control. Hour 40 the MSM concentrations of 0.125% and 0.25% showed a steady decline in rate of growth, to the extent that they were below the control from hour 40 to hour 96. Hour 40 showed the 0.5% MSM sample at a full log higher in growth than the control. 0.5% MSM at hour 48 to hour 96 declined in the growth rate to where it was 2 to 3 full logs below the control rate of growth. MSM at a concentration of 1% matched the growth rate of the growth from hour 40 to hour 96, except for hour 48 and hour 80 where it was a full log less. 2.5% MSM at hour 40 was 0.7 logs higher in growth rate compared to the control. Hour 48 showed a 0.7 log decrease in growth rate compared to the control. Hour 56 to hour 72 2.5% MSM had a growth rate that was 0.7 to 2.29 logs higher than the control. Hour 80 showed a 1 log lower growth rate for 2.5% MSM sample compared to the control and Hours 88 and 96 the growth rate was equivalent. 5% MSM at hour 40 had a growth rate of 0.7 logs higher than the control. At Hour 48, this dropped to 0.7 logs lower than the control and at Hour 56 the growth rate was equivalent to the control. Hour 64 shows a increase growth rate of 4.35 logs for the 5% MSM over the control. Hour 72 showed a decrease in growth rate, with a return to a 1.6 log increase in growth rate at hour 80 and hour 88. Hour 96 showed a 5% MSM rate of growth that was approximately 3.6 logs higher than the control.

*Bifidobacterium bifidum* showed a significant benefit to having MSM as an additive to influence growth. All MSM concentrations increased the growth rate to the point where the *Bifidobacterium bifidum* reached in maximum 16 hours before the control. The control reached a maximum of 11.54 logs of growth at hour 48. This maximum growth was reached by all MSM concentrations at hour 32. MSM concentrations of 0.125% and 0.25% show a decline in growth from Hour 40 to Hour 96, never reaching the maximum growth again. 0.5% MSM increased the growth to 0.5 logs higher than the maximum of the control. 0.5% MSM slowed the decrease of growth from hour 48 to hour 96. The 0.5% MSM delayed the die off stage to the point that at hour 96 there was 8.82 logs of growth, which was approximately 2 logs higher than the control. 1% MSM did not increase the growth of the bacteria compared to the control, but it did decrease the die off stage. From Hour 40 to Hour 64, the 1% MSM did not show a large drop in growth, there was a slow drop of 0.5 logs for Hour 48, but there was no decrease for Hours 56 and 64. Hour 72 there was a 2 log drop in growth, but at Hour 80 there was a 1 log increase of growth and at Hour 88 there is another 1 log increase of growth. Hour 96 the growth was outside the countable range and was estimated at less than 6 logs of growth. Continuing for another 8 hours, there may have been another spike in the growth to over 6 logs. 2.5% MSM at hour 40 reached 11.73 logs growth, with a drop of 1 log at hour 48. There was a steady increase of growth at Hour 56 and Hour 64, reaching a maximum of 12.26 logs, 0.72 logs higher than the control. At Hour 72 there was a 2 log drop, with a 0.7 log drop at Hour 80 for the 2.5% MSM. At Hour 88, the 2.5% MSM increased the growth 1 log, before dropping below the countable range at Hour 96. MSM at a 5% concentration was slower in increasing the growth rate compared to the other concentrations of MSM. At Hour 32, the growth was at 11.13 logs and Hour 40 the growth was 11.78 logs. At Hour 48, the growth dropped 1 log and Hour 56 there was a 0.1 log drop. At Hour 64, the growth reached the highest for all the MSM concentrations of 14.32 logs for the 5% MSM. There was a 6 log drop at hour 72, but at hour 80 the growth increased 4 logs to 12.20. At Hour 88, a 0.1 log increase was observed, before dropping to 9.60 logs of growth at Hour 96. The 5% MSM slowed the death rate considerably, extending the stationary phase out 40 hours. Once the stationary phase was reached there was a continuing increase and decrease in growth, with movement toward a lower growth pattern. These studies indicate that MSM is proceeding to the stationary phase faster for all concentrations, extending the stationary phase for concentrations over 0.5% MSM and increasing maximum growth for the concentrations at 2.5% and 5% MSM.

Example 20

Effects of Bromcresol Purple on *E. coli* when MSM is Added to the Matrix

This example shows the effects of Bromcresol Purple on E-coli when MSM is Added to the Matrix.

To investigate whether MSM functions as a carrier/transporter, the ability of MSM to transport Bromcresol into the *E. coli* was evaluated. Bromcresol Purple is an indicator dye that turns yellow in the presence of *E. coli* bacteria. It is non-toxic to the organism. To minimize potential ionic interference Lactose Broth was chosen as the preferred media for this study because it is free of both NaCl and proteins. USP<51> Antimicrobial Effectiveness for testing was used as the template to show the $LC_{100}$ (lethal concentration). MSM concentrations between 5%-16% in increments of 1% were used. All concentrations were plated out to $10^{-7}$ dilutions to ascertain the log reduction.

Materials included the following: Lot number 0604751 of OptiMSM Flake; ATCC strain 8739 *Escherichia coli* lot: 57762704; 30 mL Borosilicate glass cultures tubes were used for all OptiMSM material; Accumedia MacConkey Broth (MB) Lot: 100,974A; Diluent used was Alpha Biosciences Modified Letheen Broth (MLB) Lot: I08-09; Alpha Biosciences Trypto Soy Agar with Lecithin; and Tween 80 (TSA) Lot: F08-42.

Flake OptiMSM was weighed out using a certified Mettler Toledo AG245 balance SN: 1115210833 and aliquoted for each concentration. The material was placed into 30 mL borosilicate glass culture tubes. Material was calculated on a 10 mL volume. Material was added to each tube as follows: 5% (0.5 g), 6% (0.6 g), 7% (0.7 g), 8% (0.8 g), 9% (0.9 g), 10% (1.0 g), 11% (1.1 g), 12% (1.2 g), 13% (1.3 g), 14% (1.4 g), 15% (1.5 g), and 16% (1.6 g). MacConkey Broth was aliquoted out in 10 mLs to each tube then sterilize for 20 minutes at 121° C. Tubes were cooled to room temperature which was approximately 20° C. All tubes were then spiked with the same dilution of *Escherichia coli* that gave a level of colony forming units at $6.0 \times 10^6$/mL (6.8). The tubes were then incubated at 25° C. Daily observation for color change was performed during the first seven days. The tubes were mixed periodically to ensure that the OptiMSM was well equilibrated at all times. A positive and negative control was ascertained.

The results of these studies are as follows:
(1) Day one: showed the color change of the broth to yellow for concentration 5-7%; 8% showed slight clearing of color; and 9-16% showed no signs of change.
(2) Day two: showed same signs as day one.
(3) Day three: show a change in the 8% concentration turning to the typical yellow color.
(4) Day 4 to day 6: showed no significant signs of change.
(5) Day 7: Showed the 9% turning to a yellow color. No color change from 10%-16%.
(6) Day 14: Showed no signs for the concentration range for 10%-16%.

The concentrations tubes were streaked out on MacConkey agar to see if organism could be recovered. No organisms were observed after the 72 hour incubation. Day 30 showed no signs of change for the concentration range for 10-16%. Positive control was streaked for each time point streaked and showed signs of organism demonstrated by a classical isolation streak.

This qualitative test indicates OptiMSM having some kind of carrier affect and reducing or killing off the organism. This is demonstrated by the lack of yellow color in MSM concentrations lower than what was demonstrated in previous studies using growth medium. Color showed reduction at concentrations as low as 8% versus 11% in the growth media studies.

Example 21

Antimicrobial Study of MSM and DMSO on *Streptococcus* Organisms

This example shows the effects of MSM and DMSO on the growth of *Streptococcus* organisms.

It has been demonstrated herein that specific concentrations of MSM (such as 10% to 16% MSM) kill microorganisms. Dimethyl sulfoxide has also been observed to kill microorganisms at concentrations of 30-50%. This study evaluated the bactericidal properties of both compounds, alone and in combination, as well as their efficacy when used with a low level of penicillin

*Streptococcus pyogenes* (Lancefield group A) has a hyaluronic acid capsule and *Streptococcus Pneumonia* (no Lancefield Group identified to date) has a distinct polysaccharide capsule. These two organisms are responsible for many types of human streptococcal infections and present two different encapsulation types. Both of these organisms were used in this in vitro study. In particular, this study determined the antimicrobial effects of MSM and DMSO, both individually and in combination, on *Streptococcus pyogenes* and *Streptococcus Pneumonia*. This study also determined the most effective concentrations for antimicrobial properties for both compounds and in combination and whether combining MSM and DMSO reduces the concentrations of either compound needed to achieve microbial reduction. Further, the effectiveness of using MSM, DMSO, and the combination of the two in conjunction with an antibiotic agent was evaluated.

*Streptococcus Pneumonia* (#10341™) and *Streptococcus Pyogenes* (Lancefield group A, #10096™) were purchased from ATCC. MSM (#41631) and DMSO (#D8418) were purchased from Sigma-Aldrich. Penicillin was purchased from Henry Schein. Bacterial culture medium was purchased from Becton-Dickinson and company (#297963). The bioluminescent ATP assay kit was purchased from Promega (#G8230). *Streptococcus Pyogenes* was cultured in Brain Heart Infusion broth (BD 237500, #44 booth) overnight. Equal amounts of bacterial containing broth were used for the studies. *Streptococcus Pneumonia* was also cultured in Brain Heart Infusion broth.

Bacterial Viability Evaluation:

The bioluminescent ATP assay kit was used to evaluate the bacterial viability, based on the following reaction:

$$ATP + D\text{-Luciferin} + O_2 \rightarrow \text{Oxyluciferin} + AMP + \text{pyrophosphate} + CO_2 + \text{light (560 nm)}.$$

Bacterial ATP can be measures by direct lysis of the bacteria with a suitable detergent; the released ATP is then free to react with the luciferin/luciferase and leading to the light emission. The intensity of the emitted light is proportional to the concentration of ATP. Measurement of the light intensity using a luminometer permits direct quantitation of ATP, which is the universal indicator of viability for living microorganisms.

Both *S pyogenes* and *S pneumonia* were cultured under various conditions to determine optimal conditions to evaluate MSM, DMSO and/or Penicillin MSM, DMSO and Penicillin were diluted in culture medium according to Table 45-1. Bacterial was cultured for 7 hours for *Streptococcus pneumonia* and 18 hours for *Streptococcus pyogenes* respectively. Then the bacterial viability was evaluated by the bioluminescent ATP assay kit. The test was conducted in triplicates.

TABLE 41

Concentrations of MSM, DMSO and Penicillin evaluated.

| MSM (%) | DMSO (%) | Penicillin (µg/L) |
|---|---|---|
| 20 | 20 | 100 |
| 10 | 10 | 50 |
| 5 | 5 | 25 |
| 2.5 | 2.5 | 12.5 |
| 1.25 | 1.25 | 6.25 |
| 0.625 | 0.625 | 3.125 |
| 0.3125 | 0.3125 | 1.5625 |
| 0 | 0 | 0 |

The MSM and DMSO were diluted in culture medium according to Table 42 (for *Streptococcus pneumonia*, below left) and Table 43 (*Streptococcus pyogenes*, below right).

TABLE 42

| DMSO (%) | MSM (%) |
|---|---|
| 0 | 0 |
|   | 5 |
|   | 10 |
|   | 20 |
| 5 | 0 |
|   | 5 |
|   | 10 |
|   | 20 |
| 10 | 0 |
|   | 5 |
|   | 10 |
|   | 20 |
| 20 | 0 |
|   | 5 |
|   | 10 |
|   | 20 |

TABLE 43

| DMSO (%) | MSM (%) |
|---|---|
| 0 | 0 |
|   | 2.5 |
|   | 5 |
|   | 10 |
| 2.5 | 0 |
|   | 2.5 |
|   | 5 |
|   | 10 |
| 5 | 0 |
|   | 2.5 |
|   | 5 |
|   | 10 |
| 8 | 0 |
|   | 2.5 |
|   | 5 |
|   | 10 |

To determination the effectiveness of using MSM, DMSO in conjunction with Penicillin, the MSM, DMSO and Penicillin were diluted in culture medium according to Table 44-1 (*S. pneumonia*) and Table 44-2 (*S. pyogenes*).

TABLE 44-1

| DMSO (%) | MSM (%) | Penicillin (µg/L) |
|---|---|---|
| 5 | 5 | 25 |
|   | 10 |   |
|   | 20 |   |
| 10 | 5 |   |
|   | 10 |   |
|   | 20 |   |
| 20 | 5 |   |
|   | 10 |   |
|   | 20 |   |

TABLE 44-2

| DMSO (%) | MSM (%) | Penicillin (µg/L) |
|---|---|---|
| 2.5 | 2.5 | 3.125 |
|   | 5 |   |
|   | 10 |   |
|   | 2.5 | 6.25 |
|   | 5 |   |
|   | 10 |   |
| 5 | 2.5 | 3.125 |
|   |   | 6.25 |
| 8 |   | 3.125 |
|   |   | 6.25 |

The IC$_{50}$ of DMSO, MSM and Penicillin in *Streptococcus pneumonia* was 12.86%, 15.97% and 68.54 g/L, respectively. DMSO and MSM had synergistic effect within doses of 5% to 20% (for both drugs) in inhibiting *Streptococcus pneumonia* growth. DMSO and Penicillin also had synergistic effect within doses of 10% to 20% (for DMSO) and 25 µg/L (for Penicillin) in inhibiting *Streptococcus pneumonia* growth. Further, MSM and Penicillin had a synergistic effect within doses of 5% (for MSM) and 25 µg/L (for Penicillin) in inhibiting *Streptococcus Pneumonia* growth. When Penicillin, DMSO and MSM were used together, the greatest synergistic effect resulted from DMSO+MSM only rather than Penicillin+DMSO+MSM.

The IC$_{50}$ of DMSO, MSM and Penicillin in *Streptococcus pyogenes* was 9.07%, 10.26% and 15.25 µg/L, respectively. DMSO and MSM had a synergistic effect within doses of 2.5% to 5% (for both drugs) in inhibiting *Streptococcus Pyogenes* growth. DMSO and Penicillin had a synergistic effect within doses of 5% (for DMSO) and 6.25 µg/L (for Penicillin) in inhibiting *Streptococcus pyogenes* growth. MSM and Penicillin had a synergistic effect within doses of 2.5% to 5% (for MSM) and 3.125 to 6.25 µg/L (for Penicillin) in inhibiting *Streptococcus Pyogenes* growth. When Penicillin, DMSO and MSM were used together, the synergistic effect resulted from DMSO+MSM only rather than Penicillin+DMSO+MSM.

TABLE 45-1

Viability of *S. pneumonia* After DMSO Exposure

| DMSO Concentration | Viability of *S. pneumonia* (%) |
|---|---|
| 5 | 75.45 |
| 10 | 40.18 |
| 20 | 27.19 |

TABLE 45-2

Viability of *S. pneumonia* After MSM Exposure

| MSM Concentration | Viability of *S. pneumonia* (%) |
|---|---|
| 5 | 95.34 |
| 10 | 48.57 |
| 20 | 39.08 |

TABLE 45-3

Viability of *S. pneumonia* After Exposure to Various Concentrations of MSM in 5% DMSO

| DMSO (%) | MSM (%) | *S. pneumonia* viability (%) |
|---|---|---|
| 5 | 0 | 75.45 |
| 5 | 5 | 50.94* |
| 5 | 10 | 45.40 |
| 5 | 20 | 27.22 |

TABLE 45-4

Viability of *S. pneumonia* After Exposure to Various Concentrations of MSM in 10% DMSO

| DMSO (%) | MSM (%) | *S. pneumonia* viability (%) |
|---|---|---|
| 10 | 0 | 40.18 |
| 10 | 5 | 47.81 |

TABLE 45-4-continued

Viability of *S. pneumonia* After Exposure to Various Concentrations of MSM in 10% DMSO

| DMSO (%) | MSM (%) | *S. pneumonia* viability (%) |
|---|---|---|
| 10 | 10 | 37.42 |
| 10 | 20 | 11.95 |

TABLE 45-5

Viability of *S. pneumonia* After Exposure to Various Concentrations of MSM in 20% DMSO

| DMSO (%) | MSM (%) | *S. pneumonia* viability (%) |
|---|---|---|
| 20 | 0 | 27.19 |
| 20 | 5 | 17.60* |
| 20 | 10 | 7.76 |
| 20 | 20 | 5.15 |

TABLE 45-6

*S. pneumonia* Viability After Exposure to Various Concentrations of Penicillin

| Penicillin (µg/L) | *S. pneumonia* viability (%) |
|---|---|
| 25 | 79.82 |
| 50 | 42.70 |
| 100 | 40.93 |

TABLE 45-7

*S. pneumonia* Viability After Exposure to 25 µg/L of Penicillin with Various Concentrations of DMSO

| Penicillin (µg/L) | DMSO (%) | *S. pneumonia* viability (%) |
|---|---|---|
| 25 | 0 | 79.82 |
| 25 | 5 | 46.13 |
| 25 | 10 | 39.78 |
| 25 | 20 | 22.08 |

TABLE 45-8

*S. pneumonia* Viability After Exposure to 50 µg/L of Penicillin with Various Concentrations of DMSO

| Penicillin (µg/L) | DMSO (%) | *S. pneumonia* viability (%) |
|---|---|---|
| 50 | 0 | 42.70 |
| 50 | 5 | 46.27 |
| 50 | 10 | 37.09 |
| 50 | 20 | 19.14 |

TABLE 45-9

*S. pneumonia* Viability After Exposure to 100 µg/L of Penicillin with Various Concentrations of DMSO

| Penicillin (µg/L) | DMSO (%) | *S. pneumonia* viability (%) |
|---|---|---|
| 100 | 0 | 40.93 |
| 100 | 5 | 45.09 |
| 100 | 10 | 35.80 |
| 100 | 20 | 21.76 |

The combination of 5% MSM with 25 µg/L of penicillin exhibited a synergistic reduction in the viability of *S. pneu-*

*monia*, leading to only 41% viability (see Table 10). Synergy as compared to the expected results based on MSM alone and penicillin alone is indicated in the Tables by an "*". In contrast, 5% MSM alone reduced viability by only approximately 5%, while 25 µg/L penicillin alone reduced viability by approximately 21%. Thus, the 5% MSM/25 µg/L of penicillin combination was unexpectedly more efficacious than expected based on the results obtained with MSM or penicillin alone.

Moreover, as with DMSO, certain concentrations of MSM allowed lower concentrations of penicillin to reduce bacterial viability nearly as effectively as higher concentrations. For example, 20% MSM with 100 µg/L penicillin reduced *S. pneumonia* viability to 21.37%, 20% MSM with 50 µg/L penicillin reduced *S. pneumonia* viability to 20.75%. Thus, with use of 20% MSM, the required concentration of penicillin is reduced by one-half. Continuing this trend is the combination of 20% MSM with 25 µg/L penicillin reduced *S. pneumonia* viability to approximately 25%. Similarly, though with a less robust reduction in bacterial viability, 5% MSM allowed 25 µg/L penicillin to perform nearly identically to 100 µg/L penicillin (compare Tables 45-10 through 45-12 for 25 µg/L penicillin).

TABLE 45-10

*S. pneumonia* Viability After Exposure to 25 µg/L of Penicillin with Various Concentrations of MSM

| Penicillin (µg/L) | MSM (%) | *S. pneumonia* viability (%) |
|---|---|---|
| 25 | 0 | 79.82 |
| 25 | 5 | 41.23* |
| 25 | 10 | 41.83 |
| 25 | 20 | 25.36 |

TABLE 45-11

*S. pneumonia* Viability After Exposure to 50 µg/L of Penicillin with Various Concentrations of MSM

| Penicillin (µg/L) | MSM (%) | *S. pneumonia* viability (%) |
|---|---|---|
| 50 | 0 | 42.70 |
| 50 | 5 | 41.23 |
| 50 | 10 | 47.47 |
| 50 | 20 | 20.75 |

TABLE 45-12

*S. pneumonia* Viability After Exposure to 100 µg/L of Penicillin with Various Concentrations of MSM

| Penicillin (µg/L) | MSM (%) | *S. pneumonia* viability |
|---|---|---|
| 100 | 0 | 40.93 |
| 100 | 5 | 41.75 |
| 100 | 10 | 36.67 |
| 100 | 20 | 21.37 |

Based on the synergistic results seen in certain combinations of MSM or DMSO with penicillin, the present study was performed in order to identify the various combinations of MSM, DMSO, and penicillin that yielded synergistic reductions in bacterial viability as compared to combination the effects of combining DMSO, MSM, and penicillin on bacterial viability. This study was also designed to identify combinations of the three compounds that advantageously allow one or more of the compounds to be reduced, yet still efficaciously reduce bacterial viability.

DMSO at 5, 10, and 20% was combined individually with MSM at one of 5, 10, or 20% and penicillin at one of 25, 50, or 100 µg/L. Viability was assessed as described above. Viability data are presented in Table 45-13. The "*" symbol represents synergistic results as compared to the corresponding combination of DMSO and penicillin The "ψ" symbol represents synergistic results as compared to the corresponding combination of MSM and penicillin. The values for the reduction in bacterial viability were added together to determine the threshold reduction for synergy. For example, 5% DMSO reduces viability by approximately 25% and 25 µg/L penicillin reduced viability by approximately 21%, for a total combined reduction expected of approximately 46%. This represents 64% viability. Thus, if the combination of 5% MSM, 5% DMSO, and 25 µg/L penicillin results in less than 64% viability, synergy between the compounds has been identified.

Several combinations of MSM, DMSO, and penicillin yield synergistic improvements in bacterial reduction. For example, the combination of 5% DMSO, 5% MSM, and 25 µg/L penicillin reduced bacterial viability to approximately 52% (see Table 45-13). Five percent DMSO in combination with 25 µg/L penicillin reduced bacteria viability to approximately 64% (e.g., about a 46% reduction, based on the individual reduction seen with 5% DMSO, see Table 45-1, and the individual reduction seen with 25 µg/L penicillin). Thus, the combination of all three compounds reduced bacterial viability by about an additional 12%. Similarly, the combination of 5% MSM with 25 µg/L penicillin resulted in bacteria viability of about 74%, while the combination of all three compounds reduced viability by nearly an additional 22%.

In some combinations, synergistic results were detected with respect to both DMSO and penicillin as well as MSM plus penicillin For example, 10% DMSO in combination with 20% MSM and 25 µg/L penicillin is yielded a synergistic improved in antimicrobial activity as compared to both reference combinations. In other combinations, synergy was detected only with respect to either DMSO plus penicillin or MSM plus penicillin. For example, the combination of 5% MSM with 10% DMSO and 25 µg/L penicillin was synergistic with respect to MSM plus penicillin, but not with respect to DMSO plus penicillin.

In addition to the synergistic effects discussed above, there are several instances wherein the certain combinations of DMSO, MSM and penicillin allow for a reduction in the efficacious concentration of penicillin. For example, as shown in Table 45-13, the combination of 5% DMSO with 20% MSM yields very similar overall bacterial viability over the range of penicillin concentrations tested (from ~25% viability with 25 µg/L penicillin to ~18% viability with 100 µg/L penicillin). Additionally, 10% DMSO with 20% MSM resulted in nearly identical bacterial viabilities across the penicillin concentration range.

Similar results are seen with 20% DMSO in combination with 5, 10, or 20% MSM and any concentration of penicillin. These results reveal a slightly wider range of bacterial viability across the different penicillin concentrations, however, given that the reduction in all cases approaches approximately 90 to 95%, these combinations are all still effective.

TABLE 45-13

S. pneumonia Viability After Exposure to Various combinations of DMSO, MSM, and Penicillin

| DMSO (%) | MSM (%) | Penicillin (µg/L) | S. pneumonia viability (%) |
|---|---|---|---|
| 5 | 5 | 25 | 52.11*, Ψ |
| 5 | 5 | 50 | 43.36 |
| 5 | 5 | 100 | 53.03 |
| 5 | 10 | 25 | 51.82* |
| 5 | 10 | 50 | 44.52 |
| 5 | 10 | 100 | 31.33 |
| 5 | 20 | 25 | 24.91* |
| 5 | 20 | 50 | 19.20 |
| 5 | 20 | 100 | 18.12 |
| 10 | 5 | 25 | 44.41Ψ |
| 10 | 5 | 50 | 38.24 |
| 10 | 5 | 100 | 36.19 |
| 10 | 10 | 25 | 39.38 |
| 10 | 10 | 50 | 33.73 |
| 10 | 10 | 100 | 25.98 |
| 10 | 20 | 25 | 11.87*, Ψ |
| 10 | 20 | 50 | 11.03 |
| 10 | 20 | 100 | 10.96 |
| 20 | 5 | 25 | 12.74*, Ψ |
| 20 | 5 | 50 | 13.39Ψ |
| 20 | 5 | 100 | 9.28Ψ |
| 20 | 10 | 25 | 7.69*, Ψ |
| 20 | 10 | 50 | 7.74 |
| 20 | 10 | 100 | 5.58 |
| 20 | 20 | 25 | 4.93*, Ψ |
| 20 | 20 | 50 | 5.60 |
| 20 | 20 | 100 | 1.80 |

As discussed above, the structure of S. pyogenes differs from that of S. pneumonia, and therefore additional experiments were undertaken to evaluate the synergistic effects of various concentrations of DMSO and MSM, as well as combinations of DMSO, MSM, and penicillin.

DMSO was added to S. pyogenes cultures to final concentrations of 0.31, 0.63, 1.25, 2.50, 5.00, 10.0, or 20.0. At these concentrations, DMSO resulted in reductions in bacterial viability in a dose-dependent manner. See Table 45-14. MSM alone was added to S. pyogenes cultures to final concentrations of 0.31, 0.63, 1.25, 2.50, 5.00, 10.0, or 20.0. At these concentrations, MSM also resulted in reductions in bacterial viability in a dose-dependent manner. See Table 45-15.

TABLE 45-14

Viability of S. pyogenes After DMSO Exposure

| DMSO Concentration | Viability of S. pyogenes (%) |
|---|---|
| 0.31 | 100 |
| 0.63 | 100 |
| 1.25 | 100 |
| 2.50 | 100 |
| 5.00 | 96.66 |
| 10.0 | 14.50 |
| 20.0 | 5.14 |

TABLE 45-15

Viability of S. pyogenes After MSM Exposure

| MSM Concentration | Viability of S. pyogenes (%) |
|---|---|
| 0.31 | 100 |
| 0.63 | 100 |
| 1.25 | 100 |
| 2.50 | 100 |
| 5.00 | 95.88 |
| 10.0 | 23.94 |
| 20.0 | 15.18 |

MSM and DMSO in combination were evaluated for their antibacterial effects on S. pyogenes. DMSO at 2.5%, 5%, and 8% was combined with MSM at 0% (DMSO only control), 2.5%, 5%, and 10%. As shown in Tables 16, 17, and 18 certain combinations of MSM with DMSO are synergistic as compared to the effects of either DMSO or MSM alone. Synergistic results as compared to DMSO or MSM alone are indicated by an "*". For example, addition of 2.5% MSM to 2.5% DMSO reduced bacterial viability to approximately 65% (see Table 16), while the no effect of these concentrations of MSM and DMSO would be expected, as individually, neither compound reduced bacterial viability. The synergistic effect is also seen with 2.5% DMSO and 5% MSM, where bacterial viability is reduced by nearly 83% (as compared to an expected 4% reduction based on the compounds' effects alone). Synergy is also seen with 5% DMSO in combination with any concentration of MSM. Thus, in some embodiments, DMSO at 5% induces synergistic reductions in bacterial viability in combination with any concentration of MSM between 2.5% and 10%. In some embodiments, DMSO at 2.5% and MSM in concentrations between 2.5% and 5% are advantageously and unexpectedly synergistic at reducing bacteria viability.

TABLE 45-16

Viability of S. pyogenes After Exposure to Various Concentrations of MSM in 2.5 DMSO

| DMSO (%) | MSM (%) | S. pyogenes viability (%) |
|---|---|---|
| 2.5 | 0 | 100 |
| 2.5 | 2.5 | 65.06* |
| 2.5 | 5.0 | 17.71* |
| 2.5 | 10.0 | 16.37 |

TABLE 45-17

Viability of S. pyogenes After Exposure to Various Concentrations of MSM in 5 DMSO

| DMSO (%) | MSM (%) | S. pyogenes viability (%) |
|---|---|---|
| 5.0 | 0 | 96.66 |
| 5.0 | 2.5 | 36.21* |
| 5.0 | 5.0 | 7.87* |
| 5.0 | 10.0 | 7.64* |

TABLE 45-18

Viability of S. pyogenes After Exposure to Various Concentrations of MSM in 8 DMSO

| DMSO (%) | MSM (%) | S. pyogenes viability (%) |
|---|---|---|
| 8.0 | 0 | 9.96 |
| 8.0 | 2.5 | 14.37 |
| 8.0 | 5.0 | 5.97 |
| 8.0 | 10.0 | 5.60 |

Various concentrations of penicillin alone were evaluated for their ability to reduce viability of *S. pyogenes*. As shown in Table 45-19, penicillin decreased bacterial viability in a dose-dependent fashion.

TABLE 45-19

*S pyogenes* Viability After Exposure to Various Concentrations of Penicillin

| Penicillin (µg/L) | *S. pyogenes* viability (%) |
|---|---|
| 1.56 | 100 |
| 3.13 | 100 |
| 6.25 | 100 |
| 12.5 | 13.16 |
| 25.0 | 9.07 |
| 50 | 9.57 |
| 100 | 9.40 |

Due to the highly efficacious nature of penicillin concentrations at or above 25 µg/L, DMSO was combined with concentrations of penicillin that were less efficacious (ranging from 3.125 to 12.5 µg/L). As such, identification of synergism between DMSO and penicillin would be less likely to be mathematically obscured.

As shown in Tables 45-20, 45-21, and 45-22 (identified by an "*") several combinations of DMSO and penicillin resulted in synergistic results. For example, 5% DMSO in combination with 3.125 µg/L penicillin, based on the efficacy of the two compounds alone, would only be expected to reduce bacteria viability by about 4%. However, when combined, the actual reduction was approximately 10-fold greater (viability reduced to ~61%, see Table 45-20). Similar synergistic effects were seen when 5% DMSO was combined with 6.25 µg/L or 12.5 µg/L penicillin (see Table 45-21 and 45-22, respectively).

TABLE 45-20

*S pyogenes* Viability After Exposure to 3.13 µg/L of Penicillin with Various Concentrations of DMSO

| Penicillin (µg/L) | DMSO (%) | *S. pyogenes* viability (%) |
|---|---|---|
| 3.13 | 0 | 100 |
| 3.13 | 2.5 | 100 |
| 3.13 | 5.0 | 60.85* |
| 3.13 | 8.0 | 12.90 |

TABLE 45-21

*S pyogenes* Viability After Exposure to 6.25 µg/L of Penicillin with Various Concentrations of DMSO

| Penicillin (µg/L) | DMSO (%) | *S. pyogenes* viability (%) |
|---|---|---|
| 6.25 | 0 | 100 |
| 6.25 | 2.5 | 100 |
| 6.25 | 5.0 | 60.23* |
| 6.25 | 8.0 | 6.91* |

TABLE 45-22

*S pyogenes* Viability After Exposure to 12.5 µg/L of Penicillin with Various Concentrations of DMSO

| Penicillin (µg/L) | DMSO (%) | *S. pyogenes* viability (%) |
|---|---|---|
| 12.5 | 0 | 13.16 |
| 12.5 | 2.5 | 19.63 |

TABLE 45-22-continued

*S pyogenes* Viability After Exposure to 12.5 µg/L of Penicillin with Various Concentrations of DMSO

| Penicillin (µg/L) | DMSO (%) | *S. pyogenes* viability (%) |
|---|---|---|
| 12.5 | 5.0 | 14.77* |
| 12.5 | 8.0 | 6.43 |

Similar studies to those using DMSO were performed by combining MSM with penicillin ranging from 3.125 to 12.5 µg/L. Results are shown in Tables 45-23, 45-24, and 45-25. Synergy is indicated by an "*". As with DMSO, previously ineffective concentrations of MSM and penicillin were effective in combination at reducing bacterial viability. When taken alone, no effect would be expected from 3.13 µg/L penicillin with 2.5% MSM, however an 8% reduction in viability is detected (see Table 45-23). These effects are more pronounced with the combination of 6.25 µg/L penicillin with MSM. For example, 5% MSM with 6.25 µg/L penicillin would be expected to yield a 96% viable bacterial population (see Table 45-24). However, data indicate that viability was reduced to about 17%, nearly an 80% reduction from expected results. Synergy was not detected when 12.5 µg/L penicillin was used, due to the efficacy of that concentration of penicillin alone.

TABLE 45-23

*S pyogenes* Viability After Exposure to 3.13 µg/L of Penicillin with Various Concentrations of MSM

| Penicillin (µg/L) | MSM (%) | *S. pyogenes* viability (%) |
|---|---|---|
| 3.13 | 0 | 100 |
| 3.13 | 2.5 | 92.89* |
| 3.13 | 5.0 | 78.31* |
| 3.13 | 8.0 | 9.91* |

TABLE 45-24

*S pyogenes* Viability After Exposure to 6.25 µg/L of Penicillin with Various Concentrations of MSM

| Penicillin (µg/L) | MSM (%) | *S. pyogenes* viability (%) |
|---|---|---|
| 6.25 | 0 | 100 |
| 6.25 | 2.5 | 90.11* |
| 6.25 | 5.0 | 17.42* |
| 6.25 | 8.0 | 10.77* |

TABLE 45-25

*S pyogenes* Viability After Exposure to 12.5 µg/L of Penicillin with Various Concentrations of MSM

| Penicillin (µg/L) | MSM (%) | *S. pyogenes* viability (%) |
|---|---|---|
| 12.5 | 0 | 13.16 |
| 12.5 | 2.5 | 16.33 |
| 12.5 | 5.0 | 12.85 |
| 12.5 | 8.0 | 16.02 |

As with *S. pneumonia*, combinations of various concentrations of DMSO, MSM, and penicillin were evaluated for their effects on bacterial viability and possible synergistic activity as compared to MSM with penicillin or DMSO with penicillin. Results are shown in Table 45-26. Synergy as compared to DMSO and penicillin is indicated by an "*" while synergy as compared to MSM and penicillin is indicated by an "ψ". As can be seen by the data in Table 45-26, substantial synergy was detected across the various concentrations of compounds. Most combinations of DMSO and MSM exhibited a dose-response curve based on the concentration of penicillin used. Based on the efficacy of 12.5 μg/L alone, it is not unexpected that combinations of this concentration of penicillin with DMSO and MSM should be more effective. Of interest, the previously ineffective concentrations of penicillin are rendered effective in a dose dependent manner by combination with DMSO and MSM. For example, 2.5% DMSO with 5% MSM and 3.125 μg/L penicillin would be expected to reduce bacterial viability to between 100% and 96% (when compared to DMSO+penicillin and MSM+penicillin, respectively). However, the combination of all three reduced bacterial viability to about 19%. The expected results are similar for combinations with 6.25 μg/L penicillin, but the actual combination reduced bacterial viability even further, to about 13%. Increasing concentrations of the various compounds does not result in larger reductions in bacterial viability. For example, the combination of 8% DMSO with 2.5% MSM and 3.125 μg/L penicillin appears to be more effective than 8% DMSO with 2.5% MSM and 12.5 μg/L penicillin.

TABLE 45-26

*S. pneumonia* Viability After Exposure to Various combinations of DMSO, MSM, and Penicillin

| DMSO (%) | MSM (%) | Penicillin (μg/L) | *S. pyogenes* viability (%) |
|---|---|---|---|
| 2.5 | 2.5 | 3.125 | 91.74*, ψ |
| 2.5 | 2.5 | 6.25 | 60.55*, ψ |
| 2.5 | 2.5 | 12.5 | 8.08*, ψ |
| 2.5 | 5 | 3.125 | 18.72*, ψ |
| 2.5 | 5 | 6.25 | 13.38*, ψ |
| 2.5 | 5 | 12.5 | 9.41* |
| 2.5 | 10 | 3.125 | 16.05*, ψ |
| 2.5 | 10 | 6.25 | 11.78*, ψ |
| 2.5 | 10 | 12.5 | 11.77* |
| 5 | 2.5 | 3.125 | 14.60*, ψ |
| 5 | 2.5 | 6.25 | 10.44*, ψ |
| 5 | 2.5 | 12.5 | 9.55*, ψ |
| 8 | 2.5 | 3.125 | 9.55*, ψ |
| 8 | 2.5 | 6.25 | 10.28ψ |
| 8 | 2.5 | 12.5 | 15.55ψ |

These studies indicate that at certain concentrations MSM, DMSO or a combination thereof can inhibit *Streptococcus pyogenes* and *Streptococcus Pneumonia* supporting a possible use of such substances to prevent or inhibit *Streptococcus pyogenes* and *Streptococcus Pneumonia* growth.

Example 22

Probiotic Growth in Media Supplemented with MSM

This example describes probiotic growth in media supplemented with MSM.

*Lactobacillus acidophilus, Bifidobacterium bifidum, Lactobacillus delbrueckii*, and *Bacillus coagulans*, growth media were supplemented with MSM at 0, 0.125, 0.25, 0.5, 1.0, 2.5, and 5%. A single 5% MSM stock of MRS broth was prepared and used to make each media composition. Media for the *lactobacillus* organisms was prepared adding the appropriate amount of MSM to 99 mL of MRS broth. For *Bifidobacterium bifidum*, 99 mL of MRS broth was prepared with the respective MSM concentrations and 0.05% L-cysteine. For *Bacillus coagulans*, 99 mL of tryptic soy broth was supplemented with the appropriate amount of MSM.

These media solutions were inoculated with each probiotic organism and incubated at 35° C.±0.5° C. in $CO_2$ for a total of 72 hours for all solutions, except *Bifidobacterium bifidum*, which was grown in anaerobic conditions. Samples of each media were collected at 0, 8, 16, 24, 32, 40, 48, 56, 64, and 72 hours. *Lactobacillus* samples were plated on MRS agar, *Bifidobacterium bifidum* samples were plated on MRS+L-cysteine agar, and *Bacillus coagulans* samples were plated on tryptic soy agar. Plates were incubated at 35° C.±0.5° C. in $CO_2$ for a total of 72 hours for all solutions, except *Bacillus coagulans*, which was grown for 48 hours. Plates were then counted. Negative controls (stock media and plating controls) were free of microbial growth. Data are presented in Cfu/mL. Results from these studies are presented in the below Tables.

TABLE 46

Growth of *Lactobacillus acidophilus* in Media Fortified with MSM

| Time | 0% MSM | 0.125% MSM | 0.2% MSM | 0.50% MSM | 1% MSM | 2.5% MSM | 5% MSM |
|---|---|---|---|---|---|---|---|
| 0 | 1.48 | 1.37 | 1.37 | 1.30 | 1.48 | 1.48 | 1.52 |
| 8 | 1.48 | 2.19 | 1.43 | 2.01 | 2.25 | 2.20 | 1.37 |
| 16 | 4.87 | 4.83 | 5.74 | 3.82 | 3.79 | 4.24 | 2.69 |
| 24 | 6.97 | 7.14 | 8.19 | 6.47 | 6.77 | 5.78 | 5.36 |
| 32 | 9.47 | 9.15 | 9.85 | 9.15 | 9.05 | 9.16 | 8.91 |
| 40 | 7.08 | 9.53 | 9.50 | 9.58 | 9.49 | 9.35 | 9.25 |
| 48 | 7.27 | 9.59 | 9.32 | 10.45 | 10.98 | 10.16 | 10.88 |
| 56 | 7.20 | 10.16 | 9.26 | 9.33 | 10.90 | 11.10 | 10.01 |
| 64 | 7.29 | 9.40 | 9.37 | 9.53 | 10.34 | 11.58 | 8.95 |
| 72 | 7.19 | 8.56 | 8.36 | 8.57 | 8.68 | 8.44 | 6.66 |

TABLE 47

Growth of *Lactobacillus bulgaricus* in Media Fortified with MSM

| Time | 0% MSM | 0.125% MSM | 0.2% MSM | 0.50% MSM | 1% MSM | 2.5% MSM | 5% MSM |
|---|---|---|---|---|---|---|---|
| 0 | 2.22 | 2.29 | 2.25 | 2.23 | 2.29 | 2.26 | 2.19 |
| 8 | 3.56 | 4.15 | 4.08 | 4.42 | 4.83 | 4.57 | 3.28 |
| 16 | 8.09 | 8.22 | 8.34 | 8.28 | 8.36 | 8.09 | 7.39 |
| 24 | 8.71 | 9.04 | 9.10 | 9.05 | 9.03 | 9.01 | 8.50 |
| 32 | 9.29 | 8.55 | 9.60 | 9.54 | 9.31 | 9.15 | 9.29 |
| 40 | 9.32 | 9.29 | 9.11 | 9.40 | 9.34 | 9.27 | 9.37 |
| 48 | 10.81 | 10.94 | 11.07 | 10.82 | 11.23 | 11.37 | 10.92 |
| 56 | 7.69 | 8.00 | 8.79 | 9.14 | 8.11 | 8.23 | 10.07 |
| 64 | 8.78 | 8.59 | 8.79 | 8.80 | 6.50 | 8.75 | 10.96 |
| 72 | 6.56 | 6.74 | 6.72 | 6.72 | 6.45 | 6.51 | 8.62 |

TABLE 48

Growth of *Bacillus coagulans* in Media Fortified with MSM

| Time | 0% MSM | 0.125% MSM | 0.2% MSM | 0.50% MSM | 1% MSM | 2.5% MSM | 5% MSM |
|---|---|---|---|---|---|---|---|
| 0 | 1.43 | 1.52 | 1.67 | 1.48 | 1.30 | 1.43 | 1.56 |
| 8 | 5.05 | 4.81 | 4.94 | 4.42 | 4.98 | 5.13 | 4.61 |
| 16 | 6.75 | 6.95 | 7.19 | 6.94 | 7.29 | 7.05 | 7.56 |
| 24 | 10.34 | 9.87 | 10.34 | 10.29 | 10.30 | 10.22 | 10.48 |
| 32 | 10.70 | 11.06 | 11.25 | 11.05 | 11.42 | 11.70 | 11.55 |
| 40 | 10.70 | 11.72 | 11.34 | 10.25 | 11.02 | 10.55 | 10.85 |
| 48 | 11.07 | 11.56 | 9.94 | 10.40 | 10.38 | 10.88 | 10.22 |
| 56 | 11.35 | 9.60 | 11.45 | 10.76 | 10.86 | 10.86 | 11.1 |
| 64 | 11.01 | 12.13 | 11.37 | 10.45 | 10.40 | 10.97 | 10.75 |
| 72 | 10.92 | 10.14 | 10.94 | 10.86 | 10.70 | 11.05 | 11.81 |

TABLE 49

Growth of Bifidobacteruim bifidum in Media Fortified with MSM

| Time | 0% MSM | 0.125% MSM | 0.2% MSM | 0.50% MSM | 1% MSM | 2.5% MSM | 5% MSM |
|---|---|---|---|---|---|---|---|
| 0  | 1.67  | 1.64  | 1.82  | 1.85 | 1.48 | 1.64  | 1.00  |
| 8  | 2.30  | 1.73  | 2.08  | 1.99 | 1.70 | 1.60  | 2.29  |
| 16 | 5.33  | 6.55  | 5.22  | 6.53 | 6.81 | 6.21  | 6.71  |
| 24 | 5.86  | 2.70  | 6.15  | 3.14 | 2.75 | 2.52  | 5.72  |
| 32 | 8.80  | 3.37  | 5.03  | 3.52 | 3.37 | 3.37  | 10.32 |
| 40 | 9.71  | 4.19  | 8.14  | 4.62 | 3.48 | 3.52  | 12.02 |
| 48 | 10.60 | 6.41  | 8.55  | 4.51 | 3.90 | 3.95  | 10.54 |
| 56 | 10.42 | 9.97  | 9.00  | 6.05 | 8.32 | 8.35  | 10.92 |
| 64 | 10.65 | 11.34 | 10.19 | 9.55 | 8.02 | 8.30  | 12.04 |
| 72 | 11.21 | 10.00 | 9.10  | 7.52 | 9.52 | 10.12 | 12.43 |

These studies indicate that MSM can enhance the growth of probiotic organisms depending upon the concentration of MSM employed.

Example 23

Effect of MSM on H1N1 and Herpes Simplex Virus

This example shows the ability of MSM to enhance or reduce infectivity of Swine-like H1N1 Influenza A virus strain A/California/04/2009 (CDC ID #2009712047), Rhinovirus type 14 (ATCC #VR-284), and Herpes Simplex Virus type 1 (ATCC #VR-260). The study was performed as a Pre-treatment test of eight concentrations of MSM. Virus yield reduction/enhancement test and subsequent virus titration was conducted in three replicates. The inhibitory concentrations of MSM ($IC_{50}$ or $IC_{90}$—the concentration at which growth or activity is inhibited by 50% or 90%) were also determined in this study.

Cytotoxicity of MSM was determined prior to the test. Eight concentrations of MSM (16%. 14%, 12%, 10%, 8.0%, 6.0%, 1.0%, and 0.5%) were tested on MDCK cells (ATCC # CCL-34). MSM concentrations 16% through 8% were toxic for MDCK cells and completely destroyed cell monolayers. Concentrations 6% through 0.5% produced no visible cytotoxic effect. $TC_{50}$ (concentration at which the compound, alone, kills 50% of uninfected cells) was determined to be approximately 7%. Therefore, this concentration was the first lowest non-cytotoxic dilution used in testing.

A total of eight MSM concentrations were included in testing: 7% (~74.365 mM); 6% (~63.742 mM); 5% (~53.118 mM); 4% (~42.494 mM); 3% (~31.871 mM); 2% (~21.247 mM); 1% (~10.624 mM); and 0.5% (~5.312 mM). A detailed description of the material and methods are provided below.

Host Cells. Madin Darby Canis Kidney (MDCK [ATCC#CCL-34]) cells, MRC-5 (Human lung fibroblasts; [ATCC #CCL-171]) cells, and Vero (African green monkey kidney [ATCC#CCL-81]) cells were maintained as monolayers in disposable cell culture labware and were used for the Pre-Treatment Antiviral Test of Swine-like H1N1 Influenza A virus strain A/California/04/2009, Rhinovirus type 14 (ATCC #VR-284), and HSV-1 (ATCC #VR-260), respectively. Prior to testing, host cell cultures were seeded onto the appropriate cell culture plates. Cell monolayers were 80 to 90% confluent and less than 48 hours old before inoculation with the virus. The growth medium (GM) and maintenance medium (MM) was 1×EMEM and/or Advanced MEM with appropriate supplements.

Determination of test product cytotoxicity. The highest non-cytotoxic concentration of the test product was determined prior to the test. MDCK cell culture was washed with Phosphate Buffered Saline (PBS) and incubated with the following dilutions of a product: 16%, 14%, 12%, 10%, 8.0%, 6.0%, 1.0%, and 0.5%. Incubation was 1 hour at 37°±2° C. in a $CO_2$ incubator, After incubation, the treated cells were overlaid with MM. The plates were incubated in a $CO_2$ incubator for 3 days at 37°±2° C. Toxicity was monitored using an Inverted Compound Microscope. A cytotoxicity test performed as outlined in the Study Protocol, showed that the product concentrations 16% through 8% were toxic for MDCK cells and completely destroyed cell monolayers. Product concentrations 6% through 0.5% produced no visible cytotoxic effect. $TC_{50}$ (concentration at which the compound, alone, kills 50% of uninfected cells) was determined to be approximately 7%.

A. Pre-Treatment Test. Test Product stock solution was prepared as follows: 35.0 gram of product was diluted in 100 mL PBS and heated at 40° C. until dissolved. The 35% solution was kept at 40° C. until higher dilutions were prepared (see Project Notes [Form No. 95-G-001] in Addendum VI of this Final Report). MDCK, MRC-5 and Vero cell cultures were washed with PBS and incubated with the following product dilutions: 7%, 6%, 5%, 4%, 3%, 2%, 1%, and 0.5%. Incubation was 1 hour at 37°±2° C. in a $CO_2$, incubator. After incubation had been completed approximately 300-1000 IU (infectious units) of each of the test viruses were added to the appropriate treated cells. The testing was performed in three replicates. The plates were incubated in a $CO_2$ incubator for 6 days at the temperature appropriate for each virus. CPE was monitored using an Inverted Compound Microscope. All data resulting from the test are included in Addendum IV of this Final Report (Forms No.: 95-G-001, 91-L-002, and 07-L-002).

B. Toxicity Control for Pre-Treatment Test. MDCK, MRC-5 and Vero cell cultures were washed with PBS and incubated with the product dilutions 7% through 0.5%, Incubation was 1 hour at 37°±2° C. in a $CO_2$ incubator. After incubation, the treated cells were overlaid with MM. The plates were incubated in a $CO_2$ incubator for 6 days at the temperature appropriate for each virus. Toxicity was monitored using an Inverted Compound Microscope. The results of the cytotoxicity tests are presented in Table 50.

C. Virus Control. MDCK, MRC-5 and Vero cell cultures were washed with PBS and incubated with MM. Incubation was 1 hour at 37°±2° C. in a $CO_2$ incubator. After incubation had been completed approximately 300-1000 IU (infectious units) of each of the test viruses were added to the cells. Three replicates of Virus Control were performed. The plates were incubated in a $CO_2$ incubator for 6 days at the temperature appropriate for each virus. CPE was monitored using an Inverted Compound Microscope.

D. Negative Control. Intact cell culture monolayers served as the negative control. The GM was replaced by MM in all Negative control wells.

E. Determination of the reduction and/or enhancement of virus yield. After Virus Control had reached the maximum cytopathic effect (complete destruction of the monolayer), samples from the test wells and virus control wells were taken for titration. Ten-fold dilutions were made in MM and plated onto susceptible cells in four replicates. The results of the virus yield reduction/enhancement tests are presented in the Tables 51 through 91.

Data Analysis. Virus population titer in cell cultures were expressed as $-\log_{10}$ of the 50% titration end point for infectivity. To calculate the viral titer, a 50% tissue culture infectious dose ($TCID_{50}$) calculation—the Quantal test (Spearman-Kärber Method)—was applied.

$$\log TCID_{50}=1-d(s-0.5)$$

Where:
l=−$\log_{10}$ of the lowest dilution;
d=difference between dilution steps;
s=sum of proportions of positive wells.

1.1 The highest compound concentration that produces a cytotoxic effect was determined as 50% of the toxic compound concentration ($TC_{50}$).

1.2 The percent reduction was calculated as follows:

$$\% \text{ Reduction} = \left[1 - \frac{TCID_{50} \text{ test}}{TCID_{50} \text{ virus control}}\right] \times 100$$

1.3 $TCID_{50}$ of virus population recovered from the test and virus control was used to calculate reduction or enhancement of virus infectivity. $IC_{50}$ was determined using GraphPad Prism 5, Inc. software. $IC_{90}$ was determined experimentally when present.

Test Acceptance Criteria. A valid test requires that: 1) cells in the Negative control wells are viable and attached to the bottom of the well; 2) the medium be free of contamination in all wells of the plate; and 3) Virus Control shows the presence of virus-specific CPE.

Reductions of virus population were observed for all three test viruses. MSM at 7% concentration produced following average reductions: 1.16 $\log_{10}$ reduction (93.08% reduction) of Swine-like H1N1 Influenza A virus; 2.50 $\log_{10}$ reduction (99.68% reduction) of Herpes Simplex Virus type 1 (HSV-1); 1.25 $\log_{10}$ reduction (94.38% reduction) of Rhinovirus type 14. MSM at 6% concentration produced following average reductions: 1.00 $\log_{10}$ reduction (90.00% reduction) of Swine-like H1N1 Influenza A virus; 1.00 $\log_{10}$ reduction (90.00% reduction) of HSV-1; 0.67 $\log_{10}$ reduction (78.62% reduction) of Rhinovirus type 14.

MSM at 5% concentration produced following average reductions: 0.41 $\log_{10}$ reduction (61.10% reduction) of Swine-like H1N1 Influenza A virus; 1.34 $\log_{10}$ reduction (95.43% reduction) of HSV-1; 0.09 $\log_{10}$ reduction (18.72% reduction) of Rhinovirus type 14. MSM at 4% concentration produced following average reductions: 0.16 $\log_{10}$ reduction (30.82% reduction) of Swine-like H1N1 Influenza A virus; 1.59 $\log_{10}$ reduction (97.43% reduction) of HSV-1; 0.28 $\log_{10}$ reduction (47.52% reduction) of Rhinovirus type 14. MSM at 3% concentration produced following average reductions: 0.00 $\log_{10}$ reduction (00.00% reduction) of Swine-like H1N1 Influenza A virus; 1.00 $\log_{10}$ reduction (90.00% reduction) of HSV-1; 0.11 $\log_{10}$ reduction (22.38% reduction) of Rhinovirus type 14. MSM at 2% concentration produced following average reductions: 0.41 $\log_{10}$ reduction (61.10% reduction) of Swine-like H1N1 Influenza A virus; 0.84 $\log_{10}$ reduction (85.55% reduction) of HSV-1; 0.42 $\log_{10}$ reduction (61.98% reduction) of Rhinovirus type 14. MSM at 1% concentration produced following average reductions: 0.25 $\log_{10}$ reduction (43.77% reduction) of Swine-like H1N1 Influenza A virus; 0.67 $\log_{10}$ reduction (78.62% reduction) of HSV-1; 0.14 $\log_{10}$ reduction (27.56% reduction) of Rhinovirus type 14. MSM at 0.5% concentration produced following average reductions: 0.66 $\log_{10}$ reduction (78.12% reduction) of Swine-like H1N1 Influenza A virus; 0.25 $\log_{10}$ reduction (43.77% reduction) of HSV-1; 0.40 $\log_{10}$ reduction (60.19% reduction) of Rhinovirus type 14.

Enhancement/stimulation of virus infectivity was observed for Swine-like H1N1 Influenza A virus treated with 3% MSM. The average enhancement of virus population was 0.17 $\log_{10}$ (32.39%). A total of three MSM concentrations enhanced infectivity of Rhinovirus type 14. MSM at 5% concentration produced an average of 0.053 $\log_{10}$ enhancement (11.49%). Three percent MSM produced an average of 0.11 $\log_{10}$ enhancement (22.38%); and 1% MSM produced an average of 0.11 $\log_{10}$ enhancement (22.38%). All of the virus infectivity enhancements/stimulations determined in this study were situated within the range of normal variation for virus population and were not significant. An Inhibitory concentration of MSM at which growth or activity is inhibited by 50% ($IC_{50}$) was computed using nonlinear regression Dose-Response (GraphPad Prism 5, software). The best-fit MSM $IC_{50}$ and $IC_{50}$ values with 95% confidence intervals were calculated for each test virus. For Swine-like H1N1 Influenza A virus, the best-fit value of MSM $IC_{50}$ was 5.114 mM. $IC_{50}$ with 95% confidence interval was varying from 0.008038 mM to 3253 mM. For HSV-1, the best-fit value of MSM $IC_{50}$ was determined to be 10.13 mM with an $IC_{50}$ with 95% confidence interval varying from 7.144 mM to 14.37 mM. For Rhinovirus type 14, the best fit value of MSM $IC_{50}$ was 38.16 mM. $IC_{50}$ with 95% confidence interval was in the range of 13.07 mM to 111.4 mM. $IC_{90}$ (1.0 $\log_{10}$ reduction) were determined experimentally for HSV-1 and Swine-like Influenza A H1N1. However, due to interception of multiple MSM concentrations with the 90% reduction axis, $IC_{90}$ experimental values cannot be considered precise.

MSM tested at eight different concentrations against HSV-1, Swine-like Influenza A H1N1 and Rhinovirus produced U-shaped dose-response curves. For instance: 4% MSM (1.00 $\log_{10}$ reduction) was more effective against HSV-1 than 6% MSM (1.59 $\log_{10}$ reduction); 0.5% MSM (0.66 $\log_{10}$ reduction) was more or equally effective against Swine-like Influenza A H1N1 than 5% MSM (0.41 $\log_{10}$ reduction); concentrations 4% through 0.5% were more or equally effective against Rhinovirus than 5% MSM. It is possible, if confirmed in further research, that U-shaped MSM effects represent a stable event.

This study indicates MSM can be used as an antiviral product. Non-cytotoxic concentrations of 7% and 6% reduced populations of enveloped viruses such as HSV-1 and Swine-like Influenza A H1N1 by more than 1.0 $\log_{10}$. Tables 50 through 91 include the results for the aforementioned studies.

Table 50 presents Cytotoxicity Test for eight product concentrations performed in parallel with Pre-Treatment test using MDCK, MRC-5, and Vero cell cultures.

TABLE 50

| Test Product: Methylsulfonylmethane, lot# 0902951 | | | | | | | | |
|---|---|---|---|---|---|---|---|---|
| Cell Culture | Test Product Cytotoxicity | | | | | | | |
| Designation | 7% | 6% | 5% | 4% | 3% | 2% | 1% | 0.5% |
| Vero | 00 | 00 | 00 | 00 | 00 | 00 | 00 | 00 |
| MDCK | ++ | ++ | 00 | 00 | 00 | 00 | 00 | 00 |
| MRC-5 | ++ | 00 | 00 | 00 | 00 | 00 | 00 | 00 |

+ = CPE Present
0 = CPE not detected

Tables 51 through 58 present the Virus Control infectivity ($TCID_{50}$), the average infectivity ($TCID_{50}$), and the $\log_{10}$ and percent reductions observed in Pre-treatment test of the Test Product, Methylsulfonylmethane (Lot Number 0902951), and Swine-like H1N1 Influenza A virus strain A/California/04/2009 (CDC ID #2009712047).

TABLE 51

Reduction of Infectivity
Test Product: Methylsulfonylmethane, 7% (lot# 0902951)
Virus: Swine-like Influenza A H1N1 strain A/California/04/2009 CDC ID # 2009712047
Host Cell Line: MDCK Host Cell Line ATCC # CCL-34

| Dilutions | Virus Control | | | Test Product | | | Cell |
| --- | --- | --- | --- | --- | --- | --- | --- |
| ($-\log_{10}$) | Rep. 1 | Rep. 2 | Rep. 3 | Rep. 1 | Rep. 2 | Rep. 3 | Control |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | 00+0 | 0000 | 0+00 | |
| -5 | 00+0 | +000 | +0+0 | 0000 | 0000 | 0000 | |
| -6 | 0000 | 0000 | 0000 | 0000 | 0000 | 0000 | |
| -7 | 0000 | 0000 | 0000 | 0000 | 0000 | 0000 | |
| $TCID_{50}$ | 4.75 $\log_{10}$ | 4.75 $\log_{10}$ | 5.00 $\log_{10}$ | 3.75 $\log_{10}$ | 3.50 $\log_{10}$ | 3.75 $\log_{10}$ | |
| Average $TCID_{50}$ | | 4.83 $\log_{10}$ | | | 3.67 $\log_{10}$ | | |
| Log Reduction* | | | | 1.08 $\log_{10}$ | 1.33 $\log_{10}$ | 1.08 $\log_{10}$ | |
| Average Log Reduction | | | | | 1.16 $\log_{10}$ | | |
| Percent Reduction | | | | 91.68% | 95.32% | 91.68% | |
| Average Percent Reduction** | | | | | 93.08% | | |

+ = CPE Present
0 = CPE not detected
NT = Not Tested
Rep = Replicate
*Log Reduction = Average $TCID_{50}$ of Virus Control − $TCID_{50}$ of the Test Replicate
**Average % Reduction (calculated from average $\log_{10}$ reduction) = 100 − (1/$TCID_{50}$ Reduction)*100

TABLE 52

Reduction of Infectivity
Test Product: Methylsulfonylmethane, 6% (lot# 0902951)
Virus: Swine-like Influenza A H1N1 strain A/California/04/2009 CDC ID # 2009712047
Host Cell Line: MDCK Host Cell Line ATCC # CCL-34

| Dilutions | Virus Control | | | Test Product | | | Cell |
| --- | --- | --- | --- | --- | --- | --- | --- |
| ($-\log_{10}$) | Rep. 1 | Rep. 2 | Rep. 3 | Rep. 1 | Rep. 2 | Rep. 3 | Control |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | 0+00 | 000+ | +00+ | |
| -5 | 00+0 | +000 | +0+0 | 0000 | 0000 | 0000 | |
| -6 | 0000 | 0000 | 0000 | 0000 | 0000 | 0000 | |
| -7 | 0000 | 0000 | 0000 | 0000 | 0000 | 0000 | |
| $TCID_{50}$ | 4.75 $\log_{10}$ | 4.75 $\log_{10}$ | 5.00 $\log_{10}$ | 3.75 $\log_{10}$ | 3.75 $\log_{10}$ | 4.00 $\log_{10}$ | |
| Average $TCID_{50}$ | | 4.83 $\log_{10}$ | | | 3.67 $\log_{10}$ | | |
| Log Reduction* | | | | 1.08 $\log_{10}$ | 1.08 $\log_{10}$ | 0.83 $\log_{10}$ | |
| Average Log Reduction | | | | | 1.00 $\log_{10}$ | | |
| Percent Reduction | | | | 91.68% | 91.68% | 85.21% | |
| Average Percent Reduction** | | | | | 90.00% | | |

+ = CPE Present
0 = CPE not detected
NT = Not Tested
Rep = Replicate
*Log Reduction = Average $TCID_{50}$ of Virus Control − $TCID_{50}$ of the Test Replicate
**Average % Reduction (calculated from average $\log_{10}$ reduction) = 100 − (1/$TCID_{50}$ Reduction)*100

TABLE 53

Reduction of Infectivity
Test Product: Methylsulfonylmethane, 5% (lot# 0902951)
Virus: Swine-like Influenza A H1N1 strain A/California/04/2009 CDC ID # 2009712047
Host Cell Line: MDCK Host Cell Line ATCC # CCL-34

| Dilutions | Virus Control | | | Test Product | | | Cell |
|---|---|---|---|---|---|---|---|
| ($-\log_{10}$) | Rep. 1 | Rep. 2 | Rep. 3 | Rep. 1 | Rep. 2 | Rep. 3 | Control |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | ++++ | 0+++ | +++0 | |
| -5 | 00+0 | +000 | +0+0 | 0000 | +000 | 0000 | |
| -6 | 0000 | 0000 | 0000 | 0000 | 0000 | 0000 | |
| -7 | 0000 | 0000 | 0000 | 0000 | 0000 | 0000 | |
| $TCID_{50}$ | 4.75 $\log_{10}$ | 4.75 $\log_{10}$ | 5.00 $\log_{10}$ | 4.50 $\log_{10}$ | 4.50 $\log_{10}$ | 4.25 $\log_{10}$ | |
| Average $TCID_{50}$ | | 4.83 $\log_{10}$ | | | 4.42 $\log_{10}$ | | |
| Log Reduction* | | | | 0.33 $\log_{10}$ | 0.33 $\log_{10}$ | 0.58 $\log_{10}$ | |
| Average Log Reduction | | | | | 0.41 $\log_{10}$ | | |
| Percent Reduction | | | | 53.23% | 53.23% | 73.70% | |
| Average Percent Reduction** | | | | | 61.10% | | |

+ = CPE Present
0 = CPE not detected
NT = Not Tested
Rep = Replicate
*Log Reduction = Average $TCID_{50}$ of Virus Control − $TCID_{50}$ of the Test Replicate
**Average % Reduction (calculated from average $\log_{10}$ reduction) = 100 − (1/$TCID_{50}$ Reduction)*100

TABLE 54

Reduction of Infectivity
Test Product: Methylsulfonylmethane, 4% (lot# 0902951)
Virus: Swine-like Influenza A H1N1 strain A/California/04/2009 CDC ID # 2009712047
Host Cell Line: MDCK Host Cell Line ATCC # CCL-34

| Dilutions | Virus Control | | | Test Product | | | Cell |
|---|---|---|---|---|---|---|---|
| ($-\log_{10}$) | Rep. 1 | Rep. 2 | Rep. 3 | Rep. 1 | Rep. 2 | Rep. 3 | Control |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | ++++ | 0+++ | ++++ | |
| -5 | 00+0 | +000 | +0+0 | 00+0 | 000+ | 000+ | |
| -6 | 0000 | 0000 | 0000 | 0000 | 0000 | 0000 | |
| -7 | 0000 | 0000 | 0000 | 0000 | 0000 | 0000 | |
| $TCID_{50}$ | 4.75 $\log_{10}$ | 4.75 $\log_{10}$ | 5.00 $\log_{10}$ | 4.75 $\log_{10}$ | 4.50 $\log_{10}$ | 4.75 $\log_{10}$ | |
| Average $TCID_{50}$ | | 4.83 $\log_{10}$ | | | 4.67 $\log_{10}$ | | |
| Log Reduction* | | | | 0.08 $\log_{10}$ | 0.33 $\log_{10}$ | 0.08 $\log_{10}$ | |
| Average Log Reduction | | | | | 0.16 $\log_{10}$ | | |
| Percent Reduction | | | | 16.82% | 53.23% | 16.82% | |
| Average Percent Reduction** | | | | | 30.82% | | |

+ = CPE Present
0 = CPE not detected
NT = Not Tested
Rep = Replicate
*Log Reduction = Average $TCID_{50}$ of Virus Control − $TCID_{50}$ of the Test Replicate
**Average % Reduction (calculated from average $\log_{10}$ reduction) = 100 − (1/$TCID_{50}$ Reduction)*100

TABLE 55

Reduction of Infectivity
Test Product: Methylsulfonylmethane, 3% (lot# 0902951)
Virus: Swine-like Influenza A H1N1 strain A/California/04/2009 CDC ID # 2009712047
Host Cell Line: MDCK Host Cell Line ATCC # CCL-34

| Dilutions ($-\log_{10}$) | Virus Control | | | Test Product | | | Cell Control |
|---|---|---|---|---|---|---|---|
| | Rep. 1 | Rep. 2 | Rep. 3 | Rep. 1 | Rep. 2 | Rep. 3 | |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | ++++ | ++++ | ++++ | |
| -5 | 00+0 | +000 | +0+0 | 00++ | +00+ | 0++0 | |
| -6 | 0000 | 0000 | 0000 | 0000 | 0000 | 0000 | |
| -7 | 0000 | 0000 | 0000 | 0000 | 0000 | 0000 | |
| $TCID_{50}$ | 4.75 $\log_{10}$ | 4.75 $\log_{10}$ | 5.00 $\log_{10}$ | 5.00 $\log_{10}$ | 5.00 $\log_{10}$ | 5.00 $\log_{10}$ | |
| Average $TCID_{50}$ | | 4.83 $\log_{10}$ | | | 5.00 $\log_{10}$ | | |
| Log Reduction | | | | 0.00 $\log_{10}$ | 0.00 $\log_{10}$ | 0.00 $\log_{10}$ | |
| Average Log Reduction | | | | | 0.00 $\log_{10}$ | | |
| Percent Reduction | | | | 00.00% | 00.00% | 00.00% | |
| Average Percent Reduction | | | | | 00.00% | | |

+ = CPE Present
0 = CPE not detected
NT = Not Tested
Rep = Replicate
*Log Reduction = Average $TCID_{50}$ of Virus Control − $TCID_{50}$ of the Test Replicate
**Average % Reduction (calculated from average $\log_{10}$ reduction) = 100 − (1/$TCID_{50}$ Reduction)*100

TABLE 56

Reduction of Infectivity
Test Product: Methylsulfonylmethane, 2% (lot# 0902951)
Virus: Swine-like Influenza A H1N1 strain A/California/04/2009 CDC ID # 2009712047
Host Cell Line: MDCK Host Cell Line ATCC # CCL-34

| Dilutions ($-\log_{10}$) | Virus Control | | | Test Product | | | Cell Control |
|---|---|---|---|---|---|---|---|
| | Rep. 1 | Rep. 2 | Rep. 3 | Rep. 1 | Rep. 2 | Rep. 3 | |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | ++++ | ++++ | +000 | |
| -5 | 00+0 | +000 | +0+0 | 0000 | 000+ | 0+00 | |
| -6 | 0000 | 0000 | 0000 | 0000 | 0000 | 0000 | |
| -7 | 0000 | 0000 | 0000 | 0000 | 0000 | 0000 | |
| $TCID_{50}$ | 4.75 $\log_{10}$ | 4.75 $\log_{10}$ | 5.00 $\log_{10}$ | 4.50 $\log_{10}$ | 4.75 $\log_{10}$ | 4.00 $\log_{10}$ | |
| Average $TCID_{50}$ | | 4.83 $\log_{10}$ | | | 4.42 $\log_{10}$ | | |
| Log Reduction* | | | | 0.33 $\log_{10}$ | 0.08 $\log_{10}$ | 0.83 $\log_{10}$ | |
| Average Log Reduction | | | | | 0.41 $\log_{10}$ | | |
| Percent Reduction | | | | 53.23% | 16.82% | 85.21% | |
| Average Percent Reduction** | | | | | 61.10% | | |

+ = CPE Present
0 = CPE not detected
NT = Not Tested
Rep = Replicate
*Log Reduction = Average $TCID_{50}$ of Virus Control − $TCID_{50}$ of the Test Replicate
**Average % Reduction (calculated from average $\log_{10}$ reduction) = 100 − (1/$TCID_{50}$ Reduction)*100

TABLE 57

Reduction of Infectivity
Test Product: Methylsulfonylmethane, 1% (lot# 0902951)
Virus: Swine-like Influenza A H1N1 strain A/California/04/2009 CDC ID # 2009712047
Host Cell Line: MDCK Host Cell Line ATCC # CCL-34

| Dilutions ($-\log_{10}$) | Virus Control | | | Test Product | | | Cell Control |
| --- | --- | --- | --- | --- | --- | --- | --- |
| | Rep. 1 | Rep. 2 | Rep. 3 | Rep. 1 | Rep. 2 | Rep. 3 | |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | ++0+ | ++++ | ++++ | |
| -5 | 00+0 | +000 | +0+0 | 00+0 | 000+ | 0000 | |
| -6 | 0000 | 0000 | 0000 | 0000 | 0000 | 0000 | |
| -7 | 0000 | 0000 | 0000 | 0000 | 0000 | 0000 | |
| $TCID_{50}$ | 4.75 $\log_{10}$ | 4.75 $\log_{10}$ | 5.00 $\log_{10}$ | 4.50 $\log_{10}$ | 4.75 $\log_{10}$ | 4.50 $\log_{10}$ | |
| Average $TCID_{50}$ | | 4.83 $\log_{10}$ | | | 4.58 $\log_{10}$ | | |
| Log Reduction* | | | | 0.33 $\log_{10}$ | 0.08 $\log_{10}$ | 0.33 $\log_{10}$ | |
| Average Log Reduction | | | | | 0.25 $\log_{10}$ | | |
| Percent Reduction | | | | 53.23% | 16.82% | 53.23% | |
| Average Percent Reduction** | | | | | 43.77% | | |

+ = CPE Present
0 = CPE not detected
NT = Not Tested
Rep = Replicate
*Log Reduction = Average $TCID_{50}$ of Virus Control − $TCID_{50}$ of the Test Replicate
**Average % Reduction (calculated from average $\log_{10}$ reduction) = 100 − (1/$TCID_{50}$ Reduction)*100

TABLE 58

Reduction of Infectivity
Test Product: Methylsulfonylmethane, 0.5% (lot# 0902951)
Virus: Swine-like Influenza A H1N1 strain A/California/04/2009 CDC ID # 2009712047
Host Cell Line: MDCK Host Cell Line ATCC # CCL-34

| Dilutions ($-\log_{10}$) | Virus Control | | | Test Product | | | Cell Control |
| --- | --- | --- | --- | --- | --- | --- | --- |
| | Rep. 1 | Rep. 2 | Rep. 3 | Rep. 1 | Rep. 2 | Rep. 3 | |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | +000 | ++++ | +++0 | |
| -5 | 00+0 | +000 | +0+0 | 0000 | 0000 | 0000 | |
| -6 | 0000 | 0000 | 0000 | 0000 | 0000 | 0000 | |
| -7 | 0000 | 0000 | 0000 | 0000 | 0000 | 0000 | |
| $TCID_{50}$ | 4.75 $\log_{10}$ | 4.75 $\log_{10}$ | 5.00 $\log_{10}$ | 3.75 $\log_{10}$ | 4.50 $\log_{10}$ | 4.25 $\log_{10}$ | |
| Average $TCID_{50}$ | | 4.83 $\log_{10}$ | | | 4.17 $\log_{10}$ | | |
| Log Reduction* | | | | 1.08 $\log_{10}$ | 0.33 $\log_{10}$ | 0.58 $\log_{10}$ | |
| Average Log Reduction | | | | | 0.66 $\log_{10}$ | | |
| Percent Reduction | | | | 91.68% | 53.23% | 73.70% | |
| Average Percent Reduction** | | | | | 78.12% | | |

+ = CPE Present
0 = CPE not detected
NT = Not Tested
Rep = Replicate
*Log Reduction = Average $TCID_{50}$ of Virus Control − $TCID_{50}$ of the Test Replicate
**Average % Reduction (calculated from average $\log_{10}$ reduction) = 100 − (1/$TCID_{50}$ Reduction)*100

Tables 59 through 67 present the Virus Control infectivity ($TCID_{50}$), the average infectivity ($TCID_{50}$), and the $log_{10}$ and percent reductions observed in Pre-treatment test of the Test Product, Methylsulfonylmethane (Lot Number 0902951), and Herpes Simplex Virus type I (ATCC # VR-260).

TABLE 59

Reduction of Infectivity
Test Product: Methylsulfonylmethane, 7% (lot# 0902951)
Virus: Herpes Simplex Virus strain HF ATCC # VR-260
Host Cell Line: Vero Host Cell Line ATCC # CCL-81

| Dilutions | Virus Control | | | Test Product | | | Cell |
|---|---|---|---|---|---|---|---|
| ($-log_{10}$) | Rep. 1 | Rep. 2 | Rep. 3 | Rep. 1 | Rep. 2 | Rep. 3 | Control |
| | | | | | | | 0000 |
| -1 | NT | NT | NT | ++++ | ++++ | ++++ | |
| -2 | NT | NT | NT | ++++ | ++++ | ++++ | |
| -3 | NT | NT | NT | ++++ | +000 | 0+0+ | |
| -4 | ++++ | ++++ | ++++ | 0000 | 00+0 | 0000 | |
| -5 | ++++ | +++0 | ++++ | 0000 | 0000 | 0000 | |
| -6 | 0000 | 00+0 | +0+0 | 0000 | 0000 | 0000 | |
| -7 | 0000 | 0000 | 0000 | NT | NT | NT | |
| -8 | 0000 | 0000 | 0000 | NT | NT | NT | |
| $TCID_{50}$ | 5.50 $log_{10}$ | 5.50 $log_{10}$ | 6.00 $log_{10}$ | 3.50 $log_{10}$ | 3.00 $log_{10}$ | 3.00 $log_{10}$ | |
| Average $TCID_{50}$ | | 5.67 $log_{10}$ | | | 3.17 $log_{10}$ | | |
| Log Reduction* | | | | 2.17 $log_{10}$ | 2.67 $log_{10}$ | 2.67 $log_{10}$ | |
| Average Log Reduction | | | | | 2.50 $log_{10}$ | | |
| Percent Reduction | | | | 99.32% | 99.79% | 99.79% | |
| Average Percent Reduction** | | | | | 99.68% | | |

+ = CPE Present
0 = CPE not detected
NT = Not Tested
Rep = Replicate
*Log Reduction = Average $TCID_{50}$ of Virus Control – $TCID_{50}$ of the Test Replicate
**Average % Reduction (calculated from average $log_{10}$ reduction) = 100 – (1/$TCID_{50}$ Reduction)*100

TABLE 60

Reduction of Infectivity
Test Product: Methylsulfonylmethane, 6% (lot# 0902951)
Virus: Herpes Simplex Virus strain HF ATCC # VR-260
Host Cell Line: Vero Host Cell Line ATCC # CCL-81

| Dilutions | Virus Control | | | Test Product | | | Cell |
|---|---|---|---|---|---|---|---|
| ($-log_{10}$) | Rep. 1 | Rep. 2 | Rep. 3 | Rep. 1 | Rep. 2 | Rep. 3 | Control |
| | | | | | | | 0000 |
| -3 | NT | NT | NT | ++++ | ++++ | ++++ | |
| -4 | ++++ | ++++ | ++++ | ++++ | ++++ | +++0 | |
| -5 | ++++ | +++0 | ++++ | 000+ | 0+00 | +000 | |
| -6 | 0000 | 00+0 | +0+0 | 0000 | 0000 | 0000 | |
| -7 | 0000 | 0000 | 0000 | 0000 | 0000 | 0000 | |
| -8 | 0000 | 0000 | 0000 | 0000 | 0000 | 0000 | |
| $TCID_{50}$ | 5.50 $log_{10}$ | 5.50 $log_{10}$ | 6.00 $log_{10}$ | 4.75 $log_{10}$ | 4.75 $log_{10}$ | 4.50 $log_{10}$ | |
| Average $TCID_{50}$ | | 5.67 $log_{10}$ | | | 4.67 $log_{10}$ | | |
| Log Reduction* | | | | 0.92 $log_{10}$ | 0.92 $log_{10}$ | 1.17 $log_{10}$ | |
| Average Log Reduction | | | | | 1.00 $log_{10}$ | | |
| Percent Reduction | | | | 87.98% | 87.98% | 93.24% | |

TABLE 60-continued

Reduction of Infectivity
Test Product: Methylsulfonylmethane, 6% (lot# 0902951)
Virus: Herpes Simplex Virus strain HF ATCC # VR-260
Host Cell Line: Vero Host Cell Line ATCC # CCL-81

| Dilutions | Virus Control | | | Test Product | | | Cell |
|---|---|---|---|---|---|---|---|
| ($-\log_{10}$) | Rep. 1 | Rep. 2 | Rep. 3 | Rep. 1 | Rep. 2 | Rep. 3 | Control |
| Average Percent Reduction** | | | | | 90.00% | | |

+ = CPE Present
0 = CPE not detected
NT = Not Tested
Rep = Replicate
*Log Reduction = Average $TCID_{50}$ of Virus Control − $TCID_{50}$ of the Test Replicate
**Average % Reduction (calculated from average $\log_{10}$ reduction) = 100 − (1/$TCID_{50}$ Reduction)*100

TABLE 61

Reduction of Infectivity
Test Product: Methylsulfonylmethane, 5% (lot# 0902951)
Virus: Herpes Simplex Virus strain HF ATCC # VR-260
Host Cell Line: Vero Host Cell Line ATCC # CCL-81

| Dilutions | Virus Control | | | Test Product | | | Cell |
|---|---|---|---|---|---|---|---|
| ($-\log_{10}$) | Rep. 1 | Rep. 2 | Rep. 3 | Rep. 1 | Rep. 2 | Rep. 3 | Control |
|  |  |  |  |  |  |  | 0000 |
| -3 | NT | NT | NT | ++++ | ++++ | ++++ | |
| -4 | ++++ | ++++ | ++++ | ++0+ | ++++ | 000+ | |
| -5 | ++++ | +++0 | ++++ | 0+00 | 0000 | 0000 | |
| -6 | 0000 | 00+0 | +0+0 | 000+ | 0000 | 0000 | |
| -7 | 0000 | 0000 | 0000 | 0000 | 0000 | 0000 | |
| -8 | 0000 | 0000 | 0000 | 0000 | 0000 | 0000 | |
| $TCID_{50}$ | 5.50 $\log_{10}$ | 5.50 $\log_{10}$ | 6.00 $\log_{10}$ | 4.75 $\log_{10}$ | 4.50 $\log_{10}$ | 3.75 $\log_{10}$ | |
| Average $TCID_{50}$ | | 5.67 $\log_{10}$ | | | 4.33 $\log_{10}$ | | |
| Log Reduction* | | | | 0.92 $\log_{10}$ | 1.17 $\log_{10}$ | 1.92 $\log_{10}$ | |
| Average Log Reduction | | | | | 1.34 $\log_{10}$ | | |
| Percent Reduction | | | | 87.98% | 93.24% | 98.80 | |
| Average Percent Reduction** | | | | | 95.43% | | |

+ = CPE Present
0 = CPE not detected
NT = Not Tested
Rep = Replicate
*Log Reduction = Average $TCID_{50}$ of Virus Control − $TCID_{50}$ of the Test Replicate
**Average % Reduction (calculated from average $\log_{10}$ reduction) = 100 − (1/$TCID_{50}$ Reduction)*100

TABLE 62

Reduction of Infectivity
Test Product: Methylsulfonylmethane, 4% (lot# 0902951)
Virus: Herpes Simplex Virus strain HF ATCC # VR-260
Host Cell Line: Vero Host Cell Line ATCC # CCL-81

| Dilutions | Virus Control | | | Test Product | | | Cell |
|---|---|---|---|---|---|---|---|
| ($-\log_{10}$) | Rep. 1 | Rep. 2 | Rep. 3 | Rep. 1 | Rep. 2 | Rep. 3 | Control |
|  |  |  |  |  |  |  | 0000 |
| -3 | NT | NT | NT | ++++ | ++++ | ++++ | |
| -4 | ++++ | ++++ | ++++ | 00+0 | +0+0 | +0+0 | |

TABLE 62-continued

Reduction of Infectivity
Test Product: Methylsulfonylmethane, 4% (lot# 0902951)
Virus: Herpes Simplex Virus strain HF ATCC # VR-260
Host Cell Line: Vero Host Cell Line ATCC # CCL-81

| Dilutions | Virus Control | | | Test Product | | | Cell |
|---|---|---|---|---|---|---|---|
| ($-\log_{10}$) | Rep. 1 | Rep. 2 | Rep. 3 | Rep. 1 | Rep. 2 | Rep. 3 | Control |
| -5 | ++++ | +++0 | ++++ | 0000 | +00+ | 0000 | |
| -6 | 0000 | 00+0 | +0+0 | 0000 | 0000 | 0000 | |
| -7 | 0000 | 0000 | 0000 | 0000 | 0000 | 0000 | |
| -8 | 0000 | 0000 | 0000 | 0000 | 0000 | 0000 | |
| $TCID_{50}$ | 5.50 $\log_{10}$ | 5.50 $\log_{10}$ | 6.00 $\log_{10}$ | 3.75 $\log_{10}$ | 4.50 $\log_{10}$ | 4.00 $\log_{10}$ | |
| Average $TCID_{50}$ | | 5.67 $\log_{10}$ | | | 4.08 $\log_{10}$ | | |
| Log Reduction* | | | | 1.92 $\log_{10}$ | 1.17 $\log_{10}$ | 1.67 $\log_{10}$ | |
| Average Log Reduction | | | | | 1.59 $\log_{10}$ | | |
| Percent Reduction | | | | 98.80% | 93.24% | 97.86% | |
| Average Percent Reduction** | | | | | 97.43% | | |

+ = CPE Present
0 = CPE not detected
NT = Not Tested
Rep = Replicate
*Log Reduction = Average $TCID_{50}$ of Virus Control – $TCID_{50}$ of the Test Replicate
**Average % Reduction (calculated from average $\log_{10}$ reduction) = 100 – (1/$TCID_{50}$ Reduction)*100

TABLE 63

Reduction of Infectivity
Test Product: Methylsulfonylmethane, 3% (lot# 0902951)
Virus: Herpes Simplex Virus strain HF ATCC # VR-260
Host Cell Line: Vero Host Cell Line ATCC # CCL-81

| Dilutions | Virus Control | | | Test Product | | | Cell |
|---|---|---|---|---|---|---|---|
| ($-\log_{10}$) | Rep. 1 | Rep. 2 | Rep. 3 | Rep. 1 | Rep. 2 | Rep. 3 | Control |
| | | | | | | | 0000 |
| -3 | NT | NT | NT | ++++ | ++++ | ++++ | |
| -4 | ++++ | ++++ | ++++ | 00++ | ++++ | ++++ | |
| -5 | ++++ | +++0 | ++++ | 00+0 | 0000 | 00++ | |
| -6 | 0000 | 00+0 | +0+0 | 0000 | 0000 | 0000 | |
| -7 | 0000 | 0000 | 0000 | 0000 | 0000 | 000+ | |
| -8 | 0000 | 0000 | 0000 | 0000 | 0000 | 0000 | |
| $TCID_{50}$ | 5.50 $\log_{10}$ | 5.50 $\log_{10}$ | 6.00 $\log_{10}$ | 4.25 $\log_{10}$ | 4.50 $\log_{10}$ | 5.25 $\log_{10}$ | |
| Average $TCID_{50}$ | | 5.67 $\log_{10}$ | | | 4.67 $\log_{10}$ | | |
| Log Reduction* | | | | 1.42 $\log_{10}$ | 1.17 $\log_{10}$ | 0.42 $\log_{10}$ | |
| Average Log Reduction | | | | | 1.00 $\log_{10}$ | | |
| Percent Reduction | | | | 96.20% | 93.24% | 61.98% | |
| Average Percent Reduction** | | | | | 90.00% | | |

+ = CPE Present
0 = CPE not detected
NT = Not Tested
Rep = Replicate
*Log Reduction = Average $TCID_{50}$ of Virus Control – $TCID_{50}$ of the Test Replicate
**Average % Reduction (calculated from average $\log_{10}$ reduction) = 100 – (1/$TCID_{50}$ Reduction)*100

TABLE 64

Reduction of Infectivity
Test Product: Methylsulfonylmethane, 2% (lot# 0902951)
Virus: Herpes Simplex Virus strain HF ATCC # VR-260
Host Cell Line: Vero Host Cell Line ATCC # CCL-81

| Dilutions ($-\log_{10}$) | Virus Control | | | Test Product | | | Cell Control |
|---|---|---|---|---|---|---|---|
| | Rep. 1 | Rep. 2 | Rep. 3 | Rep. 1 | Rep. 2 | Rep. 3 | |
| | | | | | | | 0000 |
| -3 | NT | NT | NT | ++++ | ++++ | ++++ | |
| -4 | ++++ | ++++ | ++++ | ++++ | ++++ | ++++ | |
| -5 | ++++ | +++0 | ++++ | 0+++ | 0000 | 00+0 | |
| -6 | 0000 | 00+0 | +0+0 | 0000 | 0000 | 0000 | |
| -7 | 0000 | 0000 | 0000 | 0000 | 0000 | 0000 | |
| -8 | 0000 | 0000 | 0000 | 0000 | 0000 | 0000 | |
| $TCID_{50}$ | 5.50 $\log_{10}$ | 5.50 $\log_{10}$ | 6.00 $\log_{10}$ | 5.25 $\log_{10}$ | 4.50 $\log_{10}$ | 4.75 $\log_{10}$ | |
| Average $TCID_{50}$ | | 5.67 $\log_{10}$ | | | 4.83 $\log_{10}$ | | |
| Log Reduction | | | | 0.42 $\log_{10}$ | 1.17 $\log_{10}$ | 0.92 $\log_{10}$ | |
| Average Log Reduction | | | | | 0.84 $\log_{10}$ | | |
| Percent Reduction | | | | 61.98% | 93.24% | 87.98% | |
| Average Percent Reduction | | | | | 85.55% | | |

+ = CPE Present
0 = CPE not detected
NT = Not Tested
Rep = Replicate
*Log Reduction = Average $TCID_{50}$ of Virus Control − $TCID_{50}$ of the Test Replicate
**Average % Reduction (calculated from average $\log_{10}$ reduction) = 100 − (1/$TCID_{50}$ Reduction)*100

TABLE 65

Reduction of Infectivity
Test Product: Methylsulfonylmethane, 1% (lot# 0902951)
Virus: Herpes Simplex Virus strain HF ATCC # VR-260
Host Cell Line: Vero Host Cell Line ATCC # CCL-81

| Dilutions ($-\log_{10}$) | Virus Control | | | Test Product | | | Cell Control |
|---|---|---|---|---|---|---|---|
| | Rep. 1 | Rep. 2 | Rep. 3 | Rep. 1 | Rep. 2 | Rep. 3 | |
| | | | | | | | 0000 |
| -3 | NT | NT | NT | ++++ | ++++ | ++++ | |
| -4 | ++++ | ++++ | ++++ | ++++ | ++++ | ++++ | |
| -5 | ++++ | +++0 | ++++ | 00++ | 00++ | 00++ | |
| -6 | 0000 | 00+0 | +0+0 | 0000 | 0000 | 0000 | |
| -7 | 0000 | 0000 | 0000 | 0000 | 0000 | 0000 | |
| -8 | 0000 | 0000 | 0000 | 0000 | 0000 | 0000 | |
| $TCID_{50}$ | 5.50 $\log_{10}$ | 5.50 $\log_{10}$ | 6.00 $\log_{10}$ | 5.00 $\log_{10}$ | 5.00 $\log_{10}$ | 5.00 $\log_{10}$ | |
| Average $TCID_{50}$ | | 5.67 $\log_{10}$ | | | 5.00 $\log_{10}$ | | |
| Log Reduction | | | | 0.67 $\log_{10}$ | 0.67 $\log_{10}$ | 0.67 $\log_{10}$ | |
| Average Log Reduction | | | | | 0.67 $\log_{10}$ | | |
| Percent Reduction | | | | 78.62% | 78.62% | 78.62% | |
| Average Percent Reduction | | | | | 78.62% | | |

+ = CPE Present
0 = CPE not detected
NT = Not Tested
Rep = Replicate
*Log Reduction = Average $TCID_{50}$ of Virus Control − $TCID_{50}$ of the Test Replicate
**Average % Reduction (calculated from average $\log_{10}$ reduction) = 100 − (1/$TCID_{50}$ Reduction)*100

TABLE 66

Reduction of Infectivity
Test Product: Methylsulfonylmethane, 0.5% (lot# 0902951)
Virus: Herpes Simplex Virus strain HF ATCC # VR-260
Host Cell Line: Vero Host Cell Line ATCC # CCL-81

| Dilutions | Virus Control | | | Test Product | | | Cell |
|---|---|---|---|---|---|---|---|
| ($-\log_{10}$) | Rep. 1 | Rep. 2 | Rep. 3 | Rep. 1 | Rep. 2 | Rep. 3 | Control |
| | | | | | | | 0000 |
| -3 | NT | NT | NT | ++++ | ++++ | ++++ | |
| -4 | ++++ | ++++ | ++++ | ++++ | ++++ | ++++ | |
| -5 | ++++ | +++0 | ++++ | ++++ | ++0+ | ++0+ | |
| -6 | 0000 | 00+0 | +0+0 | 0000 | 0000 | 000+ | |
| -7 | 0000 | 0000 | 0000 | 0000 | 0000 | 0000 | |
| -8 | 0000 | 0000 | 0000 | 0000 | 0000 | 0000 | |
| $TCID_{50}$ | 5.50 $\log_{10}$ | 5.50 $\log_{10}$ | 6.00 $\log_{10}$ | 5.50 $\log_{10}$ | 5.25 $\log_{10}$ | 5.50 $\log_{10}$ | |
| Average $TCID_{50}$ | | 5.67 $\log_{10}$ | | | 5.42 $\log_{10}$ | | |
| Log Reduction | | | | 0.17 $\log_{10}$ | 0.42 $\log_{10}$ | 0.17 $\log_{10}$ | |
| Average Log Reduction | | | | | 0.25 $\log_{10}$ | | |
| Percent Reduction | | | | 32.39% | 61.98% | 32.39% | |
| Average Percent Reduction | | | | | 43.77% | | |

+ = CPE Present
0 = CPE not detected
NT = Not Tested
Rep = Replicate
*Log Reduction = Average $TCID_{50}$ of Virus Control − $TCID_{50}$ of the Test Replicate
**Average % Reduction (calculated from average $\log_{10}$ reduction) = 100 − (1/$TCID_{50}$ Reduction)*100

TABLE 67

Reduction of Infectivity
Test Product: Methylsulfonylmethane, 7% (lot# 0902951)
Virus: Rhinovirus type 14 strain 1059 ATCC # VR-284
Host Cell Line: MRC-5 Host Cell Line ATCC # CCL-171

| Dilutions | Virus Control | | | Test Product | | | Cell |
|---|---|---|---|---|---|---|---|
| ($-\log_{10}$) | Rep. 1 | Rep. 2 | Rep. 3 | Rep. 1 | Rep. 2 | Rep. 3 | Control |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | ++0+ | ++++ | ++++ | |
| -5 | ++++ | ++++ | ++++ | 0000 | 0000 | 0000 | |
| -6 | 0000 | 0000 | 0+0+ | 0000 | 0000 | 0000 | |
| -7 | 0000 | 0000 | 0000 | 0000 | 0000 | 0000 | |
| $TCID_{50}$ | 5.50 $\log_{10}$ | 5.50 $\log_{10}$ | 6.00 $\log_{10}$ | 4.25 $\log_{10}$ | 4.50 $\log_{10}$ | 4.50 $\log_{10}$ | |
| Average $TCID_{50}$ | | 5.67 $\log_{10}$ | | | 4.42 $\log_{10}$ | | |
| Log Reduction | | | | 1.42 $\log_{10}$ | 1.17 $\log_{10}$ | 1.17 $\log_{10}$ | |
| Average Log Reduction | | | | | 1.25 $\log_{10}$ | | |
| Percent Reduction | | | | 96.20% | 93.24% | 93.24% | |
| Average Percent Reduction | | | | | 94.38% | | |

+ = CPE Present
0 = CPE not detected
NT = Not Tested
Rep = Replicate
*Log Reduction = Average $TCID_{50}$ of Virus Control − $TCID_{50}$ of the Test Replicate
**Average % Reduction (calculated from average $\log_{10}$ reduction) = 100 − (1/$TCID_{50}$ Reduction)*100

Tables 68 through 74 present the Virus Control infectivity (TCID$_{50}$), the average infectivity (TCID$_{50}$), and the log$_{10}$ and percent reductions observed in Pre-treatment test of the Test Product, Methylsulfonylmethane (Lot Number 0902951), and Rhinovirus type 14 (ATCC # VR-284).

TABLE 68

Reduction of Infectivity
Test Product: Methylsulfonylmethane, 6% (lot# 0902951)
Virus: Rhinovirus type 14 strain 1059 ATCC # VR-284
Host Cell Line: MRC-5 Host Cell Line ATCC # CCL-171

| Dilutions | Virus Control | | | Test Product | | | Cell |
| --- | --- | --- | --- | --- | --- | --- | --- |
| (-log$_{10}$) | Rep. 1 | Rep. 2 | Rep. 3 | Rep. 1 | Rep. 2 | Rep. 3 | Control |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | ++++ | ++++ | ++++ | |
| -5 | ++++ | ++++ | ++++ | +000 | +0+0 | +0++ | |
| -6 | 0000 | 0000 | 0+0+ | 0000 | 0000 | 0000 | |
| -7 | 0000 | 0000 | 0000 | 0000 | 0000 | 0000 | |
| TCID$_{50}$ | 5.50 log$_{10}$ | 5.50 log$_{10}$ | 6.00 log$_{10}$ | 4.75 log$_{10}$ | 5.00 log$_{10}$ | 5.25 log$_{10}$ | |
| Average TCID$_{50}$ | | 5.67 log$_{10}$ | | | 5.00 log$_{10}$ | | |
| Log Reduction | | | | 0.92 log$_{10}$ | 0.67 log$_{10}$ | 0.42 log$_{10}$ | |
| Average Log Reduction | | | | | 0.67 log$_{10}$ | | |
| Percent Reduction | | | | 87.98% | 78.62% | 61.98% | |
| Average Percent Reduction | | | | | 78.62% | | |

+ = CPE Present
0 = CPE not detected
NT = Not Tested
Rep = Replicate
*Log Reduction = Average TCID$_{50}$ of Virus Control − TCID$_{50}$ of the Test Replicate
**Average % Reduction (calculated from average log$_{10}$ reduction) = 100 − (1/TCID$_{50}$ Reduction)*100

TABLE 69

Reduction of Infectivity
Test Product: Methylsulfonylmethane, 5% (lot# 0902951)
Virus: Rhinovirus type 14 strain 1059 ATCC # VR-284
Host Cell Line: MRC-5 Host Cell Line ATCC # CCL-171

| Dilutions | Virus Control | | | Test Product | | | Cell |
| --- | --- | --- | --- | --- | --- | --- | --- |
| (-log$_{10}$) | Rep. 1 | Rep. 2 | Rep. 3 | Rep. 1 | Rep. 2 | Rep. 3 | Control |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | ++++ | ++++ | ++++ | |
| -5 | ++++ | ++++ | ++++ | 0+++ | ++++ | ++++ | |
| -6 | 0000 | 0000 | 0+0+ | 0000 | 0000 | +00+ | |
| -7 | 0000 | 0000 | 0000 | 0000 | 0000 | 0000 | |
| TCID$_{50}$ | 5.50 log$_{10}$ | 5.50 log$_{10}$ | 6.00 log$_{10}$ | 5.25 log$_{10}$ | 5.50 log$_{10}$ | 6.00 log$_{10}$ | |
| Average TCID$_{50}$ | | 5.67 log$_{10}$ | | | 5.58 log$_{10}$ | | |
| Log Reduction | | | | 0.09 log$_{10}$ | 0.17 log$_{10}$ | 0.00 log$_{10}$ | |
| Average Log Reduction | | | | | 0.09 log$_{10}$ | | |
| Percent Reduction | | | | 18.72% | 32.39% | 00.00% | |

TABLE 69-continued

Reduction of Infectivity
Test Product: Methylsulfonylmethane, 5% (lot# 0902951)
Virus: Rhinovirus type 14 strain 1059 ATCC # VR-284
Host Cell Line: MRC-5 Host Cell Line ATCC # CCL-171

| Dilutions | Virus Control | | | Test Product | | | Cell |
|---|---|---|---|---|---|---|---|
| ($-\log_{10}$) | Rep. 1 | Rep. 2 | Rep. 3 | Rep. 1 | Rep. 2 | Rep. 3 | Control |
| Average Percent Reduction | | | | | 18.72% | | |

+ = CPE Present
0 = CPE not detected
NT = Not Tested
Rep = Replicate
*Log Reduction = Average $TCID_{50}$ of Virus Control − $TCID_{50}$ of the Test Replicate
**Average % Reduction (calculated from average $\log_{10}$ reduction) = 100 − (1/$TCID_{50}$ Reduction)*100

TABLE 70

Reduction of Infectivity
Test Product: Methylsulfonylmethane, 4% (lot# 0902951)
Virus: Rhinovirus type 14 strain 1059 ATCC # VR-284
Host Cell Line: MRC-5 Host Cell Line ATCC # CCL-171

| Dilutions | Virus Control | | | Test Product | | | Cell |
|---|---|---|---|---|---|---|---|
| ($-\log_{10}$) | Rep. 1 | Rep. 2 | Rep. 3 | Rep. 1 | Rep. 2 | Rep. 3 | Control |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | ++++ | ++++ | ++++ | |
| -5 | ++++ | ++++ | ++++ | 00++ | ++++ | ++++ | |
| -6 | 0000 | 0000 | 0+0+ | 0000 | 0000 | 0+00 | |
| -7 | 0000 | 0000 | 0000 | 0000 | 0000 | 0000 | |
| $TCID_{50}$ | 5.50 $\log_{10}$ | 5.50 $\log_{10}$ | 6.00 $\log_{10}$ | 5.00 $\log_{10}$ | 5.50 $\log_{10}$ | 5.75 $\log_{10}$ | |
| Average $TCID_{50}$ | | 5.67 $\log_{10}$ | | | 5.42 $\log_{10}$ | | |
| Log Reduction | | | | 0.67 $\log_{10}$ | 0.17 $\log_{10}$ | 0.00 $\log_{10}$ | |
| Average Log Reduction | | | | | 0.28 $\log_{10}$ | | |
| Percent Reduction | | | | 78.62% | 32.39% | 00.00% | |
| Average Percent Reduction | | | | | 47.52% | | |

+ = CPE Present
0 = CPE not detected
NT = Not Tested
Rep = Replicate
*Log Reduction = Average $TCID_{50}$ of Virus Control − $TCID_{50}$ of the Test Replicate
**Average % Reduction (calculated from average $\log_{10}$ reduction) = 100 − (1/$TCID_{50}$ Reduction)*100

TABLE 71

Reduction of Infectivity
Test Product: Methylsulfonylmethane, 3% (lot# 0902951)
Virus: Rhinovirus type 14 strain 1059 ATCC # VR-284
Host Cell Line: MRC-5 Host Cell Line ATCC # CCL-171

| Dilutions | Virus Control | | | Test Product | | | Cell |
|---|---|---|---|---|---|---|---|
| ($-\log_{10}$) | Rep. 1 | Rep. 2 | Rep. 3 | Rep. 1 | Rep. 2 | Rep. 3 | Control |
| | | | | | | | 0000 |
| -2 | NT | NT | NT | ++++ | ++++ | ++++ | |
| -3 | ++++ | ++++ | ++++ | ++++ | ++++ | ++++ | |

TABLE 71-continued

Reduction of Infectivity
Test Product: Methylsulfonylmethane, 3% (lot# 0902951)
Virus: Rhinovirus type 14 strain 1059 ATCC # VR-284
Host Cell Line: MRC-5 Host Cell Line ATCC # CCL-171

| Dilutions ($-\log_{10}$) | Virus Control | | | Test Product | | | Cell Control |
|---|---|---|---|---|---|---|---|
| | Rep. 1 | Rep. 2 | Rep. 3 | Rep. 1 | Rep. 2 | Rep. 3 | |
| -4 | ++++ | ++++ | ++++ | ++++ | ++++ | ++++ | |
| -5 | ++++ | ++++ | ++++ | ++0+ | ++++ | ++++ | |
| -6 | 0000 | 0000 | 0+0+ | 000+ | 0000 | 000+ | |
| -7 | 0000 | 0000 | 0000 | 0000 | 0000 | +000 | |
| $TCID_{50}$ | 5.50 $\log_{10}$ | 5.50 $\log_{10}$ | 6.00 $\log_{10}$ | 5.50 $\log_{10}$ | 5.50 $\log_{10}$ | 6.00 $\log_{10}$ | |
| Average $TCID_{50}$ | | 5.67 $\log_{10}$ | | | 5.67 $\log_{10}$ | | |
| Log Reduction | | | | 0.17 $\log_{10}$ | 0.17 $\log_{10}$ | 0.00 $\log_{10}$ | |
| Average Log Reduction | | | | | 0.11 $\log_{10}$ | | |
| Percent Reduction | | | | 32.39% | 32.39% | 00.00% | |
| Average Percent Reduction | | | | | 22.38% | | |

+ = CPE Present
0 = CPE not detected
NT = Not Tested
Rep = Replicate
*Log Reduction = Average $TCID_{50}$ of Virus Control – $TCID_{50}$ of the Test Replicate
**Average % Reduction (calculated from average $\log_{10}$ reduction) = 100 – (1/$TCID_{50}$ Reduction)*100

TABLE 72

Reduction of Infectivity
Test Product: Methylsulfonylmethane, 2% (lot# 0902951)
Virus: Rhinovirus type 14 strain 1059 ATCC # VR-284
Host Cell Line: MRC-5 Host Cell Line ATCC # CCL-171

| Dilutions ($-\log_{10}$) | Virus Control | | | Test Product | | | Cell Control |
|---|---|---|---|---|---|---|---|
| | Rep. 1 | Rep. 2 | Rep. 3 | Rep. 1 | Rep. 2 | Rep. 3 | |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | ++++ | ++++ | ++++ | |
| -5 | ++++ | ++++ | ++++ | ++++ | 0+++ | 0000 | |
| -6 | 0000 | 0000 | 0+0+ | 0000 | 00+0 | 00+0 | |
| -7 | 0000 | 0000 | 0000 | 0000 | 0000 | 0000 | |
| $TCID_{50}$ | 5.50 $\log_{10}$ | 5.50 $\log_{10}$ | 6.00 $\log_{10}$ | 5.50 $\log_{10}$ | 5.50 $\log_{10}$ | 4.75 $\log_{10}$ | |
| Average $TCID_{50}$ | | 5.67 $\log_{10}$ | | | 5.25 $\log_{10}$ | | |
| Log Reduction | | | | 0.17 $\log_{10}$ | 0.17 $\log_{10}$ | 0.92 $\log_{10}$ | |
| Average Log Reduction | | | | | 0.42 $\log_{10}$ | | |
| Percent Reduction | | | | 32.39% | 32.39% | 87.98% | |
| Average Percent Reduction | | | | | 61.98% | | |

+ = CPE Present
0 = CPE not detected
NT = Not Tested
Rep = Replicate
*Log Reduction = Average $TCID_{50}$ of Virus Control – $TCID_{50}$ of the Test Replicate
**Average % Reduction (calculated from average $\log_{10}$ reduction) = 100 – (1/$TCID_{50}$ Reduction)*100

TABLE 73

Reduction of Infectivity
Test Product: Methylsulfonylmethane, 1% (lot# 0902951)
Virus: Rhinovirus type 14 strain 1059 ATCC # VR-284
Host Cell Line: MRC-5 Host Cell Line ATCC # CCL-171

| Dilutions | Virus Control | | | Test Product | | | Cell |
|---|---|---|---|---|---|---|---|
| ($-\log_{10}$) | Rep. 1 | Rep. 2 | Rep. 3 | Rep. 1 | Rep. 2 | Rep. 3 | Control |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | ++++ | ++++ | ++++ | |
| -5 | ++++ | ++++ | ++++ | ++++ | ++0+ | ++++ | |
| -6 | 0000 | 0000 | 0+0+ | +0+0 | 0000 | 000+ | |
| -7 | 0000 | 0000 | 0000 | 0000 | 0000 | 0000 | |
| $TCID_{50}$ | 5.50 $\log_{10}$ | 5.50 $\log_{10}$ | 6.00 $\log_{10}$ | 6.00 $\log_{10}$ | 5.25 $\log_{10}$ | 5.75 $\log_{10}$ | |
| Average $TCID_{50}$ | | 5.67 $\log_{10}$ | | | 5.67 $\log_{10}$ | | |
| Log Reduction | | | | 0.00 $\log_{10}$ | 0.42 $\log_{10}$ | 0.00 $\log_{10}$ | |
| Average Log Reduction | | | | | 0.14 $\log_{10}$ | | |
| Percent Reduction | | | | 00.00% | 61.98% | 00.00% | |
| Average Percent Reduction | | | | | 27.56% | | |

+ = CPE Present
0 = CPE not detected
NT = Not Tested
Rep = Replicate
*Log Reduction = Average $TCID_{50}$ of Virus Control – $TCID_{50}$ of the Test Replicate
**Average % Reduction (calculated from average $\log_{10}$ reduction) = 100 – (1/$TCID_{50}$ Reduction)*100

TABLE 74

Reduction of Infectivity
Test Product: Methylsulfonylmethane, 0.5% (lot# 0902951)
Virus: Rhinovirus type 14 strain 1059 ATCC # VR-284
Host Cell Line: MRC-5 Host Cell Line ATCC # CCL-171

| Dilutions | Virus Control | | | Test Product | | | Cell |
|---|---|---|---|---|---|---|---|
| ($-\log_{10}$) | Rep. 1 | Rep. 2 | Rep. 3 | Rep. 1 | Rep. 2 | Rep. 3 | Control |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | ++++ | ++++ | ++++ | |
| -5 | ++++ | ++++ | ++++ | ++++ | ++++ | 0000 | |
| -6 | 0000 | 0000 | 0+0+ | 0000 | +000 | 0000 | |
| -7 | 0000 | 0000 | 0000 | 0000 | 0000 | 0000 | |
| $TCID_{50}$ | 5.50 $\log_{10}$ | 5.50 $\log_{10}$ | 6.00 $\log_{10}$ | 5.50 $\log_{10}$ | 5.75 $\log_{10}$ | 4.50 $\log_{10}$ | |
| Average $TCID_{50}$ | | 5.67 $\log_{10}$ | | | 5.25 $\log_{10}$ | | |
| Log Reduction | | | | 0.17 $\log_{10}$ | 0.00 $\log_{10}$ | 1.17 $\log_{10}$ | |
| Average Log Reduction | | | | | 0.40 $\log_{10}$ | | |
| Percent Reduction | | | | 32.39% | 00.00% | 93.24% | |
| Average Percent Reduction | | | | | 60.19% | | |

+ = CPE Present
0 = CPE not detected
NT = Not Tested
Rep = Replicate
*Log Reduction = Average $TCID_{50}$ of Virus Control – $TCID_{50}$ of the Test Replicate
**Average % Reduction (calculated from average $\log_{10}$ reduction) = 100 – (1/$TCID_{50}$ Reduction)*100

Table 75 presents the Virus Control infectivity ($TCID_{50}$), the average infectivity ($TCID_{50}$), and the $log_{10}$ and percent enhancement observed in Pre-treatment test of the Test Product, Methylsulfonylmethane (Lot Number 0902951), and Swine-like H1N1 Influenza A virus strain A/California/04/2009 (CDC ID #2009712047).

TABLE 75

Enhancement of Infectivity
Test Product: Methylsulfonylmethane, 3% (lot# 0902951)
Virus: Swine-like Influenza A H1N1 strain A/California/04/2009 CDC ID # 2009712047
Host Cell Line: MDCK Host Cell Line ATCC # CCL-34

| Dilutions | Virus Control | | | Test Product | | | Cell |
|---|---|---|---|---|---|---|---|
| ($-log_{10}$) | Rep. 1 | Rep. 2 | Rep. 3 | Rep. 1 | Rep. 2 | Rep. 3 | Control |
|  |  |  |  |  |  |  | 0000 |
| -2 | NT | NT | NT | ++++ | ++++ | ++++ |  |
| -3 | ++++ | ++++ | ++++ | ++++ | ++++ | ++++ |  |
| -4 | ++++ | ++++ | ++++ | ++++ | ++++ | ++++ |  |
| -5 | 00+0 | +000 | +0+0 | 00++ | +00+ | 0++0 |  |
| -6 | 0000 | 0000 | 0000 | 0000 | 0000 | 0000 |  |
| -7 | 0000 | 0000 | 0000 | 0000 | 0000 | 0000 |  |
| $TCID_{50}$ | 4.75 $log_{10}$ | 4.75 $log_{10}$ | 5.00 $log_{10}$ | 5.00 $log_{10}$ | 5.00 $log_{10}$ | 5.00 $log_{10}$ |  |
| Average $TCID_{50}$ |  | 4.83 $log_{10}$ |  |  | 5.00 $log_{10}$ |  |  |
| Log Stimulation |  |  |  | 0.17 $log_{10}$ | 0.17 $log_{10}$ | 0.17 $log_{10}$ |  |
| Average Log Stimulation |  |  |  |  | 0.17 $log_{10}$ |  |  |
| Percent Stimulation |  |  |  | 32.39% | 32.39% | 32.39% |  |
| Average Percent Stimulation |  |  |  |  | 32.39% |  |  |

+ = CPE Present
0 = CPE not detected
NT = Not Tested
Rep = Replicate
*Log Stimulation = Average $TCID_{50}$ of Test – $TCID_{50}$ of Replicate of the Virus Control
**Average % Stimulation (calculated from average $log_{10}$ stimulation) = 100 – (1/$TCID_{50}$ Stimulation)*100

Tables 76 through 78 the Virus Control infectivity ($TCID_{50}$), the average infectivity ($TCID_{50}$), and the $log_{10}$ and percent enhancement observed in Pre-treatment test of the Test Product, Methylsulfonylmethane (Lot Number 0902951), and Rhinovirus type 14 (ATCC # VR-284).

TABLE 76

Enhancement of Infectivity
Test Product: Methylsulfonylmethane, 5% (lot# 0902951)
Virus: Rhinovirus type 14 strain 1059 ATCC # VR-284
Host Cell Line: MRC-5 Host Cell Line ATCC # CCL-171

| Dilutions | Virus Control | | | Test Product | | | Cell |
|---|---|---|---|---|---|---|---|
| ($-log_{10}$) | Rep. 1 | Rep. 2 | Rep. 3 | Rep. 1 | Rep. 2 | Rep. 3 | Control |
|  |  |  |  |  |  |  | 0000 |
| -2 | NT | NT | NT | ++++ | ++++ | ++++ |  |
| -3 | ++++ | ++++ | ++++ | ++++ | ++++ | ++++ |  |
| -4 | ++++ | ++++ | ++++ | ++++ | ++++ | ++++ |  |
| -5 | ++++ | ++++ | ++++ | 0+++ | ++++ | ++++ |  |
| -6 | 0000 | 0000 | 0+0+ | 0000 | 0000 | +00+ |  |
| -7 | 0000 | 0000 | 0000 | 0000 | 0000 | 0000 |  |
| $TCID_{50}$ | 5.50 $log_{10}$ | 5.50 $log_{10}$ | 6.00 $log_{10}$ | 5.25 $log_{10}$ | 5.50 $log_{10}$ | 6.00 $log_{10}$ |  |
| Average $TCID_{50}$ |  | 5.67 $log_{10}$ |  |  | 5.58 $log_{10}$ |  |  |
| Log Stimulation |  |  |  | 0.08 $log_{10}$ | 0.08 $log_{10}$ | 0.00 $log_{10}$ |  |

TABLE 76-continued

Enhancement of Infectivity
Test Product: Methylsulfonylmethane, 5% (lot# 0902951)
Virus: Rhinovirus type 14 strain 1059 ATCC # VR-284
Host Cell Line: MRC-5 Host Cell Line ATCC # CCL-171

| Dilutions | Virus Control | | | Test Product | | | Cell |
|---|---|---|---|---|---|---|---|
| ($-\log_{10}$) | Rep. 1 | Rep. 2 | Rep. 3 | Rep. 1 | Rep. 2 | Rep. 3 | Control |
| Average Log Stimulation | | | | | $0.053 \log_{10}$ | | |
| Percent Stimulation | | | | 16.82% | 16.82% | 00.00% | |
| Average Percent Stimulation | | | | | 11.49% | | |

+ = CPE Present
0 = CPE not detected
NT = Not Tested
Rep = Replicate

*Log Stimulation = Average $TCID_{50}$ of Test − $TCID_{50}$ of Replicate of the Virus Control

**Average % Stimulation (calculated from average $\log_{10}$ stimulation) = 100 − (1/$TCID_{50}$ Stimulation)*100

TABLE 77

Enhancement of Infectivity
Test Product: Methylsulfonylmethane, 3% (lot# 0902951)
Virus: Rhinovirus type 14 strain 1059 ATCC # VR-284
Host Cell Line: MRC-5 Host Cell Line ATCC # CCL-171

| Dilutions | Virus Control | | | Test Product | | | Cell |
|---|---|---|---|---|---|---|---|
| ($-\log_{10}$) | Rep. 1 | Rep. 2 | Rep. 3 | Rep. 1 | Rep. 2 | Rep. 3 | Control |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | ++++ | ++++ | ++++ | |
| -5 | ++++ | ++++ | ++++ | ++0+ | ++++ | ++++ | |
| -6 | 0000 | 0000 | 0+0+ | 000+ | 0000 | 000+ | |
| -7 | 0000 | 0000 | 0000 | 0000 | 0000 | +000 | |
| $TCID_{50}$ | $5.50 \log_{10}$ | $5.50 \log_{10}$ | $6.00 \log_{10}$ | $5.50 \log_{10}$ | $5.50 \log_{10}$ | $6.00 \log_{10}$ | |
| Average $TCID_{50}$ | | $5.67 \log_{10}$ | | | $5.67 \log_{10}$ | | |
| Log Stimulation | | | | $0.17 \log_{10}$ | $0.17 \log_{10}$ | $0.00 \log_{10}$ | |
| Average Log Stimulation | | | | | $0.11 \log_{10}$ | | |
| Percent Stimulation | | | | 32.39% | 32.39% | 00.00% | |
| Average Percent Stimulation | | | | | 22.38% | | |

+ = CPE Present
0 = CPE not detected
NT = Not Tested
Rep = Replicate

*Log Stimulation = Average $TCID_{50}$ of Test − $TCID_{50}$ of Replicate of the Virus Control

**Average % Stimulation (calculated from average $\log_{10}$ stimulation) = 100 − (1/$TCID_{50}$ Stimulation)*100

TABLE 78

Enhancement of Infectivity
Test Product: Methylsulfonylmethane, 1% (lot# 0902951)
Virus: Rhinovirus type 14 strain 1059 ATCC # VR-284
Host Cell Line: MRC-5 Host Cell Line ATCC # CCL-171

| Dilutions ($-\log_{10}$) | Virus Control | | | Test Product | | | Cell Control |
|---|---|---|---|---|---|---|---|
| | Rep. 1 | Rep. 2 | Rep. 3 | Rep. 1 | Rep. 2 | Rep. 3 | |
| | | | | | | | 0000 |
| -2 | NT | NT | NT | ++++ | ++++ | ++++ | |
| -3 | ++++ | ++++ | ++++ | ++++ | ++++ | ++++ | |
| -4 | ++++ | ++++ | ++++ | ++++ | ++++ | ++++ | |
| -5 | ++++ | ++++ | ++++ | ++++ | ++0+ | ++++ | |
| -6 | 0000 | 0000 | 0+0+ | +0+0 | 0000 | 000+ | |
| -7 | 0000 | 0000 | 0000 | 0000 | 0000 | 0000 | |
| $TCID_{50}$ | 5.50 $\log_{10}$ | 5.50 $\log_{10}$ | 6.00 $\log_{10}$ | 6.00 $\log_{10}$ | 5.25 $\log_{10}$ | 5.75 $\log_{10}$ | |
| Average $TCID_{50}$ | | 5.67 $\log_{10}$ | | | 5.67 $\log_{10}$ | | |
| Log Stimulation | | | | 0.17 $\log_{10}$ | 0.17 $\log_{10}$ | 0.00 $\log_{10}$ | |
| Average Log Stimulation | | | | | 0.11 $\log_{10}$ | | |
| Percent Stimulation | | | | 32.39% | 32.39% | 00.00% | |
| Average Percent Stimulation | | | | | 22.38% | | |

\+ = CPE Present
0 = CPE not detected
NT = Not Tested
Rep = Replicate
*Log Stimulation = Average $TCID_{50}$ of Test − $TCID_{50}$ of Replicate of the Virus Control
**Average % Stimulation (calculated from average $\log_{10}$ stimulation) = 100 − (1/$TCID_{50}$ Stimulation)*100

Nonlinear Regression, Dose Versus Response:

Dose-Response (Inhibition) Analyses were performed for the test product concentrations converted into mM (test product molecular weight=94.13). Nonlinear regression analyses were as follows: log(inhibitor) vs. normalized response–Variable slope. Concentrations are presented in Table 79.

TABLE 79

| Concentration, % | Concentration, mM |
|---|---|
| 7% | 74.365 |
| 6% | 63.742 |
| 5% | 53.118 |
| 4% | 42.494 |
| 3% | 31.871 |
| 2% | 21.247 |
| 1% | 10.624 |
| 0.5% | 5.312 |

Table 80 presents the data input for Herpes Simplex Virus.

TABLE 80

| Dose, mM | Response, % reduction | | |
|---|---|---|---|
| 74.365 | 99.320 | 99.790 | 99.790 |
| 63.742 | 87.980 | 87.980 | 93.240 |
| 53.118 | 87.980 | 93.240 | 98.800 |
| 42.494 | 98.800 | 93.240 | 97.860 |
| 31.871 | 96.200 | 93.240 | 61.980 |
| 21.247 | 61.980 | 93.240 | 87.980 |
| 10.624 | 78.620 | 78.620 | 78.620 |
| 5.312 | 32.390 | 61.980 | 32.390 |

Table 81 presents transform (log of dose=X=Log(X)) of data for Herpes Simplex Virus.

TABLE 81

| Dose, mM | Response, % reduction | | |
|---|---|---|---|
| 1.871369 | 99.320 | 99.790 | 99.790 |
| 1.804426 | 87.980 | 87.980 | 93.240 |
| 1.725242 | 87.980 | 93.240 | 98.800 |
| 1.628328 | 98.800 | 93.240 | 97.860 |
| 1.503396 | 96.200 | 93.240 | 61.980 |
| 1.327298 | 61.980 | 93.240 | 87.980 |
| 1.026288 | 78.620 | 78.620 | 78.620 |
| 0.7252581 | 32.390 | 61.980 | 32.390 |

Table 82 presents of transform of normalize of the data for Herpes Simplex Virus. The percent reduction was normalized as follows: 32.39% becomes 0% for all data set; 99.79% becomes 100% for all data set.

TABLE 82

| Dose, mM | Response, % reduction | | |
|---|---|---|---|
| 1.871369 | 99.30267 | 100.000 | 100.000 |
| 1.804426 | 82.47775 | 82.47775 | 90.2819 |
| 1.725242 | 82.47775 | 90.2819 | 98.53116 |
| 1.628328 | 98.53116 | 90.2819 | 97.1365 |
| 1.503396 | 94.67358 | 90.2819 | 43.90208 |
| 1.327298 | 43.90208 | 90.2819 | 82.47775 |
| 1.026288 | 68.59051 | 68.59051 | 68.59051 |
| 0.7252581 | 0.000 | 43.90208 | 0.000 |

$IC_{50}$ computation for Herpes Simplex Virus is presented in Table 83. The best fit value for Herpes Simplex Virus $IC_{50}$ was determined 10.13 mM. However, due to a significant variation in virus reduction, $IC_{50}$ values ranging from 7.144 mM to 14.37 mM can be considered a more plausible approximation.

TABLE 83

| log (inhibitor) vs. normalized response -- Variable slope | |
|---|---|
| Best-fit values | |
| LogIC50 | 1.006 |
| HillSlope | 1.523 |
| IC50 | 10.13 |
| Std. Error | |
| LogIC50 | 0.07314 |
| HillSlope | 0.3281 |
| 95% Confidence Intervals | |
| LogIC50 | 0.8539 to 1.157 |
| HillSlope | 0.8428 to 2.204 |
| IC50 | 7.144 to 14.37 |
| Goodness of Fit | |
| Degrees of Freedom | 22 |
| R square | 0.6761 |
| Absolute Sum of Squares | 6312 |
| Sy.x | 16.94 |
| Number of points | |
| Analyzed | 24 |

Table 84 presents the data input for Swine-like Influenza virus A H1N1.

TABLE 84

| Dose, mM | Response, % reduction | | |
|---|---|---|---|
| 74.365 | 91.680 | 91.680 | 85.210 |
| 63.742 | 91.680 | 91.680 | 85.210 |
| 53.118 | 53.230 | 53.230 | 73.700 |
| 42.494 | 16.820 | 53.230 | 16.820 |
| 31.871 | 0.000 | 0.000 | 0.000 |
| 21.247 | 53.230 | 16.820 | 85.210 |
| 10.624 | 53.230 | 16.820 | 53.230 |
| 5.312 | 91.680 | 53.230 | 73.700 |

Table 85 presents transform [log of dose=X=Log(X)] of data for Swine-like Influenza virus A H1N1.

TABLE 85

| Dose, mM | Response, % reduction | | |
|---|---|---|---|
| 1.871369 | 91.680 | 91.680 | 85.210 |
| 1.804426 | 91.680 | 91.680 | 85.210 |
| 1.725242 | 53.230 | 53.230 | 73.700 |
| 1.628328 | 16.820 | 53.230 | 16.820 |
| 1.503396 | 0.000 | 0.000 | 0.000 |
| 1.327298 | 53.230 | 16.820 | 85.210 |
| 1.026288 | 53.230 | 16.820 | 53.230 |
| 0.7252581 | 91.680 | 53.230 | 73.700 |

Table 86 presents of transform of normalize of the data for Swine-like Influenza virus A H1N1. The percent reduction was normalized as follows: 0% becomes 0% for all data set; 91.68% becomes 100% for all data set.

TABLE 86

| Dose, mM | Response, % reduction | | |
|---|---|---|---|
| 1.871369 | 100.000 | 100.000 | 92.94284 |
| 1.804426 | 100.000 | 100.000 | 92.94284 |
| 1.725242 | 58.06065 | 58.06065 | 80.38831 |
| 1.628328 | 18.34642 | 58.06065 | 18.34642 |
| 1.503396 | 0.000 | 0.000 | 0.000 |
| 1.327298 | 58.06065 | 18.34642 | 92.94284 |

TABLE 86-continued

| Dose, mM | Response, % reduction | | |
|---|---|---|---|
| 1.026288 | 58.06065 | 18.34642 | 58.06065 |
| 0.7252581 | 100.000 | 58.06065 | 80.38831 |

$IC_{50}$ computation for Swine-like Influenza virus A H1N1 is presented in Table 87. The best-fit $IC_{50}$ value for Swine-like Influenza virus A H1N1 was determined 5.114 mM. $IC_{50}$ values with 95% confidence intervals ranged from 0.008038 mM to 3253 mM. In view of inconsequence of virus reduction (U-shaped curve) MSM $IC_{50}$s were determined with a significant approximation. $IC_{90}$ values can not be concluded from this data set.

TABLE 87

| log (inhibitor) vs. normalized response -- Variable slope | |
|---|---|
| Best-fit values | |
| LogIC50 | 0.7087 |
| HillSlope | 0.2135 |
| IC50 | 5.114 |
| Std. Error | |
| LogIC50 | 1.352 |
| HillSlope | 0.3534 |
| 95% Confidence Intervals | |
| LogIC50 | −2.095 to 3.512 |
| HillSlope | −0.5194 to 0.9464 |
| IC50 | 0.008038 to 3253 |
| Goodness of Fit | |
| Degrees of Freedom | 22 |
| R square | 0.01810 |
| Absolute Sum of Squares | 29296 |
| Sy.x | 36.49 |
| Number of points | |
| Analyzed | 24 |

Table 88 presents the data input for Rhinovirus type 14.

TABLE 88

| Dose, mM | Response, % reduction | | |
|---|---|---|---|
| 74.365 | 96.200 | 93.240 | 93.240 |
| 63.742 | 87.980 | 78.620 | 61.980 |
| 53.118 | 18.720 | 32.390 | 0.000 |
| 42.494 | 78.620 | 32.390 | 0.000 |
| 31.871 | 32.390 | 32.390 | 0.000 |
| 21.247 | 32.390 | 32.390 | 87.980 |
| 10.624 | 0.000 | 61.980 | 0.000 |
| 5.312 | 32.390 | 0.000 | 93.240 |

Table 89 presents transform [log of dose=X=Log(X)] of data for Rhinovirus type 14.

TABLE 89

| Dose, mM | Response, % reduction | | |
|---|---|---|---|
| 1.871369 | 96.200 | 93.240 | 93.240 |
| 1.804426 | 87.980 | 78.620 | 61.980 |
| 1.725242 | 18.720 | 32.390 | 0.000 |
| 1.628328 | 78.620 | 32.390 | 0.000 |
| 1.503396 | 32.390 | 32.390 | 0.000 |
| 1.327298 | 32.390 | 32.390 | 87.980 |
| 1.026288 | 0.000 | 61.980 | 0.000 |
| 0.7252581 | 32.390 | 0.000 | 93.240 |

Table 90 presents of transform of normalize of the data for Rhinovirus type 14. The percent reduction was normalized as follows: 0% becomes 0% for all data set; 96.20% becomes 100% for all data set.

TABLE 90

| Dose, mM | Response, % reduction | | |
|---|---|---|---|
| 1.871369 | 100.000 | 96.92308 | 96.92308 |
| 1.804426 | 91.45531 | 81.72558 | 64.42828 |
| 1.725242 | 19.45946 | 33.66944 | 0.000 |
| 1.628328 | 81.72558 | 33.66944 | 0.000 |
| 1.503396 | 33.66944 | 33.66944 | 0.000 |
| 1.327298 | 33.66944 | 33.66944 | 91.45531 |
| 1.026288 | 0.000 | 64.42828 | 0.000 |
| 0.7252581 | 33.66944 | 0.000 | 96.92308 |

$IC_{50}$ computation for Rhinovirus type 14 is presented in Table 91. The best fit $IC_{50}$ value for Rhinovirus type 14 was determined 38.16 mM. $IC_{50}$ values with 95% confidence intervals ranged from 13.07 mM to 111.4 mM. In view of inconsequence of virus reduction (U-shaped curve) MSM $IC_{50}$s were determined with a significant approximation. $IC_{90}$ values cannot be concluded from this data set.

TABLE 91

| log (inhibitor) vs. normalized response - Variable slope | |
|---|---|
| Best-fit values | |
| LogIC50 | 1.582 |
| HillSlope | 0.6280 |
| IC50 | 38.16 |
| Std. Error | |
| LogIC50 | 0.2244 |
| HillSlope | 0.4179 |
| 95% Confidence Intervals | |
| LogIC50 | 1.116 to 2.047 |
| HillSlope | −0.2387 to 1.495 |
| IC50 | 13.07 to 111.4 |
| Goodness of Fit | |
| Degrees of Freedom | 22 |
| R square | 0.1044 |
| Absolute Sum of Squares | 29118 |
| Sy.x | 36.38 |
| Number of points | |
| Analyzed | 24 |

Example 24

Effect of MSM on Algae

This example shows effects of MSM on algae activity.

Two species of Chlorella were examined for growth—Chlorella sorokiniana a freshwater species and Chlorella minutissima a marine species. The study measured the effect of algal growth in a freshwater and saltwater environment with the addition of MSM in which MSM was added at the following concentrations: 0%, 0.25%, 2%, 5%, 10% and 20%. Growth was measured on day 0, 1, 2, 3, 4, 5, 6, 7, 8, 9 and 10. The growth curves of percent transmittance of the algae were compared between the MSM concentrations with the 0% MSM concentration as a sample control for each microorganism. The MSM stock powder was supplied by Bergstrom Nutrition with certificate of analysis. The powder was the microprill formula, lot #0806809. All media, water and stock MSM powder was sterility checked prior to the study. The following media were purchased from UTEX Culture Collection of Algae: Enriched Salt Water Medium and Volvox Dextrose Medium.

The algae were grown for 48 hours in the appropriate medium. The initial suspension was enumerated for each alga and is referred to as the starting inoculums. Chlorella sorokiniana was at 381 million cells per milliliter and Chlorella minutissima was at 19 million cells per milliliter. One milliliter of the algal solution was placed into 9 mLs of medium and mixed by vortexing. This was repeated for each concentration of MSM medium mixturer. The tube of algae and MSM were incubated at room temperature with exposure to sunlight. The working MSM concentrations were prepared from a single 20.0% MSM solution and were diluted accordingly with medium to get the desired final concentration of MSM. All solutions were verified for sterility before proceeding with the study. Each dilution of MSM for each organism was set up in and analyzed in triplicate for each time interval measured. The samples were measured by percent transmittance on a UV/VIS spectrophotometer at wavelength 750 nm. The medium stock was tested for percent transmittance background levels at every time interval were measured. The results from these studies are provided in the Tables 92 and 93 below. The lower percent transmittance indicated a higher growth factor. These studies demonstrate that MSM treatment can increase growth of algae.

TABLE 92

Growth of Chlorella sorokiniana

| | | MSM Concentrations | | | | | | | |
|---|---|---|---|---|---|---|---|---|---|
| | | 0 | 0.5 | 1 | 2.5 | 5 | 10 | 20 | Medium |
| Sample Day | 0 | 80.3 | 47.3 | 48.7 | 40.6 | 35.6 | 31.2 | 19.3 | 30.2 |
| | 1 | 50.6 | 41.8 | 42.5 | 43.1 | 31.2 | 31.3 | 21.9 | 40.3 |
| | 2 | 24.5 | 29.3 | 37.5 | 44.9 | 27.4 | 29.7 | 24.1 | 82.4 |
| | 3 | 29.9 | 29.6 | 37.5 | 43.8 | 21.4 | 28.4 | 28.1 | 91.2 |
| | 4 | 25.4 | 19.0 | 17.3 | 26.1 | 18.2 | 29.0 | 31.4 | 94.5 |
| | 5 | 10.6 | 12.4 | 13.5 | 10.3 | 15.7 | 28.7 | 33.6 | 93.3 |
| | 6 | 10.5 | 12.5 | 13.0 | 10.9 | 15.9 | 27.1 | 36.8 | 97.8 |
| | 7 | 10.0 | 11.9 | 12.5 | 11.0 | 16.3 | 27.6 | 40.6 | 34.3 |
| | 8 | 10.0 | 12.2 | 12.4 | 11.2 | 17.0 | 27.1 | 40.8 | 32.2 |
| | 9 | 8.5 | 7.5 | 7.8 | 8.4 | 13.7 | 76.4 | 84.8 | 30.4 |
| | 10 | 7.4 | 6.4 | 6.6 | 6.0 | 12.8 | 93.8 | 96.7 | 18.8 |

TABLE 93

Growth of Chlorella minutissima

| | | MSM Percentage | | | | | | | |
|---|---|---|---|---|---|---|---|---|---|
| | | 0.0 | 0.5 | 1.0 | 2.5 | 5.0 | 10.0 | 20.0 | Medium |
| Sample Day | 0 | 72.4 | 93.5 | 91.1 | 82.8 | 68.9 | 49.6 | 30.0 | 105.1 |
| | 1 | 74.6 | 70.1 | 80.5 | 75.1 | 87.4 | 49.2 | 33.8 | 105.1 |
| | 2 | 51.5 | 45.4 | 40.0 | 59.5 | 76.5 | 50.8 | 51.1 | 105.1 |
| | 3 | 33.4 | 32.1 | 31.0 | 45.4 | 62.0 | 51.9 | 54.8 | 105.1 |
| | 4 | 28.2 | 27.6 | 27.9 | 33.6 | 52.9 | 52.0 | 57.3 | 105.1 |
| | 5 | 26.4 | 26.6 | 26.5 | 32.4 | 52.2 | 51.9 | 57.5 | 105.1 |
| | 6 | 25.6 | 25.1 | 25.4 | 30.0 | 50.7 | 54.9 | 57.4 | 105.1 |
| | 7 | 24.3 | 23.6 | 24.4 | 28.6 | 51.0 | 56.1 | 57.1 | 106.4 |
| | 8 | 24.1 | 22.8 | 23.7 | 27.7 | 51.9 | 58.6 | 55.8 | 107.0 |
| | 9 | 18.0 | 20.4 | 21.0 | 23.3 | 47.1 | 41.4 | 45.1 | 109.3 |
| | 10 | 14.9 | 18.9 | 19.4 | 21.1 | 44.1 | 36.7 | 30.2 | 112.0 |

Example 25

Absorption of MSM in Topical Formulation is Within Recognized Safe Levels

This example shows absorption of MSM in topical formulations is within recognized safe levels.

New Zealand White rabbits, which are an accepted animal model for dermal absorption studies, were used to assess the absorption and resultant blood levels of MSM. Rabbits were obtained from Charles River Canada (Saint-Constant, Quebec). Five male rabbits, ages 12-13 weeks and ranging in weight from 2.6 kg to 2.7 kg were used for the dermal absorption studies. Rabbits were used because of their greater skin permeability as compared to rats, pigs or humans. Thus, testing on rabbits is a more conservative approach for the safety of topical products for human use. The size of rabbit was based on the ethical restriction of collecting greater than 6 mL/kg body weight of blood within a two week period. The total volume of blood to be removed during this study was 10 mL on a single day. One animal per group was used to minimize the number of animals required Animals were housed individually in stainless steel cages with 12 hours light/dark cycles. The animal room environment was monitored daily (targeted ranges: 18-26° C. and relative humidity 25-50%). Fresh air was supplied to the room at a sufficient rate to provide approximately 15 to 17 changes of room air per hour. Clinical observations were conducted for all animals to ensure animals were in good health prior to dosing. Morbidity and mortality observations were also conducted during the study period.

Treatment groups were as shown in Table 94.

TABLE 94

Study 1 Design

| Group | Test Article | Surface Area Exposed | Volume Applied | Number of Animals | Blood Collection Times (min) |
|---|---|---|---|---|---|
| A | 10% MSM + 90% Water | 6 cm$^2$ | 0.5 mL | 1 | 0 (pre-dose), 10, 30, 120, 480 minutes |
| B | 50% DMSO + 50% Water | 6 cm$^2$ | 0.5 mL | 1 | 0 (pre-dose), 10, 30, 120, 480 minutes |
| C | 70% DMSO + 30% Water | 6 cm$^2$ | 0.5 mL | 1 | 0 (pre-dose), 10, 30, 120, 480 minute |
| D | 10% MSM + 50% DMSO + 40% Water | 6 cm$^2$ | 0.5 mL | 1 | 0 (pre-dose), 10, 30, 120, 480 minutes |
| E | 10% MSM + 70% DMSO + 20% Water | 6 cm$^2$ | 0.5 mL | 1 | 0 (pre-dose), 10, 30, 120, 480 minutes |

One day prior to the study, the rump of each rabbit was closely clipped using hair clippers. An area of 6 cm$^2$ was measured and marked to ensure equivalence in the application of the various compositions. Each product was applied by pipetting 0.5 mL of each composition into the center of the test area and spread to cover the entire test area. After the 5 minute exposure period, the compositions were removed by wiping, rinsing and drying the test area.

Prior to blood collection, animals were tranquilized with Acepromazine (1 mg/kg) by intramuscular injection in the right hind leg muscle, after which EMLA cream (lidocaine/prilocalne) was applied to both ears along the ear artery. Blood was collected by insertion of a 21 G needle (hub removed) into the ear artery. Approximately 2 mL of whole blood was collected into 4 mL vacuutainer tubes (Becton Dickinson, Mississauga, ON) containing K$_2$EDTA. Tubes were inverted to mix with the anticoagulant and stored refrigerated until plasma was separated by centrifugation. Plasma was separated from whole blood by centrifugation at 3000×g for 10 minutes. Plasma was collected, transferred and stored in a cryovial at −70° C. until further processing for MSM analysis.

Following the 5 minute exposure period to the various test products (see Table 1), blood was collected after 10 minutes, 30 minutes, 2 hours and 8 hours. Prior to the 2 and 8 hour blood collections, EMLA cream was applied to the ears (approximately 30 minutes prior to each of these blood draws) as the anesthetic effects of the EMLA cream lasts approximately 1 to 2 hours. Both EMLA cream and Acepromazine were used due to ethical considerations and to provide for the well being of the animals used in this study.

The concentrations of MSM in plasma were quantified by gas chromatography-mass spectrometry (GC/MS) based on established methods. Briefly, 450 µL of plasma sample was mixed with 50 µL of physiological saline and vortexed for 30 seconds. Following this 1 mL of Acetonitrile (Fisher, HPLC grade) was added to the mixture. The solution was vortexed vigorously for 60 seconds and centrifuged at 2000 rpm for 5 minutes. One microliter of the clear supernatant was introduced to the GC/MS system (GC/MS QP20108 EI, Shimadzu, Kyoto, Japan). The analysis was performed on a 8himadzu SHR5XLB column (0.25 mm ID×length 30 m, film 0.25 um, Kyoto, Japan). The retention time of MSM was 6.1-6.3 minutes. MSM was detected with MS and m/z 79 (M+−15) was used for monitoring MSM ion SIM profiles. Helium gas was used as the carrier gas, head pressure was 0.25 kg/cm2, make-up gas was 30 mL/min, column temperature was 80° C., injector temperature 120° C., separator temperature 200° C. and ion source temperature 250° C. The ionization energy was 70 eV. An external standard graph was prepared with MSM dissolved in acetonitrile at the following concentrations: 62.5 µg/ml, 31.3 µg/ml, 15.6 µg/ml, 7.8 µg/ml, 3.9 µg/ml, 1.9 µg/ml, 0.98 µg/ml and 0.49 µg/ml. The MSM concentration in plasma samples was calculated from the slope of the standard curve. The best fitted graph was linear with a R2 value of 0.998.

All animals were observed prior to the start of the study and all demonstrated good health. During the course of the study and subsequent to the study, all animals demonstrated good health. Morbidity, mortality and injury were assessed twice daily. No animals demonstrated any morbidity, mortality or injury.

The results of the absorption study are summarized in Table 95. Baseline plasma concentrations of MSM (prior to exposure to test articles) ranged between 4.2 µg/mL and 104.2 µg/mL. The variation in baseline is within the normal range of variation of natural MSM concentrations that have been established in prior studies. Following exposure to the various test articles, the highest plasma concentrations of MSM measured were less than or equal to approximately 140 µg/mL. This peak concentration results from exposure to 10% MSM+ 70% DMSO+20% water. When corrected for natural variation in baseline MSM concentrations, the largest change in plasma MSM was detected in the 70% DMSO+30% water group. These data suggest that variations in MSM, either due to absorption or due to metabolism of DMSO, are within the natural range of MSM concentrations.

TABLE 95

Concentration of MSM in Plasma After Exposure to MSM and DMSO

| Treatment | Time point (minute) | MSM Concentration (µg/mL) |
|---|---|---|
| 10% MSM + 90% water | 0 | 25.6 |
| | 10 | 17.6 |
| | 30 | 16.3 |
| | 120 | 14.0 |
| | 480 | 15.4 |
| 50% DMSO + 50% water | 0 | 4.2 |
| | 10 | 6.9 |
| | 30 | 6.9 |
| | 120 | 7.4 |
| | 480 | 12.6 |
| 70% DMSO + 30% water | 0 | 56.7 |
| | 10 | 89.0 |
| | 30 | 98.9 |
| | 120 | 128.7 |
| | 480 | 120.2 |
| 10% MSM + 50% DMSO + 40% water | 0 | 104.2 |
| | 10 | 116.5 |
| | 30 | 127.9 |
| | 120 | 128.4 |
| | 480 | 140.4 |
| 10% MSM + 70% DMSO + 20% water | 0 | 26.8 |
| | 10 | 37.3 |
| | 30 | 30.9 |
| | 120 | 33.9 |
| | 480 | 44.4 |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An in vitro method of enhancing fermentation efficiency of a eukaryotic microorganism for the production of beer, cider, wine, a biofuel, bread, dairy product or any combination thereof, the method comprising:
contacting, in vitro, methylsulfonylmethane (MSM), medium, and a eukaryotic microorganism capable of fermentation, wherein the MSM is provided at a concentration of 0.02%, 0.03%, 0.04%, 0.06%, 0.07%, 0.08%, 0.09%, 0.2%, 0.25%, or 0.3% by weight of the medium, wherein the MSM increases the fermentation efficiency of the eukaryotic microorganism for the production of beer, cider, wine, a biofuel, bread, dairy product or any combination thereof as compared to the fermentation efficiency of the eukaryotic microorganism for the production of beer, cider, wine, a biofuel, bread, dairy product or any combination thereof in the absence of MSM.

2. The in vitro method of claim 1, wherein the eukaryotic microorganism is yeast and the method of enhancing fermentation is for the production of beer.

3. The in vitro method of claim 1, wherein the eukaryotic microorganism is algae and the method of enhancing fermentation is for the production of biofuel.

4. The method of claim 1, wherein the concentration of MSM is 0.2% by weight of the medium.

5. An in vitro method of enhancing fermentation efficiency of a eukaryotic microorganism, the method comprising:
contacting, in vitro, methylsulfonylmethane (MSM), medium, and a eukaryotic microorganism capable of fermentation, wherein the MSM is provided at a concentration of 0.02%, 0.03%, 0.04%, 0.06%, 0.07%, 0.08%, 0.09%, 0.2%, 0.25%, or 0.3% by weight of the medium, wherein the MSM increases the fermentation efficiency of the eukaryotic microorganism by increasing production of ethanol, methanol or a combination thereof by at least 50% as compared to production of ethanol, methanol or a combination of thereof in the absence of MSM.

6. The in vitro method of claim 5, wherein the eukaryotic microorganism is yeast and the method of enhancing fermentation is for the production of beer.

7. The in vitro method of claim 5, wherein the eukaryotic microorganism is algae and the method of enhancing fermentation is for the production of biofuel.

8. The in vitro method of claim 5, wherein the MSM is provided at a concentration of 0.2% by weight of the medium.

9. The in vitro method of claim 5, wherein the MSM is provided at a concentration of 0.25% by weight of the medium.

10. An in vitro method of enhancing fermentation efficiency of a eukaryotic microorganism, the method comprising:
contacting, in vitro, methylsulfonylmethane (MSM), medium, and a eukaryotic microorganism capable of fermentation, wherein the MSM is provided at a concentration of 0.02%, 0.03%, 0.04%, 0.06%, 0.07%, 0.08%, 0.09%, 0.2%, 0.25%, or 0.3% by weight of the medium, wherein the MSM increases the fermentation efficiency by increasing carbon dioxide production by the eukaryotic microorganism by at least 50% in the presence of MSM as compared to carbon dioxide production in the absence of MSM, the eukaryotic microorganism is yeast and the method of enhancing fermentation is for the production of bread.

11. The in vitro method of claim 10, wherein the MSM is provided at a concentration of 0.2% by weight of the medium.

12. The in vitro method of claim 10, wherein the MSM is provided at a concentration of 0.25% by weight of the medium.

13. The in vitro method of claim 10, wherein the MSM is provided at a concentration of 0.3% by weight of the medium.

14. An in vitro method of enhancing fermentation efficiency of a eukaryotic microorganism, the method comprising:
contacting, in vitro, methylsulfonylmethane (MSM), medium, and a eukaryotic microorganism capable of fermentation, wherein the MSM is provided at a concentration of 0.02%, 0.03%, 0.04%, 0.06%, 0.07%, 0.08%, 0.09%, 0.2%, 0.25%, or 0.3% by weight of the medium, wherein the MSM increases the fermentation efficiency by increasing lactic acid production by the eukaryotic microorganism by at least 50% in the presence of MSM as compared to lactic acid production in the absence of MSM and the method of enhancing fermentation is for the production of a dairy product.

15. The in vitro method of claim 14, wherein the MSM is provided at a concentration of 0.2% by weight of the medium.

16. The in vitro method of claim 14, wherein the MSM is provided at a concentration of 0.25% by weight of the medium.

17. The in vitro method of claim 14, wherein the MSM is provided at a concentration of 0.3% by weight of the medium.

18. An in vitro method of enhancing fermentation efficiency of a eukaryotic microorganism for the production of beer, cider, wine, a biofuel, bread, dairy product or any combination thereof, the method comprising:

contacting, in vitro, methylsulfonylmethane (MSM), medium, and a eukaryotic microorganism capable of fermentation, wherein the MSM is provided at a concentration of 0.25% by weight of the medium, wherein the MSM increases the fermentation efficiency of the eukaryotic microorganism for the production of beer, cider, wine, a biofuel, bread, dairy product or any combination thereof as compared to the fermentation efficiency of the eukaryotic microorganism for the production of beer, cider, wine, a biofuel, bread, dairy product or any combination thereof in the absence of MSM.

19. An in vitro method of enhancing fermentation efficiency of a eukaryotic microorganism for the production of beer, cider, wine, a biofuel, bread, dairy product or any combination thereof, the method comprising:

contacting, in vitro, methylsulfonylmethane (MSM), medium, and a eukaryotic microorganism capable of fermentation, wherein the MSM is provided at a concentration of 0.3% by weight of the medium, wherein the MSM increases the fermentation efficiency of the eukaryotic microorganism for the production of beer, cider, wine, a biofuel, bread, dairy product or any combination thereof as compared to the fermentation efficiency of the eukaryotic microorganism for the production of beer, cider, wine, a biofuel, bread, dairy product or any combination thereof in the absence of MSM.

* * * * *